(12) United States Patent
Schiemann et al.

(10) Patent No.: US 9,862,717 B2
(45) Date of Patent: Jan. 9, 2018

(54) INDAZOLES

(71) Applicants: Merck Patent GmbH, Darmstadt (DE); Cancer Research Technology Ltd., London (GB)

(72) Inventors: Kai Schiemann, Seeheim-Jugenheim (DE); Aurelie Mallinger, Affleville (FR)

(73) Assignees: Merck Patent GmbH, Darmstadt (DE); Cancer Research Technology Limited, London (GB)

( * ) Notice: Subject to any disclaimer, the term of this patent is extended or adjusted under 35 U.S.C. 154(b) by 0 days.

(21) Appl. No.: 15/505,345

(22) PCT Filed: Jul. 30, 2015

(86) PCT No.: PCT/EP2015/001570
§ 371 (c)(1),
(2) Date: Feb. 21, 2017

(87) PCT Pub. No.: WO2016/026549
PCT Pub. Date: Feb. 25, 2016

(65) Prior Publication Data
US 2017/0267675 A1    Sep. 21, 2017

(30) Foreign Application Priority Data
Aug. 22, 2014 (EP) .................................... 14002929

(51) Int. Cl.
C07D 403/06    (2006.01)
C07D 471/04    (2006.01)
A61K 31/55     (2006.01)
A61K 31/437    (2006.01)
A61K 31/444    (2006.01)
A61K 31/454    (2006.01)
A61K 31/4184   (2006.01)
A61K 31/4545   (2006.01)
A61K 31/5377   (2006.01)
C07D 401/06    (2006.01)

(52) U.S. Cl.
CPC ........ *C07D 471/04* (2013.01); *A61K 31/4184* (2013.01); *A61K 31/437* (2013.01); *A61K 31/444* (2013.01); *A61K 31/454* (2013.01); *A61K 31/4545* (2013.01); *A61K 31/5377* (2013.01); *A61K 31/55* (2013.01); *C07D 401/06* (2013.01); *C07D 403/06* (2013.01)

(58) Field of Classification Search
CPC .. C07D 401/16; C07D 403/06; C07D 471/04; A61K 31/55; A61K 31/437; A61K 31/444; A61K 31/454; A61K 31/4184; A61K 31/4545; A61K 31/5377
See application file for complete search history.

(56) References Cited

U.S. PATENT DOCUMENTS 6,107,305 A     8/2000  Misra et al.
2011/0034441 A1  2/2011  Hood et al.

OTHER PUBLICATIONS

International Search Report dated Aug. 28, 2015, issued in corresponding PCT/EP2015/001570, 3 pages.

*Primary Examiner* — Timothy R Rozof
(74) *Attorney, Agent, or Firm* — Millen, White, Zelano & Branigan, P.C.

(57) ABSTRACT

The invention provides novel substituted indazole compounds according to Formula (I), their manufacture and use for the treatment of hyperproliferative diseases such as cancer, inflammatory or degenerative diseases.

15 Claims, No Drawings

INDAZOLES

FIELD OF THE INVENTION

The invention relates to a series of novel substituted indazole compounds that are useful in the treatment of hyperproliferative diseases such as cancer, as well as inflammatory or degenerative diseases, in mammals. Also encompassed by the present invention is the use of such compounds in the treatment of hyperproliferative, inflammatory or degenerative diseases in mammals, especially humans, and pharmaceutical compositions containing such compounds.

SUMMARY OF THE RELATED ART

CDK8, along with its closely related isoform CDK19, is an oncogenic transcription-regulating kinase. In contrast to better-known members of the CDK family (such as CDK1, CDK2, and CDK4/6), CDK8 plays no direct role in cell cycle progression. CDK8 knockout in embryonic stem cells prevents embryonic development, due to its essential role in the pluripotent stem cell phenotype but CDK8 depletion does not inhibit the growth of normal cells.

The role of CDK8 in cancer is due to its unique function as a regulator of several transcriptional programs involved in carcinogenesis. CDK8 has been identified as an oncogene in melanoma and colon cancer, the CDK8 gene being amplified in about 50% of the latter cancers. Higher expression of CDK8 has been associated with worse prognosis in colon, breast and ovarian cancer. The known cancer-relevant activities of CDK8 include positive regulation of Wnt/β-catenin pathway, growth factor-induced transcription and TGFα signaling. CDK8 was also shown to maintain the pluripotent phenotype of embryonic stem cells and has been associated with the cancer stem cell phenotype. DNA-damaging chemotherapeutic drugs induce TNFα, an activator of the transcription factor NFkB, in endothelial cells and in other cancer-associated stromal elements. Stroma-derived TNFα acts on tumor cells, where it induces NFkB-mediated production of related tumor-promoting cytokines CXCL1 and CXCL2. CXCL1/2 attract myeloid cells to the tumor, by binding to CXCR2 receptor on the myeloid cell surface.

Myeloid cells then secrete small calcium-binding proteins 5100A8 and A9 that are associated with chronic inflammation and cancer. 5100A8/9 act on tumor cells, promoting both their metastasis and survival of chemotherapy.

CDK8 is a cyclin dependent kinase that has a conserved function in transcription as part of the Mediator complex. Taatjes, D. J., Trends Biochem Sci 35, 315-322 (2010); Conaway, R. C. and Conaway, J. W., Curr Opin Genet Dev 21, 225-230 (2011). More recently, CDK8 has been reported to as an oncogene in both colon cancer (Firestein R. et al., Nature 455:547-51 (2008); Morris E. J. et al., Nature 455: 552-6 (2008); Starr T. K. et al., Science 323:1747-50 (2009)) and melanoma (Kapoor A. et al., Nature 468:1105-9 (2010)). CDK8 is upregulated and amplified in a subset of human colon tumors. CDK8 transforms immortalized cells and is required for colon cancer proliferation in vitro (Firestein, R. et al., Nature 455, 547-551 (2008)). CDK8 has also been found to be overexpressed and essential for proliferation in melanoma (Kapoor, A. et al., Nature 468, 1105-1109 (2010)). CDK8 has been shown to regulate several signaling pathways that are key regulators of both ES pluripotency and cancer. CDK8 activates the Wnt pathway by promoting expression of β-Catenin target genes (Firestein, R. et al., Nature 455, 547-551 (2008)) or by inhibiting E2F1, a potent inhibitor of β-Catenin transcriptional activity (Morris, E. J. et al., Nature 455, 552-556 (2008)). CDK8 promotes Notch target gene expression by phosphorylating the Notch intracellular domain, activating Notch enhancer complexes at target genes (Fryer C. J. et al., Mol Cell 16:509-20 (2004)). Lastly, CDK8 phosphorylation of SMAD proteins leads to activation of TGFβ/BMP target genes followed by degradation of the SMAD proteins to limit the target gene expression (Alarcon, C. et al., Cell 139, 757-769 (2009)).

Other compounds targeting the Wnt pathway are disclosed in, i.a. WO 2010/041054, WO 2013/110433, WO 2014/063778 or WO 2014/086453.

However, as a therapeutic directed to the Wnt pathway, and in particular to CDK8/19, has yet to be commercialized, a significant unmet medical need still exists, so that further promising Wnt pathway inhibitors have to be identified and developed.

DESCRIPTION OF THE INVENTION

It is, therefore, the object of the present invention to provide novel CDK8/19 inhibitors useful in the treatment of inflammatory or hyperproliferative diseases, such as cancer in mammals, with superior pharmacological properties both with respect to their activities as well as their solubility, metabolic clearance and bioavailability characteristics.

As a result, this invention provides novel substituted indazole compounds or their stereoisomers or tautomers, or pharmaceutically acceptable salts, that are CDK8/19 inhibitors and useful as medicaments, especially in the treatment of the diseases mentioned above and below.

The compounds are defined by Formula (I):

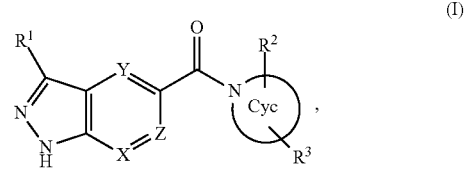

wherein:
X, Y independently are CH or N,
Z is CH, C(Hal) or N,
$R^1$ is H, LA, CA, $NH_2$, NH(LA) or (LA)NH(LA), Hal, —S(LA), —$SO_2$(LA), O(LA),
Cyc is a 3, 4, 5, 6 or 7 membered aliphatic heterocycle having 1 or 2 N atoms, or 1 N atom and 1 O atom,
$R^2$ is -LA-Ar or Ar, which is in the 2-, or 3-position with respect to the ring N atom of Cyc,
$R^3$ is H, OH, $NH_2$, COO(LA), $CONH_2$, CONH(LA), NHCO(LA), (LA)OH, NH(LA) or LA, which is in any position of Cyc,
Ar is a mono- or binuclear, aliphatic or aromatic 3, 4, 5, 6, 7, 8, 9 or 10 membered homo- or heterocycle, having 0, 1, 2, 3 or 4 N, O and/or S atoms, which may be unsubstituted, or mono- or independently disubstituted by Hal, OH, CN, LA, O(LA), S(LA),
LA is unbranched or branched alkyl, having 1, 2, 3, 4 or 5 carbon atoms, which may be saturated or partially unsaturated, wherein 1, 2 or 3 H atoms may be replaced by Hal,
CA is cycloalkyl having 3, 4, 5 or 6 carbon atoms, or cycloalkyl alkyl having 3, 4, 5 or 6 ring carbon atoms and 1 or 2 non-ring carbon atoms,
Hal is F, Cl, Br or I.

In general, all residues which occur more than once may be identical or different, i.e. are independent of one another. Above and below, the residues and parameters have the meanings indicated for the Formula (I), unless expressly indicated otherwise.

Accordingly, the invention relates, in particular, to the compounds of the Formula (I) in which at least one of the said residues has one of the preferred meanings indicated below.

Hal denotes fluorine, chlorine, bromine or iodine, in particular fluorine or chlorine, and preferably chlorine.

"LA" denotes for example methyl, ethyl, trifluoromethyl, difluoromethyl, 1,1,1-trifluoroethyl, propyl, isopropyl, butyl, isobutyl, sec-butyl or tert-butyl, isopropenyl, ethenyl, ethynyl or prop-1-ynyl.

"CA" denotes for example cyclopropyl, (cyclopropyl)methyl, cyclobutyl or (cyclopentyl)ethyl.

"Cyc" denotes, for example aziridinyl, azetidinyl, pyrrolidinyl, piperidinyl, azepanyl, preferably aziridin-1-yl, azetidin-1-yl, pyrrolidin-1-yl, piperidin-1-yl, azepan-1-yl "Ar" denotes, for example, phenyl, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, 2-, 3-, 5-, or 6-pyrazin-1- or 4-yl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-oxadiazol-2-yl, 1,3,4-thiadiazol-2- or -5-yl, 1,2,4-thiadiazol-3- or -5-yl, 1,2,3-thiadiazol-4- or -5-yl, 3- or 4-pyridazinyl, 1-, 2-, 3-, 4-, 5-, 6- or 7-indolyl, 2-, 3-, 4- or 5-isoindolyl, 2-, 6-, - or 8-purinyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 3-, 4-, 5-, 6-, 7- or 8-isoquinolinyl, 3-, 4-, 5-, 6-, 7- or 8-quinolinyl, 2-, 4-, 5-, 6-, 7- or 8-quinazolinyl, quinoxalin-2-, 3-, 4- or 5-yl, 4-, 5-, or 6-phthalazinyl, 2-, 3-, 5-, 6-, 7- or 8-2H-benzo-1,4-oxazinyl, Preferably, "Ar" denotes 2-, 3- or -4-pyridyl, phenyl, 2-, 4-, 5- or 6-pyrimidinyl, 2- or 3-pyrazinyl.

"LA-Ar" denotes, for example, 2-, 3- or 4-phenylmethyl, 2-, 3- or 4-phenylethyl, 2-, 3- or 4-pyridylmethyl, 2-, 3- or 4-pyridylethyl, In a preferred embodiment the compounds of the invention conform to Formula (I) as shown above, wherein:
X, Y, Z independently are CH or N,
R¹ is H, LA, CA, NH₂, NH(LA) or (LA)NH(LA),
Cyc is a 3, 4, 5, 6 or 7 membered aliphatic heterocycle having 1 N atom,
R² is -LA-Ar or Ar, which is in the 2-, or 3-position with respect to the ring N atom of Cyc,
R³ is H, OH, NH₂, COO(LA), CONH₂, CONH(LA) or LA, which is in any position of Cyc,
Ar is a mono- or binuclear, aliphatic or aromatic 3, 4, 5, 6, 7, 8, 9 or 10 membered homo- or heterocycle, having 0, 1, 2, 3 or 4 N, O and/or S atoms, which may be unsubstituted, or mono- or independently disubstituted by Hal, OH, CN, LA, O(LA), S(LA),
LA is unbranched or branched alkyl, having 1, 2, 3, 4 or 5 carbon atoms, which may be saturated or partially unsaturated, wherein 1, 2 or 3 H atoms may be replaced by Hal,
CA is cycloalkyl having 3, 4, 5 or 6 carbon atoms, or cycloalkyl alkyl having 3, 4, 5 or 6 ring carbon atoms and 1 or 2 non-ring carbon atoms,
Hal is F, Cl, Br or I.

In another preferred embodiment the compounds of the invention conform to Formula (I) as shown above, wherein:
X, Y independently are CH or N,
Z is CH,
R¹ is H, LA, CA, NH₂, NH(LA) or (LA)NH(LA),
Cyc is a 3, 4, 5, 6 or 7 membered aliphatic heterocycle having 1 N atom,
R² is -LA-Ar or Ar, which is in the 2-, or 3-position with respect to the ring N atom of Cyc,
R³ is H, NH₂ or LA, which is in any position of Cyc,
Ar is a mononuclear, aromatic, 6 membered homo- or heterocycle, having 0, 1 or 2 N atoms, which may be unsubstituted, or mono- or independently disubstituted by Hal, OH, CN, LA, O(LA), S(LA),
LA is unbranched or branched alkyl, having 1, 2, 3, 4 or 5 carbon atoms, which may be saturated or partially unsaturated, wherein 1, 2 or 3 H atoms may be replaced by Hal,
CA is cycloalkyl having 3, 4, 5 or 6 carbon atoms, or cycloalkyl alkyl having 3, 4, 5 or 6 ring carbon atoms and 1 or 2 non-ring carbon atoms,
Hal is F, Cl, Br or I.

In a more preferred embodiment the compounds of the invention conform to Formulae (IIa) or (IIb),

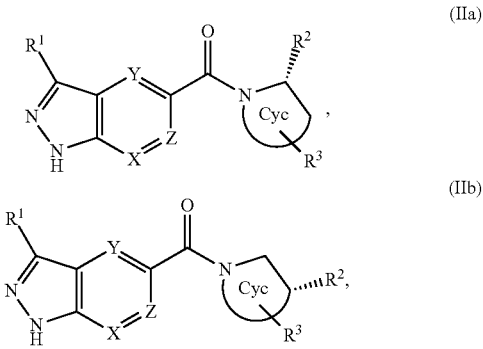

wherein all substituents have the meaning as indicated for Formula (I).

In a further preferred embodiment the compounds of the invention conform to Subformulae 1 to 26 of Formula (I) (IIa) or (IIb), wherein
in Subformula 1
Ar is a mononuclear, aromatic, 6 membered homo- or heterocycle, having 0, 1 or 2 N atoms, which is unsubstituted, or monosubstituted by Hal, LA, or O(LA),
in Subformula 2
X is N,
in Subformula 3
X is CH,
in Subformula 4
Y is CH,
in Subformula 5
Y is N,
in Subformula 6
Z is CH,
in Subformula 7
X is CH,
Y is N,
Z is CH,
in Subformula 8
X is N,
Y is CH,
Z is CH, in Subformula 9
Ar is a mononuclear, aromatic, 6 membered homo- or heterocycle, having 0, 1 or 2 N atoms, which may be unsubstituted, or mono- or independently disubstituted by Hal, OH, CN, LA, O(LA), S(LA),
X is CH,
Y is N,
Z is CH,
in Subformula 10
Ar is a mononuclear, aromatic, 6 membered homo- or heterocycle, having 0, 1 or 2 N atoms, which may be unsubstituted, or mono- or independently disubstituted by Hal, OH, CN, LA, O(LA), S(LA),
X is N,
Y is CH,
Z is CH,
in Subformula 11
$R^1$ is LA or $NH_2$, NHLA
in Subformula 12
Cyc has 4, 5 or 6 ring atoms,
in Subformula 13
$R^3$ is H, OH, $NH_2$ or methyl,
in Subformula 14
$R^3$ is H,
in Subformula 15
$R^2$ is benzyl,
$R^3$ is H, $NH_2$ or methyl,
Cyc has 6 ring atoms,
in Subformula 16
Cyc has 5 or 6 ring atoms,
$R^2$ is phenyl, which is unsubstituted, or mono- or independently disubstituted by Hal or LA,
in Subformula 17
Z is CH,
$R^2$ is benzyl or phenyl, which phenyl is unsubstituted, or mono- or independently disubstituted by Hal or LA,
in Subformula 18
X is N or CH,
Y is CH,
Z is CH,
$R^1$ is methyl, n-propyl, i-propyl, cyclopropyl, $NH_2$, NHLA
in Subformula 19
Z is CH,
Cyc has 5 ring atoms,
in Subformula 20
Z is CH,
$R^2$ is phenyl, which is unsubstituted or monosubstituted by Br, Cl, methyl or $CF_3$,
$R^3$ is H,
in Subformula 21
Z is CH,
$R^2$ is phenyl, which is unsubstituted or monosubstituted by Br, Cl, methyl or $CF_3$,
$R^3$ is H,
in Subformula 22
Z is CH,
$R^2$ is phenyl, which is unsubstituted or para-substituted by Br, Cl, methyl or $CF_3$,
$R^3$ is H,
in Subformula 23
Y is CH,
Z is CH,
$R^1$ is methyl, n-propyl, i-propyl, cyclopropyl or $NH_2$,
in Subformula 24
X is N or CH,
Y is CH,
Z is CH,
$R^1$ is methyl, n-propyl, i-propyl, cyclopropyl or $NH_2$,
Cyc has 4, 5 or 6 ring atoms,
in Subformula 25
X is N or CH,
Y is CH,
Z is CH,
$R^1$ is methyl, n-propyl, i-propyl, cyclopropyl or $NH_2$,
Cyc has 4, 5 or 6 ring atoms,
$R^2$ is phenyl, which is unsubstituted or para-substituted by Br, Cl, methyl or $CF_3$,
$R^3$ is H,
in Subformula 26
X is N or CH,
Y is CH,
Z is CH,
$R^1$ is methyl, n-propyl, i-propyl, cyclopropyl or $NH_2$,
Cyc has 5 ring atoms,
$R^2$ is phenyl, which is unsubstituted or para-substituted by Br, Cl, methyl or $CF_3$,
$R^3$ is H,
in Subformula 27
$R^1$ is methyl, n-propyl, i-propyl, cyclopropyl, methylsulfanyl, methanesulfonyl, methoxy, F or $NH_2$,
in Subformula 28
$R^3$ is H, OH, $NH_2$, methyl, acetamido, 2-hydroxyethyl or methylamino.
in Subformula 29
Z is CH or C(Hal),
Cyc has 4, 5 or 6 ring atoms, of which 1 atom is N and the other atoms are C,
$R^2$ is phenyl, which is unsubstituted or para-substituted by Br, Cl, F, methyl, methoxy, isopropyl or $CF_3$, or independently meta-/para-disubstituted by Cl and F,
$R^3$ is H.
in Subformula 30
Z is CH or C(Hal),
Cyc has 4 or 5 ring atoms, of which 1 atom is N and the other atoms are C,
$R^2$ is phenyl, which is unsubstituted or para-substituted by Br, Cl, F, methyl, methoxy, isopropyl or $CF_3$, or meta-substituted by F and para-substituted by Cl,
$R^3$ is H.
and the remaining residues have the meaning as indicated for Formula (I).

The compounds of the Formula (I) may have one or more centres of chirality. They may accordingly occur in various enantiomeric forms and be in racemic or optically active form. The invention, therefore, also relates to the optically active forms, enantiomers, racemates, diastereomers, collectively: stereoisomers, of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

An elegant method for the resolution of racemates containing ester groups (for example acetyl esters) is the use of enzymes, in particular esterases.

It is well known that atoms may have atomic masses or mass numbers which differ from the atomic masses or mass numbers of the atoms which usually occur naturally.

Examples of isotopes which are readily commercially available and which can be incorporated into a compound of the present invention by well-known methods include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively.

Incorporation of heavier isotopes, especially deuterium ($^2H$), into a compound of the invention has therapeutic advantages owing to the higher metabolic stability of this isotope-labelled compound. Higher metabolic stability translates directly into an increased in vivo half-life or lower dosages. Therefore, these isotopes are included in the definition of atoms H, C, N etc., as used in the chemical compounds of this invention.

The compounds of the present invention can be in the form of a prodrug compound. "Prodrug compound" means a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, wherein the amino group in a compound of the present invention is acylated, alkylated or phosphorylated, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated, or wherein a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like.

If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials The compounds of the present invention can be in the form of a pharmaceutically acceptable salt, a pharmaceutically acceptable solvate, or a pharmaceutically acceptable solvate of a pharmaceutically acceptable salt.

The term "pharmaceutically acceptable salts" refers to salts prepared from pharmaceutically acceptable bases or acids, including inorganic bases or acids and organic bases or acids. In cases where the compounds of the present invention contain one or more acidic or basic groups, the invention also comprises their corresponding pharmaceutically acceptable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present in salt form, and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

The term "pharmaceutically acceptable solvates" means addition forms with pharmaceutically acceptable solvents that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, e.g. a mono- or dihydrate. If the solvent is alcohol, the solvate formed is an alcoholate, e.g., a methanolate or ethanolate. If the solvent is an ether, the solvate formed is an etherate, e.g., diethyl etherate.

Therefore, the following items are also in accordance with the invention:
a) all stereoisomers or tautomers of the compounds, including mixtures thereof in all ratios,
b) prodrugs of the compounds, or stereoisomers or tautomers of these prodrugs,
c) pharmaceutically acceptable salts of the compounds and of the items mentioned under (a) and (b),
d) pharmaceutically acceptable solvates of the compounds and of the items mentioned under (a), (b) and (c).

It should be understood that all references to compounds above and below are meant to include these items, in particular pharmaceutically acceptable solvates of the compounds, or pharmaceutically acceptable solvates of their pharmaceutically acceptable salts.

Furthermore, the present invention relates to pharmaceutical compositions comprising a compound of the present invention, or its stereoisomers or tautomers, or pharmaceutically acceptable salts of each of the foregoing, including mixtures thereof in all ratios, as active ingredient, together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, such as one or more additional compounds of the present invention, or other Wnt pathway inhibitors.

The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for the treatment of cancer such as brain, lung, colon, epidermoid, squamous cell, bladder, gastric, pancreatic, breast, head & neck, renal, kidney, liver, ovarian, prostate, uterine, oesophageal, testicular, gynecological, thyroid cancer, melanoma, as well as hematologic malignancies such as acute myelogenous leukemia, multiple myeloma, chronic myelogneous leukemia, myeloid cell leukemia, Kaposi's sarcoma, or any other type of solid or liquid tumors. Preferably, the cancer to be treated is chosen from colon, lung, breast and hematological tumor types.

In addition, said compounds and pharmaceutical composition are for the treatment of inflammatory diseases such as multiple sclerosis, rheumatoid arthritis, systemic lupus, inflammatory bowel diseases or degenerative diseases such as osteoarthritis and Alzheimer's disease.

The anti-cancer treatment defined above and below may be applied as a monotherapy or may involve, in addition to the herein disclosed compounds of Formula (I), conventional surgery or radiotherapy or medicinal therapy. Such medicinal therapy, e.g. a chemotherapy or a targeted therapy, may include one or more, but preferably one, of the following anti-tumor agents:

Alkylating agents, such as altretamine, bendamustine, busulfan, carmustine, chlorambucil, chlormethine, cyclophosphamide, dacarbazine, ifosfamide, improsulfan tosilate, lomustine, melphalan, mitobronitol, mitolactol, nimustine, ranimustine, temozolomide, thiotepa, treosulfan, mechloretamine, carboquone, apaziquone, fotemustine, glufosfamide, palifosfamide, pipobroman, trofosfamide, uramustine;

Platinum Compounds, such as carboplatin, cisplatin, eptaplatin, miriplatine hydrate, oxaliplatin, lobaplatin, nedaplatin, picoplatin, satraplatin;

DNA altering agents, such as amrubicin, bisantrene, decitabine, mitoxantrone, procarbazine, trabectedin, clofarabine, amsacrin, brostallicin, pixantrone, laromustine;

Topoisomerase inhibitors, such as etoposide, irinotecan, razoxane, sobuzoxane, teniposide, topotecan, amonafide, belotecan, elliptinium acetate, voreloxin;

Microtubule modifiers, such as cabazitaxel, docetaxel, eribulin, ixabepilone, paclitaxel, vinblastine, vincristine, vinorelbine, vindesine, vinflunine, fosbretabulin, tesetaxel:

Antimetabolites, such as asparaginase, azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur, doxifluridine, elacytarabine, raltitrexed, sapacitabine, tegafur, trimetrexate;

Anticancer antibiotics, such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin, aclarubicin, peplomycin, pirarubicin;

Hormones/Antagonists, such as abarelix, abiraterone, bicalutamide, buserelin, calusterone, chlorotrianisene, degarelix, dexamethasone, estradiol, fluocortolone, fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol, acolbifene, danazol, deslorelin, epitiostanol, orteronel, enzalutamide;

Aromatase inhibitors, such as aminoglutethimide, anastrozole, exemestane, fadrozole, letrozole, testolactone, formestane;

Small molecule kinase inhibitors, such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib, afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib, cabozantinib S-malate, carfilzomib, ibrutinib, icotinib;

Photosensitizers. such as methoxsalen, porfimer sodium, talaporfin, temoporfin;

Antibodies, such as alemtuzumab, besilesomab, brentuximab vedotin, cetuximab, denosumab, ipilimumab, ofatumumab, panitumumab, rituximab, tositumomab, trastuzumab, bevacizumab, catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab, onartuzumab, pertuzumab, racotumomab, tabalumab;

Cytokines, such as aldesleukin, interferon alfa, interferon alfa2a, interferon alfa2b, tasonermin, teceleukin, oprelvekin;

Drug conjugates, such as denileukin diftitox, ibritumomab tiuxetan, iobenguane 1123, prednimustine, trastuzumab emtansine, estramustine, gemtuzumab ozogamicin, aflibercept, cintredekin besudotox, edotreotide, inotuzumab ozogamicin, naptumomab estafenatox, oportuzumab monatox, technetium (99mTc) arcitumomab, vintafolide;

Vaccines, such as sipuleucel, vitespen, emepepimut-S, oncoVAX, rindopepimut, troVax, stimuvax;

Miscellaneous agents, such as alitretinoin, bexarotene, bortezomib, everolimus, ibandronic acid, imiquimod, lenalidomide, lentinan, metirosine, mifamurtide, pamidronic acid, pegaspargase, pentostatin, sipuleucel, sizofiran, tamibarotene, temsirolimus, thalidomide, tretinoin, vismodegib, zoledronic acid, thalidomide, vorinostat, celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine, picibanil, reolysin, retaspimycin hydrochloride, trebananib, virulizin.

In particular, this invention relates to a method for inhibiting abnormal cell growth in a mammal or treating a hyperproliferative disorder that comprises administering to the mammal an amount of a compound of the present invention or pharmaceutical composition, in combination with radiotherapy, wherein the amounts of the compound or pharmaceutical composition, is in combination with the radiation therapy effective in inhibiting abnormal cell growth or treating the hyperproliferative disorder in the mammal.

Techniques for administering radiation therapy are known in the art, and these techniques can be used in the combination therapy described herein. The administration of a compound of the invention, or pharmaceutical composition, in this combination therapy can be determined as described herein. It is believed that the compounds of the present invention can render abnormal cells more sensitive to treatment with radiation for purposes of killing and/or inhibiting the growth of such cells.

Accordingly, this invention further relates to a method for sensitizing abnormal cells in a mammal to treatment with radiation which comprises administering to the mammal an amount of a compound of the present invention or pharmaceutical composition, which amount is effective in sensitizing abnormal cells to treatment with radiation. The amount of the compound in this method can be determined according to the means for ascertaining effective amounts of such compounds described herein.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray. The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating inflammatory, degenerative or hyperproliferative diseases for which compounds of the present invention are indicated, generally satisfactory results are obtained when the compounds of the present invention are administered at a daily dosage of from about 0.01 milligram to about 100 milligram per kilogram of body weight, preferably given as a single daily dose. For most large mammals, the total daily dosage is from about 0.1 milligrams to about 1000 milligrams, preferably from about 0.2 milligram to about 50 milligrams. In the case of a 70 kg adult human, the total daily dose will generally be from about 0.2 milligrams to about 200 milligrams. This dosage regimen may be adjusted to provide the optimal therapeutic response.

The invention also relates to a set (kit) consisting of separate packs of
a) an effective amount of a compound according to the invention or its stereoisomers or tautomers, or pharmaceutically acceptable salts of each of the foregoing, including mixtures thereof in all ratios, and
b) an effective amount of a further medicament active ingredient.

The set comprises suitable containers, such as boxes, individual bottles, bags or ampoules.

By way of example, the set may comprise separate ampoules, each containing an effective amount of a compound according to the invention, and an effective amount of a further medicament active ingredient in dissolved or lyophilised form.

Experimental Section

Some abbreviations that may appear in this application are as follows:

| Abbreviations | |
|---|---|
| Designation | |
| ATP | Adenosine triphosphate |
| b | Broad peak |
| calc | Calculated |
| d | Doublet |
| DIPEA, DIEA | N,N-Diisopropylethylamine |
| DMSO | Dimethyl sulfoxide |
| dppf | Bis(diphenylphosphino)ferrocene |
| EDCl | N-(3-Dimethylaminopropyl)-N'-ethylcarbodiimide hydrochloride |
| EtOH | Ethanol |
| h, hr | Hour(s) |
| HATU | 1-[Bis(dimethylamino)methylene]-1H-1,2,3-triazolo[4,5-b]pyridinium 3-oxid hexafluorophosphate |
| HPLC | High Pressure Liquid Chromatography |
| LC/MS | Liquid Chromatography coupled to Mass Spectrometry |
| LDA | Lithium diisopropylamide |
| m | Multiplet |
| mCPBA | 3-Chlor-perbenzoic acid |
| m/z | Mass-to-charge ratio |
| min | Minute |
| MS | Mass spectrometry |
| N | Normal (unit of concentration) |
| nd | Not determined |
| NMR, 1H | Nuclear Magnetic Resonance, proton |
| q | Quartette (or quartet) |
| Rf | Retention factor |
| RT | Room temperature |
| Rt | Retention time |
| s | Singlet |
| sat. | Saturated |
| t | Triplet |
| TBAF | Tetrabutylammonium fluoride |
| TBSCl | tert-Butyldimethylsilyl chloride |

| Abbreviations | |
|---|---|
| Designation | |
| tert | Tertiary |
| TFA | Trifluoro acetic acid |
| UV | Ultraviolet |

The compounds of the present invention can be prepared according to the procedures of the following Schemes and Examples, using appropriate materials and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

The invention will be illustrated, but not limited, by reference to the specific embodiments described in the following examples. Unless otherwise indicated in the schemes, the variables have the same meaning as described above.

Unless otherwise specified, all starting materials are obtained from commercial suppliers and used without further purifications. Unless otherwise specified, all temperatures are expressed in ° C. and all reactions are conducted at RT. Compounds were purified by either silica chromatography or preparative HPLC.

The present invention relates also to a process for the manufacture of compounds of Formula (I), wherein a compound of Formula (IV)

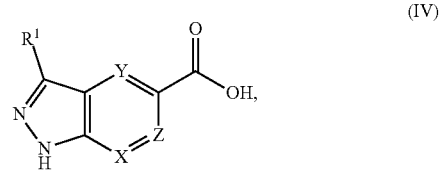

is reacted, optionally in the presence of an activating agent, with a compound of Formula (III),

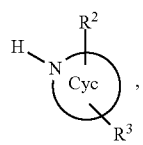

to yield a compound of Formula (I).

Those skilled in the art are aware of a number of activating agents, normally used in peptide synthesis to speed up the reaction, such as carbodiimides and triazoles. Specific examples of these agents are DCC, DIC, HBTU, HATU, HCTU, TBTU, DAPECl, PyBOP, HOBt or HOAt.

EXAMPLES

The working examples presented below are intended to illustrate particularly preferred embodiments of the invention, and are not intended to limit the scope of the specification or the claims in any way.

HPLC Methods
Method A (HPLC/MS method, polar)
  Solvent A: water+0.05% formic acid
  Solvent B: acetonitrile+0.04% formic acid
  Flow: 2.4 mL/min, wave length: 220 nm
  Gradient: 0.00 min 5% B
    2.80 min 100% B
    3.30 min 100% B
    3.40 min 5% B
  Column: Chromolith® Speed ROD RP18e 50-4.6 mm
Method B (HPLC/MS method)
  Solvent A: water+0.1% TFA
  Solvent B: acetonitrile+0.1% TFA
  Flow: 2 mL/min, wave length: 220 nm
  Gradient: 0.00 min 1% B
    0.20 min 1% B
    3.80 min 100% B
    4.20 min 100% B
    4.30 min 1% B
  Column: Chromolith® Performance RP18e 100-3 mm
Method C (HPLC/MS method)
  Solvent A: water+0.1% formic acid
  Solvent B: acetonitrile+0.08% formic acid
  Flow: 0.9 mL/min, wave length: 220 nm
  Gradient: 0.00 min 5% B
    1.00 min 100% B
    1.2 min 100% B
    1.40 min 5% B
  Column: ACQUITY UPLC® BEH C18 1.7 μm
Method D (HPLC/MS method)
  Solvent A: water+0.05% formic acid
  Solvent B: acetonitrile+0.05% formic acid
  Flow: 2.5 mL/min, wave length: 220 nm
  Gradient: 0.00 min 0% B
    1.40 min 100% B
    2.00 min 100% B
    2.20 min 0% B
  Column: Chromolith® Performance RP18e 100-3 mm
Method E (HPLC/MS method)
  Solvent A: water+5 mM $NH_4HCO_3$
  Solvent B: acetonitrile
  Flow: 1.5 mL/min, wave length: 190-400 nm
  Gradient: 0.01 min 10% B
    4.20 min 70% B
    5.20 min 70% B
    5.30 min 10% B
    5.60 min, stop
  Column: XBridge BEH C18 3.5 μM 50-4.6 mm
  Column temp: 40° C.
Method F (HPLC/MS method)
  Solvent A: water+0.05% TFA
  Solvent B: acetonitrile+0.05% TFA
  Flow: 1 mL/min, wave length: 220 nm
  Gradient: 0.01 min 5% B
    3.00 min 50% B
    5.00 min 50% B
    5.20 min 5% B
    5.60 min, stop
  Column: Shim-pack VP-ODS 50-3 mm
  Column temp: 40° C.
Method G (HPLC/MS method)
  Solvent A: water+0.05% TFA
  Solvent B: acetonitrile+0.05% TFA
  Flow: 1 mL/min, wave length: 220 nm
  Gradient: 0.01 min 5% B
    2.20 min 100% B
    3.20 min 100% B
    3.30 min 5% B
    3.60 min, stop
  Column: Shim-pack VP-ODS 50-3 mm
  Column temp: 40° C.
Method H (HPLC/MS method)
  Solvent A: water+5 mM $NH_4HCO_3$
  Solvent B: acetonitrile
  Flow: 1.5 mL/min, wave length: 190-400 nm
  Gradient: 0.01 min 5% B
    2.20 min 95% B
    3.20 min 95% B
    3.30 min 5% B
    3.60 min, stop
  Column: XBridge BEH C18 3.5 μM 50-4.6 mm
  Column temp: 40° C.
Method I (HPLC/MS method)
  Solvent A: water+0.05% TFA
  Solvent B: acetonitrile+0.05% TFA
  Flow: 1 mL/min, wave length: 220 nm
  Gradient: 0.01 min 5% B
    4.20 min 100% B
    5.20 min 100% B
    5.30 min 5% B
    5.60 min, stop
  Column: Shim-pack VP-ODS 50-3 mm
  Column temp: 40° C.
Method J (HPLC/MS method)
  Solvent A: water+0.1% TFA
  Solvent B: acetonitrile+0.1% TFA
  Flow: 1.5 mL/min, wave length: 220 nm
  Gradient: 0.01 min 10% B
    2.00 min 95% B
    2.60 min 95% B
    2.70 min 10% B
    3.00 min, stop
  Column: ACE UltraCore 2.5 Super C18, 50-3 mm
  Column temp: 40° C.
LCMS Method K:
  Analytical separation was carried out at 40° C. on a Merck Purospher STAR column (RP-18e, 30×4 mm) using a flow rate of 3 mL/min in a 2 minute gradient elution with detection at 254 nm. The mobile phase was a mixture of methanol (solvent A) and water (solvent B), both containing 0.1% formic acid. Gradient elution was as follows: 1:9 (A/B) to 9:1 (A/B) over 1.25 min, 9:1

(A/B) for 0.5 min, and then reversion back to 1:9 (A/B) over 0.15 min, finally 1:9 (A/B) for 0.1 min LCMS Method L:

Analytical separation was carried out at 30° C. on a Merck Purospher STAR column (RP-18e, 30×4 mm) using a flow rate of 1.5 mL/min in a 4 minute gradient elution with detection at 254 nm. The mobile phase was a mixture of methanol (solvent A) and water (solvent B), both containing 0.1% formic acid. Gradient elution was as follows: 1:9 (A/B) to 9:1 (A/B) over 2.5 min, 9:1 (A/B) for 1 min, and then reversion back to 1:9 (A/B) over 0.3 min, finally 1:9 (A/B) for 0.2 min.

LCMS Method M:

Analytical separation was carried out at 30° C. on a Phenomenex Kinetex XB-C18 column (30×2.1 mm, 1.7u, 100 A) using a flow rate of 0.5 mL/min in a 2 minute gradient elution with detection at 254 nm. The mobile phase was a mixture of methanol (solvent A) and water containing formic acid at 0.1% (solvent B). Gradient elution was as follows: 1:9 (A/B) to 9:1 (A/B) over 1.25 min, 9:1 (A/B) for 0.5 min, and then reversion back to 1:9 (A/B) over 0.15 min, finally 1:9 (A/B) for 0.1 min.

Chemical Synthesis

In this section experimental details are provided for a number of Example compounds according to Formula (I), and synthetic intermediates thereof.

1. [(S)-2-(4-Bromo-phenyl)-pyrrolidin-1-yl]-(3-propyl-1H-indazol-5-yl)-methanone 5 and [(R)-2-(4-bromo-phenyl)-pyrrolidin-1-yl]-(3-propyl-1H-indazol-5-yl)-methanone 6

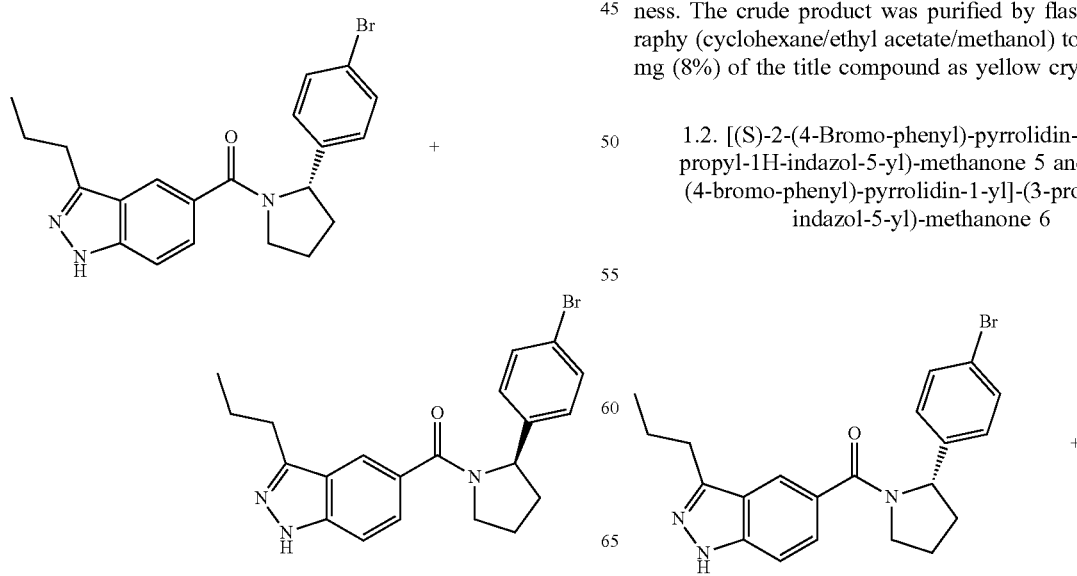

1.1 [2-(4-Bromo-phenyl)-pyrrolidin-1-yl]-(3-propyl-1H-indazol-5-yl)-methanone 4

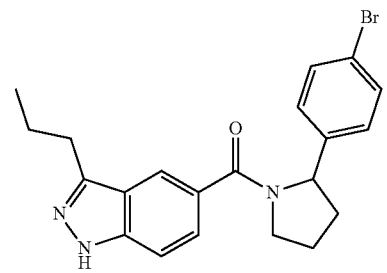 [SMILES: CCCc1n[nH]c2ccc(C(=O)N3CCCC3c3ccc(Br)cc3)cc12]

To a solution of 3-propyl-1H-indazole-5-carboxylic acid (50.0 mg, 0.24 mmol), 2-(4-bromo-phenyl)-pyrrolidine, 97% (110 mg, 0.47 mmol) and 4-methylmorpholine (0.064 mL, 0.58 mmol) in N,N-dimethyl-formamide (2 mL), 2-(1H-benzotriazole-1-yl)-1,1,3,3-tetramethylaminium tetrafluoroborate (TBTU, 83.0 mg, 0.26 mmol) and 1-hydroxybenzotriazol hydrate (9.00 mg, 0.068 mmol) were added and stirred at room temperature overnight. Water was added and the formed precipitate was filtered off and dried in vacuo. The crude product was purified by flash chromatography (dichloromethane/methanol) to yield in 52.0 mg (52%) of the title compound as yellow crystals.

Alternative Synthesis:

In a screw capped glass 3-propyl-1H-indazole-5-carboxylic acid (50.0 mg, 0.24 mmol), 2-(4-bromo-phenyl)-pyrrolidine, 97% (72.0 mg, 0.31 mmol) was dissolved in dichloromethane (5 mL), followed by N,N-diisopropylethylamine (0.12 mL, 0.73 mmol) and 1-propylphosphonic acid cyclic anhydride (50% in ethyl acetate, 0.28 mL, 0.47 mmol). The solution was stirred at room temperature overnight. The solution was triturated with ethyl acetate, washed with water, NaHCO₃ solution and brine. The organic layer was dried over sodium sulfate, filtered and evaporated to dryness. The crude product was purified by flash chromatography (cyclohexane/ethyl acetate/methanol) to yield in 7.30 mg (8%) of the title compound as yellow crystals.

1.2. [(S)-2-(4-Bromo-phenyl)-pyrrolidin-1-yl]-(3-propyl-1H-indazol-5-yl)-methanone 5 and [(R)-2-(4-bromo-phenyl)-pyrrolidin-1-yl]-(3-propyl-1H-indazol-5-yl)-methanone 6

-continued

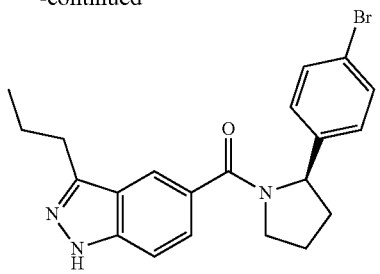

52.0 mg (0.13 mmol) of the racemic mixture dissolved in methanol (1 mL) were separated into the contained enantiomerically pure materials by chiral HPLC in 25 μL/run portions to yield in 19.9 mg (38%) of light yellow crystals as 5 and 19.4 mg (37%) of light yellow crystals as 6. HPLC/MS (chiral): Rt 2.40 min (method below, 5), Rt 3.32 min (method below, 6).

Instrument: SFC Berger Minigram, column: ChiralPak AD-H, eluent: $CO_2$/methanol+0.5% diethyl amine 60:40, isocratic, flow: 5 mL/min, detection: 220 nm.

According to these procedures compounds 8, 9, 11 and 12 were synthesized.

2. (S)-2-(4-Chloro-phenyl)-pyrrolidin-1-yl]-(3-methyl-1H-pyrazolo[3,4-b]pyridin-5-yl)-methanone 13 and [(R)-2-(4-chloro-phenyl)-pyrrolidin-1-yl]-(3-methyl-1H-pyrazolo[3,4-b]pyridin-5-yl)-methanone 14

2.1. 3-Methyl-1H-pyrazolo[3,4-b]pyridine-5-carboxylic acid

Methyl 3-methyl-1H-pyrazolo[3,4-b]pyridine-5-carboxylate (500 mg, 2.54 mmol) was dissolved in tetrahydrofurane (100 mL). Lithium hydroxide (180 mg, 7.60 mmol) dissolved in water (50 mL) were added and stirred at room temperature overnight. The reaction mixture was acidified to pH 5 using 1 N HCl and the precipitate was filtered off, washed with methyl tert-butyl ether and dried in vacuo to result in 377 mg (83%) of the title compound as white crystals. HPLC: (purity) 99%. HPLC MS: Room temperature 1.21 min (method A).

2.2. [2-(4-Chloro-phenyl)-pyrrolidin-1-yl]-(3-methyl-1H-pyrazolo[3,4-b]pyridin-5-yl)-methanone 10

To a solution of 3-methyl-1H-pyrazolo[3,4-b]pyridine-5-carboxylic acid (510 mg, 2.74 mmol), 2-(4-chloro-phenyl)-pyrrolidine hydrochloride (1.00 g, 4.56 mmol) and 4-methylmorpholin (0.064 mL, 0.58 mmol) in N,N-dimethylformamide (2 mL) was added 2-(1H-benzotriazole-1-yl)-1,1,3,3-tetramethylaminium tetrafluoroborate (TBTU, 83.0 mg, 0.26 mmol) and 1-hydroxybenzotriazol hydrate (9.00 mg, 0.068 mmol) at room temperature. It was stirred at room temperature overnight. Water was added to the mixture, and the aqueous layer was extracted with ethyl acetate. The product was found in the aqueous phase. It was evaporated to dryness and the crude product was purified by flash chromatography (dichlormethane/methanol) to yield in 667 mg (71%) of the title compound as yellow crystals.

2.3. (S)-2-(4-Chloro-phenyl)-pyrrolidin-1-yl]-(3-methyl-1H-pyrazolo[3,4-b]pyridin-5-yl)-methanone 13 and [(R)-2-(4-Chloro-phenyl)-pyrrolidin-1-yl]-(3-methyl-1H-pyrazolo[3,4-b]pyridin-5-yl)-methanone 14

100 mg (0.56 mmol) of the racemic mixture dissolved in methanol (1 mL) were separated into the contained enantiomerically pure materials by chiral HPLC in 60 µL/run portions to yield in 39.1 mg (39%) of light yellow crystals as 13 and 40.2 mg (40%) of light yellow crystals as 14. HPLC/MS (chiral): Rt 3.84 min (method below, 13), Rt 5.96 min (method below, 14).

Instrument: SFC Berger Minigram, column: ChiralPak AD-H, eluent: $CO_2$/methanol+0.5% diethyl amine 60:40, isocratic, flow: 5 mL/min, detection: 220 nm.

According to these procedures compounds 1-3, 7, 15-30, 32-34, 36-41 and 43-46, 55-69, 94-95, 121-123, 125, 127, 129, 130, 136-139, 141-146, 149-150, 157-160, 162 and 170 were synthesized.

3. [(S)-2-(4-Chloro-phenyl)-pyrrolidin-1-yl]-(3-isobutyl-1H-indazol-5-yl)-methanone 35 and [(R)-2-(4-chloro-phenyl)-pyrrolidin-1-yl]-(3-isobutyl-1H-indazol-5-yl)-methanone 31

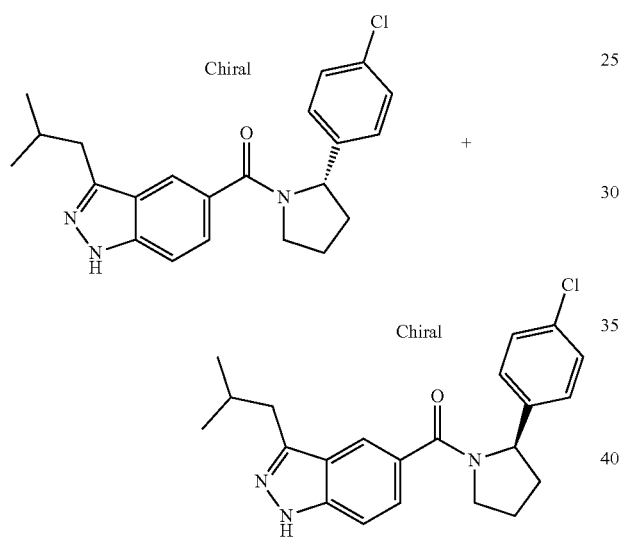

3.1. 3-Iodo-1H-indazole-5-carboxylic acid

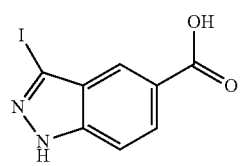 [SMILES: O=C(O)c1ccc2[nH]nc(I)c2c1]

Into a 25-mL round-bottom flask was placed 1H-indazole-5-carboxylic acid (200 mg, 1.23 mmol), N,N-dimethylformamide (3 mL), potassium hydroxide (138 mg, 2.46 mmol) and iodine (470 mg, 1.85 mmol). The solution was stirred for 3 h at 25° C. The reaction was quenched by the addition of 10 mL of $Na_2S_2O_3$. The pH value of the solution was adjusted to 6 with hydrogen chloride solution (10%). The solids were collected by filtration. This resulted in 300 mg (84%) of 3-iodo-1H-indazole-5-carboxylic acid as a white solid.

3.2. 3-(2-Methylprop-1-en-1-yl)-1H-indazole-5-carboxylic acid

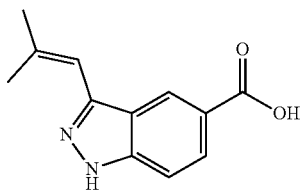 [SMILES: CC(C)=Cc1n[nH]c2ccc(C(=O)O)cc12]

Into a 250 mL round-bottom flask purged and maintained with an inert atmosphere of nitrogen, was placed 3-iodo-1H-indazole-5-carboxylic acid (2.00 g, 6.94 mmol), 4,4,5,5-tetramethyl-2-(2-methylprop-1-en-1-yl)-1,3,2-dioxaborolane (1.90 g, 10.4 mmol), Pd(PPh$_3$)$_4$ (800 mg, 0.69 mmol), potassium carbonate (2.86 g, 20.7 mmol), dioxane (40 mL) and water (10 mL). The solution was stirred for 3 h at 90° C. The pH value of the solution was adjusted to 6 with hydrogen chloride solution (10%). The solids were collected by filtration. This resulted in 1.30 g (87%) of 3-(2-methylprop-1-en-1-yl)-1H-indazole-5-carboxylic acid as a yellow solid.

3.3 3-(2-Methylpropyl)-1H-indazole-5-carboxylic acid

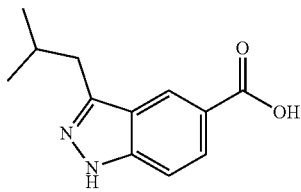 [SMILES: CC(C)Cc1n[nH]c2ccc(C(=O)O)cc12]

Into a 2000 mL sealed tube were placed 3-(2-methylprop-1-en-1-yl)-1H-indazole-5-carboxylic acid (1.20 g, 5.55 mmol) and palladium on carbon (2.00 g, 18.8 mmol). This was followed by the addition of methanol (800 mL). To the above mixture hydrogen was introduced and hydrogen chloride solution (4 mL, 10%) was added. The solution was stirred for 4 h at 60° C. The solids were filtered off. The mixture was concentrated under vacuum. This resulted in 1.00 g (83%) of 3-(2-methylpropyl)-1H-indazole-5-carboxylic acid as a yellow solid.

3.4. [(S)-2-(4-Chloro-phenyl)-pyrrolidin-1-yl]-(3-isobutyl-1H-indazol-5-yl)-methanone 35 and [(R)-2-(4-Chloro-phenyl)-pyrrolidin-1-yl]-(3-isobutyl-1H-indazol-5-yl)-methanone 31

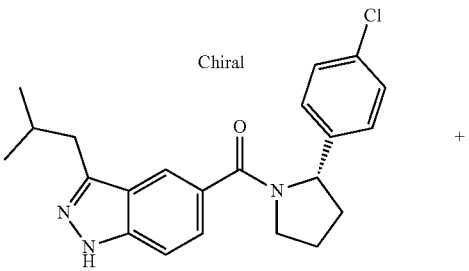

-continued

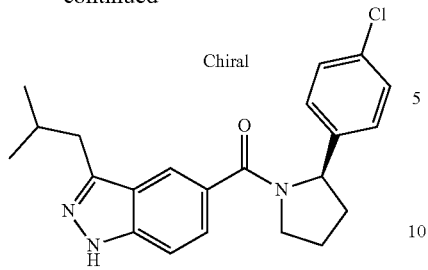

Into a 25-mL round-bottom flask, was placed 3-(2-methylpropyl)-1H-indazole-5-carboxylic acid (120 mg, 0.55 mmol), 2-(4-chlorophenyl)pyrrolidine (150 mg, 0.83 mmol), 1-[bis(dimethylamino)methylene]-1H-1,2,3-triazolo[4,5-b]pyridinium 3-oxid hexafluorophosphate (HATU, 208 mg, 0.55 mmol), N,N-diisopropylethylamine (212 mg, 1.64 mmol) and N,N-dimethylformamide (2 mL). The solution was stirred for 1 h at room temperature. The mixture was concentrated under vacuum. The remainder was purified by prep-HPLC to result in 80 mg (38%) racemic material. The racemic mixture was purified by chiral-prep-HPLC (column: ChiralPak IC, 2*25 cm, 5 μm, mobile phase: hexane/isopropanol (hold 50% isopropanol in 25 min), Detector: UV 254/220 nm). 20 mg (10%) of 5-[[(2S)-2-(4-chlorophenyl)pyrrolidin-1-yl]carbonyl]-3-(2-methylpropyl)-1H-indazole 35 as a white solid and 20 mg (10%) of 5-[[(2R)-2-(4-chlorophenyl)pyrrolidin-1-yl]carbonyl]-3-(2-methylpropyl)-1H-indazole 31 as a white solid were obtained.

According to these general procedures compound 42 was synthesized 4. (3-Amino-1H-indazol-5-yl)-[2-(4-chloro-phenyl)-pyrrolidin-1-yl]-methanone 78

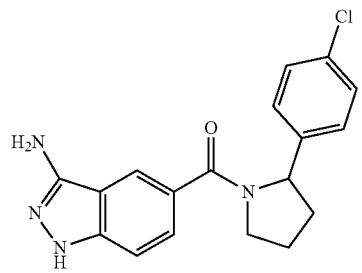 [SMILES: Nc1n[nH]c2ccc(C(=O)N3CCCC3c3ccc(Cl)cc3)cc12]

4.1. 3-Amino-1H-indazole-5-carboxylic acid

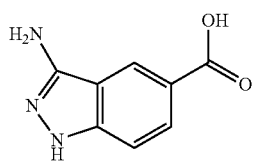

3-Cyano-4-fluoro-benzoic acid (2.00 g, 12.1 mmol) and hydrazinium hydroxide (0.60 mL, 12.1 mmol) were dissolved in 1-butanol (40 mL) and stirred at 110° C. overnight. The crystals formed after cooling to room temperature were filtered off, washed with methyl tert-butyl ether and dried in vacuo at 40° C. to yield in 1.16 g (66%) of the title compound as beige crystals. LC/MS: Rt 0.99 min (method A).

4.2 (3-Amino-1H-indazol-5-yl)-[2-(4-chloro-phenyl)-pyrrolidin-1-yl]-methanone

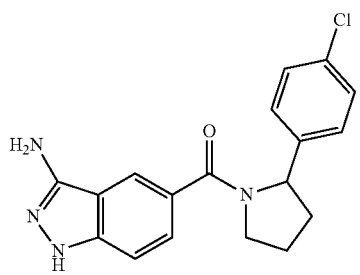 [SMILES: Nc1n[nH]c2ccc(C(=O)N3CCCC3c3ccc(Cl)cc3)cc12]

To a solution of 3-amino-1H-indazole-5-carboxylic acid (50.0 mg, 0.28 mmol), 2-(4-chloro-phenyl)-pyrrolidine hydrochloride (123 mg, 0.56 mmol) and 4-methylmorpholine (0.064 mL, 0.58 mmol) in N,N-dimethyl-formamide (2 mL), 2-(1H-benzotriazole-1-yl)-1,1,3,3-tetramethylaminium tetrafluoroborate (TBTU, 83.0 mg, 0.26 mmol) and 1-hydroxybenzotriazol hydrate (9.00 mg, 0.068 mmol) were added and stirred at room temperature overnight. Water was added to the mixture, and the precipitate was filtered off and dried in vacuo. The crude product was purified by preparative HPLC to yield in 48.0 mg (50%) of the tile compound as an off-white solid.

4.3. (3-Amino-1H-indazol-5-yl)-[(S)-2-(4-chloro-phenyl)-pyrrolidin-1-yl]-methanone 79 and (3-amino-1H-indazol-5-yl)-[(R)-2-(4-chloro-phenyl)-pyrrolidin-1-yl]-methanone 80

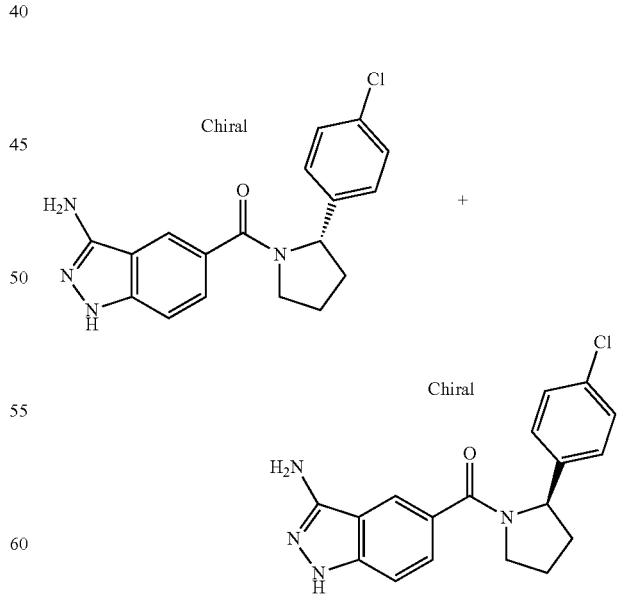

45.0 mg (0.13 mmol) of the racemic mixture dissolved in methanol (1 mL) were separated into the contained enantiomerically pure materials by chiral HPLC in 90 μL/run portions to yield in 22.1 mg (49%) of light yellow crystals as 79 and 20.0 mg (44%) of light yellow crystals as 80. HPLC/MS (chiral): Rt 3.47 min (method below, 79), Rt 6.45 min (method below, 80).

Instrument: SFC Berger Minigram, column: ChiralPak AD-H, eluent: $CO_2$/methanol+0.5% diethyl amine 60:40, isocratic, flow: 5 mL/min, UV detection: 220 nm.

According to these general procedures compounds 74-77, 81-93, 104-118, 120, 124, 131-135, 147, 148 and 167 were synthesized.

5. [2-(4-Chloro-phenyl)-pyrrolidin-1-yl]-(3-cyclopropyl-1H-pyrazolo[3,4-b]pyridin-5-yl)-methanone 70

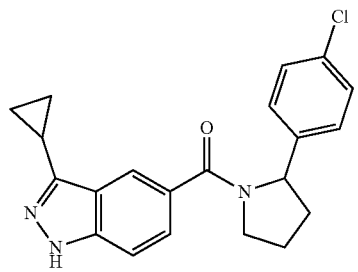 [SMILES: O=C(c1ccc2[nH]nc(C3CC3)c2c1)N1CCCC1c1ccc(Cl)cc1]

5.1. 1-(3-Cyclopropyl-1H-indazole-5-carbonyl)-1,3-dimethyl-urea

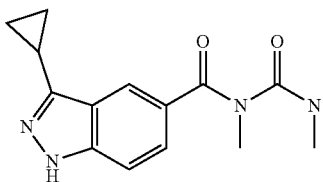 [SMILES: CNC(=O)N(C)C(=O)c1ccc2[nH]nc(C3CC3)c2c1]

A mixture of 3-amino-5-cyclopropyl-1H-pyrazole (250 mg, 2.03 mmol) and 1,3-dimethyl-2,4-dioxo-1,2,3,4-tetrahydropyrimidine-5-carbaldehyde (360 mg, 2.03 mmol) in glacial acetic acid (20 mL) was refluxed for 6 h. After cooling the solvent was evaporated under reduced pressure. The residue was dissolved in methanol and the solution was allowed to stand overnight. The mixture was diluted with diethyl ether, the crystals formed were filtered off and dried in vacuo to obtain 246 mg (44%) of the title compound as light beige crystals.

5.2. 3-Cyclopropyl-1H-indazole-5-carboxylic acid

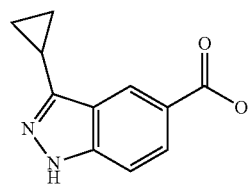 [SMILES: O=C(O)c1ccc2[nH]nc(C3CC3)c2c1]

A mixture of 1-(3-cyclopropyl-1H-pyrazolo[3,4-b]pyridine-5-carbonyl)-1,3-dimethyl-urea (246 mg, 0.89 mmol) and sodium hydroxide solution, 10% (8 mL) was heated and stirred for 2 h at 60° C. After cooling, the reaction mixture was filtered, and the filtrate was acidified with diluted HCl. The mixture was extracted with dichloromethane. The organic phase was allowed to stand overnight to form a suspension. The crystals were filtered off, washed with water and dried in vacuo to yield in 133 mg (74%) of the title compound as white crystals.

5.3. [2-(4-Chloro-phenyl)-pyrrolidin-1-yl]-(3-cyclopropyl-1H-pyrazolo[3,4-b]pyridin-5-yl)-methanone 70

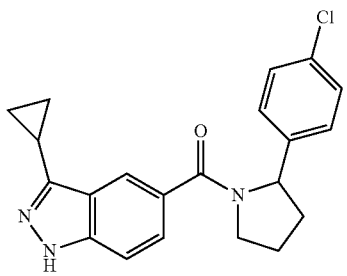 [SMILES: O=C(c1ccc2[nH]nc(C3CC3)c2c1)N1CCCC1c1ccc(Cl)cc1]

To a solution of 3-cyclopropyl-1H-pyrazolo[3,4-b]pyridine-5-carboxylic acid (100 mg, 0.49 mmol), 2-(4-chlorophenyl)-pyrrolidine (152 mg, 0.84 mmol) and 4-methylmorpholine (0.064 mL, 0.58 mmol) in N,N-dimethyl-formamide (2 mL), O-(1H-benzotriazol-1-yl)-N,N,N',N'-tetramethyluroniumtetrafluoroborate (TBTU, 83.0 mg, 0.26 mmol) and 1-hydroxybenzotriazolhydrat (9.00 mg, 0.07 mmol) were added and stirred at room temperature overnight. Water was added to the mixture, extracted with ethyl acetate twice and the combined organic phases was dried with $Na_2SO_4$, filtered and evaporated to dryness. The crude product was purified by preparative HPLC (acetonitrile/water). The combined fractions were made alkaline with 1 N NaOH, extracted twice with dichloromethane, the combined organic phases were dried over $Na_2SO_4$, filtered and evaporated to dryness to yield in 92.3 mg of the title compound as white crystals.

According to these general procedures compounds 71-73, 152-153 and 168-169 were synthesized.

6. (S)-2-(4-Chloro-phenyl)-pyrrolidin-1-yl]-(3-methyl-1H-pyrazolo[3,4-b]pyridin-5-yl)-methanone 155 and [(R)-2-(4-chloro-phenyl)-pyrrolidin-1-yl]-(3-methyl-1H-pyrazolo[3,4-h]pyridin-5-yl)-methanone 156

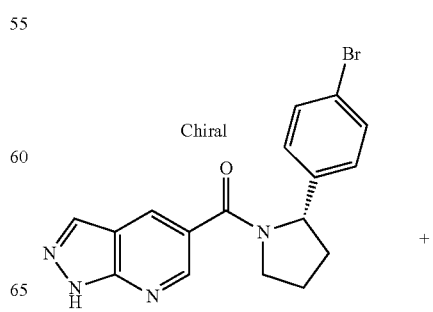

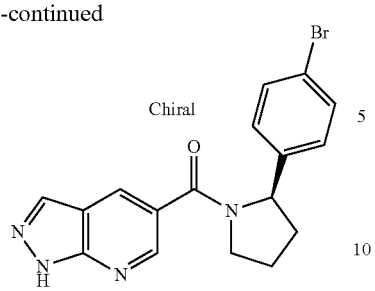

6.1. [2-(4-Bromo-phenyl)-pyrrolidin-1-yl]-(1H-pyrazolo[3,4-b]pyridin-5-yl)-methanone 154

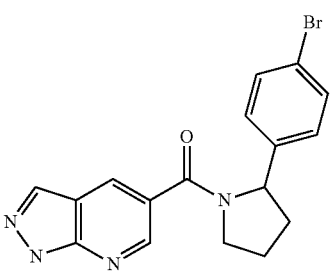 [SMILES: O=C(c1cnc2[nH]ncc2c1)N1CCCC1c1ccc(Br)cc1]

To a solution of 1H-Indazole-5-carboxylic acid (100 mg, 0.60 mmol), 2-(4-bromo-phenyl)-pyrrolidine hydrochloride (280 mg, 1.02 mmol) and 4-methylmorpholin (0.064 mL, 0.58 mmol) in N,N-dimethylformamide (2 mL) was added 2-(1H-benzotriazole-1-yl)-1,1,3,3-tetramethylaminium tetrafluoroborate (TBTU, 83.0 mg, 0.26 mmol) and 1-hydroxybenzotriazol hydrate (9.00 mg, 0.068 mmol) at room temperature. It was stirred at room temperature overnight. Water was added to the mixture, and the aqueous layer was extracted with ethyl acetate. The product was found in the aqueous phase. It was evaporated to dryness and the crude product was purified by flash chromatography (dichlormethane/methanol) to yield in 41.1 mg (19%) of the title compound as white crystals.

6.2. (S)-2-(4-Chloro-phenyl)-pyrrolidin-1-yl]-(3-methyl-1H-pyrazolo[3,4-b]pyridin-5-yl)-methanone 155 and [(R)-2-(4-chloro-phenyl)-pyrrolidin-1-yl]-(3-methyl-1H-pyrazolo[3,4-b]pyridin-5-yl)-methanone 156

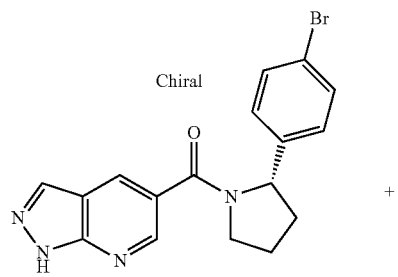

+

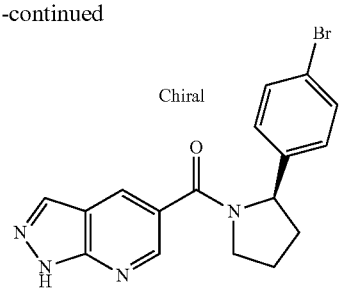

35.5 mg (0.096 mmol) of the racemic mixture dissolved in methanol (0.5 mL) were separated into the contained enantiomerically pure materials by chiral HPLC in 60 µL/run portions to yield in 13.8 mg (39%) of light yellow crystals as 155 and 14.2 mg (40%) of light yellow crystals as 156. HPLC/MS (chiral): Rt 4.66 min (method below, 155), Rt 7.33 min (method below, 156).

Instrument: SFC Berger Minigram, column: ChiralPak AD-H, eluent: CO$_2$/methanol+0.5% diethyl amine 60:40, isocratic, flow: 5 mL/min, detection: 220 nm.

7. [(S)-2-(4-Bromo-phenyl)-pyrrolidin-1-yl]-(3-methyl-1H-indazol-5-yl)-methanone 49

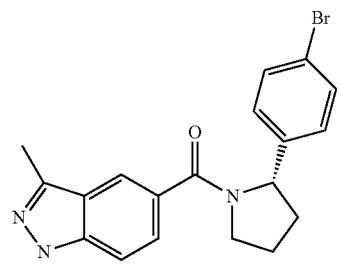 [SMILES: Cc1n[nH]c2ccc(C(=O)N3CCC[C@H]3c3ccc(Br)cc3)cc12]

7.1. 5-Bromo-3-methyl-1H-indazole

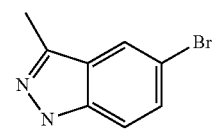

To a 50 mL sealed tube purged and maintained with an inert atmosphere of nitrogen, were added 1-(5-bromo-2-fluorophenyl)ethan-1-one (6.00 g, 27.7 mmol) and hydrazine hydrate (30 mL). The solution was stirred for 14 h at 117° C. The reaction mixture was concentrated under vacuum. The residue was dissolved in water and extracted with 3 times with 20 mL of ethyl acetate. The organic layers were combined, dried over anhydrous sodium sulfate and concentrated. The residue was purified by a silica gel column eluting with petroleum ether:ethyl acetate (5:1). The collected fractions were combined and concentrated under vacuum. This resulted in 3.00 g (51%) of 5-bromo-3-methyl-1H-indazole as a yellow solid.

7.2. 3-Methyl-1H-indazole-5-carboxylic acid methyl ester

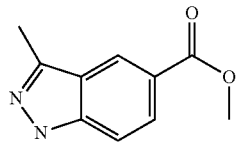

To a 50 mL steel tank reactor purged and maintained with an atmosphere of carbon monoxide (5 atm), were added 5-bromo-3-methyl-1H-indazole (1.00 g, 4.74 mmol), Pd(dppf)Cl$_2$.CH$_2$Cl$_2$ (400 mg, 0.49 mmol), potassium acetate (1.40 g, 14.3 mmol), N,N-dimethylformamide (5 mL) and methanol (25 mL). The solution was stirred for 14 h at 80° C. The reaction mixture was concentrated under vacuum. The residue was dissolved in water and extracted 3 times with 20 mL of ethyl acetate. The organic layers were combined, dried over anhydrous sodium sulfate and concentrated. The residue was purified by a silica gel column eluting with ethyl acetate/petroleum ether (3:7). This resulted in 750 mg (83%) of 3-Methyl-1H-indazole-5-carboxylic acid methyl ester as a yellow solid.

7.3. 3-Methyl-1H-indazole-5-carboxylic acid

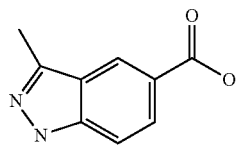

To a 100 mL round-bottom flask were added 3-Methyl-1H-indazole-5-carboxylic acid methyl ester (500 mg, 2.63 mmol), sodium hydroxide (210 mg, 5.25 mmol), tetrahydrofuran (50 mL) and water (13 mL). The solution was stirred for 2 h at 50° C. The reaction mixture was concentrated under vacuum. The residue was dissolved in 30 mL of water. The pH value of the solution was adjusted to 3 with HCl solution (1 M). The precipitate was collected by filtration. This resulted in 300 mg (65%) of 3-methyl-1H-indazole-5-carboxylic acid as a yellow solid.

7.4 [(S)-2-(4-Bromo-phenyl)-pyrrolidin-1-yl]-(3-methyl-1H-indazol-5-yl)-methanone 49

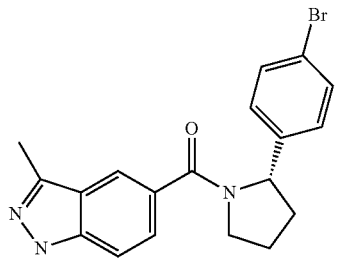 [SMILES: Cc1n[nH]c2ccc(C(=O)N3CCC[C@H]3c3ccc(Br)cc3)cc12]

To a 25-mL round-bottom flask, were added 3-methyl-1H-indazole-5-carboxylic acid (80.0 mg, 0.45 mmol), 2-(4-chlorophenyl)pyrrolidine (124 mg, 0.68 mmol), diisopropylethylamine (176 mg, 1.36 mmol), 1-[bis(dimethylamino)methylene]-1H-1,2,3-triazolo[4,5-b]pyridinium 3-oxid hexafluorophosphate (HATU, 207 mg, 0.54 mmol) and N,N-dimethylformamide (5 mL). The solution was stirred for 3 h at 25° C. The reaction mixture was concentrated under vacuum. The residue was dissolved in water and extracted 3 times with 10 mL ethyl acetate. The organic layers were combined. The crude product (200 mg) was purified by Prep-HPLC (acetonitrile/water). The racemic product (150 mg, 87%) was further purified by chiral preparative HPLC with the following conditions: Column: Phenomenex Lux 5μ Cellulose-4, 250*21.2 mm, 5 μm; mobile phase: hexane and ethanol (20% ethanol in hexane isocratic in 21 min); Detector, UV 254/220 nm. This resulted in 80.0 mg (46%) of 5-[[(2S)-2-(4-bromophenyl)pyrrolidin-1-yl]carbonyl]-3-methyl-1H-indazole 49 as a white solid.

According to these general procedures compounds 47, 48 and 50 were synthesized.

8. [(S)-2-(4-Chloro-phenyl)-pyrrolidin-1-yl]-(3-methyl-1H-pyrazolo[4,3-b]pyridin-5-yl)-methanone 51

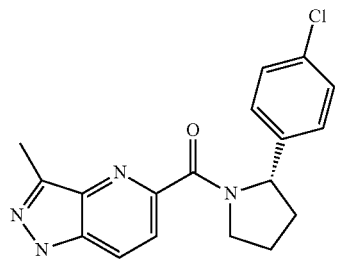 [SMILES: Cc1n[nH]c2ccc(C(=O)N3CCC[C@H]3c3ccc(Cl)cc3)nc12]

8.1. 3-Methyl-1H-pyrazolo[4,3-b]pyridine

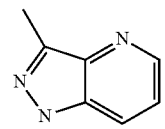

To a 50 mL sealed tube were added 1-(3-fluoropyridin-2-yl)ethan-1-one (2.00 g, 14.4 mmol) and hydrazine hydrate (25 mL). The solution was stirred for 3 h at 130° C. The reaction mixture was washed 3 times with 50 mL of ethyl acetate, dried over anhydrous sodium sulfate and concentrated. The residue was purified by a silica gel column eluting with ethyl acetate/petroleum ether (2:3). This resulted in 900 mg (47%) of 3-methyl-1H-pyrazolo[4,3-b]pyridine as a yellow solid.

8.2. 3-Methyl-1-trityl-1H-pyrazolo[4,3-b]pyridine

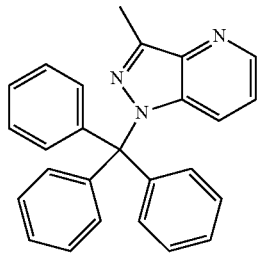 [SMILES: Cc1nn(C(c2ccccc2)(c2ccccc2)c2ccccc2)c2cccnc12]

To a 100 mL round-bottom flask purged and maintained with an inert atmosphere of nitrogen were added 3-methyl-1H-pyrazolo[4,3-b]pyridine (2.43 g, 18.3 mmol) and N,N-dimethylformamide (20 mL) at 0° C. Then sodium hydride (660 mg, 27.5 mmol) and after 30 min (chlorodiphenylmethyl)benzene (5.60 g, 20.1 mmol) was added to the reaction mixture. The solution was stirred for 2 h at 25° C. The reaction was then quenched by the addition of 5 ml of NH$_4$Cl solution. The mixture was concentrated under vacuum. The residue was dissolved in 20 mL of ethyl acetate, washed 3 times with 30 mL of water, dried over anhydrous sodium sulfate and concentrated. The residue was purified by a silica gel column eluting with petroleum ether:ethyl acetate (3:1). This resulted in 3.00 g (44%) of 3-methyl-1-(triphenylmethyl)-1H-pyrazolo[4,3-b]pyridine as a yellow solid.

8.3. 3-Methyl-1H-trityl-1H-pyrazolo[4,3-b]pyridine 4-oxide

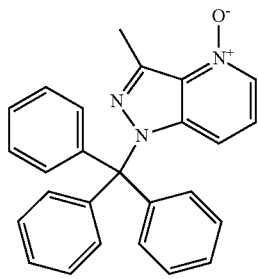 [SMILES: Cc1nn(C(c2ccccc2)(c2ccccc2)c2ccccc2)c2ccc[n+]([O-])c12]

To a 50 mL round-bottom flask were added 3-methyl-1-(triphenylmethyl)-1H-pyrazolo[4,3-b]pyridine (3.00 g, 7.99 mmol) and dichloromethane (20 mL) at 0° C. Then meta-chloroperoxybenzoic acid (1.50 g, 8.69 mmol) was added. The solution was stirred for 2 h at 25° C. The reaction mixture was washed 3 times with 20 mL sodium carbonate solution, dried over anhydrous sodium sulfate and concentrated under vacuum. The residue was purified by a silica gel column eluting with dichloromethane/ethyl acetate (1:1). This resulted in 2.70 g (86%) of 3-methyl-1-trityl-1H-pyrazolo[4,3-b]pyridine 4-oxide as a off-white solid.

8.4. 5-Chloro-3-methyl-1H-pyrazolo[4,3-b]pyridine

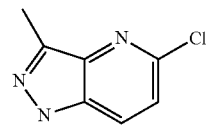

To a 50 mL sealed tube, were added 3-methyl-1-trityl-1H-pyrazolo[4,3-b]pyridine 4-oxide (2.84 g, 7.25 mmol), phosphoryl chloride (20 mL). The solution was stirred for 1 h at 130° C. The reaction was then quenched by the addition of 20 mL water/ice slurry. Sodium hydroxide solution (6 M) was used to adjust the pH of the mixture to 7. The solution was extracted with 5 times with 200 mL of dichloromethane and the organic layers were combined, dried over anhydrous sodium sulfate and concentrated. The residue was purified by a silica gel column eluting with dichloromethane/methanol (20:1). This resulted in 1.40 g (98%) of 5-chloro-3-methyl-1H-pyrazolo[4,3-b]pyridine as an off-white solid.

8.5. 3-Methyl-1H-pyrazolo[4,3-b]pyridine-5-carboxylic acid methyl ester

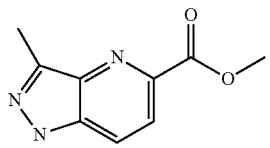

To a 250 mL steel tank reactor purged and maintained with an atmosphere of carbon monoxide (5 atm), were added 5-chloro-3-methyl-1H-pyrazolo[4,3-b]pyridine (1.20 g, 7.16 mmol), methanol (160 mL), potassium acetate (2.10 g, 21.4 mmol) and Pd(dppf)Cl$_2$.CH$_2$Cl$_2$ (585 mg, 0.72 mmol). The solution was stirred for 14 h at 80° C. The reaction mixture was concentrated under vacuum. The residue was dissolved in 50 mL of water. The solution was extracted 3 times with 60 mL of ethyl acetate and the organic layers were combined and concentrated. The residue was purified by a silica gel column eluting with ethyl acetate/petroleum ether (3:2). This resulted in 720 mg (53%) of 3-methyl-1H-pyrazolo[4,3-b]pyridine-5-carboxylic acid methyl ester as a off-white solid.

8.6. 3-Methyl-H-pyrazolo[4,3-b]pyridine-5-carboxylic acid

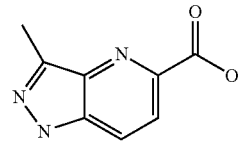

To a 50 mL round-bottom flask, were added 3-methyl-1H-pyrazolo[4,3-b]pyridine-5-carboxylic acid methyl ester (720 mg, 3.77 mmol), tetrahydrofuran (10 mL), water (2 mL) and sodium hydroxide (226 mg, 5.65 mmol). The solution was stirred for 2 h at 50° C. The reaction mixture was concentrated under vacuum. The residue was dissolved in 20 mL of water. The solid formed was filtered out. HCl solution (1 M) was added to adjust the pH to 7. The precipitate was collected by filtration. This resulted in 350 mg (52%) of 3-methyl-1H-pyrazolo[4,3-b]pyridine-5-carboxylic acid as an off-white solid.

8.7. [(S)-2-(4-Chloro-phenyl)-pyrrolidin-1-yl]-(3-methyl-1H-pyrazolo[4,3-b]pyridin-5-yl)-methanone 51

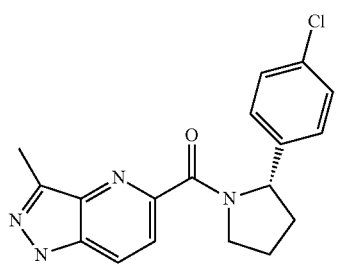

To a 25 mL round-bottom flask were added 3-methyl-1H-pyrazolo[4,3-b]pyridine-5-carboxylic acid (170 mg, 0.96 mmol), 2-(4-chlorophenyl)pyrrolidine (261 mg, 1.44 mmol), N,N-dimethylformamide (4 mL), 1-[bis(dimethylamino)methylene]-1H-1,2,3-triazolo[4,5-b]pyridinium 3-oxid hexafluorophosphate (HATU, 401 mg, 1.05 mmol) and diisopropylethylamine (372 mg, 2.88 mmol). The solution was stirred for 1 h at 25° C. The mixture was concentrated under vacuum. The residue was purified by preparative HPLC (acetonitrile/water). The racemic product (80.0 mg, 24%) was further purified by chiral preparative HPLC with the following conditions: Column: Phenomenex Lux 5u Cellulose-4, 250*21.2 mm, 5 μm; mobile phase: hexane and methanol (20% methanol in hexane isocratic in 12 min); Detector, UV 254/220 nm. This resulted in 35 mg (11%) of (2S)-2-(4-chlorophenyl)-1-([3-methyl-1H-pyrazolo[4,3-b]pyridin-5-yl]carbonyl)pyrrolidine as a white solid.

According to these general procedures compounds 52, 53 and 54 were synthesized.

9. (3-Amino-1H-pyrazolo[3,4-b]pyridin-5-yl)-[(S)-2-(4-bromo-phenyl)-pyrrolidin-1-yl]-methanone 98

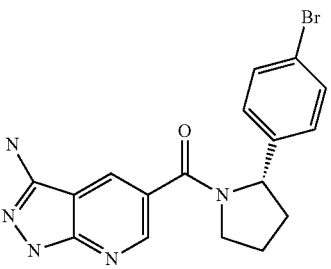 [SMILES: Nc1n[nH]c2ncc(C(=O)N3CCC[C@H]3c3ccc(Br)cc3)cc12]

9.1. 5-Bromo-1H-pyrazolo[3,4 -b]pyridin-3-ylamine

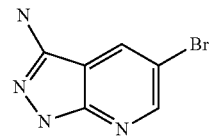

Into a 100mL sealed tube, was added 5-bromo-2-chloropyridine-3-carbonitrile (2.50 g, 11.5 mmol) and hydrazine hydrate (30 mL). The solution was stirred for 3 h at 130° C. The reaction mixture was concerntrated under vacuum. The residue was dissolved in 30ml of water. Precipitation occurred. The precipitates were collected by filtration. This resulted in 2.00 g (82%) of 5-bromo-1H-pyrazolo[3,4-b]pyridin-3-amine as a yellow solid.

9.2. 3-Amino-1H-pyrazolo[3,4-b]pyridine-5-carboxylic acid methyl ester

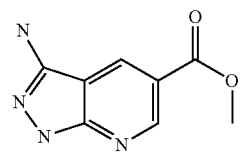

To a 30 mL steel tank reactor purged and maintained with an atmosphere of carbon monoxide (5 atm), was placed 5-bromo-1H-pyrazolo[3,4-b]pyridin-3-amine (500 mg, 2.35 mmol), Pd(dppf)Cl$_2$.CH$_2$Cl$_2$ (192 mg, 0.24 mmol), potassium acetate (691 mg, 7.04 mmol), N,N-dimethylformamide (5 mL) and methanol (5 mL). The mixture was stirred for 14 h at 80° C. and then concentrated under vacuum. The solution was extracted 3 times with 20 mL of ethyl acetate and the organic layers were combined. The residue was purified by a silica gel column eluting with ethyl acetate/petroleum ether (7:3). This resulted in 200 mg (44%) of methyl 3-amino-1H-pyrazolo[3,4-b]pyridine-5-carboxylate as a light brown solid.

9.3. 3-Amino-1H-pyrazolo[3,4-b]pyridine-5-carboxylic acid

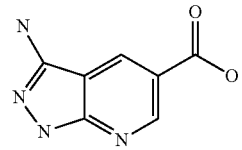 [SMILES: Nc1n[nH]c2ncc(C(=O)O)cc12]

To a 25-mL round-bottom flask was added methyl 3-amino-1H-pyrazolo[3,4-b]pyridine-5-carboxylate (200 mg, 1.04 mmol), tetrahydrofuran (8 mL), water (2 mL) and sodium hydroxide (84.0 mg, 2.10 mmol). The solution was stirred for 3 h at 50° C. The mixture was concentrated under vacuum. The residue was dissolved in 10 mL of water. The pH value of the solution was adjusted to 3 with hydrogen chloride (1 mol/L). The precipitates were collected by filtration. This resulted in 100 mg (54%) of 3-amino-1H-pyrazolo[3,4-b]pyridine-5-carboxylic acid as a yellow solid.

9.4. (3-Amino-1H-pyrazolo[3,4-b]pyridin-5-yl)-[(S)-2-(4-bromo-phenyl)-pyrrolidin-1-yl]-methanone 98

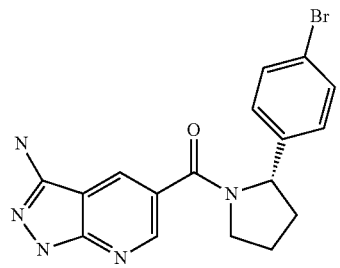 [SMILES: Nc1n[nH]c2ncc(C(=O)N3CCC[C@H]3c3ccc(Br)cc3)cc12]

Into a 25-mL round-bottom flask, was placed 3-amino-1H-pyrazolo[3,4-b]pyridine-5-carboxylic acid (40 mg, 0.22 mmol), 2-(4-bromophenyl)pyrrolidine (76.0 mg, 0.34 mmol), N,N-dimethylformamide (5 mL), 1-[bis(dimethylamino)methylene]-1H-1,2,3-triazolo[4,5-b]pyridinium 3-oxid hexafluorophosphate (HATU, 94 mg, 0.25 mmol), diisopropylethylamine (87.0 mg, 0.67 mmol). The solution was stirred for 1 h at 25° C. The mixture was concentrated under vacuum. The residue was dissolved in 10 mL of ethyl acetate. The mixture was washed three times with 10 mL of water. The crude product was purified by preparative HPLC (acetonitrile/water). The crude product (50 mg, 59%) was purified by chiral preparative HPLC with the following conditions: Column: Chiralpak IC, 2*25 cm, 5 µm; mobile phase: hexane-HPLC and ethanol-HPLC (hold 50% ethanol-HPLC in 20 min); Detector, UV 254/220 nm. This resulted in 19 mg (21%) of 5-[[(2S)-2-(4-bromophenyl)pyrrolidin-1-yl]carbonyl]-1H-pyrazolo[3,4-b]pyridin-3-amine as an off-white solid.

According to these general procedures compounds 96, 97 and 99 were synthesized.

10. [2-(4-Chloro-phenyl)-pyrrolidin-1-yl]-(3-trifluoromethyl-1H-pyrazolo[3,4-b]pyridin-5-yl)-methanone (177)

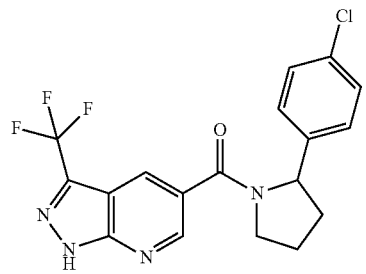 [SMILES: O=C(c1cnc2[nH]nc(C(F)(F)F)c2c1)N1CCCC1c1ccc(Cl)cc1]

10.1. 1,3-Dimethyl-1-(3-trifluoromethyl-1H-pyrazolo[3,4-b]pyridine-5-carbonyl)-urea

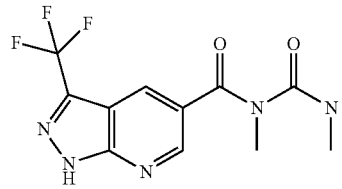 [SMILES: CNC(=O)N(C)C(=O)c1cnc2[nH]nc(C(F)(F)F)c2c1]

A mixture of 5-trifluoromethyl-2H-pyrazol-3-ylamine (500 mg, 3.31 mmol) and 1,3-dimethyl-2,4-dioxo-1,2,3,4-tetrahydropyrimidine-5-carbaldehyde (586 mg, 3.31 mmol) in acetic acid (glacial, 40 mL) was refluxed for 6 h. After cooling the solvent was evaporated under reduced pressure. The residue was dissolved in methanol, the solution was allowed to stand overnight, the precipitated crystals were suspended in diethyl ether, filtered off and dried. The crude product was purified by flash chromatography (dichloromethane/methanol) to yield in 630 mg (49%) of the title compound as a colorless solid. HPLC (purity) 77%. HPLC/MS: Rt 1.66 min (method A).

10.2. 3-Trifluoromethyl-1H-pyrazolo[3,4-b]pyridine-5-carboxylic acid

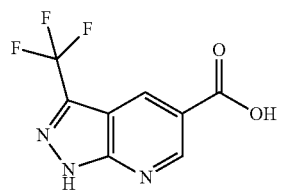 [SMILES: O=C(O)c1cnc2[nH]nc(C(F)(F)F)c2c1]

A mixture of 1,3-dimethyl-1-(3-trifluoromethyl-1H-pyrazolo[3,4-b]pyridine-5-carbonyl)-urea (630 mg, 1.61 mmol) and sodium hydroxide solution in water (10%, 16 mL) was heated and stirred for 2 h at 60° C. After cooling, the reaction mixture was filtered, and the filtrate was acidified with dilute HCl. The precipitated formed was filtered off, washed with water and dried to yield in 206 mg (51%) of the title compound as a beige solid.

HPLC (purity) 92%. HPLC/MS: Rt 1.58 min.

10.3. [2-(4-Chloro-phenyl)-pyrrolidin-1-yl]-(3-trifluoromethyl-1H-pyrazolo[3,4-b]pyridin-5-yl)-methanone

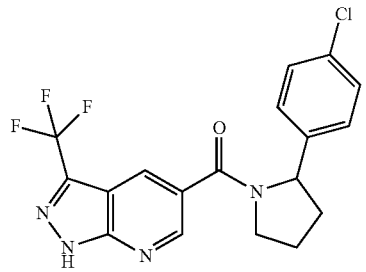

To a solution of 3-trifluoromethyl-1H-pyrazolo[3,4-b]pyridine-5-carboxylic acid (100 mg, 0.40 mmol), 2-(4-chloro-phenyl)-pyrrolidine (115 mg, 0.60 mmol) and 4-methylmorpholine (0.064 mL, 0.58 mmol) in N,N-dimethylformamide (2 mL) was added at RT N-(3-dimethylaminopropyl)-N-ethylcarbodiimide hydrochloride, DAPECl (92.0 mg, 0.48 mmol) and 1-hydroxybenzotriazole hydrate (9.00 mg, 0.07 mmol) and the reaction mixture was stirred at RT overnight. The mixture was poured into water, the precipitate was filtered off and dried in vacuo. The crude product was purified by flash chromatography (n-heptane/ethyl acetate) to yield in 69.0 mg (44%) of the title compound as a white solid. 1H NMR (400 MHz, DMSO-d6) ppm=8.90, 8.55, 8.49, 7.84 (4×s, 2H, ratio=2:3 mixture of rotamers), 7.46, 7.38, 7.23, 7.02 (2×d, J=8.2 Hz, 2×d, J=7.7 Hz, 4H, ratio=2:3 mixture of rotamers), 5.23-5.10, 4.98-4.87 (2×m, 1H, ratio=2:3 mixture of rotamers), 3.97-3.76, 3.66-3.24 (1×m, 1×m+HDO, 2H), 2.46-2.30 (m, 1H), 2.03-1.68 (m, 3H).

62.7 mg of the racemic mixture was separated by prep HPLC (SFC Berger Minigram, column: ChiralPak AD-H, solvent: CO2/Methanol 85:15, flow rate: 5 ml/min, wavelength: 220 nm) to yield in compounds 180 (26.6 mg, 42%) and 181 (26.3 mg, 42%) as white solids.

Analog to these procedures cpds 183 and 184 were synthesized.

11. [(S)-2-(4-Chloro-phenyl)-pyrrolidin-1-yl]-(3-methyl-1H-pyrazolo[3,4-c]pyridin-5-yl)-methanone (190)

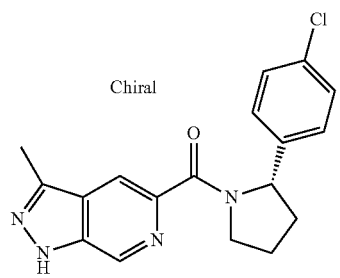 [SMILES: Cc1n[nH]c2cnc(C(=O)N3CCC[C@H]3c3ccc(Cl)cc3)cc12]

11.1. 1-(2-bromo-5-fluoropyridin-4-yl)ethan-1-one

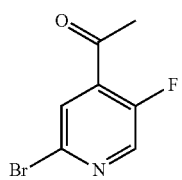

Into a 250 mL three-necked round-bottom flask purged and maintained with an inert atmosphere of nitrogen was placed a solution of LDA (35.0 mL, 258 mmol) in tetrahydrofuran (30 mL). This was followed by the addition of a solution of 2-bromo-5-fluoropyridine (5.00 g, 28.4 mmol) in tetrahydrofuran (20 mL) at −78° C. The mixture was stirred for 2 h at −78° C. To the mixture was added a solution of N-methoxy-N-methylacetamide (6.40 g, 62.1 mmol) in tetrahydrofuran (20 mL) at −78° C. The solution was warmed up to RT and stirred for 3 h at RT. The mixture was then quenched by the addition of 100 mL of water. The solution was extracted with 200 mL of ethyl acetate and the organic layer was dried over anhydrous sodium sulfate and concentrated under vacuum. The residue was purified over silica gel column with petrol ether/ethyl acetate (50:1). This resulted in 4.00 g (65%) of 1-(2-bromo-5-fluoropyridin-4-yl)ethan-1-one as yellow oil.

11.2 5-bromo-3-methyl-1H-pyrazolo[3,4-c]pyridine

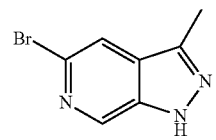

Into a 30 mL sealed tube, was placed 1-(2-bromo-5-fluoropyridin-4-yl)ethan-1-one (2.00 g, 9.17 mmol), NH2NH2*water (500 mg, 9.99 mmol) and ethane-1,2-diol (10 mL). The solution was stirred for 4 h at 165° C. in an oil bath. The mixture was diluted with 100 mL of water. The solids were collected by filtration. This resulted in 1.70 g (87%) of 5-bromo-3-methyl-1H-pyrazolo[3,4-c]pyridine as a yellow solid.

11.3. Methyl 3-methyl-1H-pyrazolo[3,4-c]pyridine-5-carboxylate

Into a 30 mL sealed tube was placed 5-bromo-3-methyl-1H-pyrazolo[3,4-c]pyridine (900 mg, 4.24 mmol), Pd(dppf)Cl2 (315 mg, 0.43 mmol), KOAc (1.25 g, 12.7 mmol) and N,N-dimethylformamide (10 mL). This was followed by the addition of methanol (10 mL) and CO gas. The solution was stirred for 1 h overnight at 80° C. in an oil bath. The mixture was concentrated under vacuum. The residue was purified over a silica gel column with dichloromethane/methanol (20:1). This resulted in 0.60 g (74%) of methyl 3-methyl-1H-pyrazolo[3,4-c]pyridine-5-carboxylate as a brown solid.

11.4 3-methyl-1H-pyrazolo[3,4-c]pyridine-5-carboxylic acid

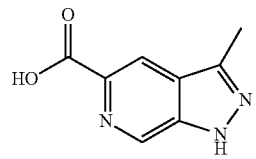

Into a 50 mL round-bottom flask was placed methyl 3-methyl-1H-pyrazolo[3,4-c]pyridine-5-carboxylate (300 mg, 1.57 mmol), LiOH*H₂O (328 mg, 7.82 mmol), tetrahydrofuran (20 mL) and water (5 mL). The solution was stirred for 5 h at 60° C. in an oil bath. The mixture was concentrated under vacuum. The pH of the solution was adjusted to 4 with hydrogen chloride (1 M). The solids were collected by filtration. This resulted in 190 mg (68%) of 3-methyl-1H-pyrazolo[3,4-c]pyridine-5-carboxylic acid as a yellow solid. 11.5 [(S)-2-(4-Chloro-phenyl)-pyrrolidin-1-yl]-(3-methyl-1H-pyrazolo[3,4-c]pyridin-5-yl)-methanone

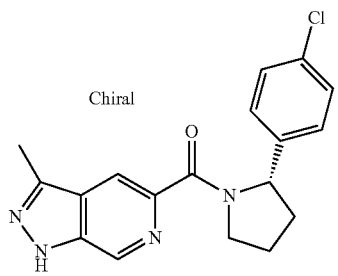 [SMILES: Cc1n[nH]c2cnc(C(=O)N3CCC[C@H]3c3ccc(Cl)cc3)cc12]

Into a 25 mL round-bottom flask was placed 3-methyl-1H-pyrazolo[3,4-c]pyridine-5-carboxylic acid (130 mg, 0.73 mmol), (S)-2-(4-chlorophenyl)pyrrolidine (172 mg, 0.95 mmol), HATU (277 mg, 0.73 mmol), diethyl acetate (282 mg, 2.18 mmol) and N,N-dimethylformamide (4 mL). The solution was stirred for 3 h at RT. The mixture was concentrated under vacuum. The crude product was purified by prep-HPLC (acetonitrile/water). This resulted in 20.0 mg (8%) of (2S)-2-(4-chlorophenyl)-1-([3-methyl-1H-pyrazolo[3,4-c]pyridin-5-yl]carbonyl)pyrrolidine as a white solid. 1H NMR (300 MHz, DMSO-d6) ppm=13.40 (m, 1H), 9.00 (s, 0.67H), 8.72 (s, 0.33H), 8.14 (s, 0.67H), 7.83 (s, 0.33H), 7.40-7.32 (m, 3H), 7.15-6.98 (m, 1H), 5.84-5.82 (m, 0.33H), 5.26-5.21 (m, 0.67H), 4.10-4.02 (m, 0.67H), 3.87-3.70 (m, 1.33H), 2.55 (s, 2H), 2.41 (s, 1H), 2.38-2.27 (m, 1H), 1.87-1.68 (m, 3H).

Analog to these procedures 189 was synthesized.

12. [(S)-2-(4-Chloro-phenyl)-pyrrolidin-1-yl]-(6-fluoro-3-methyl-1H-indazol-5-yl)-methanone (206)

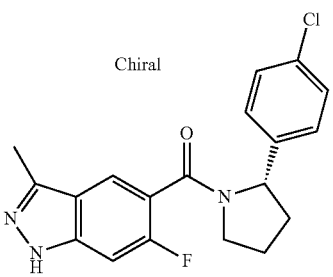 [SMILES: Cc1n[nH]c2cc(F)c(C(=O)N3CCC[C@H]3c3ccc(Cl)cc3)cc12]

12.1. 5-bromo-6-fluoro-3-methyl-1H-indazole

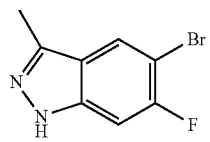

Into a 50 mL round-bottom flask was placed ethane-1,2-diol (30 mL), 1-(5-bromo-2,4-difluorophenyl)ethan-1-one (5.95 g, 25.3 mmol), NH₂NH₂*H₂O (1.90 g, 38.0 mmol). The solution was stirred for 20 h at 120° C. in an oil bath. The mixture was diluted with 200 mL of water and extracted three times with 70 mL of ethyl acetate. The combined organic layers were concentrated under vacuum. This resulted in 4.45 g (77%) of 5-bromo-6-fluoro-3-methyl-1H-indazole as a yellow solid.

12.2. Methyl 6-fluoro-3-methyl-1H-indazole-5-carboxylate

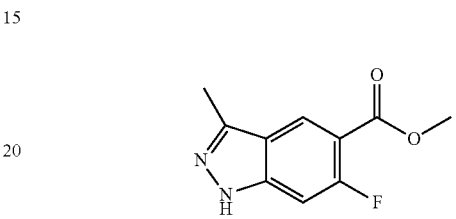

Into a 250 mL sealed tube was placed methanol (180 mL), N,N-dimethylformamide (10 mL), 5-bromo-6-fluoro-3-methyl-1H-indazole (4.00 g, 17.5 mmol), Pd(dppf)Cl₂*dichloromethane (2.55 g, 3.12 mmol) and potassium acetate (5.15 g, 52.4 mmol). The solution was stirred for 20 h at 80° C. in an oil bath. The mixture was concentrated under vacuum. The residue was diluted with 100 mL of water. The solution was extracted three time with 50 mL of ethyl acetate and the combined organic layers were evaporated to dryness. The residue was purified over a silica gel column with ethyl acetate/hexane (1:3). This resulted in 2.64 g (73%) of methyl 6-fluoro-3-methyl-1H-indazole-5-carboxylate as a yellow solid.

12.3 6-fluoro-3-methyl-1H-indazole-5-carboxylic acid

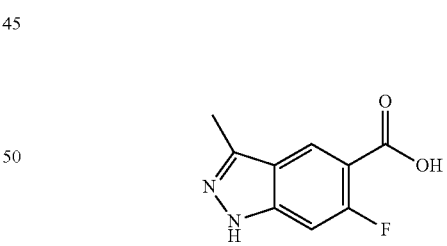

Into a 100 mL round-bottom flask was placed tetrahydrofuran (50 mL), methyl 6-fluoro-3-methyl-1H-indazole-5-carboxylate (2.64 g, 12.7 mmol), water (10 mL) and LiOH (1.52 g, 63.47 mmol). The solution was stirred for 4 h at 60° C. in an oil bath. The mixture was concentrated under vacuum. The pH of the solution was adjusted to 4 with hydrogen chloride (12 M). The solids were collected by filtration and discarded. The filtrate was concentrated under vacuum to result in 2.21 g (90%) of 6-fluoro-3-methyl-1H-indazole-5-carboxylic acid as a light yellow solid.

12.4. [(S)-2-(4-Chloro-phenyl)-pyrrolidin-1-yl]-(6-fluoro-3-methyl-1H-indazol-5-yl)-methanone (206)

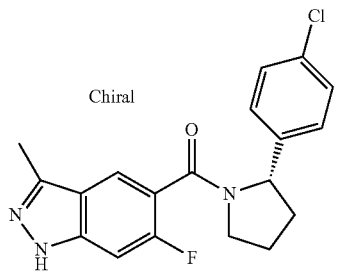 [SMILES: Cc1n[nH]c2cc(F)c(C(=O)N3CCC[C@H]3c3ccc(Cl)cc3)cc12]

Into a 25 mL round-bottom flask was placed N,N-dimethylformamide (5 mL), 6-fluoro-3-methyl-1H-indazole-5-carboxylic acid (200 mg, 1.03 mmol), (2S)-2-(4-chlorophenyl)pyrrolidine (243.261 mg, 1.34 mmol), diethyl acetate (399 mg, 3.09 mmol) and HATU (392 mg, 1.03 mmol). The solution was stirred for 1 h at 25° C. The solids were filtered off and the crude product was purified by prep-HPLC (acetonitrile/water) to result in 60 mg (16%) of 5-[[(2S)-2-(4-chlorophenyl)pyrrolidin-1-yl]carbonyl]-6-fluoro-3-methyl-1H-indazole as a white solid. 1H NMR (300 MHz, CDCl$_3$) ppm=7.78 (d, 0.65H), 7.33-7.12 (m, 2.33H), 7.09-7.06 (m, 1.90H), 6.93-6.78 (m, 1.17H), 5.36-5.32 (m, 0.69H), 4.72-4.68 (m, 0.38H), 4.00-3.90 (m, 0.75H), 3.70-3.66 (m, 0.65H), 3.49-3.45 (m, 0.65H), 2.57-2.45 (s, 2H), 2.43-2.39 (m, 1.02H), 2.38-2.36 (s, 1.18H), 2.07-2.00 (m, 1.14H), 1.96-1.85 (m, 2.14H).

Analog to these procedures 203 was synthesized

13. [(S)-2-(4-Chloro-phenyl)-pyrrolidin-1-yl]-(3-methanesulfonyl-1H-indazol-5-yl)-methanone (220)

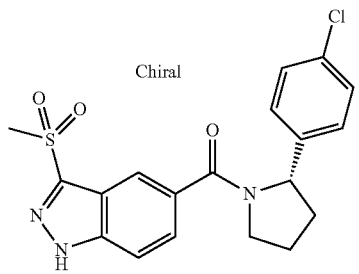 [SMILES: CS(=O)(=O)c1n[nH]c2ccc(C(=O)N3CCC[C@H]3c3ccc(Cl)cc3)cc12]

13.1. 3-Methylsulfanyl-1H-indazole-5-carboxylic acid

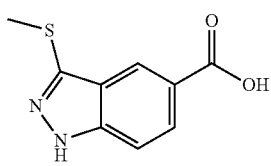

Into a 2 mL microwave vial 3-iodo-1H-indazole-5-carboxylic acid ethyl ester (100 mg, 0.32 mmol), copper(I) iodide (6.02 mg, 0.03 mmol) and sodium methanethiolate (123 µL, 1.58 mmol) were weighed in and dissolved in dry dimethyl sulfoxide (4 mL) and water (0.6 mL). The mixture was reacted at 120° C. for 2 h under microwave irradiation. The mixture was diluted with 0.5 N HCl solution (25 mL) and extracted with ethyl acetate twice (50 mL). The combined organic layers were evaporated to dryness and purified by flash chromatography (ethyl acetate/methanol) to yield in 3-methylsulfanyl-1H-indazole-5-carboxylic acid (62.0 mg, 77%) as a colorless oil.

13.2. [(S)-2-(4-Chloro-phenyl)-pyrrolidin-1-yl]-(3-methylsulfanyl-1H-indazol-5-yl)-methanone (210)

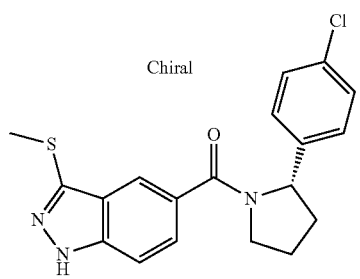 [SMILES: CSc1n[nH]c2ccc(C(=O)N3CCC[C@H]3c3ccc(Cl)cc3)cc12]

3-Methylsulfanyl-1H-indazole-5-carboxylic acid (62.0 mg, 0.24 mmol), (S)-2-(4-Chloro-phenyl)-pyrrolidine hydrochloride (63.8 mg, 0.29 mmol) and O-(1H-Benzotriazol-1-yl)-N,N,N',N'-tetramethyluronium tetrafluorborate (TBTU, 157 mg, 0.49 mmol) were weighed in and dissolved in N,N-dimethylformamide (2 mL) and 4-methylmorpholine (82.1 µL, 0.73 mmol). The clear solution was stirred at RT for 30 min. The reaction mixture was poured into sat. ammonium chloride solution (30 mL). The precipitate was filtered off, washed with water (10 mL) and dried at 70° C. under vacuum overnight to give [(S)-2-(4-chloro-phenyl)-pyrrolidin-1-yl]-(3-methylsulfanyl-1H-indazol-5-yl)-methanone (26.2 mg, 27%) as an off-white solid.

13.3. [(S)-2-(4-Chloro-phenyl)-pyrrolidin-1-yl]-(3-methanesulfonyl-1H-indazol-5-yl)-methanone (220)

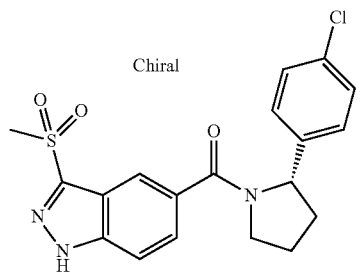 [SMILES: CS(=O)(=O)c1n[nH]c2ccc(C(=O)N3CCC[C@H]3c3ccc(Cl)cc3)cc12]

Into a 12 mL screw cap jar [(S)-2-(4-Chloro-phenyl)-pyrrolidin-1-yl]-(3-methylsulfanyl-1H-indazol-5-yl)-methanone (17.5 mg, 0.04 mmol) and Oxone®, monopersulfate (Potassium peroxymonosulfate, 54.1 mg, 0.09 mmol) were weighed in and suspended in N,N-dimethylformamide (1 mL). The mixture was stirred at RT for 3 days. The suspension was quenched with NaHSO$_3$ solution (3 mL, 39% in water). The mixture was diluted with water and neutralized with solid NaHCO$_3$. It was extracted with ethyl acetate twice (30 mL). The combined organic layers were dried, filtered, evaporated to dryness and further purified by flash chromatography (dichloromethane/methanol) to yield in 12.4 mg (71%) of [(S)-2-(4-chloro-phenyl)-pyrrolidin-1-yl]-(3-methanesulfonyl-1H-indazol-5-yl)-methanone as a white solid.

14. [(S)-2-(4-Chloro-phenyl)-pyrrolidin-1-yl]-(3-fluoro-1H-indazol-5-yl)-methanone (216)

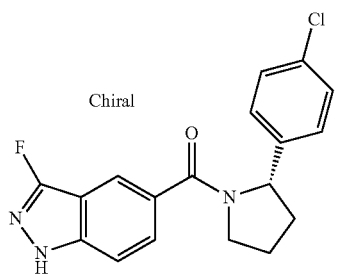 [SMILES: O=C(c1ccc2[nH]nc(F)c2c1)N1CCC[C@H]1c1ccc(Cl)cc1]

14.1. 3-Fluoro-1H-indazole-5-carboxylic acid

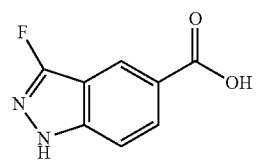 [SMILES: O=C(O)c1ccc2[nH]nc(F)c2c1]

A screw cap bottle was charged with 1H-indazole-5-carboxylic acid (64.0 mg, 0.38 mmol) and was suspended in acetonitrile (8 mL) and acetic acid (glacial, 1 mL). To this cloudy suspension 1-(chloromethyl)-4-fluoro-1,4-diazoniabicyclo[2.2.2]octane ditetrafluoroborate (214 mg, 0.57 mmol) dissolved in 1 mL acetonitrile was added dropwise and the mixture was stirred overnight at 60° C. and for 4 days at 80° C. The mixture was evaporated to dryness, the residue was dissolved in ethyl acetate and washed twice with water and once with brine. The organic phase was dried with sodium sulfate and the organic phase was evaporated to dryness. The residue was separated by preparative chromatography (acetonitrile/water) to yield in 16 mg (23%) of a white solid.

14.2. [(S)-2-(4-Chloro-phenyl)-pyrrolidin-1-yl]-(3-fluoro-1H-indazol-5-yl)-methanone (216)

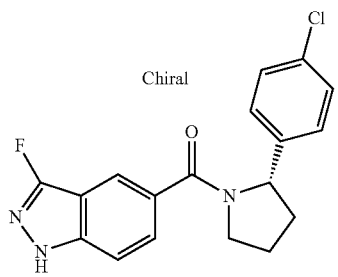 [SMILES: O=C(c1ccc2[nH]nc(F)c2c1)N1CCC[C@H]1c1ccc(Cl)cc1]

To a solution of 3-fluoro-1H-indazole-5-carboxylic acid (16.0 mg, 0.09 mmol) in N,N-dimethylformamide (3 mL), (S)-2-(4-chloro-phenyl)-pyrrolidine hydrochloride (23.0 mg, 0.11 mmol), 4-methylmorpholine (0.03 mL, 0.26 mmol) and [(benzotriazol-1-yloxy)-dimethylamino-methylene]-dimethyl-ammonium tetrafluoroborate (TBTU), 56.5 mg, 0.18 mmol) were added and the mixture was stirred for 5 min at 60° C. The mixture was diluted with ethyl acetate, washed once with 1N NaOH solution, with water and brine. The organic layer was separated and dried with sodium sulfate, filtered and evaporated to dryness. The residue was purified by preparative chromatography (acetonitrile/water) to yield in 17 mg (55%) of the title compound as an off-white solid. 1H NMR (400 MHz, DMSO-d6, 90° C.) ppm=12.43 (s, 1H), 7.78 (s, 1H), 7.54-7.39 (m, 2H), 7.34-7.18 (m, 4H), 5.12 (t, J=6.7 Hz, 1H), 3.86-3.76 (m, 1H), 3.69-3.58 (m, 1H), 2.43-2.33 (m, 1H), 1.94-1.83 (m, 2H), 1.83-1.72 (m, 1H).

15. [(S)-2-(1H-Indazol-5-yl)-pyrrolidin-1-yl]-(3-methyl-1H-pyrazolo[3,4-b]pyridin-5-yl)-methanone (245) and [(R)-2-(1H-Indazol-5-yl)-pyrrolidin-1-yl]-(3-methyl-1H-pyrazolo[3,4-b]pyridin-5-yl)-methanone (246)

15.1. Tert-butyl 2-(1H-indazol-5-yl)-1H-pyrrole-1-carboxylate

Into a 250 mL round-bottom flask purged and maintained with an inert atmosphere of nitrogen was placed sodium carbonate (1.08 g, 10.1 mmol), water (20 mL), ethylene glycol dimethyl ether (100 mL), 5-bromo-1H-indazole (1.00 g, 5.08 mmol), [1-[(tert-butoxy)carbonyl]-1H-pyrrol-2-yl] boronic acid (1.29 g, 6.09 mmol) and Pd(PPh$_3$)$_4$ (586 mg, 0.51 mmol). The solution was stirred for 4 h at 95° C. in an oil bath and was diluted with 50 mL of water after cooling. The solution was extracted twice with 50 mL of dichloromethane and the combined organic layers were concentrated to dryness. The residue was purified over a silica gel column with ethyl acetate/petroleum ether (1:10). This resulted in 1 g (70%) of tert-butyl 2-(1H-indazol-5-yl)-1H-pyrrole-1-carboxylate as yellow oil.

15.2. 5-(pyrrolidin-2-yl)-1H-indazole

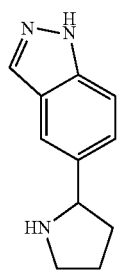 [SMILES: c1cc2[nH]ncc2cc1C1CCCN1]

Into a 20 mL pressure tank reactor purged and maintained with an atmosphere of hydrogen was placed tert-butyl 2-(1H-indazol-5-yl)-1H-pyrrole-1-carboxylate (500 mg, 1.76 mmol), ethanol (5.00 mL), hydrogen chloride (1 N, 0.50 mL) and PtO$_2$ (40.1 mg, 0.18 mmol). The solution was stirred for 5 days at 60° C. in an oil bath. The mixture was concentrated under vacuum. The residue was purified over a silica gel column with methanol/water (1:99). This resulted in 200 mg (61%) of 5-(pyrrolidin-2-yl)-1H-indazole as yellow oil.

15.3 [(S)-2-(1H-Indazol-5-yl)-pyrrolidin-1-yl]-(3-methyl-1H-pyrazolo[3,4-b]pyridin-5-yl)-methanone (245) and [(R)-2-(1H-Indazol-5-yl)-pyrrolidin-1-yl]-(3-methyl-1H-pyrazolo[3,4-b]pyridin-5-yl)-methanone (246)

Were prepared according to the general procedures to yield in 29 mg (7%) of the title compound as a white solids. 1H NMR (245, 300 Hz, DMSO-d6) ppm=13.11 (s, 1H), 12.76 (s, 1H), 8.52 (s, 1H), 8.40-8.09 (m, 1H), 7.95 (s, 1H), 7.62-7.50 (m, 1H), 7.50-7.35 (m, 1H), 7.22 (s, 1H), 5.24 (s, 1H), 3.92-3.90 (m, 1H), 3.79-3.72 (m, 1H), 2.42-2.31 (m, 4H), 1.97-1.90 (m, 3H).

16. [(2S,4R)-2-(4-Chloro-phenyl)-4-methylamino-pyrrolidin-1-yl]-(3-methyl-1H-pyrazolo[3,4-b]pyridin-5-yl)-methanone (254)

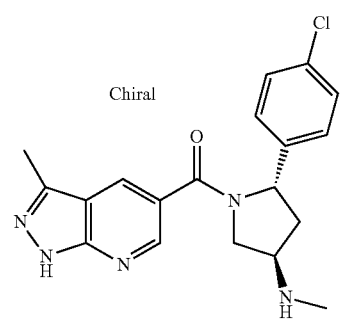 [SMILES: CN[C@@H]1C[C@@H](c2ccc(Cl)cc2)N(C(=O)c2cnc3[nH]nc(C)c3c2)C1]

16.1. (3S)-3-[(tert-butyldimethylsilyl)oxy]-4-chlorobutanenitrile

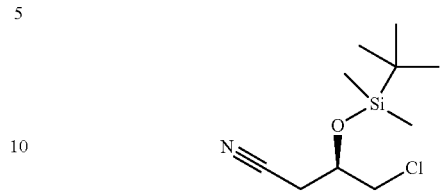

Into a 250 mL round-bottom flask was placed (3S)-4-chloro-3-hydroxybutanenitrile (5.00 g, 41.8 mmol), N,N-dimethylformamide (80 mL), TBSCl (8.10 g, 53.74 mmol), imidazole (5.60 g, 82.3 mmol). The reaction mixture was stirred for 1 h overnight at RT. The solution was diluted with 200 mL of ethyl acetate. The mixture was concentrated under vacuum. The residue was purified over a silica gel column with ethyl acetate/petroleum ether (1:10). This resulted in 7.80 g (80%) of (3S)-3-[(tert-butyldimethylsilyl)oxy]-4-chlorobutanenitrile as a colorless liquid.

16.2. (3S)-3-[(tert-butyldimethylsilyl)oxy]-5-(4-chlorophenyl)-3,4-dihydro-2H-pyrrole

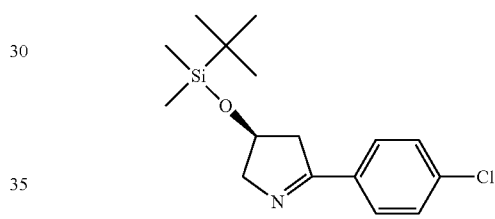

Into a 50 mL 3-necked round-bottom flask purged and maintained with an inert atmosphere of nitrogen was placed (3S)-3-[(tert-butyldimethylsilyl)oxy]-4-chlorobutanenitrile (300 mg, 1.28 mmol) in methyl tert.butyl ether (5 mL). This was followed by the addition of bromo(4-chlorophenyl)magnesium (3.80 mL, 17.6 mmol) at 0° C. The mixture was stirred for 3 h at 25° C. To the mixture was added ethylene glycol dimethyl ether (5 mL) and the solution was stirred for 2 h at RT. The solution was diluted with 50 mL of ethyl acetate. The mixture was concentrated under vacuum. The residue was purified over a silica gel column with petrol ether/ethyl acetate (50:1). This resulted in 240 mg (60%) of (3S)-3-[(tert-butyldimethylsilyl)oxy]-5-(4-chlorophenyl)-3,4-dihydro-2H-pyrrole as brown oil.

16.3. (2RS,4S)-4-[(tert-butyldimethylsilyl)oxy]-2-(4-chlorophenyl)pyrrolidine

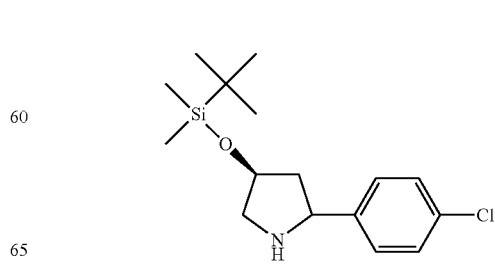

Into a 50 mL round-bottom flask was placed (3S)-3-[(tert-butyldimethylsilyl)oxy]-5-(4-chlorophenyl)-3,4-dihydro-2H-pyrrole (300 mg, 0.97 mmol) in ethanol (6 mL). This was followed by the addition of PtO$_2$ (30 mg, 0.13 mmol). The solution was stirred under hydrogen atmosphere for 1 h overnight at RT. The solids were filtered off and discarded. The filtrate was concentrated under vacuum to result in 300 mg (99%) of (2RS,4S)-4-[(tert-butyldimethylsilyl)oxy]-2-(4-chlorophenyl)pyrrolidine as brown oil.

16.4. (2RS,4S)-4-[(tert-butyldimethylsilyl)oxy]-2-(4-chlorophenyl)-1-({3-methyl-1H-pyrazolo[3,4-b]pyridin-5-yl}carbonyl)pyrrolidine

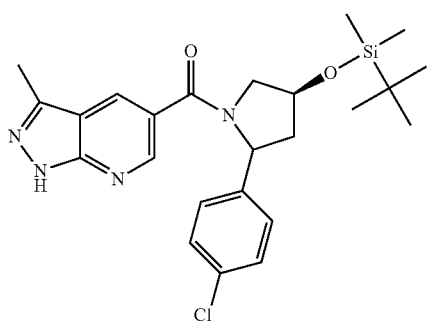 [SMILES: Cc1n[nH]c2ncc(C(=O)N3C[C@@H](O[Si](C)(C)C(C)(C)C)CC3c3ccc(Cl)cc3)cc12]

Into a 50 mL round-bottom flask was placed 3-methyl-1H-pyrazolo[3,4-b]pyridine-5-carboxylic acid (300 mg, 1.69 mmol), (2RS,4S)-4-[(tert-butyldimethylsilyl)oxy]-2-(4-chlorophenyl)pyrrolidine (631 mg, 2.02 mmol), HATU (640 mg, 1.68 mmol), diethyl acetate (652 mg, 5.04 mmol) and N,N-dimethylformamide (5 mL). The solution was stirred for 3 h at RT. The mixture was concentrated under vacuum. The residue was purified over a silica gel column with dichloromethane/methanol (50:1). This resulted in 250 mg (31%) of (2RS,4S)-4-[(tert-butyldimethylsilyl)oxy]-2-(4-chlorophenyl)-1-([3-methyl-1H-pyrazolo[3,4-b]pyridin-5-yl]carbonyl)pyrrolidine as a yellow 16.5. (3S,5RS)-5-(4-chlorophenyl)-1-({3-methyl-1H-pyrazolo[3,4-b]pyridin-5-yl}carbonyl)pyrrolidin-3-ol

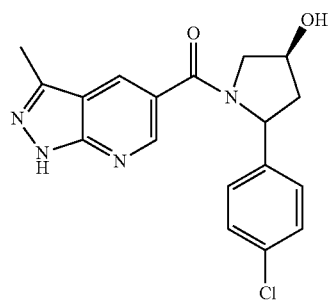 [SMILES: Cc1n[nH]c2ncc(C(=O)N3C[C@@H](O)CC3c3ccc(Cl)cc3)cc12]

Into a 25 mL round-bottom flask was placed (2RS,4S)-4-[(tert-butyldimethylsilyl)oxy]-2-(4-chlorophenyl)-1-([3-methyl-1H-pyrazolo[3,4-b]pyridin-5-yl]carbonyl)pyrrolidine (200 mg, 0.42 mmol) in tetrahydrofuran (5 mL). TBAF (2 mL, 7.65 mmol) was added at 0° C. and the solution was stirred for 30 min at 0° C. in a water/ice bath. The mixture was concentrated under vacuum. The residue was applied onto a silica gel column with dichloromethane/methanol (20:1). This resulted in 140 mg (92%) of (3S,5RS)-5-(4-chlorophenyl)-1-([3-methyl-1H-pyrazolo[3,4-b]pyridin-5-yl]carbonyl)pyrrolidin-3-ol as a yellow solid.

16.6. (3S,5RS)-5-(4-chlorophenyl)-1-({3-methyl-1H-pyrazolo[3,4-b]pyridin-5-yl}carbonyl)pyrrolidin-3-yl methanesulfonate

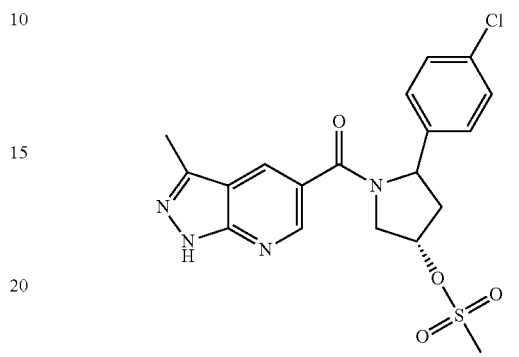

Into a 25 mL round-bottom flask was placed (3S,5RS)-5-(4-chlorophenyl)-1-([3-methyl-1H-pyrazolo[3,4-b]pyridin-5-yl]carbonyl)pyrrolidin-3-ol (140 mg, 0.39 mmol), dichloromethane (10 mL), triethylamine (119 mg, 1.18 mmol), mesyl chloride (58.0 mg, 0.51 mmol). The solution was stirred for 2 h at 0° C. in a water/ice bath. The solution was diluted with 50 mL of dichloromethane. The mixture was dried over sodium sulfate and concentrated under vacuum. This resulted in 140 mg (82%) of (3S,5RS)-5-(4-chlorophenyl)-1-([3-methyl-1H-pyrazolo[3,4-b]pyridin-5-yl]carbonyl)pyrrolidin-3-yl methanesulfonate as yellow oil.

16.7. [(2S,4R)-2-(4-Chloro-phenyl)-4-methylamino-pyrrolidin-1-yl]-(3-methyl-1H-pyrazolo[3,4-b]pyridin-5-yl)-methanone

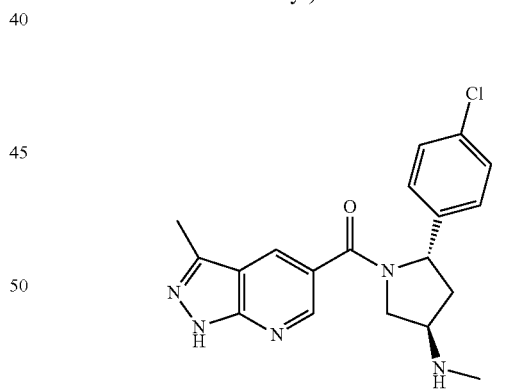

Into a 30 mL sealed tube, was placed (3S,5RS)-5-(4-chlorophenyl)-1-([3-methyl-1H-pyrazolo[3,4-b]pyridin-5-yl]carbonyl)pyrrolidin-3-yl methanesulfonate (140 mg, 0.32 mmol), methyl amine (434 mg, 13.97 mmol) and ethanol (8 mL). The solution was stirred for 1 overnight at 100° C. in an oil bath. The mixture was concentrated under vacuum. The crude product was purified by prep-HPLC (acetonitrile/water) to yield in 5.00 mg (4%) of [(2S,4R)-2-(4-chloro-phenyl)-4-methylamino-pyrrolidin-1-yl]-(3-methyl-1H-pyrazolo[3,4-b]pyridin-5-yl)-methanone as a white solid. 1H NMR (400 MHz, DMSO-d6) ppm=13.38 (s, 1H), 8.69 (s, 1H), 8.52 (s, 1H), 7.46 (d, J=8 Hz, 2H), 7.38 (d, J=8 Hz, 2H), 5.20 (m, 1H), 4.11-4.07 (m, 1H), 3.46-3.41 (m, 2H), 2.59 (s, 3H), 2.37-2.15 (m, 5H), 1.84 (m, 2H).

17. [(3S,4R)-3-(4-Chloro-phenyl)-4-hydroxy-pyrrolidin-1-yl]-(3-methyl-1H-pyrazolo[3,4-b]pyridin-5-yl)-methanone (256)

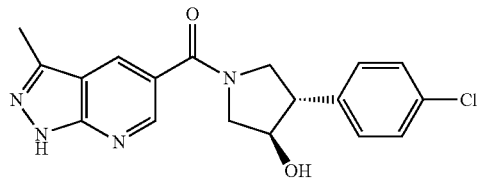 [SMILES: Cc1n[nH]c2ncc(C(=O)N3C[C@H](c4ccc(Cl)cc4)[C@@H](O)C3)cc12]

17.1. Tert-butyl 3-(4-chlorophenyl)-4-hydroxypyrrolidine-1-carboxylate

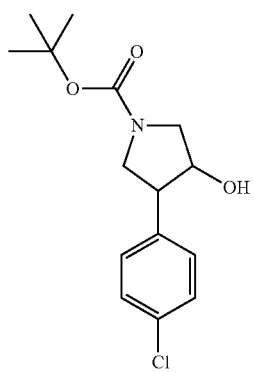 [SMILES: CC(C)(C)OC(=O)N1CC(O)C(c2ccc(Cl)cc2)C1]

Into a 100 mL three-neck round-bottom flask purged and maintained with an inert atmosphere of nitrogen was placed 1-bromo-4-chlorobenzene (2.33 g, 12.2 mmol) in tetrahydrofuran (20 mL). To this solution n-BuLi (5.40 mL, 2.5 mol/L) was added dropwise with stirring at −80° C. over 30 min. To the mixture was then added BF$_3$*Et$_2$O (1.80 mL, 14.2 mmol) dropwise with stirring at −80° C. within 10 min. A solution of tert-butyl 6-oxa-3-azabicyclo[3.1.0]hexane-3-carboxylate (1.00 g, 5.40 mmol) in tetrahydrofuran (3 mL) was added dropwise with stirring again at −80° C. The solution was stirred for 3 h at −80° C. The reaction was then quenched by the addition of 20 mL of aqueous sodium bicarbonate. The mixture was extracted twice with 20 mL of tetrahydrofuran/ethyl acetate (1:1) and the combined organic layers were concentrated under vacuum. The residue was purified over a silica gel column with petrol ether/ethyl acetate (5:2). This resulted in 600 mg (37%) of tert-butyl 3-(4-chlorophenyl)-4-hydroxypyrrolidine-1-carboxylate as colorless oil.

17.2. 4-(4-chlorophenyl)pyrrolidin-3-ol

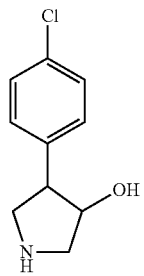 [SMILES: OC1CNCC1c1ccc(Cl)cc1]

Into a 50 mL round-bottom flask was placed tert-butyl 3-(4-chlorophenyl)-4-hydroxypyrrolidine-1-carboxylate (600 mg, 2.01 mmol) in dichloromethane (15 mL) and trifluoroacetic acid (3 mL) was added at RT. The solution was stirred for 2 h at RT. The mixture was concentrated under vacuum. The residue was purified over a silica gel column with methanol/water (1:99). This resulted in 300 mg (75%) of 4-(4-chlorophenyl)pyrrolidin-3-ol as colorless oil.

17.3. [(3S,4R)-3-(4-Chloro-phenyl)-4-hydroxy-pyrrolidin-1-yl]-(3-methyl-1H-pyrazolo[3,4-b]pyridin-5-yl)-methanone (256) and [(3R,4S)-3-(4-Chloro-phenyl)-4-hydroxy-pyrrolidin-1-yl]-(3-methyl-1H-pyrazolo[3,4-b]pyridin-5-yl)-methanone (255)

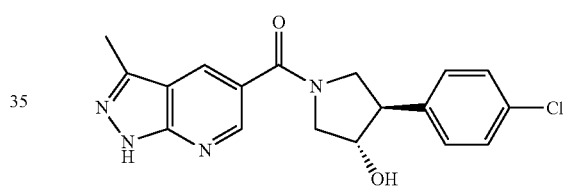

Into a 25 mL round-bottom flask was placed 3-methyl-1H-pyrazolo[3,4-b]pyridine-5-carboxylic acid (150 mg, 0.85 mmol), 4-(4-chlorophenyl)pyrrolidin-3-ol (201 mg, 1.02 mmol), N,N-dimethylformamide (5 mL), EDCl (325 mg, 1.69 mmol) and 4-dimethylaminopyridine (155 mg, 1.27 mmol). The solution was stirred for 3 h at RT. The residue was purified over a silica gel column with methanol/dichloromethane (3:10). The crude product was purified by prep. HPLC (acetonitrile/water). This resulted in 30 mg (10%) of racemic trans-[3-(4-chloro-phenyl)-4-hydroxy-pyrrolidin-1-yl]-(3-methyl-1H-pyrazolo[3,4-b]pyridin-5-yl)-methanone as a white solid. The racemic mixture was then purified via chiral HPLC (Chiralpak IB4.6*250 mm, 5 μm, 100% methanol (0.1% diethylamine) to yield in [(3S,4R)-3-(4-Chloro-phenyl)-4-hydroxy-pyrrolidin-1-yl]-(3-methyl-1H-pyrazolo[3,4-b]pyridin-5-yl)-methanone (256) and [(3R,4S)-3-(4-Chloro-phenyl)-4-hydroxy-pyrrolidin-1-yl]-(3-methyl-1H-pyrazolo[3,4-b]pyridin-5-yl)-methanone (255). 1H NMR (256, 300 Hz, DMSO-d6) ppm=13.15 (s, 1H), 8.65-8.64 (m, 1H), 8.36-8.35 (m, 1H), 7.38-7.33 (m, 4H), 5.30-5.00 (m, 1H), 4.27-4.25 (m, 1H), 4.04-3.98 (m, 1H), 3.86-3.80 (m, 1H), 3.65-3.59 (m, 1H), 3.46-3.40 (m, 1H), 3.32-3.24 (m, 1H), 2.52 (s, 3H).

18. 3-(4-chlorophenyl)morpholino)(3-methyl-1H-indazol-5-yl)methanone (178)

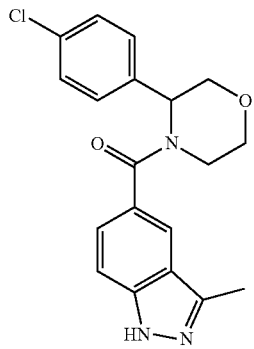 [SMILES: Cc1n[nH]c2ccc(C(=O)N3CCOCC3c3ccc(Cl)cc3)cc12]

To 3-methyl-1H-indazole-5-carboxylic acid (40 mg, 0.23 mmol) in N,N-dimethyl formamide (1.9 mL) was added HATU (104 mg, 0.272 mmol), 3-(4-chlorophenyl)morpholine hydrochloride (53 mg, 0.23 mmol) and DIPEA (87 µL, 0.50 mmol). The reaction mixture was stirred at RT overnight, concentrated and the crude material was purified via Biotage column chromatography (dichloromethane/ethanol 99/1 to 93/7) and by prepTLC (1 mm, dichloromethane/ethanol, 98/2). The product was then filtered on a SCX-2 column and released with 1N NH$_3$ in methanol to give the title compound (5 mg, 6% yield). $^1$H NMR (500 MHz, CD$_3$OD) ppm=7.86-7.85 (m, 1H), 7.60-7.51 (m, 3H), 7.47-7.40 (m, 3H), 5.70-5.40 (bs, 1H), 4.49 (d, J=12.4 Hz, 1H), 4.00-4.64 (bs, 1H), 4.00 (dd, J=12.4, 3.6 Hz, 1H), 3.94-3.83 (m, 1H), 3.73-3.64 (m, 1H), 3.39-3.30 (m, 1H), 2.56 (s, 3H). LC-MS (ESI, m/z, method L) Rt=2.71 min-356/358 (M+H)$^+$. ESI-HRMS: Found: 356.1153 calculated for C$_{19}$H$_{19}$$^{35}$ClN$_3$O$_2$(M+H)$^+$: 356.1160.

19. (2-(4-chlorophenyl)-4-methylpiperazin-1-yl)(3-methyl-1H-indazol-5-yl)methanone (244)

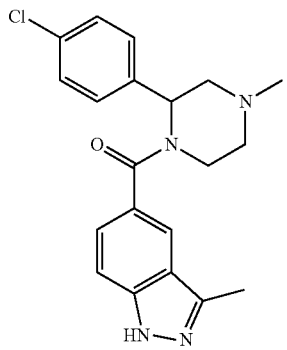

19.1. 3-(4-chlorophenyl)-1-methylpiperazine

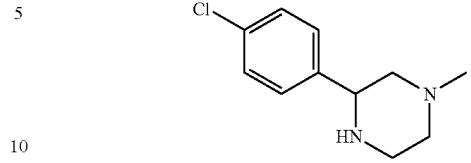

To a solution of 2-(4-chlorophenyl)piperazine (200 mg, 1.02 mmol) and triethylamine (1.08 mL, 7.73 mmol) in acetone (3.2 mL) was added methyl iodide (70 µL, 1.1 mmol) dropwise at 0° C. The reaction was stirred at RT overnight. 1 additional equivalent of methyl iodide and 1 mL of acetone were added. The reaction was stirred at RT for another 5 h. Saturated NH$_4$Cl solution and ethyl acetate were added, the aqueous layer was extracted with ethyl acetate three times and the organic layer was dried over MgSO$_4$, filtrated and concentrated. The crude mixture was used in the following step without purification.

19. 2. (2-(4-chlorophenyl)-4-methylpiperazin-1-yl)(3-methyl-1H-indazol-5-yl)methanone

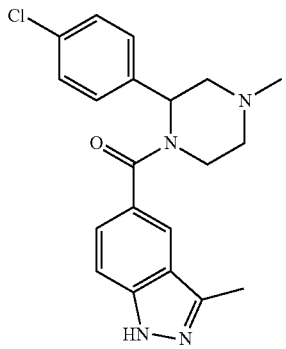

To 3-methyl-1H-indazole-5-carboxylic acid (92 mg, 0.52 mmol), HATU (238 mg, 0.626 mmol) and 3-(4-chlorophenyl)-1-methylpiperazine (110 mg, 0.522 mmol) were added DIPEA (200 µL, 1.15 mmol) and N,N-dimethyl formamide (4.4 mL). The reaction mixture was stirred at RT for 2 h and the solvent was evaporated (V10). The crude was purified via Biotage column chromatography (dichloromethane/ethanol 99:1 to 80:20) followed by prep HPLC. The product was filtered on a SCX column and released with 1N NH$_3$ in methanol to give the title compound (30 mg, 16% yield). $^1$H NMR (500 MHz, CD$_3$OD) ppm=7.84 (s, 1H), 7.55-7.34 (m, 6H), 5.64 (bs, 1H), 3.92 (bs, 1H), 3.51-3.44 (m, 1H), 3.27-3.18 (m, 1H), 2.78-2.72 (m, 1H), 2.54 (s, 3H), 2.53-2.48 (m, 1H), 2.29 (s, 3H), 2.20-2.14 (m, 1H). LC-MS (ESI, m/z, method L) Rt=0.96 min-369/371 (M+H)$^+$. ESI-HRMS: Found: 369.1471 calculated for C$_{20}$H$_{22}$$^{35}$ClN$_4$O (M+H)$^+$: 369.1477.

20. (S)-(2-(4-chlorophenyl)pyrrolidin-1-yl)(3-methoxy-1H-pyrazolo[3,4-b]pyridin-5-yl)methanone (243)

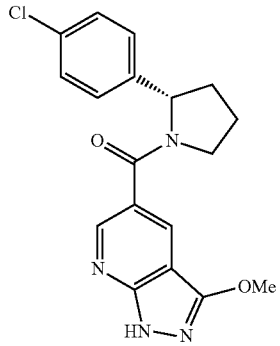 [SMILES: COc1n[nH]c2ncc(C(=O)N3CCC[C@H]3c3ccc(Cl)cc3)cc12]

20.1. 3-methoxy-1H-pyrazolo[3,4-b]pyridine-5-carbonitrile

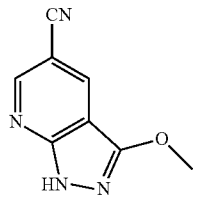

5-Bromo-3-methoxy-1H-pyrazolo[3,4-b]pyridine (300 mg, 1.32 mmol), Pd(PPh$_3$)$_4$ (152 mg, 0.132 mmol) and zinc cyanide (170 mg, 1.45 mmol) were loaded in a microwave vial and N,N-dimethyl formamide (8.7 mL) was added. The reaction mixture was stirred at 60° C. overnight. The solvent was evaporated and the crude mixture was purified via biotage column chromatography (dichloromethane/ethanol 99:1 to 96:4) to give the title compound (160 mg containing 17% of triphenylphosphine oxide, 58% corrected yield). $^1$H NMR (500 MHz, CD$_3$OD) ppm=8.72 (d, J=2.0 Hz, 1H), 8.55 (d, J=2.0 Hz, 1H), 4.11 (s, 3H). LC-MS (ESI, m/z, method M) Rt=0.96 min-175 (M+H)$^+$. 20.2. 3-methoxy-1H-pyrazolo[3,4-b]pyridine-5-carboxylic acid

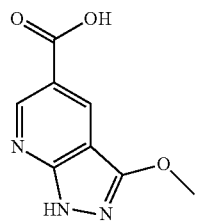

To 3-methoxy-1H-pyrazolo[3,4-b]pyridine-5-carbonitrile (160 mg, 0.919 mmol) in ethanol (7.1 mL) was added 2 M NaOH (6.9 mL, 13.78 mmol). The reaction was heated at 100° C. for 12 h. HCl in dioxane (13.8 mL, 13.78 mmol) was added to the reaction mixture and the reaction mixture was concentrated under vacuum. The crude was used in the next step without purification.

20.3. (S)-(2-(4-chlorophenyl)pyrrolidin-1-yl)(3-methoxy-1H-pyrazolo[3,4-b]pyridin-5-yl)methanone

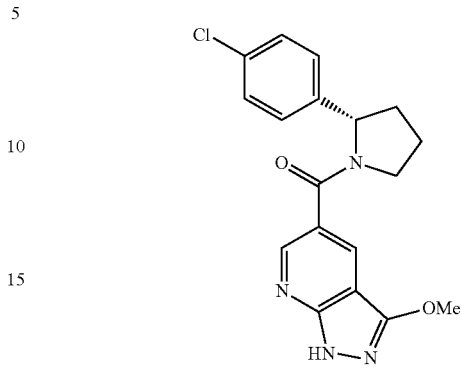

To 3-methoxy-1H-pyrazolo[3,4-b]pyridine-5-carboxylic acid (59 mg, 0.31 mmol), (S)-2-(4-chlorophenyl)pyrrolidine hydrochloride (67 mg, 0.31 mmol) and HATU (139 mg, 0.367 mmol) were added N,N-dimethyl formamide (2.5 mL) and DIPEA (117 µL, 0.672 mmol). The reaction mixture was stirred at RT for 1 h30 and then concentrated (V10), dry loaded on silica and purified by Biotage column chromatography (snap 25 g, dichloromethane/ethanol 99:1 to 95:5) and by prepTLC (0.5 mm, dichloromethane/ethanol 98:2) to give the title compound (18 mg, 16% yield). $^1$H NMR (500 MHz, CD$_3$OD, 2 rotamers) ppm=8.72 (s, 0.6H), 8.39 (s, 0.6H), 8.26 (s, 0.4H), 7.86 (s, 0.4H), 7.37 (d, J=8.1 Hz, 1.2H), 7.32 (d, J=8.1 Hz, 1.2H), 7.17 (d, J=8.0 Hz, 0.8H), 6.97 (d, J=8.0 Hz, 0.8H), 5.21 (t, J=7.3 Hz, 0.6H), 5.02-4.96 (m, 0.4H), 4.09 (s, 1.8H), 4.01 (s, 1.2H), 4.00-3.85 (m, 1.4H), 3.75-3.68 (m, 0.6H), 2.50-2.40 (m, 1H), 2.08-1.98 (m, 1.4H), 1.96-1.83 (m, 1.6H). LC-MS (ESI, m/z, method L) Rt=2.67 min-357/359 (M+H)$^+$. ESI-HRMS: Found: 357.1111 calculated for C$_{18}$H$_{18}$$^{35}$ClN$_4$O$_2$(M+H)$^+$: 357.1113.

21. (S)-(2-(4-fluorophenyl)pyrrolidin-1-yl)(3-methyl-1H-pyrazolo[4,3-b]pyridin-5-yl)methanone (242)

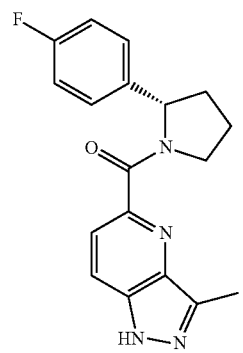 [SMILES: Cc1n[nH]c2ccc(C(=O)N3CCC[C@H]3c3ccc(F)cc3)nc12]

To 3-methyl-1H-pyrazolo[4,3-b]pyridine-5-carboxylic acid (40 mg, 0.23 mmol), HATU (103 mg, 0.271 mmol) and (S)-2-(4-fluorophenyl)pyrrolidine hydrochloride (45.5 mg, 0.226 mmol) were added DIPEA (87 µL, 0.50 mmol) and N,N-dimethyl formamide (1.9 mL). The reaction mixture was stirred at RT for 1 h. The reaction mixture was then concentrated (V10), dry loaded on silica and purified via Biotage column chromatography (dichloromethane/ethanol 99:1 to 85:15) and by prepTLC (0.5 mm, dichloromethane/ethanol 98:2) to give the title compound (16 mg, 22% yield). $^1$H NMR (500 MHz, CDC$_3$, 2 rotamers) ppm=7.97 (d, J=8.7 Hz, 0.45H), 7.79 (d, J=8.7 Hz, 0.45H), 7.66 (d, J=8.7 Hz, 0.55H), 7.59 (d, J=8.7 Hz, 0.55H), 7.32-7.26 (m, 0.90H), 7.01-6.93 (m, 2H), 6.82-6.76 (m, 1.1H), 5.89-5.84 (m, 0.55H), 5.42-5.37 (m, 0.45H), 4.39 (dt, J=12.3, 6.8 Hz, 0.45H), 4.11 (dt, J=12.3, 6.8 Hz, 0.45H), 4.06-3.94 (m, 1.1H), 2.73 (s, 1.35H), 2.48 (s, 1.65H), 2.52-2.37 (m, 1.1H), 2.10-1.85 (m, 2.9H). $^{19}$F NMR (470 MHz, CDCl$_3$) ppm=−116.35. LC-MS (ESI, m/z, method L) Rt=2.55 min-325 (M+H)$^+$. ESI-HRMS: Found: 325.1456 calculated for C$_{18}$H$_{18}$FN$_4$O (M+H)$^+$: 325.1459.

22. (2-(4-chloro-3-fluorophenyl)pyrrolidin-1-yl)(3-methyl-1H-pyrazolo[4,3-b]pyridin-5-yl)methanone 260)

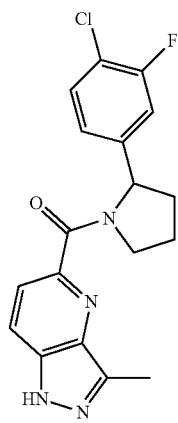 [SMILES: Cc1n[nH]c2ccc(C(=O)N3CCCC3c3ccc(Cl)c(F)c3)nc12]

22.1. tert-butyl 2-(4-chloro-3-fluorophenyl)-1H-pyrrole-1-carboxylate

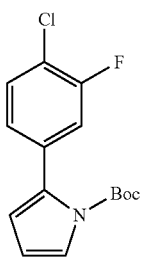 [SMILES: CC(C)(C)OC(=O)n1cccc1-c1ccc(Cl)c(F)c1]

(1-(tert-butoxycarbonyl)-1H-pyrrol-2-yl)boronic acid (0.625 g, 2.96 mmol), sodium carbonate (1.05 g, 9.87 mmol) and Pd(PPh$_3$)$_4$ (0.285 g, 0.247 mmol) were loaded in a flask and then DME (50 mL), water (10 mL) and 4-bromo-1-chloro-2-fluorobenzene (0.300 mL, 2.47 mmol) were added. The reaction mixture was stirred at 95° C. for 3 h30. Water and dichloromethane were added and the layers were separated. The aqueous layer was extracted with dichloromethane and the organic layers were dried and concentrated. The crude was purified via biotage column chromatography (cyclohexane/dichloromethane 100/0 to 90/10) to give the title compound (600 mg, 82% yield). $^1$H NMR (500 MHz, CDCl$_3$) ppm=7.38-7.34 (m, 2H), 7.15 (dd, J=10.0, 2.0 Hz, 1H), 7.11-7.08 (m, 1H), 6.24-6.20 (m, 2H), 1.43 (s, 9H). LC-MS (ESI, m/z. method K) Rt=1.67 min-196/198 (M-Boc+H)$^+$.

22.2. 2-(4-chloro-3-fluorophenyl)pyrrolidine

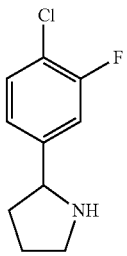

To tert-butyl 2-(4-chloro-3-fluorophenyl)-1H-pyrrole-1-carboxylate (600 mg, 2.03 mmol) in ethanol (11.9 mL) was added HCl (867 μl, 9.13 mmol) and PtO$_2$ (60 mg). After 27 h at 13-C, the reaction mixture was filtered on celite and the filtrate was concentrated. Methanol (2 mL) and 4 N HCl in dioxane (2 mL) were added to the residue obtained. After 2 h at RT, the reaction mixture was concentrated. The crude mixture was filtered on a SCX2 column and the product was released with 1N NH$_3$ in methanol and used in the next step without further purification. $^1$H NMR (500 MHz, CDCl$_3$) ppm=7.30 (dd, J=8.2, 7.6 Hz, 1H), 7.22-7.15 (m, 1H), 7.11-7.04 (m, 1H), 4.11 (t, J=7.7 Hz, 1H), 3.16 (ddd, J=10.1, 7.7, 5.3 Hz, 1H), 3.02 (ddd, J=10.1, 8.2, 6.7 Hz, 1H), 2.23-2.12 (m, 1H), 1.96-1.77 (m, 2H), 1.63-1.55 (m, 1H). LC-MS (ESI, m/z, method K) Rt=0.69 min-200/202 (M+H)$^+$.

22.3. (2-(4-chloro-3-fluorophenyl)pyrrolidin-1-yl)(3-methyl-1H-pyrazolo[4,3-b]pyridin-5-yl)methanone

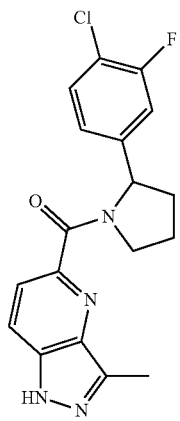 [SMILES: Cc1n[nH]c2ccc(C(=O)N3CCCC3c3ccc(Cl)c(F)c3)nc12]

3-methyl-1H-pyrazolo[4,3-b]pyridine-5-carboxylic acid (80 mg, 0.45 mmol) was mixed with N,N-dimethyl formamide (2.3 mL) and triethylamine (126 μl, 0.903 mmol). The suspension was cooled in an ice/acetone bath. Ethyl chloroformate (43 μl, 0.45 mmol) was added to the cold solution and the reaction was stirred for 15 min. A solution of 2-(4-chloro-3-fluorophenyl)pyrrolidine hydrochloride (107 mg, 0.452 mmol) in N,N-dimethyl formamide (2 mL) was added to the reaction mixture which was stirred for another 30 min in the cold bath. The reaction was stirred at RT overnight. Water and dichloromethane were added to the reaction mixture. The layers were separated and the aqueous layer was extracted with ethyl acetate three times. The organic layers were dried over MgSO₄ and concentrated under vacuum. The crude material was dissolved in methanol (3 mL) and cesium carbonate (147 mg, 0.452 mmol) was added. The reaction mixture was stirred at 40° C. for 1 h. After evaporation of the solvent, the crude was purified via biotage column chromatography (dichloromethane/ethanol, 98/2 to 94/6) and by filtration on a SCX column to give the title compound (18 mg, 11% yield). ¹H NMR (500 MHz, CDCl₃, 2 rotamers) ppm=7.98 (d, J=8.8 Hz, 0.5H), 7.85 (dd, J=8.8, 5.5 Hz, 1H), 7.71 (d, J=8.8 Hz, 0.5H), 7.29 (t, J=8.1 Hz, 0.5H), 7.17 (dd, J=8.3, 7.4 Hz, 0.5H), 7.09 (dd, J=10.0, 2.0 Hz, 0.5H), 7.05 (dd, J=8.1, 2.1 Hz, 0.5H), 6.88 (dd, J=10.0, 2.0 Hz, 0.5H), 6.81 (dd, J=8.3, 2.1 Hz, 0.5H), 5.92 (dd, J=7.5, 2.7 Hz, 0.5H), 5.34 (dd, J=7.8, 5.3 Hz, 0.5H), 4.38 (dt, J=11.7, 6.9 Hz, 0.5H), 4.11 (dt, J=11.7, 6.9 Hz, 0.5H), 4.02-3.94 (m, 1H), 2.75 (s, 1.5H), 2.49-2.34 (m, 2.5H), 2.10-1.82 (m, 3H). LC-MS (ESI, m/z, method K) Rt=1.40 min-359/361 (M+H)⁺. ESI-HRMS: Found: 359.1086 calculated for C₁₈H₁₇³⁵ClFN₄O (M+H)⁺: 359.1069.

23. (S)-(3-Methyl-1H-pyrazolo[4,3-b]pyridin-5-yl)(2-(4-(trifluoromethyl)phenyl) pyrrolidin-1-yl)methanone (257)

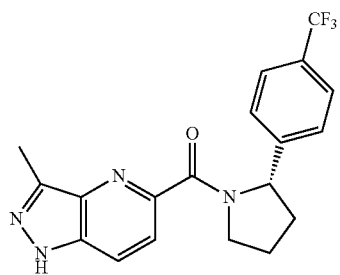 [SMILES: Cc1n[nH]c2ccc(C(=O)N3CCC[C@H]3c3ccc(C(F)(F)F)cc3)nc12]

23.1. 3-Methyl-1H-pyrazolo[4,3-b]pyridine

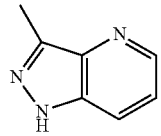

A solution of 1-(3-fluoropyridin-2-yl)ethanone (1.00 g, 7.19 mmol) in hydrazine monohydrate (12 mL, 247.00 mmol) was heated at 130° C. for 3 h under microwave irradiation. Water (50 mL) was added and the mixture extracted with ethyl acetate (3×25 mL). The combined organic layers were dried (MgSO4), filtered, and concentrated in vacuo. Purified by Biotage (SNAP 50 g column, ethyl acetate/ethanol 95/5→70/30) to give a cream colored solid (575 mg, 60%). 1H NMR (500 MHz, DMSO-d6) δ 12.87 (br s, 1H), 8.46 (dd, J=4.3, 1.4 Hz, 1H), 7.91 (dd, J=8.5, 1.4 Hz, 1H), 7.33 (dd, J=8.5, 4.3 Hz, 1H), 2.53 (s, 3H). 13C NMR (126 MHz, DMSO-d6) δ 144.51, 142.04, 139.94, 133.42, 121.12, 118.49, 11.24. LCMS (Method M) Rt 0.52 min, [M+H]+ 134; HRMS calcd. for C7H8N3: 134.0718, found: 134.0726.

23.2. 3-Methyl-1-trityl-1H-pyrazolo[4,3-b]pyridine

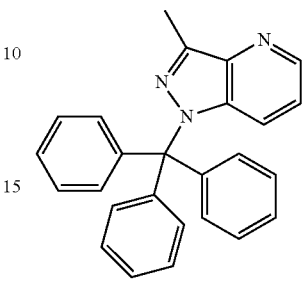

To a solution of 3-methyl-1H-pyrazolo[4,3-b]pyridine (497 mg, 3.73 mmol) in DMF (10 mL) at 0° C. was added NaH (60% in mineral oil; 300 mg, 7.50 mmol) and the mixture allowed to warm to RT and stirred for 20 min. Trityl chloride (1.35 g, 4.84 mmol) was then added and the mixture stirred at RT for 2.5 h. The reaction was quenched with sat. aq. NH4Cl (5 mL) and the mixture concentrated in vacuo. The residue was taken up in ethyl acetate (75 mL) and washed with water (3×50 mL). The organic layer was dried (MgSO4), filtered, concentrated in vacuo, and the residue purified by Biotage (SNAP 50 g column, cyclohexane/dichloromethane 100/0→50/50) to give an off-white solid (1.086 g, 77%). 1H NMR (500 MHz, CDCl3) δ 8.47 (dd, J=4.4, 1.3 Hz, 1H), 7.32-7.27 (m, 15H), 6.90 (dd, J=8.7, 4.4 Hz, 1H), 6.59 (dd, J=8.7, 1.3 Hz, 1H), 2.69 (s, 3H). 13C NMR (126 MHz, CDCl3) δ 144.43, 142.72 (3×ArC), 142.66, 135.23, 130.46, 130.18 (6×ArCH), 127.73 (6×ArCH), 127.52 (3×ArCH), 121.35, 119.81, 78.48, 11.32. LCMS (Method M) Rt 1.67 min, [M+H]+ 376; HRMS calcd. for C26H22N3: 376.1814, found: 376.1816.

23.3. 3-Methyl-1-trityl-1H-pyrazolo[4,3-b]pyridine 4-oxide

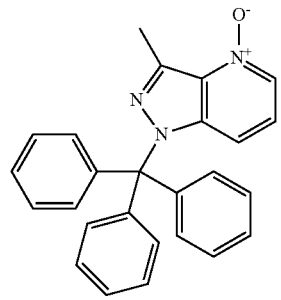 [SMILES: Cc1nn(C(c2ccccc2)(c2ccccc2)c2ccccc2)c2ccc[n+]([O-])c12]

To a solution of 3-methyl-1-trityl-1H-pyrazolo[4,3-b]pyridine (108 mg, 0.29 mmol) in dichloromethane (0.8 mL) at 0° C. was added mCPBA (77%; 80 mg, 0.36 mmol). The mixture was then allowed to warm to RT and stirred for 1.5 h. The reaction mixture was then diluted with dichloromethane (10 mL) and washed with sat. aq. NaHCO3 (3×10 mL). The organic layer was filtered through a phase separator and concentrated in vacuo. The resulting residue was purified by Biotage (SNAP 10 g column, dichloromethane/ethyl acetate 100/0→70/30) to give a white solid (94 mg, 83%). 1H NMR (500 MHz, CDCl3) δ 8.03 (d, J=6.0 Hz, 1H), 7.35-7.29 (m, 9H), 7.21-7.18 (m, 6H), 6.75 (dd, J=8.8, 6.0 Hz, 1H), 6.19 (d, J=8.8 Hz, 1H), 2.85 (s, 3H). 13C NMR (126 MHz, CDCl3) δ 142.01 (3×ArCH), 139.70, 138.83, 132.14, 130.26, 130.10 (6×ArCH), 127.82 (6×ArCH), 120.97, 113.41, 79.14, 14.26. LCMS (Method K) Rt 1.54 min, [M+H]+ 392; HRMS calcd. for $C_{26}H_{22}N_3O$: 392.1757, found: 392.1744.

23.4. 3-Methyl-1-trityl-1H-pyrazolo[4,3-b]pyridine-5-carbonitrile

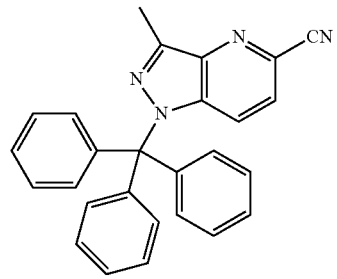 [SMILES: Cc1nn(C(c2ccccc2)(c2ccccc2)c2ccccc2)c2ccc(C#N)nc12]

To a suspension of 3-methyl-1-trityl-1H-pyrazolo[4,3-b]pyridine 4-oxide (94 mg, 0.24 mmol) and triethylamine (0.05 mL, 0.36 mmol) in a mixture of acetonitrile (1 mL) and dichloromethane (0.2 mL) was added TMS-CN (0.07 mL, 0.52 mmol). The resulting mixture was heated at reflux for 18 h. The mixture was then allowed to cool to RT, concentrated in vacuo, and the residue purified by Biotage (SNAP 10 g column, dichloromethane/ethyl acetate 100/0→70/30) to give a colorless oil (81 mg, 84%). 1H NMR (500 MHz, CDCl3) δ 7.35-7.29 (m, 9H), 7.25-7.20 (m, 7H), 6.59 (d, J=8.8 Hz, 1H), 2.67 (s, 3H). LCMS (Method M) Rt 1.14 min (mass not found; only mass for trityl).

23.5. 3-Methyl-1-trityl-1H-pyrazolo[4,3-b]pyridine-5-carboxylic acid

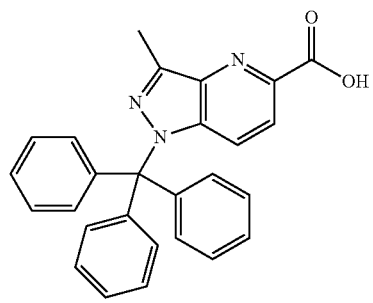 [SMILES: Cc1nn(C(c2ccccc2)(c2ccccc2)c2ccccc2)c2ccc(C(=O)O)nc12]

3-Methyl-1-trityl-1H-pyrazolo[4,3-b]pyridine-5-carbonitrile (112 mg, 0.28 mmol) was taken up in ethanol (1.5 mL) and 2 M NaOH (1 mL, 2.00 mmol) was added. The resulting mixture was heated at 130° C. for 1 h under microwave irradiation. The pH was then adjusted to 3 with 2 M HCl and extracted with dichloromethane (3×20 mL). The combined organic layers were filtered through a phase separator, concentrated in vacuo, and the residue purified by Biotage (SNAP 10 g column, dichloromethane/ethyl acetate 100/0→75/25) to give a white solid (67 mg, 57%). 1H NMR (500 MHz, CDCl3) δ 7.85 (d, J=8.9 Hz, 1H), 7.39-7.26 (m, 9H), 7.26-7.12 (m, 6H), 6.72 (d, J=8.9 Hz, 1H), 2.68 (s, 3H). LCMS (Method M) Rt 1.54 min, [M+Na]+442; HRMS calcd. for C27H21 N3O2Na: 442.1531, found: 442.1542.

23.6. (S)-(3-Methyl-1-trityl-1H-pyrazolo[4,3-b]pyridin-5-yl)(2-(4-(trifluoromethyl)phenyl)pyrrolidin-1-yl)methanone

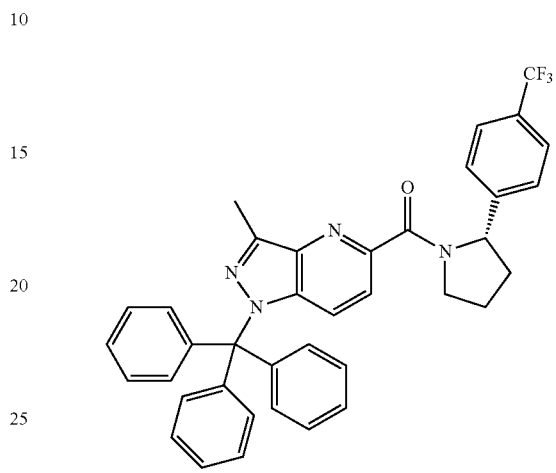

To a mixture of 3-methyl-1-trityl-1H-pyrazolo[4,3-b]pyridine-5-carboxylic acid (67 mg, 0.16 mmol) and (S)-2-(4-(trifluoromethyl)phenyl)pyrrolidine hydrochloride (70 mg, 0.28 mmol) in DMF (0.8 mL) was added HATU (95 mg, 0.25 mmol) and DIPEA (0.3 mL, 1.72 mmol), and the resulting mixture stirred at RT for 18 h. The mixture was then concentrated in vacuo and the residue purified by Biotage (SNAP 10 g column, cyclohexane/ethyl acetate 100/0→70/30) to give the title compound as a mixture of rotamers (78 mg). LCMS (Method M) Rt 1.71 min, [M+H]+ 617; HRMS calcd. for C38H32F3N4O: 617.2528, found: 617.2556.

23.7. (S)-(3-Methyl-1H-pyrazolo[4,3-b]pyridin-5-yl)(2-(4-(trifluoromethyl)phenyl)pyrrolidin-1-yl)methanone (257)

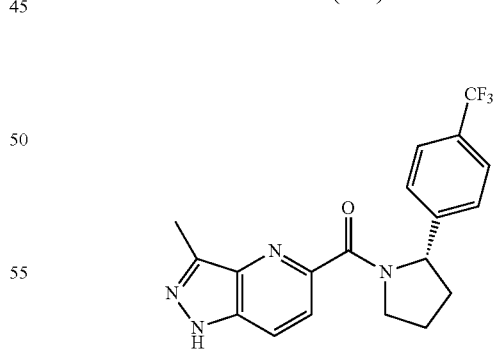

To a solution of (S)-(3-methyl-1-trityl-1H-pyrazolo[4,3-b]pyridin-5-yl)(2-(4-(trifluoromethyl)phenyl)pyrrolidin-1-yl)methanone (78 mg, 0.13 mmol) in dichloromethane (0.8 mL) was added TFA (0.2 mL, 2.60 mmol) and the resulting mixture stirred at RT for 45 min. The reaction was then quenched with sat. aq. NaHCO3 (6 mL) and extracted with ethyl acetate (3×10 mL). The combined organic layers were dried (MgSO4), filtered, and concentrated in vacuo. The residue was purified by Biotage (SNAP 10 g column, cyclohexane/ethyl acetate 100/0→0/100) to give the title compound as a mixture of rotamers (46 mg, 97%). 1H NMR (500 MHz, CDCl3) δ 7.98 (d, J=8.7 Hz, 1H), 7.82-7.74 (m, 2H), 8.00-7.55 (m, 3H), 7.47-7.42 (m, 4H), 7.21 (d, J=8.0 Hz, 2H), 6.02-5.97 (m, 1H), 5.47 (br dd, J=7.8, 5.2 Hz, 1H), 4.45 (dt, J=12.0, 6.9 Hz, 1H), 4.19 (dt, J=12.4, 6.8 Hz, 1H), 4.08-4.01 (m, 2H), 2.72 (s, 3H), 2.51-2.42 (m, 2H), 2.32 (s, 3H), 2.10-1.98 (m, 4H), 1.96-1.89 (m, 2H). 13C NMR (126 MHz, CDCl3) δ 167.01, 166.48, 148.93, 148.40, 148.00, 147.45 (2×C), 144.98, 144.60, 138.60, 138.10, 133.43, 133.12, 129.10, 128.84, 128.59, 125.91 (4×C), 125.51 (q, J=3.8 Hz, 2×C), 125.8 (q, J=3.8 Hz, 2×C), 123.14, 122.99, 122.26, 121.97, 117.95, 117.80, 65.88, 63.12, 62.14, 51.04, 48.52, 36.40, 34.15, 25.13, 21.35, 14.13, 10.93, 10.51. LCMS (Method M) Rt 1.31 min, [M+H]+ 375; HRMS calcd. for C19H18F3N4O: 375.1433, found: 375.1429.

24. (3-Amino-1H-pyrazolo[4,3-b]pyridin-5-yl)-[(S)-2-(4-chloro-phenyl)-pyrrolidin-1-yl]-methanone (265)

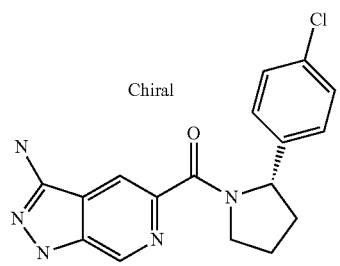 [SMILES: Nc1n[nH]c2cnc(C(=O)N3CCC[C@H]3c3ccc(Cl)cc3)cc12]

24.1. 5-Bromo-1H-pyrazolo[3,4-c]pyridin-3-ylamine

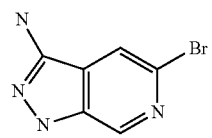 [SMILES: Nc1n[nH]c2cnc(Br)cc12]

Into a 10-mL sealed tube, was placed 2-bromo-5-fluoro-pyridine-4-carbonitrile (700 mg, 3.13 mmol, 90%), DMSO (5 mL) and NH2NH2.H2O (2.5 mL). The mixture was stirred for 3 h at 120° C. The reaction mixture was diluted with 50 mL of water. The organic layer was isolated and the aqueous layer was extracted with 50 mL of ethyl acetate. The combined organic layers were washed with 20 mL of sodium chloride twice, dried over Na2SO4, filtered and evaporated to dryness. This resulted in 600 mg (81%) of 5-bromo-1H-pyrazolo[3,4-c]pyridin-3-amine as a yellow solid.

24.2. 3-Amino-1H-pyrazolo[3,4-c]pyridine-5-carboxylic acid methyl ester

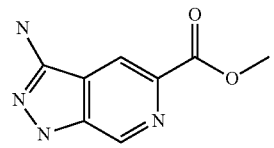

Into a 20-mL pressure tank purged and maintained with an atmosphere of CO(g), was placed 5-bromo-1H-pyrazolo[3,4-c]pyridin-3-amine (600 mg, 2.53 mmol, 90%), Pd(dppf)Cl2.CH2Cl2 (104 mg, 0.13 mmol), AcOK (498 mg, 5.07 mmol), methanol (5 mL) and N,N-dimethylformamide (5 mL). The resulting solution was stirred overnight at 80° C. The resulting solution was diluted with 10 mL of water and extracted with 50 mL of ethyl acetate. The organic layer was evaporated to dryness. This resulted in 500 mg (72%) of methyl 3-amino-1H-pyrazolo[3,4-c]pyridine-5-carboxylate as an orange solid.

24.3. 3-Amino-1H-pyrazolo[3,4-c]pyridine-5-carboxylic acid

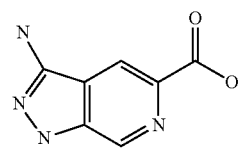 [SMILES: Nc1n[nH]c2cnc(C(=O)O)cc12]

Into a 50-mL round-bottom flask, was placed LiOH (99.7 mg, 4.16 mmol), water (3 mL), tetrahydrofuran (10 mL) and methyl 3-amino-1H-pyrazolo[3,4-c]pyridine-5-carboxylate (500 mg, 2.08 mmol, 80%). The solution was stirred for 20 h at 50° C. The mixture was concentrated by evaporation and 10 mL of water were added. The pH value of the solution was adjusted to 2 with hydrogen chloride solution (2N). The mixture was extracted twice with 30 mL of ethyl acetate and the organic layers were combined. The organic phase was washed twice with 20 mL of water, dried over sodium sulfate and after filtration was evaporated to dryness. This resulted in 400 mg (76%) of 3-amino-1H-pyrazolo[3,4-c]pyridine-5-carboxylic acid as a yellow solid.

24.4 (3-Amino-1H-pyrazolo[4,3-b]pyridin-5-yl)-[(S)-2-(4-chloro-phenyl)-pyrrolidin-1-yl]-methanone (265)

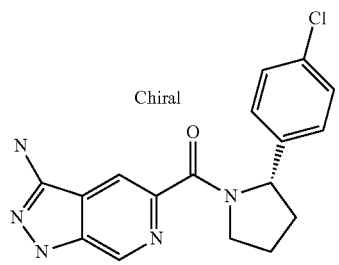 [SMILES: Nc1n[nH]c2cnc(C(=O)N3CCC[C@H]3c3ccc(Cl)cc3)cc12]

Into a 10-mL round-bottom flask, was placed 3-amino-1H-pyrazolo[3,4-c]pyridine-5-carboxylic acid (100 mg, 0.39 mmol, 70%), 2-(4-chlorophenyl)pyrrolidine (112 mg, 0.59 mmol), 4-dimethylaminopyridine (82.3 mg, 0.67 mmol), EDCl (215 mg, 1.12 mmol) and N,N-dimethylformamide (5 mL). The reaction mixture was stirred for 3 h at RT. The mixture was concentrated under vacuum. The residue was applied onto a silica gel column with methanol:dichloromethane (3:10). The crude racemic product was purified by prep-HPLC (acetonitrile/water), followed by a chiral-Prep-HPLC separation (Chiralpak IB4.6*250 mm, 5 µM, 100% methanol (0.1% diethylamine) to yield in 13 mg (9%) of (3-Amino-1H-pyrazolo[4,3-b]pyridin-5-yl)-[(S)-2-(4-chloro-phenyl)-pyrrolidin-1-yl]-methanone as a white solid. 1H NMR (300 Hz, DMSO-d6) ppm=11.84 (s, 1H), 8.65-8.64 (m, 1H), 8.13 (s, 1H), 7.27 (s, 4H), 5.60-5.20 (m, 3H), 4.12-3.90 (m, 1H), 3.90-3.70 (m, 1H), 2.41-2.29 (m, 1H), 1.99-1.77 (m, 4H). LCMS (Method J) Rt 1.17 min, [M+H]+ 342.

The remaining cpds were synthesized from the described or commercially available carboxylic acids with described or commercially available amines as described in 2.2., partially followed by a chiral separation as described in 2.3 resulting in 2 or more distinct enantiomeres. Hereby, cpds 171-176, 179, 182, 185-188, 191-202, 204-205, 207-209, 211-215, 217-219, 221-241, 247-253, 258-259 and 261-264 were synthesized.

Biological Activity
Biochemical Assay for CDK8 Inhibitory Activity

FRET based Lanthascreen binding competition assay: A dye-labeled ATP competitive probe served as a FRET acceptor upon binding to CDK8 labeled with a strepavidin -Eu-chelate (via a biotinylated anti His antibody). The result was a fluorescence signal at 647 nm. In case this probe was competed by an inhibitor, such a signal cannot be generated any more. The CDK8 used for this assay was a protein co-expressed with CycC.

The assay procedure for an assay in a 1536 well plate was performed according to the following: 2 µL CDK8/biotin-anti-His Ab/SA-Eu mix in Assay buffer were pipetted into the wells of a micro plate.

1 µL compound in 20 mM Hepes buffer/5% DMSO was added. The plate was shaken for 30 sec and incubated for 20 min at RT.

2 µL Alexa647-probe in assay buffer were added. The plate was shaken for 30 sec again and incubated for 60 min at RT in the dark.

Then the plate was read out on a Perkin Elmer Envision (mode LANCE/TRF, excitation 340 nm emission 650 nm).

The assay buffer was 50 mM Hepes pH 7.5 (Merck #1.10110), 10 mM $MgCl_2$ (Merck #1.05833), 1 mM EGTA (Merck #1.08435), 0.01% Brij-35 (Pierce #28316).

The final concentrations of the reaction components in 5 µl total assay volume were: 1% DMSO (Merck #1.02950), 5 nM CDK8 (CDK8/CycC Invitrogen #PV4402), 2 nM biotin-a-His Ab (Invitrogen #PV6089), 2 nM SA-Europium (Invitrogen #PV5899), 10 nM Alexa647-Tracer (Invitrogen #PV5592).

The compound dilutions for dose respond curves were 30, 10, 3.2, 1, 0.32, 0.2, 0.032, 0.01, 0.0032, 0.001 µM (final) or optional (as 1:5 dilution) 30, 6, 1.2, 0.24, 0.048, 0.0096, 0.0019, 0.0004, 8e-5, 2e-5 µM.

The readouts were fitted to $IC_{50}$ curves using Genedata Condoseo.

To assess the inhibitory potential of the compounds on CDK8, $IC_{50}$-values were determined, as shown in Table 1 below, whereby the following classification is used:

| | |
|---|---|
| $IC_{50}$ <10 nM | "A" |
| 10 nM ≤ $IC_{50}$ <0.1 µM | "B" |
| 0.1 µM ≤ $IC_{50}$ <1 µM | "C" |
| 1 µM ≤ $IC_{50}$ <10 µM | "D" |

TABLE 1

| No. | Structure | [M + 1]+ | RT [min] (HPLC method) | IC50 [µM] | Chemical Name | NMR |
|---|---|---|---|---|---|---|
| 1 | (structure) | 385, 387 | 2.03 (A) | A | [2-(4-Bromo-phenyl)-pyrrolidin-1-yl]-(3-methyl-1H-pyrazolo[3,4-b]pyridin-5-yl)-methanone | 1H NMR (400 MHz, DMSO-d6) ppm = 13.50-13.19 (m, 1H), 8.75-6.91 (m, 6H), 5.22-4.92 (m, 1H), 4.03-3.51 (m, 2H), 2.58-2.30 (m, 4H), 2.01-1.64 (m, 3H). |
| 2 | (structure) | 385, 387 | 2.02 (A) | A | [(S)-2-(4-Bromo-phenyl)-pyrrolidin-1-yl]-(3-methyl-1H-pyrazolo[3,4-b]pyridin-5-yl)-methanone | 1H NMR (400 MHz, DMSO-d6) ppm = 13.48-13.19 (m, 1H), 8.74-6.93 (m, 6H), 5.20-4.94 (m, 1H), 4.03-3.52 (m, 2H), 2.60-2.29 (m, 4H), 2.01-1.68 (m, 3H). |

TABLE 1-continued

| No. | Structure | [M + 1]+ | RT [min] (HPLC method) | IC50 [μM] | Chemical Name | NMR |
|---|---|---|---|---|---|---|
| 3 | 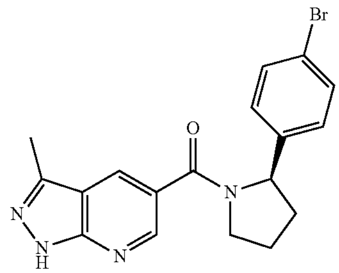 [SMILES: Cc1n[nH]c2ncc(C(=O)N3CCC[C@@H]3c3ccc(Br)cc3)cc12] | 385, 387 | 2.03 (A) | C | [(R)-2-(4-Bromo-phenyl)-pyrrolidin-1-yl]-(3-methyl-1H-pyrazolo[3,4-b]pyridin-5-yl)-methanone | 1H NMR (400 MHz, DMSO-d6) ppm = 13.50-13.18 (m, 1H), 8.76-6.89 (m, 6H), 5.22-4.94 (m, 1H), 4.03-3.52 (m, 2H), 2.59-2.30 (m, 4H), 2.00-1.68 (m, 3H). |
| 4 | 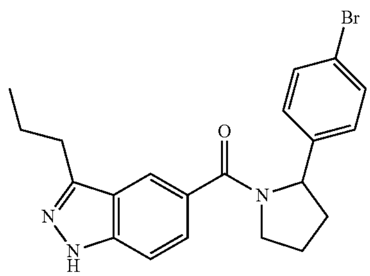 | 412, 414 | 2.38 (A) | A | [2-(4-Bromo-phenyl)-pyrrolidin-1-yl]-(3-propyl-1H-indazol-5-yl)-methanone | 1H NMR (400 MHz, DMSO-d6) ppm = 12.96-12.52 (m, 1H), 8.10-6.92 (m, 7H), 5.22-4.88 (m, 1H), 4.03-3.46 (m, 2H), 3.03-2.22 (m, 3H), 2.01-1.33 (m, 5H), 1.07-0.73 (m, 3H). |
| 5 | 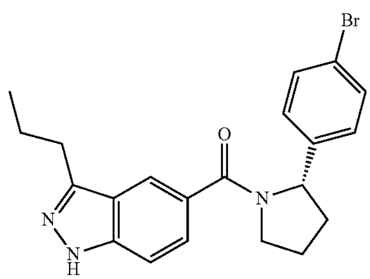 [SMILES: CCCc1n[nH]c2ccc(C(=O)N3CCC[C@H]3c3ccc(Br)cc3)cc12] | 412, 414 | 2.38 (A) | A | [(S)-2-(4-Bromo-phenyl)-pyrrolidin-1-yl]-(3-propyl-1H-indazol-5-yl)-methanone | 1H NMR (400 MHz, DMSO-d6) ppm = 12.89-12.62 (m, 1H), 8.09-6.99 (m, 7H), 5.20-4.89 (m, 1H), 3.98-3.48 (m, 2H), 3.02-2.21 (m, 3H), 2.00-1.36 (m, 5H), 1.05-0.76 (m, 3H). |
| 6 | 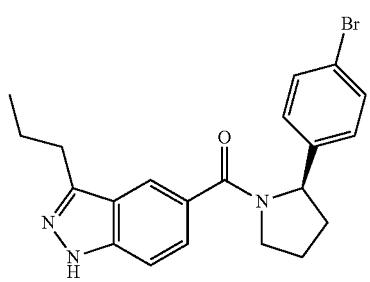 [SMILES: CCCc1n[nH]c2ccc(C(=O)N3CCC[C@@H]3c3ccc(Br)cc3)cc12] | 412, 414 | 2.32 (A) | C | [(R)-2-(4-Bromo-phenyl)-pyrrolidin-1-yl]-(3-propyl-1H-indazol-5-yl)-methanone | 1H NMR (400 MHz, DMSO-d6) ppm = 12.88-12.62 (m, 1H), 8.09-6.99 (m, 7H), 5.19-4.89 (m, 1H), 3.98-3.48 (m, 2H), 3.02-2.20 (m, 3H), 2.00-1.34 (m, 5H), 1.06-0.76 (m, 3H). |
| 9 | 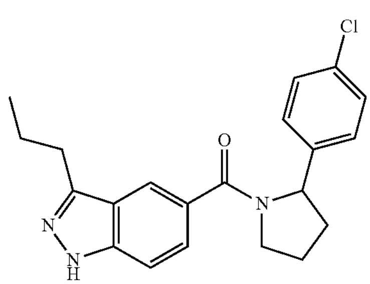 [SMILES: CCCc1n[nH]c2ccc(C(=O)N3CCCC3c3ccc(Cl)cc3)cc12] | 368 | 2.29 (A) | A | [2-(4-Chloro-phenyl)-pyrrolidin-1-yl]-(3-propyl-1H-indazol-5-yl)-methanone | 1H NMR (400 MHz, DMSO-d6) ppm = 12.89-12.58 (m, 1H), 8.12-6.99 (m, 7H), 5.25-4.86 (m, 1H), 4.00-3.44 (m, 2H), 3.03-2.19 (m, 3H), 2.00-1.33 (m, 5H), 1.06-0.71 (m, 3H). |

TABLE 1-continued

| No. | Structure | [M + 1]⁺ | RT [min] (HPLC method) | IC50 [μM] | Chemical Name | NMR |
|---|---|---|---|---|---|---|
| 10 | 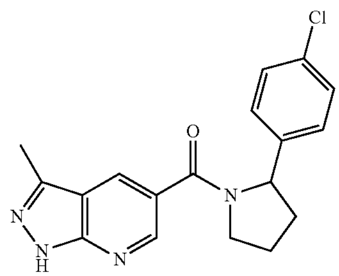 [SMILES: Cc1n[nH]c2ncc(C(=O)N3CCCC3c3ccc(Cl)cc3)cc12] | 341 | 1.99 (A) | A | [2-(4-Chloro-phenyl)-pyrrolidin-1-yl]-(3-methyl-1H-pyrazolo[3,4-b]pyridin-5-yl)-methanone | 1H NMR (400 MHz, DMSO-d6) ppm = 13.51-13.19 (m, 1H), 8.76-6.96 (m, 6H), 5.25-4.95 (m, 1H), 4.03-3.51 (m, 2H), 2.62-2.28 (m, 4H), 2.01-1.68 (m, 3H). |
| 11 | 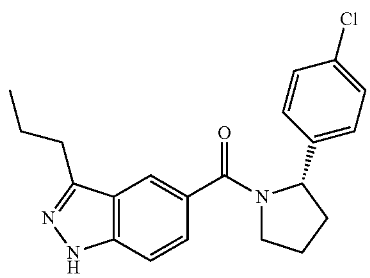 | 368 | 2.2 (A) | A | [(S)-2-(4-Chloro-phenyl)-pyrrolidin-1-yl]-(3-propyl-1H-indazol-5-yl)-methanone | 1H NMR (500 MHz, DMSO-d6) ppm = 12.88-12.59 (m, 1H), 8.10-7.02 (m, 7H), 5.22-4.90 (m, 1H), 3.99-3.48 (m, 2H), 3.01-2.21 (m, 3H), 2.01-1.35 (m, 5H), 1.06-0.74 (m, 3H). |
| 12 | 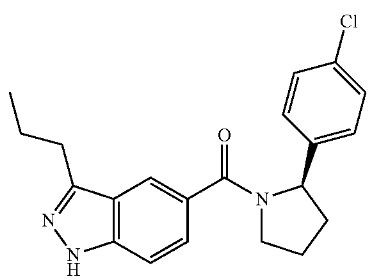 [SMILES: CCCc1n[nH]c2ccc(C(=O)N3CCC[C@@H]3c3ccc(Cl)cc3)cc12] | 368 | 2.29 (A) | C | [(R)-2-(4-Chloro-phenyl)-pyrrolidin-1-yl]-(3-propyl-1H-indazol-5-yl)-methanone | 1H NMR (500 MHz, DMSO-d6) ppm = 12.92-12.58 (m, 1H), 8.12-7.00 (m, 7H), 5.24-4.88 (m, 1H), 3.99-3.47 (m, 2H), 3.03-2.20 (m, 3H), 2.00-1.35 (m, 5H), 1.06-0.73 (m, 3H). |
| 13 | 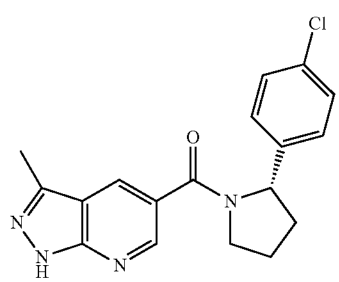 | 341 | 1.99 (A) | A | [(S)-2-(4-Chloro-phenyl)-pyrrolidin-1-yl]-(3-methyl-1H-pyrazolo[3,4-b]pyridin-5-yl)-methanone | 1H NMR (400 MHz, DMSO-d6) ppm = 13.10 (s, 1H), 8.52 (s, 1H), 8.35-8.08 (m, 1H), 7.39-7.14 (m, 4H), 5.20-5.07 (m, 1H), 3.90-3.82 (m, 1H), 3.73-3.62 (m, 1H), 2.53-2.33 (m, 4H), 1.97-1.84 (m, 2H), 1.84-1.73 (m, 1H). |
| 14 | 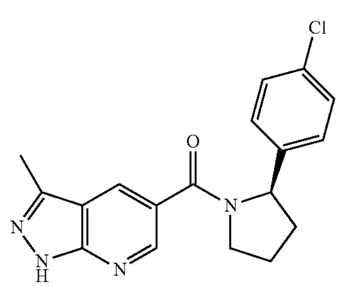 | 341 | 1.98 (A) | C | [(R)-2-(4-Chloro-phenyl)-pyrrolidin-1-yl]-(3-methyl-1H-pyrazolo[3,4-b]pyridin-5-yl)-methanone | 1H NMR (400 MHz, DMSO-d6, 90° C.) ppm = 13.10 (s, 1H), 8.52 (s, 1H), 8.34-8.08 (m, 1H), 7.44-7.14 (m, 4H), 5.21-5.06 (m, 1H), 3.91-3.81 (m, 1H), 3.74-3.59 (m, 1H), 2.53-2.34 (m, 4H), 1.97-1.84 (m, 2H), 1.84-1.73 (m, 1H). |

TABLE 1-continued

| No. | Structure | [M + 1]+ | RT [min] (HPLC method) | IC50 [μM] | Chemical Name | NMR |
|---|---|---|---|---|---|---|
| 15 | 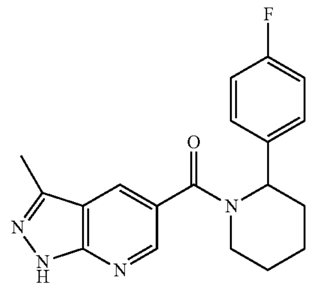 [SMILES: Cc1n[nH]c2ncc(C(=O)N3CCCCC3c3ccc(F)cc3)cc12] | 339 | 2.05 (A) | B | [2-(4-Fluoro-phenyl)-piperidin-1-yl]-(3-methyl-1H-pyrazolo[3,4-b]pyridin-5-yl)-methanone | 1H NMR (400 MHz, DMSO-d6) ppm = 13.40 (s, 1H), 8.59-8.53 (m, 1H), 8.39-8.30 (m, 1H), 7.44-7.36 (m, 2H), 7.27-7.19 (m, 2H), 5.73-5.36 (m, 1H), 4.14-3.67 (m, 1H), 2.97-2.82 (m, 1H), 2.55-2.38 (m, 4H), 2.02-1.89 (m, 1H), 1.71-1.32 (m, 4H). |
| 16 | 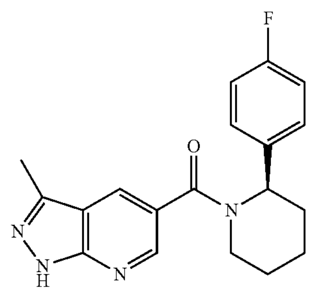 [SMILES: Cc1n[nH]c2ncc(C(=O)N3CCCC[C@@H]3c3ccc(F)cc3)cc12] | 339 | 2.05 (A) | | [(R)-2-(4-Fluoro-phenyl)-piperidin-1-yl]-(3-methyl-1H-pyrazolo[3,4-b]pyridin-5-yl)-methanone | 1H NMR (400 MHz, DMSO-d6) ppm = 13.41 (s, 1H), 8.60-8.53 (m, 1H), 8.40-8.31 (m, 1H), 7.46-7.34 (m, 2H), 7.29-7.18 (m, 2H), 5.74-5.39 (m, 1H), 4.02-3.65 (m, 1H), 2.97-2.81 (m, 1H), 2.58-2.35 (m, 4H), 2.02-1.88 (m, 1H), 1.71-1.33 (m, 4H). |
| 17 | 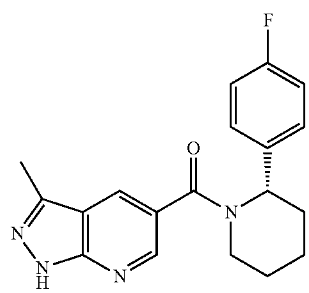 [SMILES: Cc1n[nH]c2ncc(C(=O)N3CCCC[C@H]3c3ccc(F)cc3)cc12] | 339 | 2.05 (A) | B | [(S)-2-(4-Fluoro-phenyl)-piperidin-1-yl]-(3-methyl-1H-pyrazolo[3,4-b]pyridin-5-yl)-methanone | 1H NMR (400 MHz, DMSO-d6) ppm = 13.41 (s, 1H), 8.57 (s, 1H), 8.36 (s, 1H), 7.47-7.34 (m, 2H), 7.28-7.17 (m, 2H), 5.78-5.32 (m, 1H), 4.10-3.70 (m, 1H), 2.98-2.81 (m, 1H), 2.57-2.35 (m, 4H), 2.03-1.88 (m, 1H), 1.73-1.32 (m, 4H). |
| 18 | 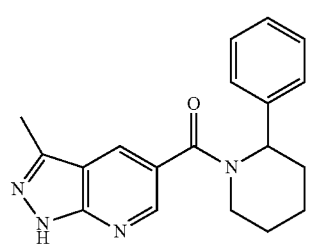 [SMILES: Cc1n[nH]c2ncc(C(=O)N3CCCCC3c3ccccc3)cc12] | 321 | 2.02 (A) | B | (3-Methyl-1H-pyrazolo[3,4-b]pyridin-5-yl)-(2-phenyl-piperidin-1-yl)-methanone | 1H NMR (400 MHz, DMSO-d6) ppm = 13.41 (s, 1H), 8.59-8.54 (m, 1H), 8.38-8.33 (m, 1H), 7.48-7.25 (m, 5H), 5.84-5.31 (m, 1H), 4.05-3.53 (m, 1H), 3.00-2.83 (m, 1H), 2.55-2.38 (m, 4H), 2.02-1.90 (m, 1H), 1.70-1.31 (m, 4H). |
| 19 | 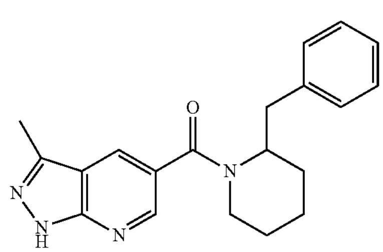 [SMILES: Cc1n[nH]c2ncc(C(=O)N3CCCCC3Cc3ccccc3)cc12] | 335 | 1.99 (A) | C | (2-Benzyl-piperidin-1-yl)-(3-methyl-1H-pyrazolo[3,4-b]pyridin-5-yl)-methanone | 1H NMR (400 MHz, DMSO-d6) ppm = 13.31 (s, 1H), 8.30-6.70 (m, 7H), 5.07-2.59 (m, 5H), 2.46 (s, 3H), 1.96-1.27 (m, 6H). |

TABLE 1-continued

| No. | Structure | [M + 1]+ | RT [min] (HPLC method) | IC50 [μM] | Chemical Name | NMR |
|---|---|---|---|---|---|---|
| 20 | 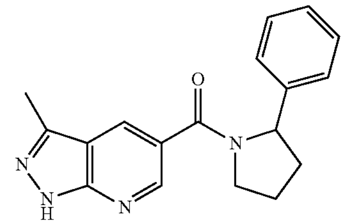 [SMILES: Cc1n[nH]c2ncc(C(=O)N3CCCC3c3ccccc3)cc12] | 307 | 1.82 (A) | A | (3-Methyl-1H-pyrazolo[3,4-b]pyridin-5-yl)-(2-phenyl-pyrrolidin-1-yl)-methanone | 1H NMR (400 MHz, DMSO-d6) ppm = 13.47-13.19 (m, 1H), 8.75-7.82 (m, 2H), 7.45-6.98 (m, 5H), 5.26-4.96 (m, 1H), 4.04-3.53 (m, 2H), 2.63-2.26 (m, 4H), 2.00-1.70 (m, 3H). |
| 21 | 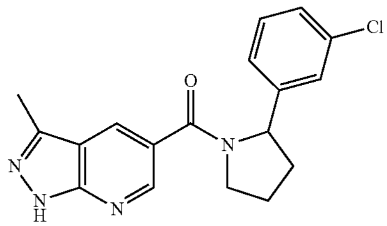 [SMILES: Cc1n[nH]c2ncc(C(=O)N3CCCC3c3cccc(Cl)c3)cc12] | 341 | 1.96 (A) | B | [2-(3-Chloro-phenyl)-pyrrolidin-1-yl]-(3-methyl-1H-pyrazolo[3,4-b]pyridin-5-yl)-methanone | 1H NMR (400 MHz, DMSO-d6) ppm = 13.53-13.26 (m, 1H), 8.75-7.85 (m, 2H), 7.50-6.97 (m, 4H), 5.18-4.98 (m, 1H), 4.09-3.25 (m, 2H), 2.58-2.30 (m, 4H), 1.99-1.67 (m, 3H). |
| 22 | 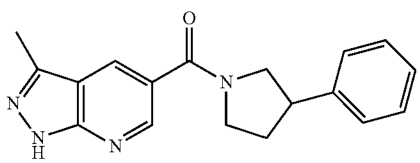 | 307 | 1.89 (A) | B | (3-Methyl-1H-pyrazolo[3,4-b]pyridin-5-yl)-(3-phenyl-pyrrolidin-1-yl)-methanone | 1H NMR (400 MHz, DMSO-d6) ppm = 13.46-13.32 (m, 1H), 8.71-8.63 (m, 1H), 8.49-8.41 (m, 1H), 7.41-7.18 (m, 5H), 4.06-3.35 (m, 5H), 2.57-2.48 (m, 3H), 2.38-2.22 (m, 1H), 2.15-1.94 (m, 1H). |
| 23 | 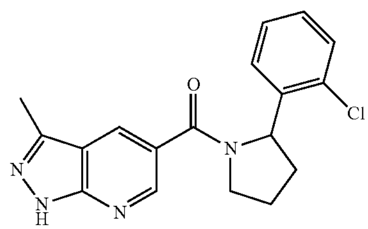 [SMILES: Cc1n[nH]c2ncc(C(=O)N3CCCC3c3ccccc3Cl)cc12] | 341 | 1.97 (A) | B | [2-(2-Chloro-phenyl)-pyrrolidin-1-yl]-(3-methyl-1H-pyrazolo[3,4-b]pyridin-5-yl)-methanone | 1H NMR (400 MHz, DMSO-d6) ppm = 13.47-13.23 (m, 1H), 8.75-7.86 (m, 2H), 7.59-7.19 (m, 4H), 5.49-5.27 (m, 1H), 4.09-3.58 (m, 2H), 2.62-2.28 (m, 4H), 2.04-1.64 (m, 3H). |
| 24 | 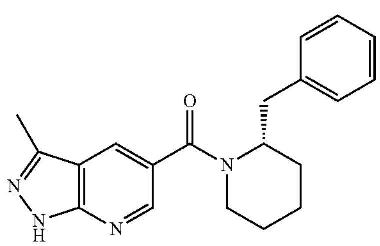 | 335 | 1.99 (A) | C | ((S)-2-Benzyl-piperidin-1-yl)-(3-methyl-1H-pyrazolo[3,4-b]pyridin-5-yl)-methanone | 1H NMR (400 MHz, DMSO-d6) ppm = 13.30 (s, 1H), 8.24-6.76 (m, 7H), 5.29-3.60 (m, 2H), 3.28-2.58 (m, 3H), 2.46 (s, 3H), 1.90-1.35 (m, 6H). |
| 25 | 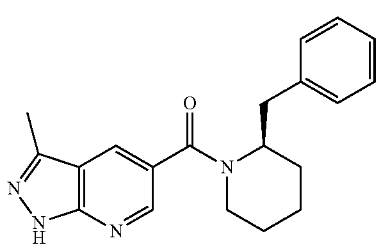 [SMILES: Cc1n[nH]c2ncc(C(=O)N3CCCC[C@@H]3Cc3ccccc3)cc12] | 335 | 1.99 (A) | | ((R)-2-Benzyl-piperidin-1-yl)-(3-methyl-1H-pyrazolo[3,4-b]pyridin-5-yl)-methanone | 1H NMR (400 MHz, DMSO-d6) ppm = 13.31 (s, 1H), 8.27-6.73 (m, 7H), 5.48-3.69 (m, 2H), 3.38-2.96 (m, 3H), 2.46 (s, 3H), 1.91-1.34 (m, 6H). |

TABLE 1-continued

| No. | Structure | [M + 1]+ | RT [min] (HPLC method) | IC50 [μM] | Chemical Name | NMR |
|---|---|---|---|---|---|---|
| 26 | 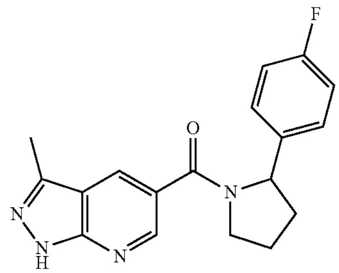 [SMILES: Cc1n[nH]c2ncc(C(=O)N3CCCC3c3ccc(F)cc3)cc12] | 325 | 1.86 (A) | A | [2-(4-Fluoro-phenyl)-pyrrolidin-1-yl]-(3-methyl-1H-pyrazolo[3,4-b]pyridin-5-yl)-methanone | 1H NMR (400 MHz, DMSO-d6) ppm = 13.46-13.14 (m, 1H), 8.73-7.82 (m, 2H), 7.49-6.91 (m, 4H), 5.23-4.97 (m, 1H), 4.03-3.51 (m, 2H), 2.61-2.28 (m, 4H), 1.98-1.69 (m, 3H). |
| 27 | 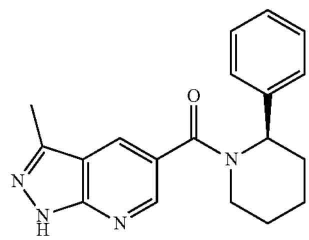 [SMILES: Cc1n[nH]c2ncc(C(=O)N3CCCC[C@@H]3c3ccccc3)cc12] | 321 | 2.01 (A) | | (3-Methyl-1H-pyrazolo[3,4-b]pyridin-5-yl)-((R)-2-phenyl-piperidin-1-yl)-methanone | 1H NMR (400 MHz, DMSO-d6) ppm = 13.41 (s, 1H), 8.60-8.33 (m, 2H), 7.46-7.26 (m, 5H), 5.87-5.28 (m, 1H), 4.20-3.68 (m, 1H), 2.99-2.85 (m, 1H), 2.58-2.40 (m, 4H), 2.04-1.90 (m, 1H), 1.72-1.34 (m, 4H). |
| 28 | 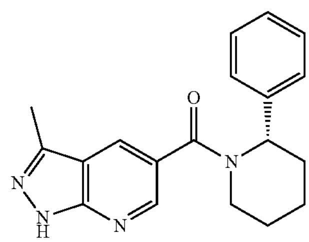 [SMILES: Cc1n[nH]c2ncc(C(=O)N3CCCC[C@H]3c3ccccc3)cc12] | 321 | 2.01 (A) | B | (3-Methyl-1H-pyrazolo[3,4-b]pyridin-5-yl)-((S)-2-phenyl-piperidin-1-yl)-methanone | 1H NMR (400 MHz, DMSO-d6) ppm = 13.40 (s, 1H), 8.61-8.33 (m, 2H), 7.47-7.25 (m, 5H), 5.81-5.36 (m, 1H), 4.10-3.68 (m, 1H), 3.00-2.83 (m, 1H), 2.56-2.39 (m, 4H), 2.03-1.89 (m, 1H), 1.71-1.32 (m, 4H). |
| 29 | 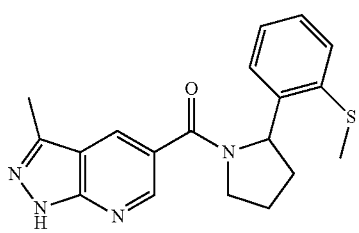 | 353 | 1.95 (A) | | (3-Methyl-1H-pyrazolo[3,4-b]pyridin-5-yl)-[2-(2-methylsulfanyl-phenyl)-pyrrolidin-1-yl]-methanone | 1H NMR (400 MHz, DMSO-d6) ppm = 13.47-13.18 (m, 1H), 8.75-7.77 (m, 2H), 7.48-6.95 (m, 4H), 5.51-5.15 (m, 1H), 4.07-3.53 (m, 2H), 2.60-1.60 (m, 10H). |
| 30 | 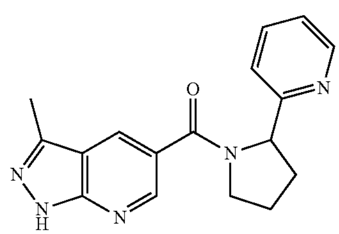 [SMILES: Cc1n[nH]c2ncc(C(=O)N3CCCC3c3ccccn3)cc12] | 308 | 1.28 (A) | C | (3-Methyl-1H-pyrazolo[3,4-b]pyridin-5-yl)-(2-pyridin-2-yl-pyrrolidin-1-yl)-methanone | 1H NMR (400 MHz, DMSO-d6) ppm = 13.48-13.17 (m, 1H), 8.77-6.92 (m, 6H), 5.30-4.99 (m, 1H), 3.99-3.56 (m, 2H), 2.62-2.30 (m, 4H), 2.01-1.79 (m, 3H). |
| 31 | 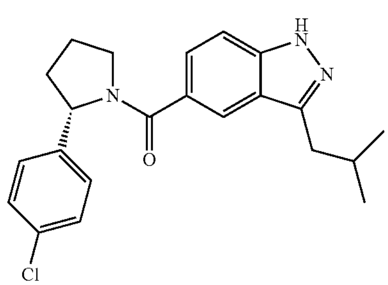 [SMILES: CC(C)Cc1n[nH]c2ccc(C(=O)N3CCC[C@H]3c3ccc(Cl)cc3)cc12] | 382 | 2.13 (G) | A | [(S)-2-(4-Chloro-phenyl)-pyrrolidin-1-yl]-(3-isobutyl-1H-indazol-5-yl)-methanone | 1H NMR (300 MHz, DMSO-d6) ppm = 12.54 (s, 1H), 7.75 (s, 1H), 7.40-7.07 (m, 6H), 5.09 (m, 1H), 3.83-3.53 (m, 2H), 2.81 (m, 2H), 2.25 (m, 1H), 2.09-1.75 (m, 4H), 0.85 (m, 6H). |

TABLE 1-continued

| No. | Structure | [M + 1]+ | RT [min] (HPLC method) | IC50 [µM] | Chemical Name | NMR |
|---|---|---|---|---|---|---|
| 32 | 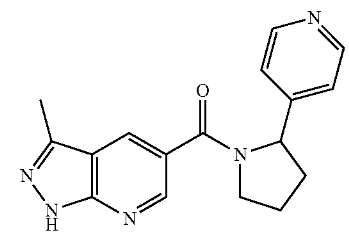 | 308 | 1.15 (A) | C | (3-Methyl-1H-pyrazolo[3,4-b]pyridin-5-yl)-(2-pyridin-4-yl-pyrrolidin-1-yl)-methanone | |
| 33 | 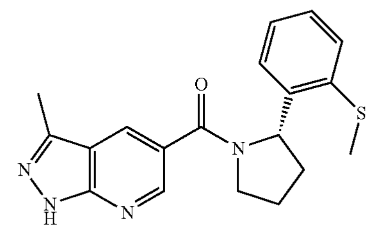 | 353 | 1.96 (A) | C | (3-Methyl-1H-pyrazolo[3,4-b]pyridin-5-yl)-[(S)-2-(2-methylsulfanyl-phenyl)-pyrrolidin-1-yl]-methanone | |
| 34 | 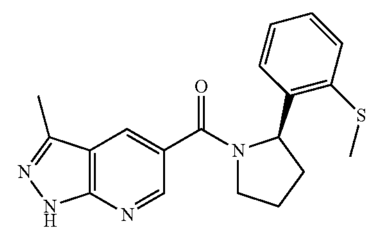 [SMILES: CSc1ccccc1[C@H]1CCCN1C(=O)c1cnc2[nH]nc(C)c2c1] | 353 | 1.96 (A) | C | (3-Methyl-1H-pyrazolo[3,4-b]pyridin-5-yl)-[(R)-2-(2-methylsulfanyl-phenyl)-pyrrolidin-1-yl]-methanone | |
| 35 | 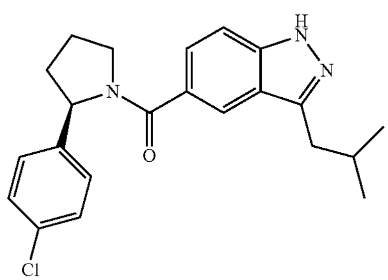 [SMILES: CC(C)Cc1n[nH]c2ccc(C(=O)N3CCC[C@@H]3c3ccc(Cl)cc3)cc12] | 382 | 2.13 (G) | | [(R)-2-(4-Chloro-phenyl)-pyrrolidin-1-yl]-(3-isobutyl-1H-indazol-5-yl)-methanone | 1H NMR (300 MHz, d6-DMSO-d6): ppm = 12.54 (s, 1H), 7.70 (s, 1H), 7.56-7.24 (m, 6H), 5.09 (m, 1H), 3.83-3.69 (m, 2H), 2.83 (m, 2H), 2.25 (m, 1H), 1.98-1.71 (m, 4H), 0.85 (m, 6H). |
| 36 | 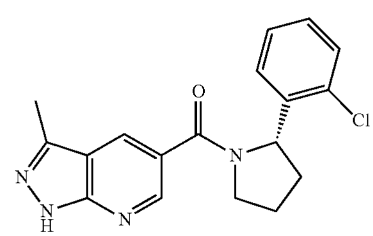 [SMILES: Cc1n[nH]c2ncc(C(=O)N3CCC[C@H]3c3ccccc3Cl)cc12] | 341 | 1.96 (A) | B | [(S)-2-(2-Chloro-phenyl)-pyrrolidin-1-yl]-(3-methyl-1H-pyrazolo[3,4-b]pyridin-5-yl)-methanone | 1H NMR (400 MHz, DMSO-d6) ppm = 13.51-13.18 (m, 1H), 8.75-7.82 (m, 2H), 7.61-7.16 (m, 4H), 5.51-5.26 (m, 1H), 4.09-3.58 (m, 2H), 2.62-2.28 (m, 4H), 2.06-1.64 (m, 3H). |
| 37 | 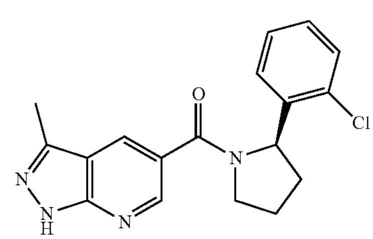 [SMILES: Cc1n[nH]c2ncc(C(=O)N3CCC[C@@H]3c3ccccc3Cl)cc12] | 341 | 1.96 (A) | C | [(R)-2-(2-Chloro-phenyl)-pyrrolidin-1-yl]-(3-methyl-1H-pyrazolo[3,4-b]pyridin-5-yl)-methanone | 1H NMR (400 MHz, DMSO-d6) ppm = 13.47-13.19 (m, 1H), 8.77-7.84 (m, 2H), 7.59-7.18 (m, 4H), 5.52-5.25 (m, 1H), 4.09-3.58 (m, 2H), 2.61-2.27 (m, 4H), 2.05-1.65 (m, 3H). |

TABLE 1-continued

| No. | Structure | [M + 1]⁺ | RT [min] (HPLC method) | IC50 [μM] | Chemical Name | NMR |
|---|---|---|---|---|---|---|
| 38 | 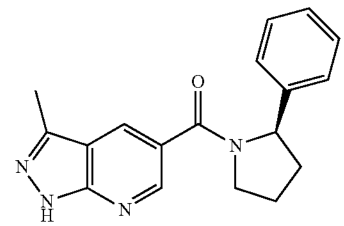 [SMILES: Cc1n[nH]c2ncc(C(=O)N3CCC[C@@H]3c3ccccc3)cc12] | 307 | 1.82 (A) | C | (3-Methyl-1H-pyrazolo[3,4-b]pyridin-5-yl)-((R)-2-phenyl-pyrrolidin-1-yl)-methanone | 1H NMR (400 MHz, DMSO-d6) ppm = 13.47-13.18 (m, 1H), 8.76-7.79 (m, 2H), 7.48-6.96 (m, 5H), 5.30-4.95 (m, 1H), 4.11-3.51 (m, 2H), 2.63-2.22 (m, 4H), 2.01-1.70 (m, 3H). |
| 39 | 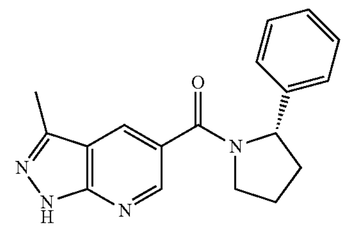 | 307 | 1.82 (A) | A | (3-Methyl-1H-pyrazolo[3,4-b]pyridin-5-yl)-((S)-2-phenyl-pyrrolidin-1-yl)-methanone | 1H NMR (400 MHz, DMSO-d6) ppm = 13.51-13.17 (m, 1H), 8.75-7.80 (m, 2H), 7.45-6.98 (m, 5H), 5.27-4.95 (m, 1H), 4.10-3.53 (m, 2H), 2.62-2.25 (m, 4H), 1.99-1.71 (m, 3H). |
| 40 | 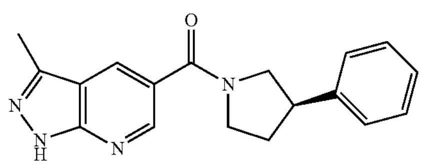 [SMILES: Cc1n[nH]c2ncc(C(=O)N3CC[C@H](c4ccccc4)C3)cc12] | 307 | 1.89 (A) | C | (3-Methyl-1H-pyrazolo[3,4-b]pyridin-5-yl)-((R)-3-phenyl-pyrrolidin-1-yl)-methanone | 1H NMR (400 MHz, DMSO-d6) ppm = 13.45-13.33 (m, 1H), 8.67 (s, 1H), 8.49-8.41 (m, 1H), 7.40-7.18 (m, 5H), 4.07-3.25 (m, 5H), 2.56-2.47 (m, 3H), 2.38-2.22 (m, 1H), 2.14-1.94 (m, 1H). |
| 41 | 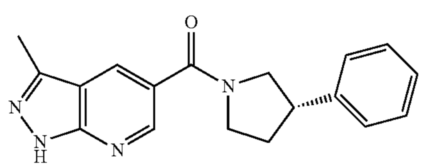 [SMILES: Cc1n[nH]c2ncc(C(=O)N3CC[C@@H](c4ccccc4)C3)cc12] | 307 | 1.89 (A) | B | (3-Methyl-1H-pyrazolo[3,4-b]pyridin-5-yl)-((S)-3-phenyl-pyrrolidin-1-yl)-methanone | 1H NMR (400 MHz, DMSO-d6) ppm = 13.44-13.33 (m, 1H), 8.70-8.64 (m, 1H), 8.48-8.41 (m, 1H), 7.40-7.18 (m, 5H), 4.07-3.28 (m, 5H), 2.58-2.45 (m, 3H), 2.38-2.22 (m, 1H), 2.16-1.95 (m, 1H). |
| 43 | 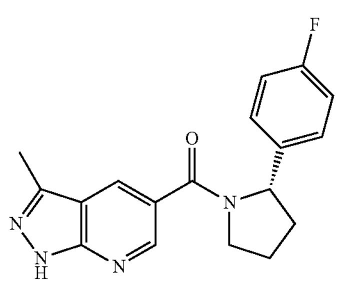 [SMILES: Cc1n[nH]c2ncc(C(=O)N3CCC[C@H]3c3ccc(F)cc3)cc12] | 325 | 1.86 (A) | A | [(S)-2-(4-Fluoro-phenyl)-pyrrolidin-1-yl]-(3-methyl-1H-pyrazolo[3,4-b]pyridin-5-yl)-methanone | 1H NMR (400 MHz, DMSO-d6) ppm = 13.48-13.19 (m, 1H), 8.78-7.81 (m, 2H), 7.53-6.94 (m, 4H), 5.26-4.95 (m, 1H), 4.04-3.50 (m, 2H), 2.61-2.24 (m, 4H), 2.01-1.67 (m, 3H). |
| 44 | 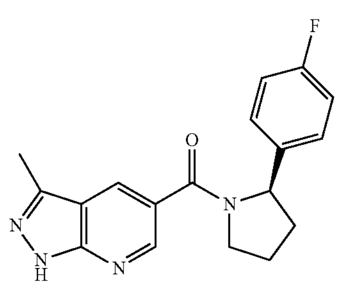 [SMILES: Cc1n[nH]c2ncc(C(=O)N3CCC[C@@H]3c3ccc(F)cc3)cc12] | 325 | 1.86 (A) | C | [(R)-2-(4-Fluoro-phenyl)-pyrrolidin-1-yl]-(3-methyl-1H-pyrazolo[3,4-b]pyridin-5-yl)-methanone | 1H NMR (400 MHz, DMSO-d6) ppm = 13.49-13.18 (m, 1H), 8.75-7.83 (m, 2H), 7.50-6.96 (m, 4H), 5.24-4.97 (m, 1H), 4.04-3.50 (m, 2H), 2.61-2.27 (m, 4H), 1.99-1.68 (m, 3H). |

| No. | Structure | [M + 1]+ | RT [min] (HPLC method) | IC50 [μM] | Chemical Name | NMR |
|---|---|---|---|---|---|---|
| 45 | 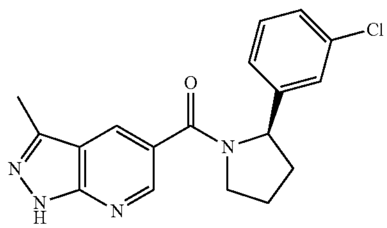 [SMILES: Cc1n[nH]c2ncc(C(=O)N3CCC[C@@H]3c3cccc(Cl)c3)cc12] | 341 | 1.96 (A) | C | [(r)-2-(3-Chloro-phenyl)-pyrrolidin-1-yl]-(3-methyl-1H-pyrazolo[3,4-b]pyridin-5-yl)-methanone | 1H NMR (400 MHz, DMSO-d6) ppm = 13.51-13.19 (m, 1H), 8.79-7.80 (m, 2H), 7.55-6.98 (m, 4H), 5.21-4.98 (m, 1H), 4.09-3.53 (m, 2H), 2.61-2.25 (m, 4H), 1.99-1.68 (m, 3H). |
| 46 | 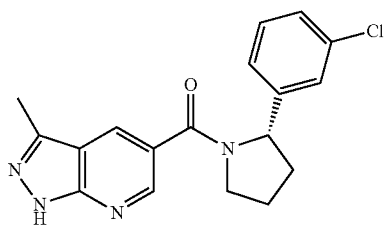 [SMILES: Cc1n[nH]c2ncc(C(=O)N3CCC[C@H]3c3cccc(Cl)c3)cc12] | 341 | 1.96 (A) | B | [(S)-2-(3-Chloro-phenyl)-pyrrolidin-1-yl]-(3-methyl-1H-pyrazolo[3,4-b]pyridin-5-yl)-methanone | 1H NMR (400 MHz, DMSO-d6) ppm = 13.51-13.20 (m, 1H), 8.79-7.81 (m, 2H), 7.51-6.96 (m, 4H), 5.21-4.97 (m, 1H), 4.09-3.53 (m, 2H), 2.60-2.27 (m, 4H), 2.00-1.67 (m, 3H). |
| 47 | 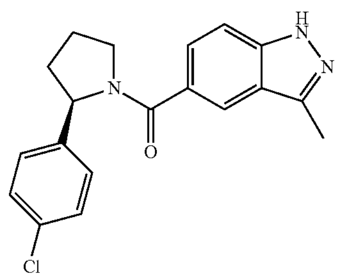 [SMILES: Cc1n[nH]c2ccc(C(=O)N3CCC[C@@H]3c3ccc(Cl)cc3)cc12] | 340 | 1.97 (D) | C | [(R)-2-(4-Chloro-phenyl)-pyrrolidin-1-yl]-(3-methyl-1H-indazol-5-yl)-methanone | 1H NMR (300 MHz, DMSO-d6) ppm = 12.49 (s, 1H), 7.76 (s, 1H), 7.40 (s, 2H), 7.33-7.28 (m, 4H), 5.12 (s, 1H), 3.83-3.77 (m, 1H), 3.67 (s, 1H), 2.48-2.40 (m, 3H), 2.38-2.34 (m, 1H), 1.88-1.74 (m, 3H) |
| 48 | 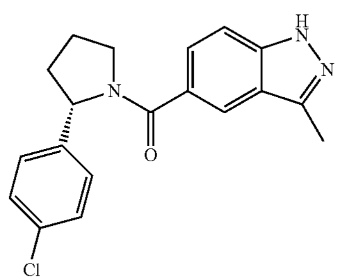 [SMILES: Cc1n[nH]c2ccc(C(=O)N3CCC[C@H]3c3ccc(Cl)cc3)cc12] | 340 | 1.97 (D) | A | [(S)-2-(4-Chloro-phenyl)-pyrrolidin-1-yl]-(3-methyl-1H-indazol-5-yl)-methanone | 1H NMR (300 MHz, DMSO-d6) ppm = 12.49 (s, 1H), 7.76 (s, 1H), 7.40 (s, 2H), 7.33-7.28 (m, 4H), 5.12 (s, 1H), 3.83-3.77 (m, 1H), 3.67 (s, 1H), 2.48-2.40 (m, 3H), 2.38-2.34 (m, 1H), 1.88-1.74 (m, 3H) |
| 49 | 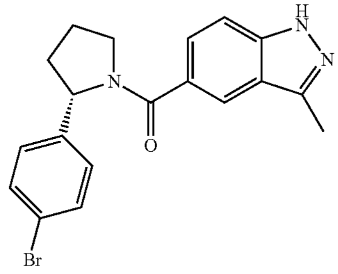 [SMILES: Cc1n[nH]c2ccc(C(=O)N3CCC[C@H]3c3ccc(Br)cc3)cc12] | 384/ 386 | 2.00 (D) | A | [(S)-2-(4-Bromo-phenyl)-pyrrolidin-1-yl]-(3-methyl-1H-indazol-5-yl)-methanone | 1H NMR (300 MHz, DMSO-d6) ppm = 12.50 (s, 1H), 7.76 (s, 1H), 7.47-7.40 (m, 4H), 7.22-7.20 (d, 2H), 5.10-5.08 (t, 1H), 3.83-3.77 (m, 1H), 3.66-3.64 (m, 1H), 2.48-2.40 (m, 3H), 2.38-2.32 (m, 1H), 1.90-1.74 (m, 3H) |

TABLE 1-continued

| No. | Structure | [M + 1]⁺ | RT [min] (HPLC method) | IC50 [μM] | Chemical Name | NMR |
|---|---|---|---|---|---|---|
| 50 | 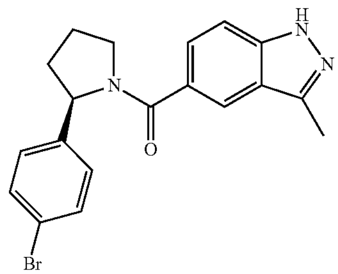 [SMILES: Cc1n[nH]c2ccc(C(=O)N3CCC[C@@H]3c3ccc(Br)cc3)cc12] | 384/ 386 | 2.00 (D) | C | [(R)-2-(4-Bromo-phenyl)-pyrrolidin-1-yl]-(3-methyl-1H-indazol-5-yl)-methanone | 1 H NMR (300 MHz, DMSO-d6) ppm = 12.50 (s, 1H), 7.76 (s, 1H), 7.47-7.40 (m, 4H), 7.22-7.20 (d, 2H), 5.10 (s, 1H), 3.85-3.77 (m, 1H), 3.66-3.65 (m, 1H), 2.48-2.45 (m, 3H), 2.40-2.31 (m, 1H), 1.90-1.72 (m, 3H) |
| 51 | 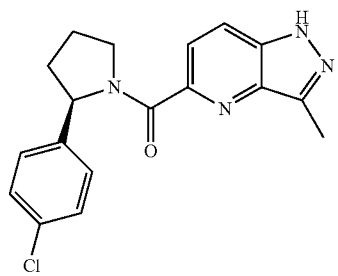 [SMILES: Cc1n[nH]c2ccc(C(=O)N3CCC[C@@H]3c3ccc(Cl)cc3)nc12] | 341 | 1.87 (G) | C | [(R)-2-(4-Chloro-phenyl)-pyrrolidin-1-yl]-(3-methyl-1H-pyrazolo[4,3-b]pyridin-5-yl)-methanone | 1H NMR (300 MHz, DMSO-d6) ppm = 12.74 (m, 1H), 7.93-7.05 (m, 6H), 5.78-5.28 (m, 1H), 4.13-3.88 (m, 2H), 2.57-2.25 (m, 4H), 1.91-1.89 (m, 3H) |
| 52 | 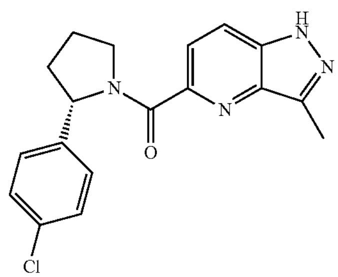 [SMILES: Cc1n[nH]c2ccc(C(=O)N3CCC[C@H]3c3ccc(Cl)cc3)nc12] | 341 | 2.68 (I) | A | [(S)-2-(4-Chloro-phenyl)-pyrrolidin-1-yl]-(3-methyl-1H-pyrazolo[4,3-b]pyridin-5-yl)-methanone | 1H NMR (300 MHz, DMSO-d6) ppm = 12.76 (m, 1H), 7.93-7.04 (m, 6H), 5.77-5.28 (m, 1H), 4.14-3.87 (m, 2H), 2.57-2.35 (m, 4H), 1.91-1.89 (m, 3H) |
| 53 | 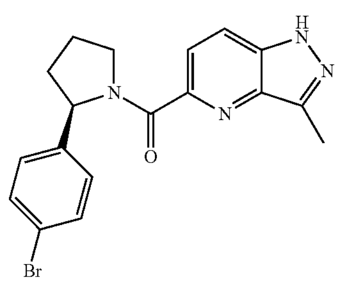 | 386, 388 | 2.74 (I) | C | [(R)-2-(4-Bromo-phenyl)-pyrrolidin-1-yl]-(3-methyl-1H-pyrazolo[4,3-b]pyridin-5-yl)-methanone | 1H NMR (300 MHz, DMSO-d6) ppm = 12.97-12.72 (m, 1H), 7.94-6.98 (m, 6H), 5.76-5.21 (m, 1H), 4.12-3.88 (m, 2H), 2.57-2.35 (m, 4H), 1.91 (m, 3H) |
| 54 | 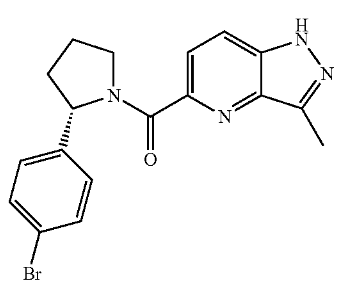 [SMILES: Cc1n[nH]c2ccc(C(=O)N3CCC[C@H]3c3ccc(Br)cc3)nc12] | 386, 388 | 2.74 (I) | A | [(S)-2-(4-Bromo-phenyl)-pyrrolidin-1-yl]-(3-methyl-1H-pyrazolo[4,3-b]pyridin-5-yl)-methanone | 1H NMR (300 MHz, DMSO-d6) pp = 12.77 (m, 1H), 7.71-6.99 (m, 6H), 5.76-5.26 (m, 1H), 4.13-3.88 (m, 2H), 2.57-2.35 (m, 4H), 1.91-1.89 (m, 3H) |

TABLE 1-continued

| No. | Structure | [M + 1]+ | RT [min] (HPLC method) | IC50 [μM] | Chemical Name | NMR |
|---|---|---|---|---|---|---|
| 55 | 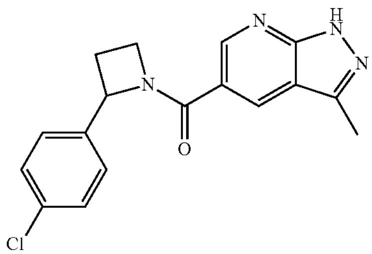 [SMILES: Cc1n[nH]c2ncc(C(=O)N3CCC3c3ccc(Cl)cc3)cc12] | 327 | 1.82 (G) | B | [2-(4-Chloro-phenyl)-azetidin-1-yl]-(3-methyl-1H-pyrazolo[3,4-b]pyridin-5-yl)-methanone | 1H NMR (300 Hz, DMSO-d6) ppm = 13.16 (s, 1H), 8.66 (s, 1H), 8.28 (s, 1H), 7.45-7.29 (m, 4H), 5.56-5.51 (m, 1H), 4.50-4.48 (m, 1H), 4.24-4.17 (m, 1H), 2.99-2.71 (m, 1H), 2.62 (s, 3H), 2.25-2.11 (m, 1H). |
| 56 | 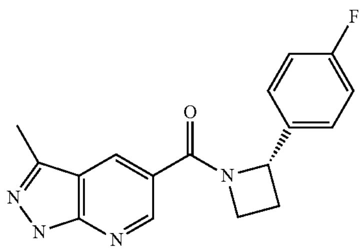 [SMILES: Cc1n[nH]c2ncc(C(=O)N3CC[C@H]3c3ccc(F)cc3)cc12] | 311 | 1.79 (A) | B | [(S)-2-(4-Fluoro-phenyl)-azetidin-1-yl]-(3-methyl-1H-pyrazolo[3,4-b]pyridin-5-yl)-methanone | 1H NMR (400 MHz, T = 363 K, DMSO-d6) ppm = 13.15 (s, 1H), 8.65 (s, 1H), 8.27 (s, 1H), 7.57-7.37 (m, 2H), 7.24-7.00 (m, 2H), 5.55 (dd, J = 8.8, 6.0 Hz, 1H), 4.62-4.38 (m, 1H), 4.32-4.08 (m, 1H), 2.87-2.71 (m, 1H), 2.47 (s, 3H), 2.25-2.07 (m, 1H). |
| 57 | 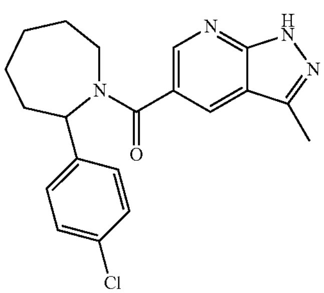 [SMILES: Cc1n[nH]c2ncc(C(=O)N3CCCCCC3c3ccc(Cl)cc3)cc12] | 369 | 1.42 (J) | C | [2-(4-Chloro-phenyl)-azepan-1-yl]-(3-methyl-1H-pyrazolo[3,4-b]pyridin-5-yl)-methanone | 1H NMR (300 Hz, DMSO-d6) ppm = 8.23 (s, 1H), 7.91 (s, 1H), 7.30-7.17 (m, 4H), 5.05 (m, 1H), 4.12 (m, 1H), 2.35 (s, 3H), 2.27-2.18 (m, 2H), 1.82-1.62 (m, 5H), 1.46-1.35 (m, 3H). |
| 58 | 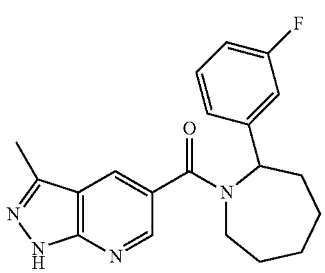 [SMILES: Cc1n[nH]c2ncc(C(=O)N3CCCCCC3c3cccc(F)c3)cc12] | 353 | 1.41 (D) | B | [2-(3-Fluoro-phenyl)-azepan-1-yl]-(3-methyl-1H-pyrazolo[3,4-b]pyridin-5-yl)-methanone | 1H NMR (400 MHz, DMSO-d6) ppm = 13.40, 13.33 (2 × s, 1H, ratio = 1:0, 8 mixture of rotamers), 8.51, 8.34, 8.17, 7.83 (4 × s, 2H, ratio 1:0, 8 mixture of rotamers), 7.52-7.35 (m, 1H), 7.32-7.17 (m, 1H), 7.17-7.03 (m, 1H), 7.03-6.87 (m, 1H), 5.54, 4, 73 (2 × dd, J = 12.0, 5.4 Hz, J = 11.0, 6.5 Hz 1H, ratio 1:0, 7 mixture of rotamers), 4.55-4.30, 3.90-3.64 (2 × m, 1H, ratio 1:0, 7 mixture of rotamers), 3.50-3.35, 3.23-3.01 (2 × m, 1H, 1:0, 7 mixture of rotamers), 2.54, 2.44-2.30 (1 × s, 1 × m, 4H), 1.96-1.26 (m, 7H). |

TABLE 1-continued

| No. | Structure | [M + 1]+ | RT [min] (HPLC method) | IC50 [μM] | Chemical Name | NMR |
|---|---|---|---|---|---|---|
| 59 | 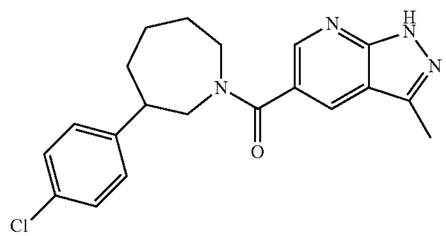 [SMILES: Cc1n[nH]c2ncc(C(=O)N3CCCCC(c4ccc(Cl)cc4)C3)cc12] | 3690 | 1.37 (J) | B | [3-(4-Chloro-phenyl)-azepan-1-yl]-(3-methyl-1H-pyrazolo[3,4-b]pyridin-5-yl)-methanone | 1H NMR (300 Hz, DMSO-d6) ppm = 13.11 (s, 1H), 8.50 (s, 1H), 8.23 (s, 1H), 7.27-7.22 (m, 4H), 3.91-3.82 (m, 1H), 3.78-3.68 (m, 1H), 3.54-3.50 (m, 1H), 3.37-3.29 (m, 1H), 2.98 (s, 1H), 2.48 (s, 3H), 1.91-1.72 (m, 5H), 1.55-1.51 (m, 1H). |
| 60 | 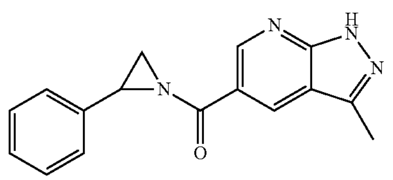 [SMILES: Cc1n[nH]c2ncc(C(=O)N3CC3c3ccccc3)cc12] | 279 | | | (3-Methyl-1H-pyrazolo[3,4-b]pyridin-5-yl)-(2-phenyl-aziridin-1-yl)-methanone | |
| 61 | 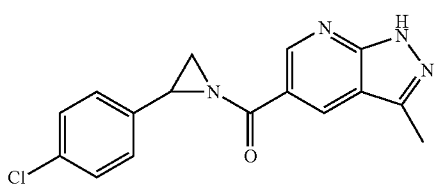 [SMILES: Cc1n[nH]c2ncc(C(=O)N3CC3c3ccc(Cl)cc3)cc12] | 313 | | | [2-(4-Chloro-phenyl)-aziridin-1-yl]-(3-methyl-1H-pyrazolo[3,4-b]pyridin-5-yl)-methanone | |
| 62 | 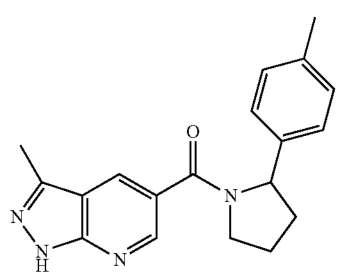 [SMILES: Cc1ccc(C2CCCN2C(=O)c2cnc3[nH]nc(C)c3c2)cc1] | 321 | 1.31 (D) | A | (3-Methyl-1H-pyrazolo[3,4-b]pyridin-5-yl)-(2-p-tolyl-pyrrolidin-1-yl)-methanone | 1H NMR (400 MHz, T = 363 K, DMSO-d6) ppm = 13.07 (s, 1H), 8.61-8.42 (m, 1H), 8.30-8.02 (m, 1H), 7.21-6.94 (m, 4H), 5.18-4.98 (m, 1H), 3.90-3.78 (m, 1H), 3.75-3.60 (m, 1H), 2.44 (s, 3H), 2.40-2.29 (m, 1H), 2.25 (s, 3H), 1.98-1.82 (m, J = 5.9 Hz, 2H), 1.85-1.73 (m, 1H). |
| 63 | 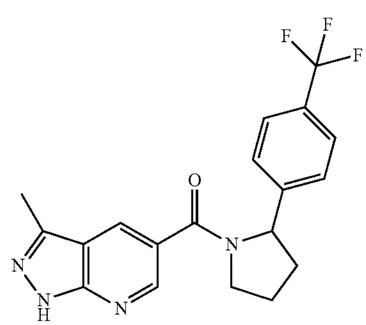 [SMILES: Cc1n[nH]c2ncc(C(=O)N3CCCC3c3ccc(C(F)(F)F)cc3)cc12] | 375 | 2.58 (B) | A | (3-Methyl-1H-pyrazolo[3,4-b]pyridin-5-yl)-[2-(4-trifluoromethyl-phenyl)-pyrrolidin-1-yl]-methanone | |

TABLE 1-continued

| No. | Structure | [M + 1]+ | RT [min] (HPLC method) | IC50 [μM] | Chemical Name | NMR |
|---|---|---|---|---|---|---|
| 64 | 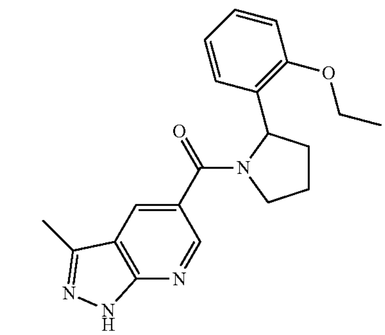 [SMILES: CCOc1ccccc1C1CCCN1C(=O)c1cnc2[nH]nc(C)c2c1] | 351 | 3.24 (F) | | [2-(2-Ethoxy-phenyl)-pyrrolidin-1-yl]-(3-methyl-1H-pyrazolo[3,4-b]pyridin-5-yl)-methanone | 1H NMR (300 Hz, DMSO-d6) ppm = 13.08 (s, 1H), 8.44 (s, 1H), 8.10 (s, 1H), 7.17-7.12 (m, 2H), 6.90-6.85 (m, 2H), 5.32 (s, 1H), 3.99-3.71 (m, 4H), 2.36 (s, 3H), 2.34-2.27 (m, 1H), 1.91-1.72 (m, 3H), 1.24 (s, 3H). |
| 65 | 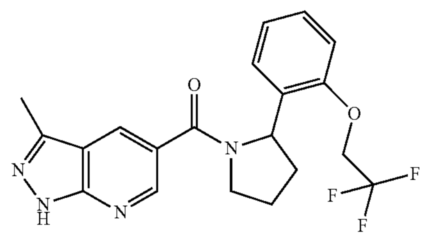 [SMILES: Cc1n[nH]c2ncc(C(=O)N3CCCC3c3ccccc3OCC(F)(F)F)cc12] | 405 | 3.43 (F) | C | (3-Methyl-1H-pyrazolo[3,4-b]pyridin-5-yl)-{2-[2-(2,2,2-trifluoro-ethoxy)-phenyl]-pyrrolidin-1-yl}-methanone | 1H NMR (300 Hz, DMSO-d6) ppm = 13.09 (s, 1H), 8.51 (s, 1H), 8.22 (s, 1H), 7.26-7.19 (m, 2H), 7.04-6.99 (m, 2H), 5.36 (s, 1H), 4.70-4.60 (m, 2H), 3.84-3.80 (m, 1H), 3.69 (s, 1H), 2.48 (s, 3H), 2.38-2.32 (m, 1H), 1.91-1.76 (m, 3H). |
| 66 | 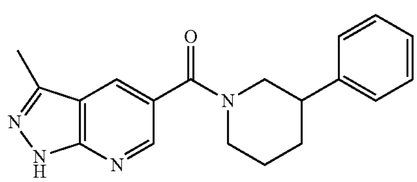 [SMILES: Cc1n[nH]c2ncc(C(=O)N3CCCC(c4ccccc4)C3)cc12] | 321 | 1.35 (D) | C | (3-Methyl-1H-pyrazolo[3,4-b]pyridin-5-yl)-(3-phenyl-piperidin-1-yl)-methanone | 1H NMR (400 MHz, DMSO-d6) ppm = 13.40 (s, 1H), 8.55 (d, J = 2.0 Hz, 1H), 8.33 (d, J = 1.9 Hz, 1H), 7.65-6.83 (m, 5H), 4.91-4.25 (m, 1H), 3.94-3.47 (m, 1H), 3.28-2.70 (m, 3H), 2.53 (s, 3H), 2.07-1.50 (m, 4H). |
| 67 | 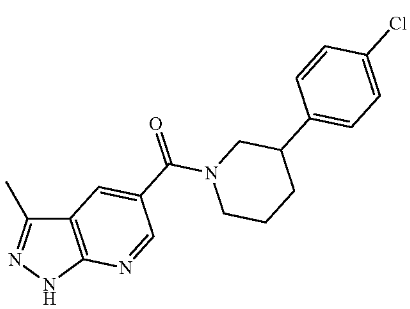 [SMILES: Cc1n[nH]c2ncc(C(=O)N3CCCC(c4ccc(Cl)cc4)C3)cc12] | 355 | 3.64 (F) | B | [3-(4-Chloro-phenyl)-piperidin-1-yl]-(3-methyl-1H-pyrazolo[3,4-b]pyridin-5-yl)-methanone | 1HNMR (300 Hz, DMSO-d6) ppm = 13.13 (s, 1H), 8.50 (s, 1H), 8.22 (s, 1H), 7.34-7.25 (m, 4H), 4.10 (m, 2H), 3.10-2.99 (m, 2H), 2.88-2.84 (m, 1H), 2.51 (s, 3H), 1.97-1.90 (m, 1H), 1.81-1.64 (m, 3H). |
| 68 | 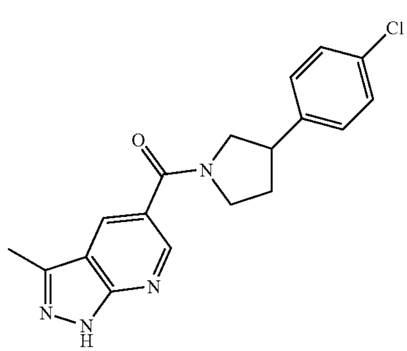 [SMILES: Cc1n[nH]c2ncc(C(=O)N3CCC(c4ccc(Cl)cc4)C3)cc12] | 341 | 1.23 (J) | A | [3-(4-Chloro-phenyl)-pyrrolidin-1-yl]-(3-methyl-1H-pyrazolo[3,4-b]pyridin-5-yl)-methanone | 1H NMR (300 Hz, DMSO-d6) ppm = 13.13 (s, 1H), 8.64 (s, 1H), 8.35 (s, 1H), 7.33-7.30 (m, 4H), 3.94 (s, 1H), 3.69-3.60 (m, 2H), 3.55-3.43 (m, 2H), 2.51 (s, 3H), 2.33-2.26 (m, 1H), 2.05-1.98 (m, 1H). |

TABLE 1-continued

| No. | Structure | [M + 1]+ | RT [min] (HPLC method) | IC50 [μM] | Chemical Name | NMR |
|---|---|---|---|---|---|---|
| 69 | 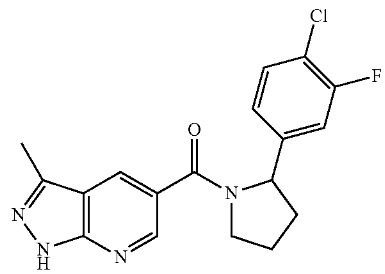 [SMILES: Cc1n[nH]c2ncc(C(=O)N3CCCC3c3ccc(Cl)c(F)c3)cc12] | 359 | 1.88 (I) | B | [2-(4-Chloro-3-fluoro-phenyl)-pyrrolidin-1-yl]-(3-methyl-1H-pyrazolo[3,4-b]pyridin-5-yl)-methanone | 1H NMR (300 Hz, DMSO-d6) ppm = 13.14 (s, 1H), 8.60 (s, 1H), 8.33 (s, 1H), 7.51-7.46 (m, 1H), 7.36-7.20 (m, 2H), 5.20-5.18 (m, 1H), 3.95-3.89 (m, 1H), 3.80-3.60 (m, 1H), 2.60-2.50 (m, 3H), 2.47-2.35 (m, 1H), 1.99-1.80 (m, 3H). |
| 70 | 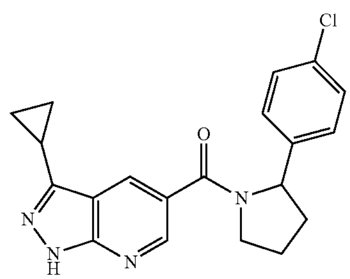 [SMILES: O=C(c1cnc2[nH]nc(C3CC3)c2c1)N1CCCC1c1ccc(Cl)cc1] | 367 | 1.42 (D) | B | [2-(4-Chloro-phenyl)-pyrrolidin-1-yl]-(3-cyclopropyl-1H-pyrazolo[3,4-b]pyridin-5-yl)-methanone | 1H NMR (400 MHz, DMSO-d6) ppm = 13.36, 13.22 (2 × s, 1H, ratio = 2:1 mixture of rotamers), 8.75-8.62, 8.62-8.51, 8.34-8.17, 7.90-7.73 (4 × m, 2H), 7.52-7.41, 7.41-7.33, 7.33-7.24, 7.16-7.00 (4 × m, 4H), 5.23-5.09, 5.09-4.93 (2 × m, 1H, ratio = 2:1 mixture of rotamers), 4.03-3.88, 3.88-3.73, 3.67-3.52 (3 × m, 2H), 2.46-2.27, 2.15-2.02, 2.02-1.66 (3 × m, 5H), 1.11-0.66 (m, 4H). |
| 71 | 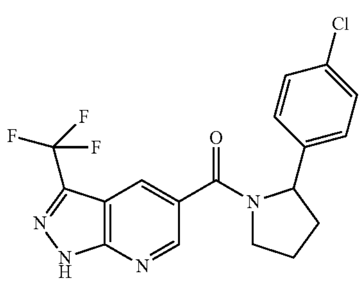 [SMILES: O=C(c1cnc2[nH]nc(C(F)(F)F)c2c1)N1CCCC1c1ccc(Cl)cc1] | 395 | 2.26 (A) | B | [2-(4-Chloro-phenyl)-pyrrolidin-1-yl]-(3-trifluoromethyl-1H-pyrazolo[3,4-b]pyridin-5-yl)-methanone | 1H NMR (400 MHz, DMSO-d6) ? 8.90, 8.55, 8.49, 7.84 (4 × s, 2H, ratio = 2:3 mixture of rotamers), 7.46, 7.38, 7.23, 7.02 (2 × d, J = 8.2 Hz, 2 × d, J = 7.7 Hz, 4H, ratio = 2:3 mixture of rotamers), 5.23-5.10, 4.98-4.87 (2 × m, 1H, ratio = 2:3 mixture of rotamers), 3.97-3.76, 3.66-3.24 (1 × m, 1 × m + HDO, 2H), 2.46-2.30 (m, 1H), 2.03-1.68 (m, 3H). |
| 72 | 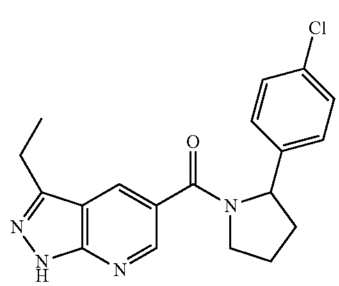 [SMILES: CCc1n[nH]c2ncc(C(=O)N3CCCC3c3ccc(Cl)cc3)cc12] | 355 | | | [2-(4-Chloro-phenyl)-pyrrolidin-1-yl]-(3-ethyl-1H-pyrazolo[3,4-b]pyridin-5-yl)-methanone | |

TABLE 1-continued

| No. | Structure | [M + 1]+ | RT [min] (HPLC method) | IC50 [μM] | Chemical Name | NMR |
|---|---|---|---|---|---|---|
| 73 | 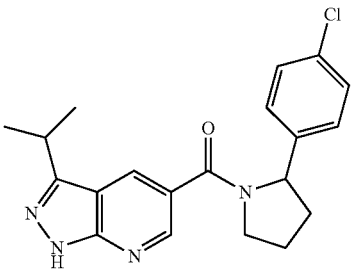 [SMILES: CC(C)c1n[nH]c2ncc(C(=O)N3CCCC3c3ccc(Cl)cc3)cc12] | 387 | | | [2-(4-Chloro-phenyl)-pyrrolidin-1-yl]-(3-isopropyl-1H-pyrazolo[3,4-b]pyridin-5-yl)-methanone | |
| 74 | 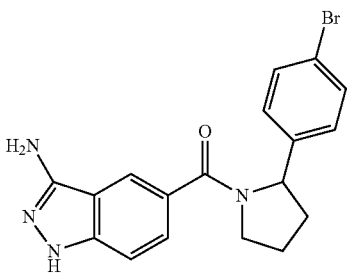 | 385, 387 | 1.93 (A) | A | (3-Amino-1H-indazol-5-yl)-[2-(4-bromo-phenyl)-pyrrolidin-1-yl]-methanone | 1H NMR (400 MHz, DMSO-d6) ppm = 11.73-11.37 (m, 1H), 8.09 (s, 1H), 7.57-6.92 (m, 6H), 6.06-5.18 (m, 2H), 5.14 (t, J = 7.0 Hz, 1H), 3.98-3.54 (m, 2H), 2.44-2.33 (m, 1H), 1.95-1.66 (m, 3H). |
| 76 | 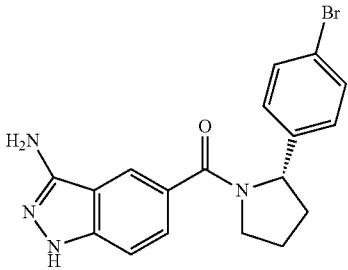 [SMILES: Nc1n[nH]c2ccc(C(=O)N3CCC[C@H]3c3ccc(Br)cc3)cc12] | 385, 387 | 1.93 (A) | A | (3-Amino-1H-indazol-5-yl)-[(S)-2-(4-bromo-phenyl)-pyrrolidin-1-yl]-methanone | 1H NMR (400 MHz, DMSO-d6) ppm = 11.57 (s, 1H), 8.09 (s, 1H), 7.60-6.90 (m, 6H), 5.68-5.29 (m, 2H), 5.14 (t, J = 7.0 Hz, 1H), 4.00-3.54 (m, 2H), 2.48-2.31 (m, 1H), 1.96-1.66 (m, 3H). |
| 77 | 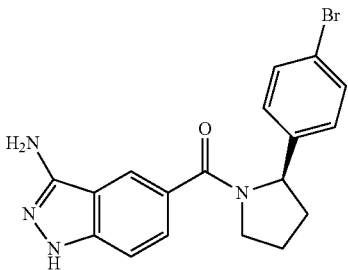 [SMILES: Nc1n[nH]c2ccc(C(=O)N3CCC[C@@H]3c3ccc(Br)cc3)cc12] | 385, 387 | 1.93 (A) | C | (3-Amino-1H-indazol-5-yl)-[(R)-2-(4-bromo-phenyl)-pyrrolidin-1-yl]-methanone | 1H NMR (400 MHz, DMSO-d6) ppm = 11.57 (s, 1H), 8.09 (s, 1H), 7.61-6.91 (m, 6H), 5.70-5.29 (m, 2H), 5.14 (t, J = 7.0, 1H), 3.95-3.52 (m, 2H), 2.45-2.33 (m, 1H), 1.93-1.67 (m, 3H). |
| 78 | 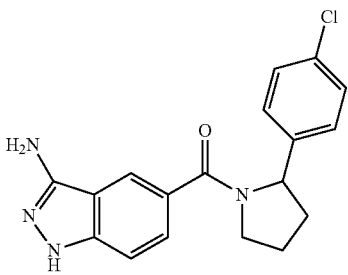 [SMILES: Nc1n[nH]c2ccc(C(=O)N3CCCC3c3ccc(Cl)cc3)cc12] | 341 | 1.89 (A) | A | (3-Amino-1H-indazol-5-yl)-[2-(4-chloro-phenyl)-pyrrolidin-1-yl]-methanone | 1H NMR (400 MHz, DMSO-d6) ppm = 11.70-11.38 (m, 1H), 8.31-7.74 (m, 1H), 7.62-6.84 (m, 6H), 5.67-5.27 (m, 2H), 5.16 (t, J = 7.0 Hz, 1H), 4.04-3.47 (m, 2H), 2.44-2.33 (m, 1H), 1.96-1.67 (m, 3H). |

TABLE 1-continued

| No. | Structure | [M + 1]+ | RT [min] (HPLC method) | IC50 [μM] | Chemical Name | NMR |
|---|---|---|---|---|---|---|
| 79 | 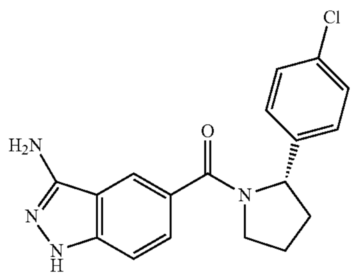 | 341 | 1.89 (A) | A | (3-Amino-1H-indazol-5-yl)-[(S)-2-(4-chloro-phenyl)-pyrrolidin-1-yl]-methanone | 1H NMR (500 MHz, DMSO-d6) ppm = 11.62-11.37 (m, 1H), 8.34-7.72 (m, 1H), 7.63-6.88 (m, 6H), 5.57-5.26 (m, 2H), 5.19-5.02 (m, 1H), 3.96-3.52 (m, 2H), 2.44-2.33 (m, 1H), 1.95-1.68 (m, 3H). |
| 80 | 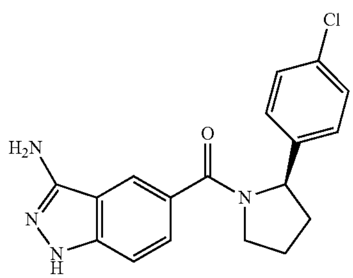 [SMILES: Nc1n[nH]c2ccc(C(=O)N3CCC[C@@H]3c3ccc(Cl)cc3)cc12] | 341 | 1.89 (A) | C | (3-Amino-1H-indazol-5-yl)-[(R)-2-(4-chloro-phenyl)-pyrrolidin-1-yl]-methanone | 1H NMR (500 MHz, DMSO-d6) ppm = 11.64-11.43 (m, 1H), 8.15-8.01 (m, 1H), 7.54-6.90 (m, 6H), 5.60-5.32 (m, 2H), 5.20-5.11 (m, 1H), 3.98-3.52 (m, 2H), 2.43-2.34 (m, 1H), 1.95-1.67 (m, 3H). |
| 81 | 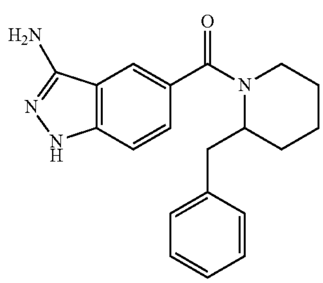 [SMILES: Nc1n[nH]c2ccc(C(=O)N3CCCCC3Cc3ccccc3)cc12] | 335 | 2.29 (B) | C | (3-Amino-1H-indazol-5-yl)-(2-benzyl-piperidin-1-yl)-methanone | |
| 82 | 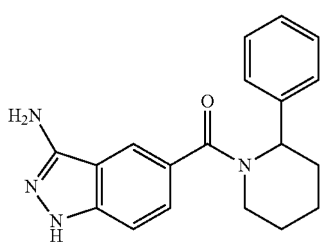 [SMILES: Nc1n[nH]c2ccc(C(=O)N3CCCCC3c3ccccc3)cc12] | 321 | 2.29 (B) | B | (3-Amino-1H-indazol-5-yl)-(2-phenyl-piperidin-1-yl)-methanone | |
| 83 | 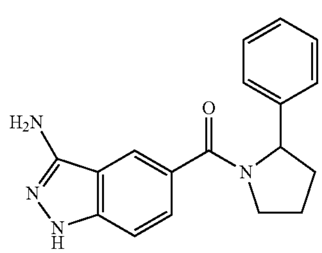 [SMILES: Nc1n[nH]c2ccc(C(=O)N3CCCC3c3ccccc3)cc12] | 307 | 2.16 (B) | B | (3-Amino-1H-indazol-5-yl)-(2-phenyl-pyrrolidin-1-yl)-methanone | |
| 84 | 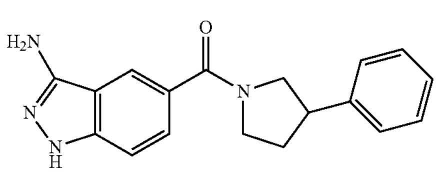 [SMILES: Nc1n[nH]c2ccc(C(=O)N3CCC(c4ccccc4)C3)cc12] | 307 | 1.77 (A) | C | (3-Amino-1H-indazol-5-yl)-(3-phenyl-pyrrolidin-1-yl)-methanone | 1H NMR (400 MHz, DMSO-d6) ppm = 11.68-11.49 (m, 1H), 8.06-7.99 (m, 1H), 7.50-7.44 (m, 1H), 7.40-7.18 (m, 6H), 6.01-5.09 (m, 2H), 4.06-3.38 (m, 5H), 2.37-2.18 (m, 1H), 2.15-1.92 (m, 1H). |

TABLE 1-continued

| No. | Structure | [M + 1]⁺ | RT [min] (HPLC method) | IC50 [μM] | Chemical Name | NMR |
|---|---|---|---|---|---|---|
| 85 | 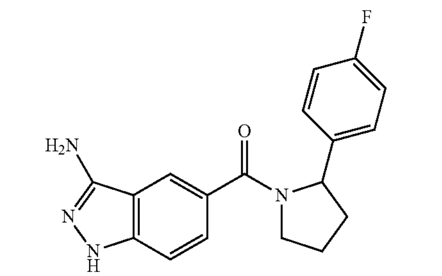 [SMILES: Nc1n[nH]c2ccc(C(=O)N3CCCC3c3ccc(F)cc3)cc12] | 325 | 1.76 (A) | A | (3-Amino-1H-indazol-5-yl)-[2-(4-fluoro-phenyl)-pyrrolidin-1-yl]-methanone | 1H NMR (400 MHz, DMSO-d6) ppm = 11.75-11.35 (m, 1H), 8.19-7.99 (m, 1H), 7.54-6.92 (m, 6H), 5.66-5.30 (m, 2H), 5.23-5.07 (m, 1H), 4.05-3.48 (m, 2H), 2.44-2.29 (m, 1H), 1.95-1.65 (m, 3H). |
| 86 | 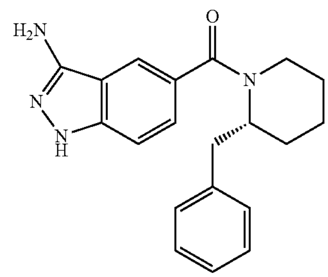 | 335 | 2.31 (B) | B | (3-Amino-1H-indazol-5-yl)-((S)-2-benzyl-piperidin-1-yl)-methanone | |
| 87 | 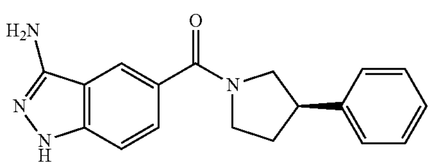 [SMILES: Nc1n[nH]c2ccc(C(=O)N3CC[C@H](c4ccccc4)C3)cc12] | 307 | 1.78 (A) | C | (3-Amino-1H-indazol-5-yl)-((R)-3-phenyl-pyrrolidin-1-yl)-methanone | 1H NMR (500 MHz, DMSO-d6) ppm = 11.55 (s, 1H), 8.02 (s, 1H), 7.46 (dd, J = 8.7, 1.6, 1H), 7.41-7.17 (m, 6H), 5.47 (s, 2H), 4.01-3.38 (m, 5H), 2.35-2.21 (m, 1H), 2.15-1.92 (m, 1H). |
| 88 | 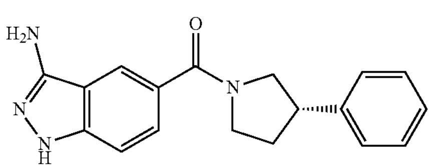 [SMILES: Nc1n[nH]c2ccc(C(=O)N3CC[C@@H](c4ccccc4)C3)cc12] | 307 | 1.78 (A) | C | (3-Amino-1H-indazol-5-yl)-((S)-3-phenyl-pyrrolidin-1-yl)-methanone | 1H NMR (400 MHz, DMSO-d6) ppm = 11.55 (s, 1H), 8.02 (s, 1H), 7.46 (dd, J = 8.6, 1.6, 1H), 7.40-7.18 (m, 6H), 5.47 (s, 2H), 4.03-3.34 (m, 5H), 2.32-2.21 (m, 1H), 2.16-1.93 (m, 1H). |
| 89 | 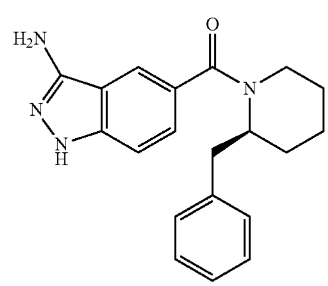 [SMILES: Nc1n[nH]c2ccc(C(=O)N3CCCC[C@H]3Cc3ccccc3)cc12] | 335 | 2.31 (B) | C | (3-Amino-1H-indazol-5-yl)-((R)-2-benzyl-piperidin-1-yl)-methanone | 1H NMR (400 MHz, DMSO-d6, 90° C.) ppm = 11.30 (s, 1H), 7.59 (s, 1H), 7.29-7.07 (m, 6H), 6.94 (dd, J = 8.5, 1.6 Hz, 1H), 5.12 (s, 2H), 4.51 (s, 1H), 4.04-3.91 (m, 1H), 3.15 (td, J = 13.2, 2.9 Hz, 1H), 3.08-2.97 (m, 1H), 2.92 (dd, J = 13.5, 7.9 Hz, 1H), 1.91-1.76 (m, 1H), 1.74-1.52 (m, 4H), 1.52-1.38 (m, 1H). |

TABLE 1-continued

| No. | Structure | [M + 1]+ | RT [min] (HPLC method) | IC50 [µM] | Chemical Name | NMR |
|---|---|---|---|---|---|---|
| 90 | 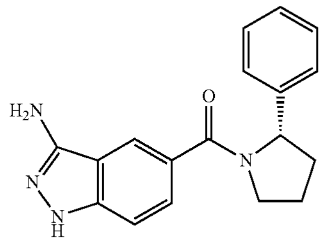 [SMILES: Nc1n[nH]c2ccc(C(=O)N3CCC[C@H]3c3ccccc3)cc12] | 307 | 2.10 (B) | A | (3-Amino-1H-indazol-5-yl)-((S)-2-phenyl-piperidin-1-yl)-methanone | |
| 91 | 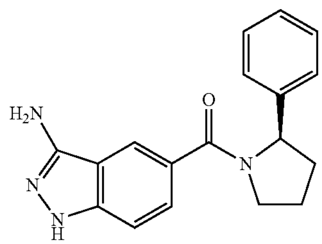 [SMILES: Nc1n[nH]c2ccc(C(=O)N3CCC[C@@H]3c3ccccc3)cc12] | 307 | 2.10 (B) | B | (3-Amino-1H-indazol-5-yl)-((R)-2-phenyl-piperidin-1-yl)-methanone | |
| 92 | 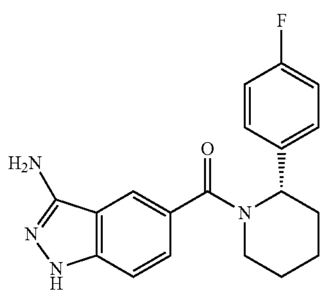 [SMILES: Nc1n[nH]c2ccc(C(=O)N3CCCC[C@H]3c3ccc(F)cc3)cc12] | 339 | 2.36 (B) | B | (3-Amino-1H-indazol-5-yl)-[(S)-2-(4-fluoro-phenyl)-piperidin-1-yl]-methanone | 1H NMR (400 MHz, DMSO-d6) ppm = 11.57 (s, 1H), 7.91 (s, 1H), 7.41-7.19 (m, 6H), 5.63-5.54 (m, 1H), 5.52-5.45 (m, 2H), 3.98-3.82 (m, 1H), 2.88-2.77 (m, 1H), 2.46-2.38 (m, 1H), 1.96-1.85 (m, 1H), 1.71-1.60 (m, 1H), 1.59-1.49 (m, 2H), 1.47-1.34 (m, 1H). |
| 93 | 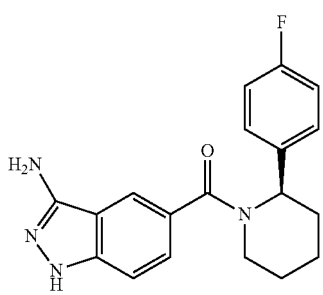 [SMILES: Nc1n[nH]c2ccc(C(=O)N3CCCC[C@@H]3c3ccc(F)cc3)cc12] | 339 | 2.36 (B) | | (3-Amino-1H-indazol-5-yl)-[(R)-2-(4-fluoro-phenyl)-piperidin-1-yl]-methanone | 1H NMR (400 MHz, DMSO-d6) ppm = 11.57 (s, 1H), 7.94-7.89 (m, 1H), 7.40-7.19 (m, 6H), 5.66-5.52 (m, 1H), 5.52-5.42 (m, 2H), 3.99-3.83 (m, 1H), 2.89-2.77 (m, 1H), 2.47-2.37 (m, 1H), 1.97-1.84 (m, 1H), 1.69-1.61 (m, 1H), 1.58-1.50 (m, 2H), 1.47-1.32 (m, 1H). |
| 94 | 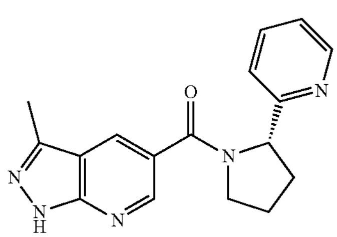 | 308 | 1.76 (A) | | (3-Methyl-1H-pyrazolo[3,4-b]pyridin-5-yl)-((S)-2-pyridin-2-yl-pyrrolidin-1-yl)-methanone | 1H NMR (400 MHz, DMSO-d6, temperature: 363 K) ppm = 13.11 (s, 1H), 8.81-8.36 (m, 2H), 8.36-7.97 (m, 1H), 7.81-7.56 (m, 1H), 7.46-6.92 (m, 2H), 5.31-5.15 (m, 1H), 3.92-3.80 (m, 1H), 3.80-3.63 (m, 1H), 2.49 (s, 3H), 2.45-2.36 (m, 1H), 2.05-1.87 (m, 3H). |

TABLE 1-continued

| No. | Structure | [M + 1]+ | RT [min] (HPLC method) | IC50 [μM] | Chemical Name | NMR |
|---|---|---|---|---|---|---|
| 95 | 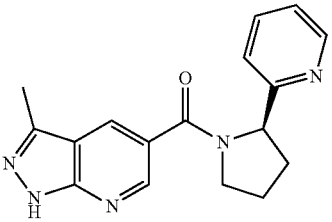 [SMILES: Cc1n[nH]c2ncc(C(=O)N3CCC[C@@H]3c3ccccn3)cc12] | 308 | 1.76 (A) | | (3-Methyl-1H-pyrazolo[3,4-b]pyridin-5-yl)-((R)-2-pyridin-2-yl-pyrrolidin-1-yl)-methanone | 1H NMR (400 MHz, DMSO-d6, temperature: 363 K) ppm = 13.52-12.70 (m, 1H), 8.77-8.40 (m, 2H), 8.40-7.99 (m, 1H), 7.87-7.56 (m, 1H), 7.42-7.05 (m, 2H), 5.38-5.04 (m, 1H), 3.97-3.81 (m, 1H), 3.81-3.61 (m, 1H), 2.49 (s, 3H), 2.45-2.24 (m, 1H), 2.06-1.87 (m, 3H). |
| 96 | 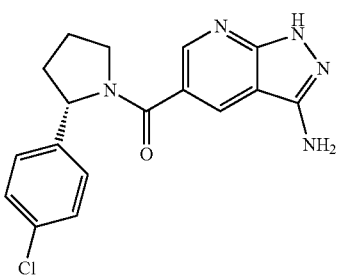 | 342 | 2.61 (E) | B | (3-Amino-1H-pyrazolo[3,4-b]pyridin-5-yl)-[(S)-2-(4-chloro-phenyl)-pyrrolidin-1-yl]-methanone | 1H NMR (300 MHz, DMSO-d6): ppm = 11.91 (s, 1H), 8.45 (s, 1H), 8.34 (s, 1H), 7.30-7.29 (s, 4H), 5.40 (s, 2H), 5.18 (m, 1H), 3.87-3.85 (m, 1H), 3.68 (m, 1H), 2.37 (m, 1H), 1.89-1.78 (m, 3H) |
| 97 | 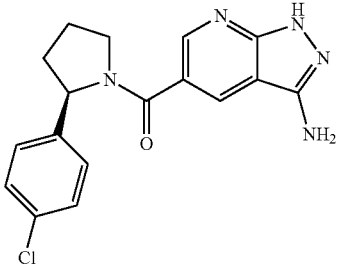 [SMILES: Nc1n[nH]c2ncc(C(=O)N3CCC[C@@H]3c3ccc(Cl)cc3)cc12] | 342 | 2.61 (E) | | (3-Amino-1H-pyrazolo[3,4-b]pyridin-5-yl)-[(R)-2-(4-chloro-phenyl)-pyrrolidin-1-yl]-methanone | 1H NMR (300 MHz, DMSO-d6): ppm = 11.91 (s, 1H), 8.45 (s, 1H), 8.34 (s, 1H), 7.33-7.28 (m, 4H), 5.40 (s, 2H), 5.21-5.16 (m, 1H), 3.88-3.82 (m, 1H), 3.69-3.66 (m, 1H), 2.41-2.37 (m, 1H), 1.92-1.76 (m, 3H) |
| 98 | 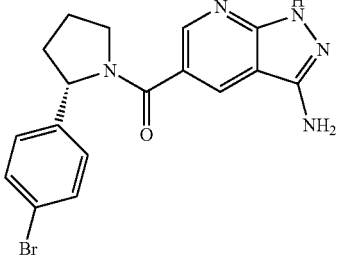 | 386, 388 | 1.61 (H) | B | (3-Amino-1H-pyrazolo[3,4-b]pyridin-5-yl)-[(S)-2-(4-bromo-phenyl)-pyrrolidin-1-yl]-methanone | 1H NMR (300 MHz, DMSO-d6) ppm = 11.91 (s, 1H), 8.45 (s, 1H), 8.34 (s, 1H), 7.45 (d, J = 8.4, 2H), 7.22 (d, J = 8.1, 2H), 5.40 (s, 2H), 5.19-5.15 (m, 1H), 3.87-3.84 (m, 1H), 3.69-3.65 (m, 1H), 2.41-2.37 (m, 1H), 1.91-1.77 (m, 3H) |
| 99 | 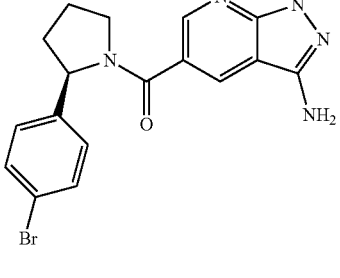 | 386, 388 | 1.61 (H) | | (3-Amino-1H-pyrazolo[3,4-b]pyridin-5-yl)-[(R)-2-(4-bromo-phenyl)-pyrrolidin-1-yl]-methanone | 1H NMR (300 MHz, DMSO-d6) ppm = 11.91 (s, 1H), 8.45 (s, 1H), 8.34 (s, 1H), 7.45 (d, J = 8.1, 2H), 7.22 (d, J = 7.8, 2H), 5.40 (s, 2H), 5.19-5.15 (m, 1H), 3.90-3.82 (m, 1H), 3.69-3.63 (m, 1H), 2.41-2.34 (m, 1H), 1.90-1.75 (m, 3H) |

TABLE 1-continued

| No. | Structure | [M + 1]+ | RT [min] (HPLC method) | IC50 [µM] | Chemical Name | NMR |
|---|---|---|---|---|---|---|
| 100 | 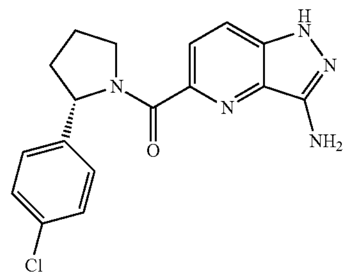 [SMILES: Nc1n[nH]c2ccc(C(=O)N3CCC[C@H]3c3ccc(Cl)cc3)nc12] | 342 | | | (3-Amino-1H-pyrazolo[4,3-b]pyridin-5-yl)-[(S)-2-(4-chloro-phenyl)-pyrrolidin-1-yl]-methanone | |
| 101 | 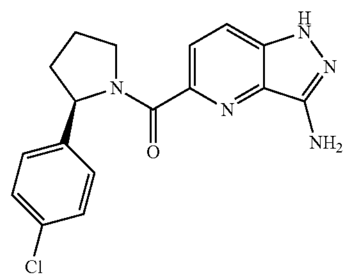 [SMILES: Nc1n[nH]c2ccc(C(=O)N3CCC[C@@H]3c3ccc(Cl)cc3)nc12] | 342 | | | (3-Amino-1H-pyrazolo[4,3-b]pyridin-5-yl)-[(R)-2-(4-chloro-phenyl)-pyrrolidin-1-yl]-methanone | |
| 102 | 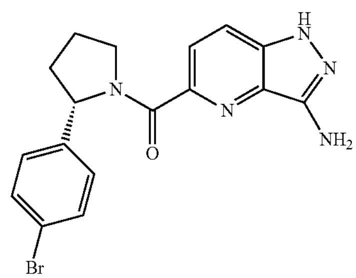 [SMILES: Nc1n[nH]c2ccc(C(=O)N3CCC[C@H]3c3ccc(Br)cc3)nc12] | 386, 388 | | | (3-Amino-1H-pyrazolo[4,3-b]pyridin-5-yl)-[(S)-2-(4-bromo-phenyl)-pyrrolidin-1-yl]-methanone | |
| 103 | 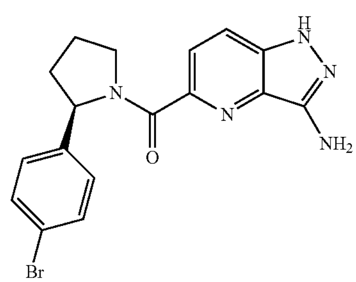 [SMILES: Nc1n[nH]c2ccc(C(=O)N3CCC[C@@H]3c3ccc(Br)cc3)nc12] | 386, 388 | | | (3-Amino-1H-pyrazolo[4,3-b]pyridin-5-yl)-[(R)-2-(4-bromo-phenyl)-pyrrolidin-1-yl]-methanone | |
| 104 | 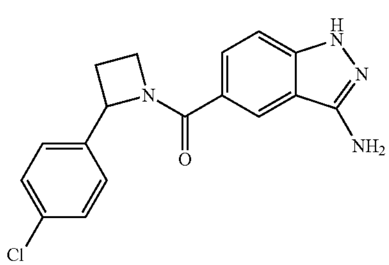 [SMILES: Nc1n[nH]c2ccc(C(=O)N3CCC3c3ccc(Cl)cc3)cc12] | 327 | 1.07 (F) | B | (3-Amino-1H-indazol-5-yl)-[2-(4-chloro-phenyl)-azetidin-1-yl]-methanone | 1H NMR (300 Hz, DMSO-d6) ppm = 11.38 (s, 1H), 8.08 (s, 1H), 7.50-7.35 (m, 5H), 7.20-7.17 (m, 1H), 5.51-5.49 (m, 1H), 5.24 (s, 2H), 4.52-4.50 (m, 1H), 4.17-4.15 (m, 1H), 2.88-2.65 (m, 1H), 2.20-2.03 (m, 1H). |

TABLE 1-continued

| No. | Structure | [M + 1]+ | RT [min] (HPLC method) | IC50 [μM] | Chemical Name | NMR |
|---|---|---|---|---|---|---|
| 105 | 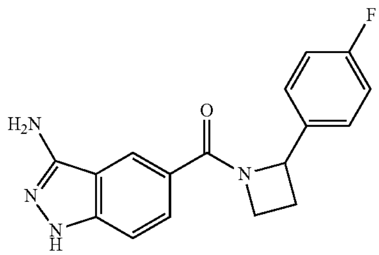 [SMILES: Nc1n[nH]c2ccc(C(=O)N3CCC3c3ccc(F)cc3)cc12] | 311 | 1.21 (D) | B | (3-Amino-1H-indazol-5-yl)-[2-(4-fluoro-phenyl)-azetidin-1-yl]-methanone | 1H NMR (400 MHz, DMSO-d6) ppm = 11.61 (s, 1H), 8.39-7.89 (m, br, 1H), 7.73-7.33 (m, br, 3H), 7.33-6.76 (m, br, 3H), 5.82-5.30 (m, br, 3H), 4.90-4.35 (m, br, 1H), 4.35-4.03 (m, br, 1H), 2.87-2.62 (m, br, 1H), 2.26-1.94 (m, br, 1H). |
| 106 | 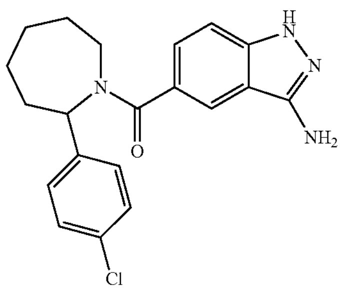 [SMILES: Nc1n[nH]c2ccc(C(=O)N3CCCCCC3c3ccc(Cl)cc3)cc12] | 369 | 1.34 (J) | C | (3-Amino-1H-indazol-5-yl)-[2-(4-chloro-phenyl)-azepan-1-yl]-methanone | 1H NMR (300 Hz, DMSO-d6) ppm = 11.29 (s, 1H), 7.67 (s, 1H), 7.37-7.26 (m, 2H), 7.19-7.10 (m, 3H), 7.37 (s, 1H), 5.12 (s, 2H), 4.30-3.90 (m, 1H), 3.24-3.10 (m, 1H), 2.41-2.30 (m, 2H), 2.00-1.35 (m, 7H). |
| 107 | 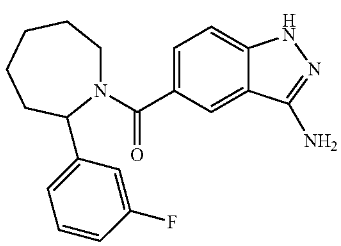 [SMILES: Nc1n[nH]c2ccc(C(=O)N3CCCCCC3c3cccc(F)c3)cc12] | 353 | 1.99 (A) | C | (3-Amino-1H-indazol-5-yl)-[2-(3-fluoro-phenyl)-azepan-1-yl]-methanone | 1H NMR (400 MHz, DMSO-d6) ppm = 11.54, 11.49 (2 × s, 1H, ratio 1:1 mixture of rotamers), 7.79, 7.66 (2 × s, 1H, ratio 1:1 mixture of rotamers), 7.53-7.33, 7.33-7.12, 7.12-7.01, 7.01-6.70 (4 × m, 6H) 5.65-5.50, 4.95-4.74 (2 × m, 1H, ratio 1:1 mixture of rotamers), 5.46, 5.36 (2 × s, 2H, ratio 1:1 mixture of rotamers), 4.53-4.23, 3.89-3.68 (2 × m, 1H, ratio 1:1 mixture of rotamers), 3.50-3.15, 2.99-2.84 (1 × m + H2O, 1 × m, 1H), 2.47-2.26 (m, 1H), 2.02-1.14 (m, 7H). |
| 108 | 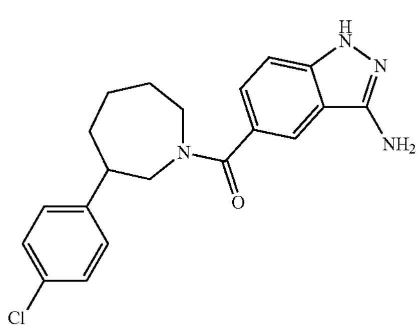 [SMILES: Nc1n[nH]c2ccc(C(=O)N3CCCCC(c4ccc(Cl)cc4)C3)cc12] | 369 | 1.30 (F) | | (3-Amino-1H-indazol-5-yl)-[3-(4-chloro-phenyl)-azepan-1-yl]-methanone | 1H NMR (300 Hz, DMSO-d6) ppm = 11.30 (s, 1H), 7.80 (s, 1H), 7.32-7.15 (m, 6H), 5.16 (s, 2H), 4.05-3.82 (m, 1H), 3.81-3.55 (m, 1H), 3.54-3.35 (m, 1H), 3.34-3.12 (m, 1H), 3.12-2.90 (m, 1H), 1.93-1.60 (m, 5H), 1.75-1.72 (m, 1H). |

TABLE 1-continued

| No. | Structure | [M + 1]+ | RT [min] (HPLC method) | IC50 [μM] | Chemical Name | NMR |
|---|---|---|---|---|---|---|
| 109 | 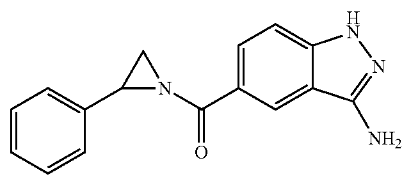 [SMILES: Nc1n[nH]c2ccc(C(=O)N3CC3c3ccccc3)cc12] | 279 | | | (3-Amino-1H-indazol-5-yl)-(2-phenyl-aziridin-1-yl)-methanone | |
| 110 | 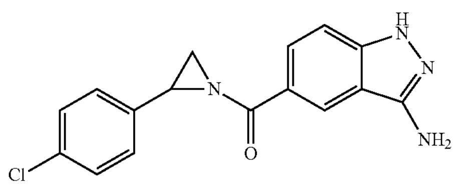 [SMILES: Nc1n[nH]c2ccc(C(=O)N3CC3c3ccc(Cl)cc3)cc12] | 313 | | | (3-Amino-1H-indazol-5-yl)-[2-(4-chloro-phenyl)-aziridin-1-yl]-methanone | |
| 111 | 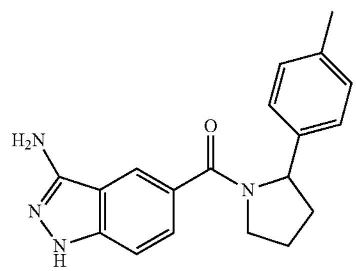 [SMILES: Cc1ccc(C2CCCN2C(=O)c2ccc3[nH]nc(N)c3c2)cc1] | 321 | | | (3-Amino-1H-indazol-5-yl)-(2-p-tolyl-pyrrolidin-1-yl)-methanone | |
| 112 | 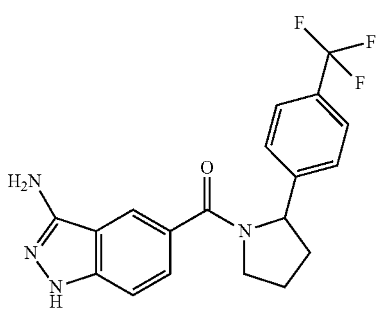 [SMILES: Nc1n[nH]c2ccc(C(=O)N3CCCC3c3ccc(C(F)(F)F)cc3)cc12] | 375 | 1.98 (A) | B | (3-Amino-1H-indazol-5-yl)-[2-(4-trifluoromethyl-phenyl)-pyrrolidin-1-yl]-methanone | 1H NMR (400 MHz, DMSO-d6, TE = 363 K) ppm = 11.35 (s, 1H), 8.00 (s, 1H), 7.64 (d, J = 8.2 Hz, 2H), 7.51 (d, J = 7.9 Hz, 2H), 7.39 (d, J = 8.4 Hz, 1H), 7.21 (d, J = 8.6 Hz, 1H), 5.40-5.24 (m, 1H), 5.19 (s, 2H), 3.95-3.82 (m, 1H), 3.75-3.61 (m, 1H), 2.49-2.37 (m, 1H), 2.03-1.71 (m, 3H). |
| 113 | 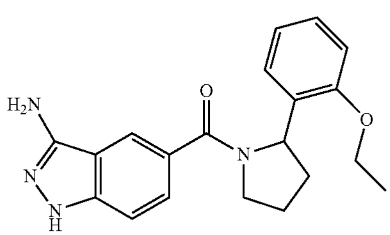 [SMILES: CCOc1ccccc1C1CCCN1C(=O)c1ccc2[nH]nc(N)c2c1] | 351 | 1.10 (F) | C | (3-Amino-1H-indazol-5-yl)-[2-(2-ethoxy-phenyl)-pyrrolidin-1-yl]-methanone | 1H NMR (300 Hz, DMSO-d6) ppm = 11.28 (s, 1H), 7.91 (s, 1H), 7.29 (s, 1H), 7.17-7.12 (m, 3H), 6.92-6.85 (m, 2H), 5.40-5.38 (m, 1H), 5.12 (s, 2H), 4.05-4.01 (m, 2H), 3.86-3.78 (m, 1H), 3.66-3.64 (m, 1H), 2.36-2.30 (m, 1H), 1.87-1.80 (m, 2H), 1.77-1.72 (m, 1H), 1.40-1.20 (m, 3H). |

TABLE 1-continued

| No. | Structure | [M + 1]+ | RT [min] (HPLC method) | IC50 [µM] | Chemical Name | NMR |
|---|---|---|---|---|---|---|
| 114 | 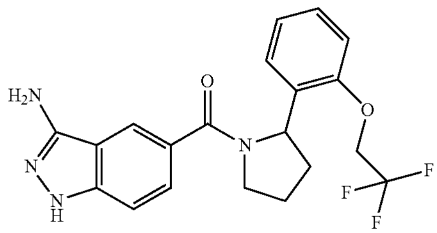 [SMILES: Nc1n[nH]c2ccc(C(=O)N3CCCC3c3ccccc3OCC(F)(F)F)cc12] | 405 | 1.23 (F) | C | (3-Amino-1H-indazol-5-yl)-{2-[2-(2,2,2-trifluoro-ethoxy)-phenyl]-pyrrolidin-1-yl}-methanone | 1H NMR (300 Hz, DMSO-d6) ppm = 11.32 (s, 1H), 7.95 (s, 1H), 7.42-7.30 (m, 1H), 7.29-7.12 (m, 3H), 7.10-6.99 (m, 2H), 5.49-5.38 (m, 1H), 5.25-5.05 (m, 2H), 4.81-4.55 (m, 2H), 3.92-3.75 (m, 1H), 3.72-3.55 (m, 1H), 2.40-2.30 (m, 1H), 1.92-1.65 (m, 3H). |
| 115 | 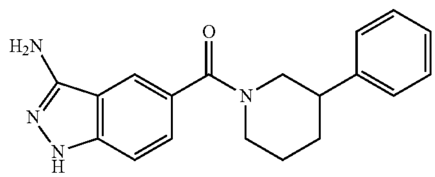 [SMILES: Nc1n[nH]c2ccc(C(=O)N3CCCC(c4ccccc4)C3)cc12] | 321 | 1.21 (J) | C | (3-Amino-1H-indazol-5-yl)-[3-(4-chloro-phenyl)-piperidin-1-yl]-methanone | 1H NMR (300 Hz, DMSO-d6) ppm = 11.33 (s, 1H), 7.82 (s, 1H), 7.33-7.25 (m, 6H), 5.17 (s, 2H), 4.16-4.12 (m, 2H), 3.10-3.03 (m, 1H), 2.95-2.90 (m, 1H), 2.83-2.76 (m, 1H), 2.10-1.88 (m, 1H), 1.88-1.50 (m, 3H). |
| 116 | 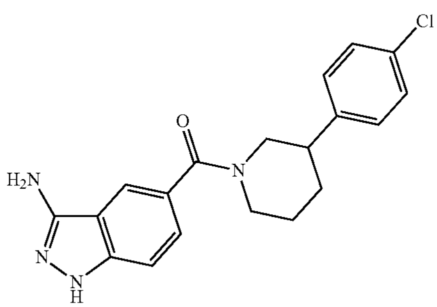 [SMILES: Nc1n[nH]c2ccc(C(=O)N3CCCC(c4ccc(Cl)cc4)C3)cc12] | 355 | 1.21 (F) | C | (3-Amino-1H-indazol-5-yl)-[3-(4-chloro-phenyl)-piperidin-1-yl]-methanone | 1H NMR (300 Hz, DMSO-d6) ppm = 11.33 (s, 1H), 7.82 (s, 1H), 7.33-7.25 (m, 6H), 5.17 (s, 2H), 4.16-4.12 (m, 2H), 3.10-3.03 (m, 1H), 2.95-2.90 (m, 1H), 2.83-2.76 (m, 1H), 2.10-1.88 (m, 1H), 1.88-1.50 (m, 3H). |
| 117 | 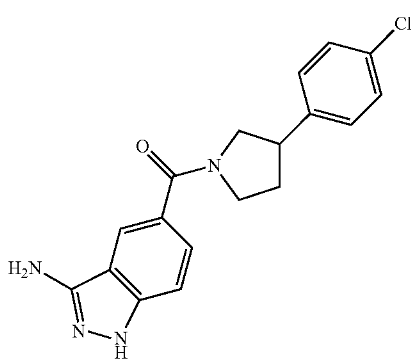 [SMILES: Nc1n[nH]c2ccc(C(=O)N3CCC(c4ccc(Cl)cc4)C3)cc12] | 341 | 1.15 (F) | B | (3-Amino-1H-indazol-5-yl)-[3-(4-chloro-phenyl)-pyrrolidin-1-yl]-methanone | 1H NMR (300 Hz, DMSO-d6) ppm = 11.33 (s, 1H), 7.96 (s, 1H), 7.45-7.21 (m, 6H), 5.19 (s, 2H), 3.94-3.89 (m, 1H), 3.89-3.63 (m, 2H), 3.59-3.41 (m, 2H), 3.38-3.28 (m, 1H), 2.03-1.96 (m, 1H). |
| 118 | 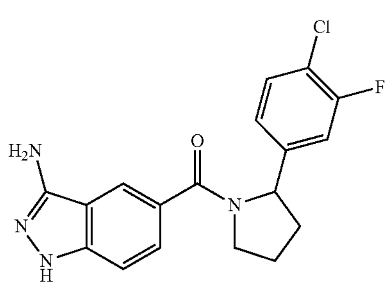 [SMILES: Nc1n[nH]c2ccc(C(=O)N3CCCC3c3ccc(Cl)c(F)c3)cc12] | 359 | 2.98 (F) | | (3-Amino-1H-indazol-5-yl)-[2-(4-chloro-3-fluoro-phenyl)-pyrrolidin-1-yl]-methanone | 1H NMR (300 Hz, DMSO-d6) ppm = 11.37 (s, 1H), 8.01 (s, 1H), 7.51-7.40 (m, 2H), 7.29-7.16 (m, 3H), 5.22 (s, 3H), 3.91-3.87 (m, 1H), 3.68-3.66 (m, 1H), 2.48-2.37 (m, 1H), 1.94-1.78 (m, 3H). |

TABLE 1-continued

| No. | Structure | [M + 1]+ | RT [min] (HPLC method) | IC50 [μM] | Chemical Name | NMR |
|---|---|---|---|---|---|---|
| 120 | 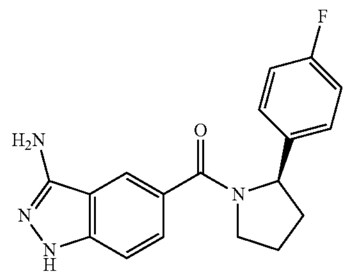 [SMILES: Nc1n[nH]c2ccc(C(=O)N3CCC[C@@H]3c3ccc(F)cc3)cc12] | 325 | 2.27 (B) | C | (3-Amino-1H-indazol-5-yl)-[(R)-2-(4-fluoro-phenyl)-pyrrolidin-1-yl]-methanone | 1H NMR (400 MHz, DMSO-d6, 363 K) ppm = 7.96 (s, 1H), 7.37 (d, J = 7.9 Hz, 1H), 7.32-7.23 (m, 2H), 7.19 (d, J = 8.6 Hz, 1H), 7.06 (t, J = 8.8 Hz, 2H), 5.32-5.07 (m, 1H), 3.95-3.77 (m, 1H), 3.71-3.57 (m, 1H), 2.44-2.27 (m, 1H), 2.01-1.69 (m, 3H). |
| 121 | 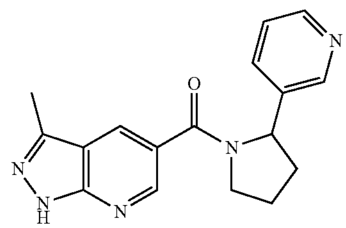 [SMILES: Cc1n[nH]c2ncc(C(=O)N3CCCC3c3cccnc3)cc12] | 308 | 1.65 (B) | | (3-Methyl-1H-pyrazolo[3,4-b]pyridin-5-yl)-(2-pyridin-3-yl-pyrrolidin-1-yl)-methanone | |
| 122 | 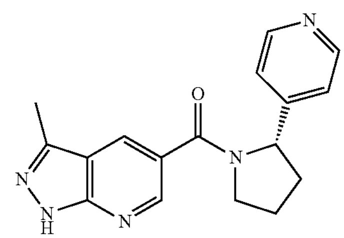 [SMILES: Cc1n[nH]c2ncc(C(=O)N3CCC[C@H]3c3ccncc3)cc12] | 308 | 0.90 (D) | C | (3-Methyl-1H-pyrazolo[3,4-b]pyridin-5-yl)-((S)-2-pyridin-4-yl-pyrrolidin-1-yl)-methanone | 1H NMR (400 MHz, DMSO-d6, 363 K) ppm = 13.12 (s, 1H), 8.58 (s, 1H), 8.46 (d, J = 5.4 Hz, 2H), 8.31 (s, 1H), 7.46-7.13 (m, 2H), 5.27-5.06 (m, 1H), 3.95-3.80 (m, 1H), 3.79-3.61 (m, 1H), 2.56-2.38 (m, 4H), 2.02-1.85 (m, 2H), 1.85-1.70 (m, 1H). |
| 123 | 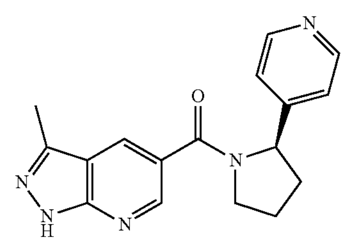 [SMILES: Cc1n[nH]c2ncc(C(=O)N3CCC[C@@H]3c3ccncc3)cc12] | 308 | 0.90 (D) | | (3-Methyl-1H-pyrazolo[3,4-b]pyridin-5-yl)-((R)-2-pyridin-4-yl-pyrrolidin-1-yl)-methanone | 1H NMR (400 MHz, DMSO-d6, 363 K) ppm = 13.12 (s, 1H), 8.58 (s, 1H), 8.46 (d, J = 5.5 Hz, 2H), 8.31 (s, 1H), 7.41-7.13 (m, 2H), 5.31-5.04 (m, 1H), 3.99-3.77 (m, 1H), 3.77-3.59 (m, 1H), 2.63-2.33 (m, 4H), 2.05-1.86 (m, 2H), 1.86-1.72 (m, 1H). |
| 124 | 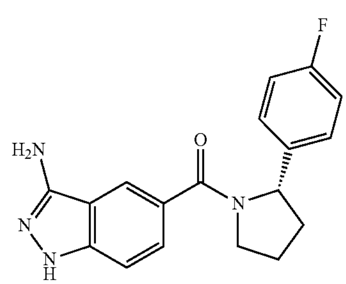 [SMILES: Nc1n[nH]c2ccc(C(=O)N3CCC[C@H]3c3ccc(F)cc3)cc12] | 325 | 2.27 (B) | B | (3-Amino-1H-indazol-5-yl)-[(S)-2-(4-fluoro-phenyl)-pyrrolidin-1-yl]-methanone | 1H NMR (400 MHz, DMSO-d6, 363 K) ppm = 7.97 (s, 1H), 7.37 (d, J = 8.5 Hz, 1H), 7.32-7.22 (m, 2H), 7.20 (d, J = 8.6 Hz, 1H), 7.06 (t, J = 8.8 Hz, 2H), 5.24-5.09 (m, 1H), 3.89-3.76 (m, 1H), 3.69-3.55 (m, 1H), 2.44-2.27 (m, 1H), 2.01-1.67 (m, 3H). |

TABLE 1-continued

| No. | Structure | [M + 1]+ | RT [min] (HPLC method) | IC50 [μM] | Chemical Name | NMR |
|---|---|---|---|---|---|---|
| 125 | 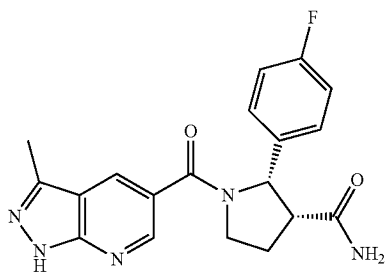 [SMILES: Cc1n[nH]c2ncc(C(=O)N3CC[C@@H](C(N)=O)[C@H]3c3ccc(F)cc3)cc12] | 368 | 1.33 (B) | | (2S,3R)-2-(4-Fluoro-phenyl)-1-(3-methyl-1H-pyrazolo[3,4-b]pyridine-5-carbonyl)-pyrrolidine-3-carboxylic acid amide | 1H NMR (400 MHz, 363 K, DMSO-d6) ppm = 13.13 (s, 1H), 8.59-8.28 (m, 1H), 7.35-7.08 (m, 2H), 7.09-6.96 (m, 3H), 5.65-5.21 (m, 1H), 4.18-3.93 (m, 1H), 3.80-3.61 (m, 1H), 3.36-3.24 (m, 1H), 2.46 (s, 3H), 2.39-2.26 (m, 1H), 2.05-1.94 (m, 1H). |
| 127 | 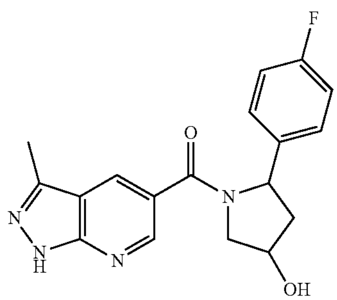 [SMILES: Cc1n[nH]c2ncc(C(=O)N3CC(O)CC3c3ccc(F)cc3)cc12] | 341 | 2.06 (B) | C | [2-(4-Fluoro-phenyl)-4-hydroxy-pyrrolidin-1-yl]-(3-methyl-1H-pyrazolo[3,4-b]pyridin-5-yl)-methanone | 1H NMR (400 MHz, DMSO-d, 363 K) ppm = 13.13 (s, 1H), 8.54 (s, 1H), 8.25 (s, 1H), 7.44-7.27 (m, 2H), 7.10-6.99 (m, 2H), 5.16 (t, J = 7.7 Hz, 1H), 4.90 (d, J = 4.1 Hz, 1H), 4.41-4.27 (m, 1H), 3.92-3.80 (m, 1H), 3.69 (dd, J = 10.8, 6.5 Hz, 1H), 2.64 (ddd, J = 14.2, 8.1, 6.4 Hz, 1H), 1.81 (dt, J = 12.8, 7.2 Hz, 1H). |
| 129 | 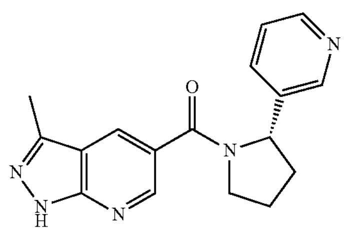 [SMILES: Cc1n[nH]c2ncc(C(=O)N3CCC[C@H]3c3cccnc3)cc12] | 308 | 1.65 (B) | C | (3-Methyl-1H-pyrazolo[3,4-b]pyridin-5-yl)-((S)-2-pyridin-3-yl-pyrrolidin-1-yl)-methanone | 1H NMR (400 MHz, DMSO-d6, 363 K) ppm = 13.14 (s, 1H), 8.75-8.46 (m, 2H), 8.42 (d, J = 3.6 Hz, 1H), 8.37-8.14 (m, 1H), 7.82-7.57 (m, 1H), 7.31 (dd, J = 7.8, 4.8 Hz, 1H), 5.22 (t, J = 6.6 Hz, 1H), 3.99-3.85 (m, 1H), 3.82-3.61 (m, 1H), 2.63-2.34 (m, 4H), 2.08-1.78 (m, 3H). |
| 130 | 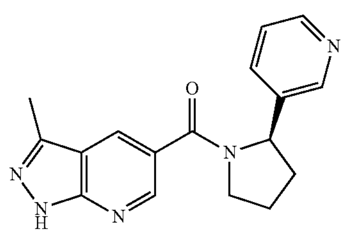 [SMILES: Cc1n[nH]c2ncc(C(=O)N3CCC[C@@H]3c3cccnc3)cc12] | 308 | 1.65 (B) | | (3-Methyl-1H-pyrazolo[3,4-b]pyridin-5-yl)-((R)-2-pyridin-3-yl-pyrrolidin-1-yl)-methanone | 1H NMR (400 MHz, DMSO-d6, 363 K) ppm = 13.14 (s, 1H), 8.65-8.46 (m, 2H), 8.42 (d, J = 3.5 Hz, 1H), 8.37-8.18 (m, 1H), 7.80-7.63 (m, 1H), 7.31 (dd, J = 7.7, 4.8 Hz, 1H), 5.22 (t, J = 6.7 Hz, 1H), 4.01-3.88 (m, 1H), 3.79-3.63 (m, 1H), 2.58-2.39 (m, 4H), 2.06-1.79 (m, 3H). |
| 131 | 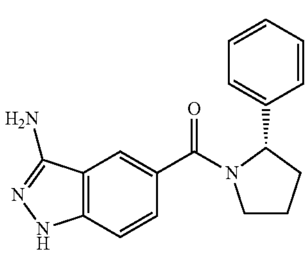 [SMILES: Nc1n[nH]c2ccc(C(=O)N3CCC[C@H]3c3ccccc3)cc12] | 307 | 0.88 (C) | C | (3-Amino-1H-indazol-5-yl)-((S)-2-phenyl-pyrrolidin-1-yl)-methanone | 1H NMR (400 MHz, DMSO-d6) ppm = 11.91-11.34 (m, 1H), 8.15-7.94 (m, 1H), 7.57-7.41 (m, 1H), 7.41-7.17 (m, 6H), 6.23-4.92 (m, 2H), 4.04-3.20 (m, 5H), 2.36-1.91 (m, 2H). |

TABLE 1-continued

| No. | Structure | [M + 1]⁺ | RT [min] (HPLC method) | IC50 [μM] | Chemical Name | NMR |
|---|---|---|---|---|---|---|
| 132 | 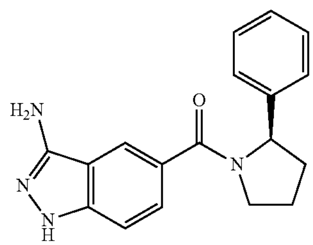 [SMILES: Nc1n[nH]c2ccc(C(=O)N3CCC[C@@H]3c3ccccc3)cc12] | 307 | 0.89 (C) | C | (3-Amino-1H-indazol-5-yl)-((R)-2-phenyl-pyrrolidin-1-yl)-methanone | 1H NMR (400 MHz, DMSO-d6) ppm = 11.90-11.30 (m, 1H), 8.15-7.94 (m, 1H), 7.55-7.41 (m, 1H), 7.40-7.17 (m, 6H), 6.02-5.30 (m, 2H), 4.04-3.25 (m, 5H), 2.40-1.91 (m, 2H). |
| 133 | 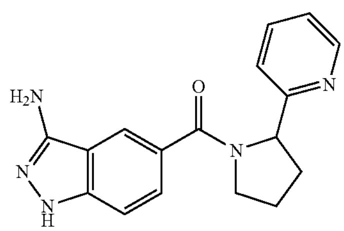 [SMILES: Nc1n[nH]c2ccc(C(=O)N3CCCC3c3ccccn3)cc12] | 308 | 1.64 (B) | | (3-Amino-1H-indazol-5-yl)-(2-pyridin-2-yl-pyrrolidin-1-yl)-methanone | 1H NMR (400 MHz, DMSO-d6-TFA Exchange) ppm = 8.93 (d, J = 5.9 Hz, 1H), 8.67-8.57 (m, 1H), 8.46 (s, 1H), 8.22 (d, J = 8.0 Hz, 1H), 8.05-7.94 (m, 2H), 7.61-7.54 (m, 1H), 5.53-5.39 (m, 1H), 4.17-4.01 (m, 1H), 3.86-3.68 (m, 1H), 2.71-2.52 (m, 1H), 2.16-1.96 (m, 3H). |
| 134 | 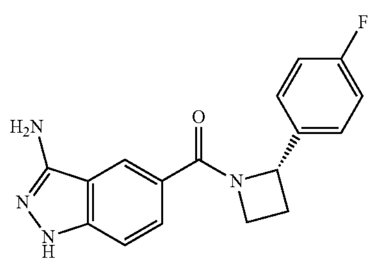 [SMILES: Nc1n[nH]c2ccc(C(=O)N3CC[C@H]3c3ccc(F)cc3)cc12] | 311 | 1.20 (D) | B | (3-Amino-1H-indazol-5-yl)-[(S)-2-(4-fluoro-phenyl)-azetidin-1-yl]-methanone | 1H NMR (400 MHz, T = 363 K, DMSO-d6) ppm = 11.39 (s, 1H), 8.09 (s, 1H), 7.51 (d, J = 8.6 Hz, 1H), 7.49-7.43 (m, 2H), 7.21 (d, J = 8.7 Hz, 1H), 7.18-7.09 (m, 2H), 5.58-5.50 (m, 1H), 5.25 (s, 2H), 4.59-4.45 (m, 1H), 4.22-4.11 (m, 1H), 2.85-2.71 (m, 1H), 2.22-2.10 (m, 1H). |
| 135 | 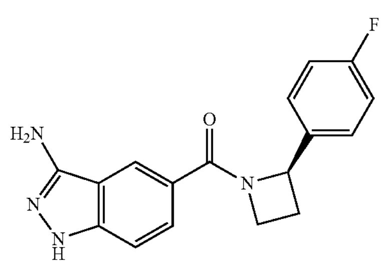 [SMILES: Nc1n[nH]c2ccc(C(=O)N3CC[C@@H]3c3ccc(F)cc3)cc12] | 311 | 1.20 (D) | C | (3-Amino-1H-indazol-5-yl)-[(R)-2-(4-fluoro-phenyl)-azetidin-1-yl]-methanone | 1H NMR (400 MHz, DMSO-d6) ppm = 11.60 (s, 1H), 8.26-8.06 (m, 1H), 7.67-7.35 (m, 3H), 7.35-7.01 (m, 3H), 5.66-5.38 (m, 3H), 4.86-4.37 (m, 1H), 4.30-4.04 (m, 1H), 2.92-2.68 (m, 1H), 2.22-2.04 (m, 1H). |
| 136 | 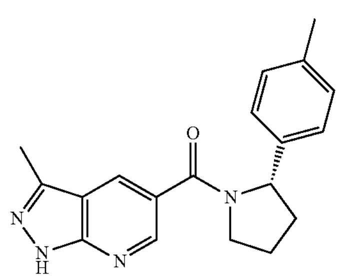 [SMILES: Cc1ccc([C@@H]2CCCN2C(=O)c2cnc3[nH]nc(C)c3c2)cc1] | 321 | 1.32 (D) | A | (3-Methyl-1H-pyrazolo[3,4-b]pyridin-5-yl)-((S)-2-p-tolyl-pyrrolidin-1-yl)-methanone | 1H NMR (400 MHz, T = 363 K, DMSO-d6) ppm = 13.10 (s, 1H), 8.52 (s, 1H), 8.17 (s, 1H), 7.11 (s, 4H), 5.20-5.05 (m, 1H), 3.93-3.80 (m, 1H), 3.78-3.65 (m, 1H), 2.47 (s, 3H), 2.28 (s, 3H), 2.43-2.33, 1.99-1.76 (2 × m, 4H). |

TABLE 1-continued

| No. | Structure | [M + 1]+ | RT [min] (HPLC method) | IC50 [μM] | Chemical Name | NMR |
|---|---|---|---|---|---|---|
| 137 | 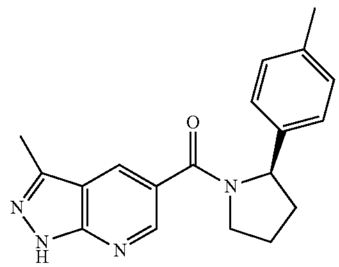 [SMILES: Cc1ccc([C@H]2CCCN2C(=O)c2cnc3[nH]nc(C)c3c2)cc1] | 321 | 1.32 (D) | D | (3-Methyl-1H-pyrazolo[3,4-b]pyridin-5-yl)-((R)-2-p-tolyl-pyrrolidin-1-yl)-methanone | 1H NMR (400 MHz, T = 363 K, DMSO-d6) ppm = 13.06 (s, 1H), 8.49 (s, 1H), 8.14 (s, 1H), 7.23-7.01 (m, 4H), 5.14-5.01 (m, 1H), 3.91-3.77 (m, 1H), 3.77-3.60 (m, 1H), 2.44 (s, 3H), 2.40-2.31 (m, 1H), 2.25 (s, 3H), 1.96-1.84, 1.84-1.72 (m, 1H). |
| 138 | 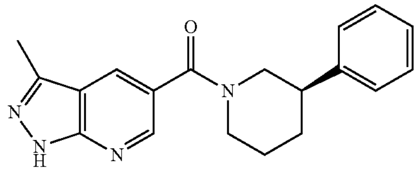 [SMILES: Cc1n[nH]c2ncc(C(=O)N3CCC[C@H](c4ccccc4)C3)cc12] | 321 | 1.33 (D) | | (3-Methyl-1H-pyrazolo[3,4-b]pyridin-5-yl)-((R)-3-phenyl-piperidin-1-yl)-methanone | 1H NMR (400 MHz, DMSO-d6) ppm = 13.40 (s, 1H), 8.55 (d, J = 1.9 Hz, 1H), 8.33 (d, J = 1.9 Hz, 1H), 7.46-7.09 (m, 5H), 4.82-4.29 (m, 1H), 3.92-3.47 (m, 1H), 3.27-2.74 (m, 3H), 2.53 (s, 3H), 2.03-1.92 (m, 1H), 1.87-1.71 (m, 2H), 1.71-1.54 (m, 1H). |
| 139 | 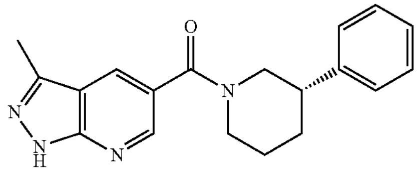 [SMILES: Cc1n[nH]c2ncc(C(=O)N3CCC[C@@H](c4ccccc4)C3)cc12] | 321 | 1.33 (D) | C | (3-Methyl-1H-pyrazolo[3,4-b]pyridin-5-yl)-((S)-3-phenyl-piperidin-1-yl)-methanone | 1H NMR (400 MHz, DMSO-d6) ppm = 13.40 (s, 1H), 8.55 (d, J = 1.9 Hz, 1H), 8.33 (d, J = 1.8 Hz, 1H), 7.47-7.05 (m, 5H), 4.74-4.33 (m, 1H), 3.95-3.46 (m, 1H), 3.27-2.74 (m, 3H), 2.53 (s, 3H), 2.04-1.92 (m, 1H), 1.87-1.70 (m, 2H), 1.70-1.54 (m, 1H). |
| 141 | 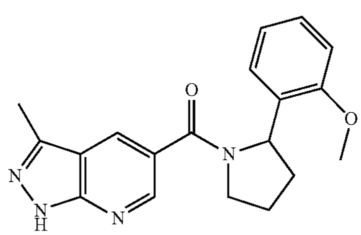 | 337 | 1.29 (D) | C | [2-(2-Methoxy-phenyl)-pyrrolidin-1-yl]-(3-methyl-1H-pyrazolo[3,4-b]pyridin-5-yl)-methanone | 1H NMR (400 MHz, DMSO-d6) ppm = 13.40, 13.24 (2 × s, 1H, ratio = 3:2 mixture of rotamers), 8.69, 8.54, 8.23, 7.83 (4 × s, 2H), 7.37-7.27, 7.27-7.08, 7.04-6.97, 6.97-6.89, 6.83-6.73 (5 × m, 4H), 5.52-5.38, 5.23-5.11 (2 × m, 1 H, ratio = 3:2 mixture of rotamers), 4.00-3.90, 3.84-3.76, 3.61-3.50 (3 × m, 2H), 3.86, 3.48 (2 × s, 3H), 2.56, 2.30 (2 × s, 3H), 2.38-2.20, 2.03-1.60 (2 × m, 4H). |
| 142 | 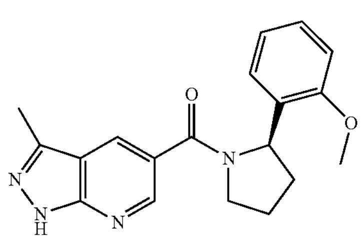 [SMILES: COc1ccccc1[C@H]1CCCN1C(=O)c1cnc2[nH]nc(C)c2c1] | 337 | 1.28 (D) | | [(R)-2-(2-Methoxy-phenyl)-pyrrolidin-1-yl]-(3-methyl-1H-pyrazolo[3,4-b]pyridin-5-yl)-methanone | 1H NMR (400 MHz, T = 363 K, DMSO-d6) ppm = 13.05 (s, 1H), 8.59-8.29 (m, 1H), 8.29-7.87 (m, 1H), 7.27-7.10 (m, 2H), 6.98-6.77 (m, 2H), 5.44-5.22 (m, 1H), 3.92-3.51 (m, 5H), 2.43 (s, 3H), 2.39-2.24, 1.95-1.85, 1.78-1.67 (3 × m, 4H). |

TABLE 1-continued

| No. | Structure | [M + 1]+ | RT [min] (HPLC method) | IC50 [µM] | Chemical Name | NMR |
|---|---|---|---|---|---|---|
| 143 | 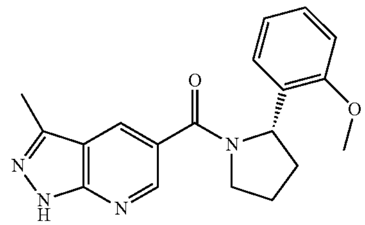 [SMILES: COc1ccccc1[C@@H]1CCCN1C(=O)c1cnc2[nH]nc(C)c2c1] | 337 | 1.28 (D) | B | [(S)-2-(2-Methoxy-phenyl)-pyrrolidin-1-yl]-(3-methyl-1H-pyrazolo[3,4-b]pyridin-5-yl)-methanone | 1H NMR (400 MHz, DMSO-d6) ppm = 13.42, 13.26 (2 × s, 1H, ratio 3:2 mixture of rotamers), 8.70, 8.55, 8.24, 7.84 (4 × s, 2H, ratio 3:2 mixture of rotamers), 7.49-7.28, 7.28-7.09, 7.09-6.99, 6.99-6.87, 6.87-6.66 (5 × m, 4H), 5.67-5.31, 5.31-5.02 (2 × m, 1H, ratio 3:2 mixture of rotamers), 4.05-3.67, 3.67-3.43 (2 × m + s, 5H), 2.57, 2.45-2.17 (1 × s + 1 × m + s, 4H), 2.07-1.55 (m, 3H). |
| 144 | 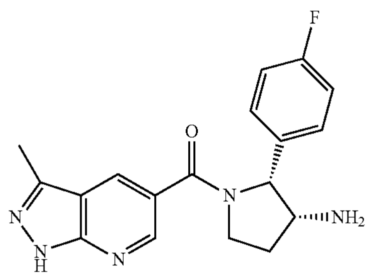 [SMILES: Cc1n[nH]c2ncc(C(=O)N3CC[C@@H](N)[C@H]3c3ccc(F)cc3)cc12] | 340 | 1.08 (A) | B | [(2R,3R)-3-Amino-2-(4-fluoro-phenyl)-pyrrolidin-1-yl]-(3-methyl-1H-pyrazolo[3,4-b]pyridin-5-yl)-methanone | 1H NMR (400 MHz, T = 363 K, DMSO-d6) ppm = 13.12 (s, 1H), 8.66-8.40 (m, 1H), 8.14 (s, 1H), 7.39-7.18 (m, 2H), 7.18-7.00 (m, 2H), 5.19-4.71 (m, 1H), 4.05-3.85 (m, 1H), 3.78-3.59 (m, 3H), 2.45 (s, 3H), 2.14-2.02 (m, 1H), 1.75-1.58 (m, 1H). |
| 145 | 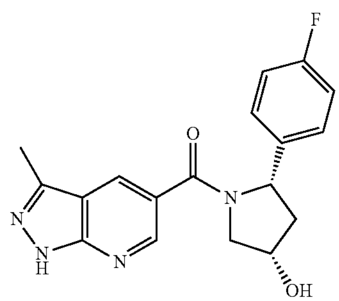 [SMILES: Cc1n[nH]c2ncc(C(=O)N3C[C@@H](O)C[C@H]3c3ccc(F)cc3)cc12] | 341 | 1.13 (D) | C | [(2S,4S)-2-(4-Fluoro-phenyl)-4-hydroxy-pyrrolidin-1-yl]-(3-methyl-1H-pyrazolo[3,4-b]pyridin-5-yl)-methanone | |
| 147 | 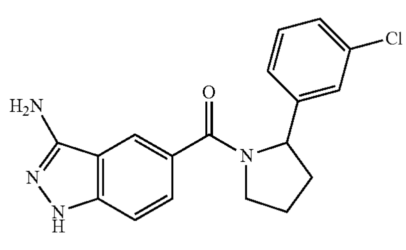 [SMILES: Nc1n[nH]c2ccc(C(=O)N3CCCC3c3cccc(Cl)c3)cc12] | 342 | 2.38 (B) | C | (3-Amino-1H-indazol-5-yl)-[2-(3-chloro-phenyl)-pyrrolidin-1-yl]-methanone | |
| 148 | 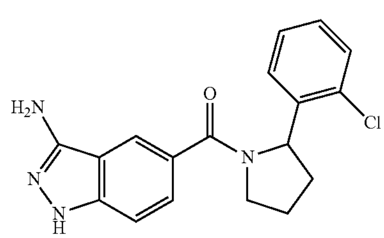 [SMILES: Nc1n[nH]c2ccc(C(=O)N3CCCC3c3ccccc3Cl)cc12] | 341 | 2.37 (B) | C | (3-Amino-1H-indazol-5-yl)-[2-(2-chloro-phenyl)-pyrrolidin-1-yl]-methanone | |

TABLE 1-continued

| No. | Structure | [M + 1]+ | RT [min] (HPLC method) | IC50 [μM] | Chemical Name | NMR |
|---|---|---|---|---|---|---|
| 149 | 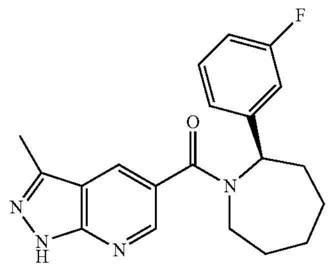 [SMILES: Cc1n[nH]c2ncc(C(=O)N3CCCCC[C@@H]3c3cccc(F)c3)cc12] | 353 | 1.40 (D) | | [(R)-2-(3-Fluoro-phenyl)-azepan-1-yl]-(3-methyl-1H-pyrazolo[3,4-b]pyridin-5-yl)-methanone | 1H NMR (400 MHz, DMSO-d6) ppm = 13.39, 13.34 (2 × s, 1H, ration 1:0, 8 mixture of rotamers), 8.51, 8.34, 8.18, 7.83 (4 × d, J = 1.7 Hz, 2H, ratio 1:0, 8 mixture of rotamers), 7.51-7.34, 7.24-7.19, 7.18-7.04, 6.97-6.88 (4 × m, 4H), 5.54-5.15, 5.15-4.73 (2 × dd, J = 11.0, 6.1 Hz, 1H, ration 1:0, 8 mixture of rotamers), 4.51-4.12, 4.12-3.76 (2 × d, J = 14.6 Hz, 1H, ratio 1:0, 8 mixture of rotamers), 3.45-3.25, 3.19-3.07 (2 × m + H2O, 1H), 2.55, 2.45-2.37 (1 × s, 1 × m, 4H), 2.02-1.21 (m, 7H). |
| 150 | 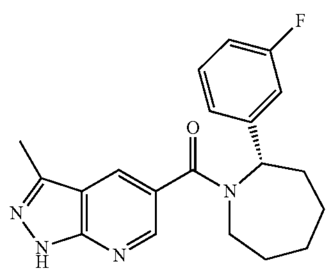 [SMILES: Cc1n[nH]c2ncc(C(=O)N3CCCCC[C@H]3c3cccc(F)c3)cc12] | 353 | 1.40 (D) | C | [(S)-2-(3-Fluoro-phenyl)-azepan-1-yl]-(3-methyl-1H-pyrazolo[3,4-b]pyridin-5-yl)-methanone | 1H NMR (400 MHz, DMSO-d6) ppm = 13.46-13.28 (m, 1H), 8.53-8.48, 8.36-8.32, 8.20-8.15, 7.85-7.80 (4 × m, 1H), 7.46-7.38 (m, 1H), 7.28-7.18 (m, 1H), 7.15-7.03 (m, 1H), 7.02-6.90 (m, 1H), 5.59-5.47, 4.77-4.67 (2 × m, 1H, ratio = 3:4 mixture of rotamers), 4.47-4.34, 3.82-3.69 (2 × m, 1H, ratio = 3:4 mixture of rotamers), 3.44-3.34, 3.16-3.07 (2 × m, 1H, ratio = 3:4 mixture of rotamers), 2.54, 2.44-2.29, 1.99-1.27 (1 × s, 2 × m, 11H). |
| 152 | 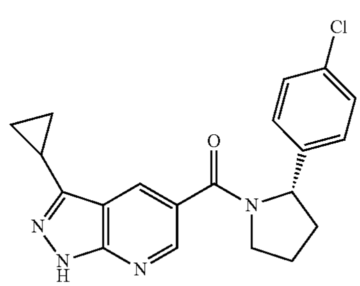 [SMILES: O=C(c1cnc2[nH]nc(C3CC3)c2c1)N1CCC[C@H]1c1ccc(Cl)cc1] | 367 | 1.41 (D) | A | [(S)-2-(4-Chloro-phenyl)-pyrrolidin-1-yl]-(3-cyclopropyl-1H-pyrazolo[3,4-b]pyridin-5-yl)-methanone | 1H NMR (400 MHz, T = 363 K, DMSO-d6) ppm = 13.08 (s, 1H), 8.62-8.47 (m, 1H), 8.34-8.08 (m, 1H), 7.38-7.22 (m, 4H), 5.21-5.07 (m, 1H), 3.94-3.82 (m, 1H), 3.80-3.66 (m, 1H), 2.47-2.36 (m, 1H), 2.35-2.19 (m, 1H), 2.01-1.87 (m, 2H), 1.87-1.76 (m, 1H), 1.06-0.97 (m, 2H), 0.97-0.86 (m, 2H). |

TABLE 1-continued

| No. | Structure | [M + 1]+ | RT [min] (HPLC method) | IC50 [μM] | Chemical Name | NMR |
|---|---|---|---|---|---|---|
| 153 | 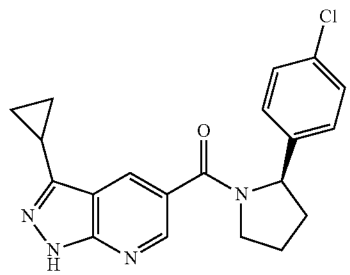 [SMILES: O=C(c1cnc2[nH]nc(C3CC3)c2c1)N1CCC[C@@H]1c1ccc(Cl)cc1] | 367 | 1.41 (D) | C | [(R)-2-(4-Chloro-phenyl)-pyrrolidin-1-yl]-(3-cyclopropyl-1H-pyrazolo[3,4-b]pyridin-5-yl)-methanone | 1H NMR (400 MHz, DMSO-d6) ppm = 13.37, 13.24 (2 × s, 1H) ratio 2, 5:1 mixture of rotamers, 8.71, 8.57, 8.29, 7.84 (4 × s, 2H) ratio 2, 5:1 mixture of rotamers, 7.58-7.21, 7.21-6.99 (2 × m, 4H), 5.34-5.09, 5.09-4.83 (2 × m, 1H) ratio 2, 5:1 mixture of rotamers, 4.05-3.90, 3.90-3.71, 3.71-3.48 (3 × m, 2H), 2.49-2.22, 2.20-2.02, 2.02-1.61 (3 × m, 5H), 1.19-0.62 (m, 4H). |
| 154 | 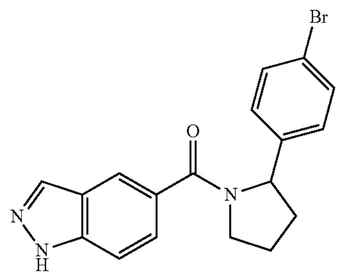 [SMILES: O=C(c1ccc2[nH]ncc2c1)N1CCCC1c1ccc(Br)cc1] | 370, 372 | 1.41 (D) | B | [2-(4-Bromo-phenyl)-pyrrolidin-1-yl]-(1H-indazol-5-yl)-methanone | 1H NMR (400 MHz, DMSO-d6, 363 K) ? 12.97 (s, 1H), 8.09 (s, 1H), 7.92 (s, 1H), 7.62-7.33 (m, 4H), 7.33-7.12 (m, 2H), 5.22-5.09 (m, 1H), 3.92-3.74 (m, 1H), 3.74-3.53 (m, 1H), 2.45-2.28 (m, 1H), 2.03-1.67 (m, 3H). |
| 155 | 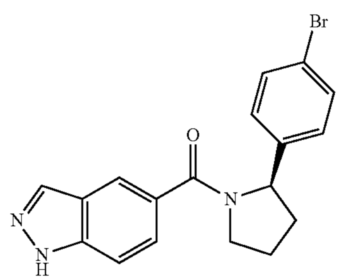 [SMILES: O=C(c1ccc2[nH]ncc2c1)N1CCC[C@@H]1c1ccc(Br)cc1] | 370, 372 | 1.39 (D) | | [(R)-2-(4-Bromo-phenyl)-pyrrolidin-1-yl]-(1H-indazol-5-yl)-methanone | 1H NMR (400 MHz, T = 363 K, DMSO-d6) ppm = 12.98 (s, 1H), 8.10 (s, 1H), 7.93 (s, 1H), 7.56-7.40 (m, 4H), 7.29-7.17 (m, 2H), 5.20-5.10 (m, 1H), 3.88-3.77 (m, 1H), 3.72-3.60 (m, 1H), 2.47-2.35 (m, 1H), 1.96-1.73 (m, 3H). |
| 156 | 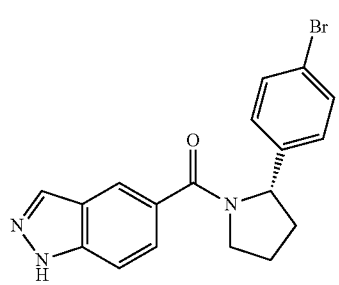 [SMILES: O=C(c1ccc2[nH]ncc2c1)N1CCC[C@H]1c1ccc(Br)cc1] | 370, 372 | 1.39 (D) | B | [(S)-2-(4-Bromo-phenyl)-pyrrolidin-1-yl]-(1H-indazol-5-yl)-methanone | 1H NMR (400 MHz, T = 363 K, DMSO-d6) ppm = 12.98 (s, 1H), 8.09 (s, 1H), 7.93 (s, 1H), 7.59-7.36 (m, 4H), 7.34-7.13 (m, 2H), 5.21-5.10 (m, 1H), 3.89-3.77 (m, 1H), 3.72-3.57 (m, 1H), 2.47-2.35 (m, 1H), 1.85 (dtd, J = 40.4, 12.7, 6.8 Hz, 3H). |

TABLE 1-continued

| No. | Structure | [M + 1]+ | RT [min] (HPLC method) | IC50 [μM] | Chemical Name | NMR |
|---|---|---|---|---|---|---|
| 157 | 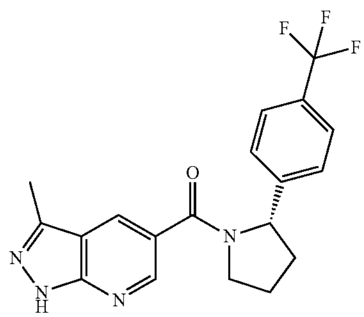 [SMILES: Cc1n[nH]c2ncc(C(=O)N3CCC[C@H]3c3ccc(C(F)(F)F)cc3)cc12] | 375 | 1.39 (D) | A | (3-Methyl-1H-pyrazolo[3,4-b]pyridin-5-yl)-[(S)-2-(4-trifluoromethyl-phenyl)-pyrrolidin-1-yl]-methanone | 1H NMR (400 MHz, DMSO-d6) ppm = 13.43, 13.25 (2 × s, 1H, ratio = 3:1 mixture of rotamers), 8.78-8.67, 8.60-8.51, 8.31-8.21, 7.87-7.78 (4 × m, 2H), 7.75-7.67, 7.67-7.60, 7.60-7.49, 7.32-7.19 (4 × m, 4H), 5.29-5.19, 5.15-5.05 (2 × m, 1H, ratio = 3:1 mixture of rotamers), 4.04-3.94, 3.90-3.78, 3.67-3.57 (3 × m, 2H), 2.55 (s, 3H), 2.50-2.37, 2.35-2.24, 2.05-1.68 (3 × m, 4H). |
| 158 | 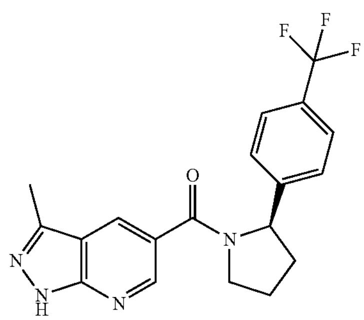 [SMILES: Cc1n[nH]c2ncc(C(=O)N3CCC[C@@H]3c3ccc(C(F)(F)F)cc3)cc12] | 375 | 1.39 (D) | | (3-Methyl-1H-pyrazolo[3,4-b]pyridin-5-yl)-[(R)-2-(4-trifluoromethyl-phenyl)-pyrrolidin-1-yl]-methanone | 1H NMR (400 MHz, T = 363 K, DMSO-d6) ppm = 13.15 (s, 1H), 8.68-8.51 (m, 1H), 8.42-8.12 (m, 1H), 7.70-7.59 (m, 2H), 7.59-7.45 (m, 2H), 5.31-5.21 (m, 1H), 3.97-3.88 (m, 1H), 3.78-3.67 (m, 1H), 2.57-2.41 (m, 1H), 2.02-1.90 (m, 2H), 1.84 (dq, J = 12.6, 6.9, 6.4 Hz, 1H). |
| 159 | 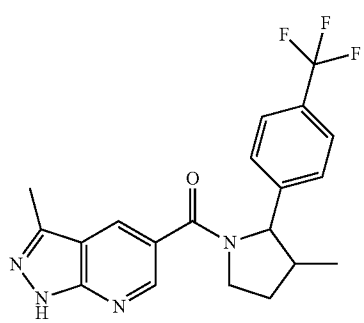 [SMILES: Cc1n[nH]c2ncc(C(=O)N3CCC(C)C3c3ccc(C(F)(F)F)cc3)cc12] | 389 | 2.68 (B) | B | (3-Methyl-1H-pyrazolo[3,4-b]pyridin-5-yl)-[3-methyl-2-(4-trifluoromethyl-phenyl)-pyrrolidin-1-yl]-methanone | |
| 160 | 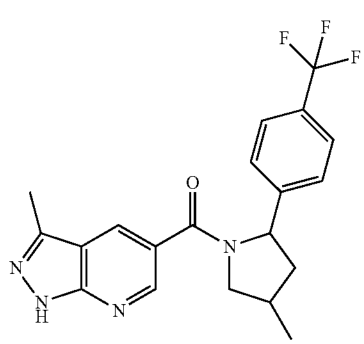 [SMILES: Cc1n[nH]c2ncc(C(=O)N3CC(C)CC3c3ccc(C(F)(F)F)cc3)cc12] | 389 | 1.45 (D) | C | (3-Methyl-1H-pyrazolo[3,4-b]pyridin-5-yl)-[4-methyl-2-(4-trifluoromethyl-phenyl)-pyrrolidin-1-yl]-methanone | 1H NMR (400 MHz, DMSO-d6, 363 K) ppm = 13.16 (s, 1H), 8.63 (s, 1H), 8.34 (s, 1H), 7.76-7.28 (m, 4H), 5.27-5.11 (m, 1H), 3.92-3.69 (m, 1H), 3.69-3.47 (m, 1H), 2.68-2.58 (m, 1H), 2.53 (s, 3H), 2.40-2.25 (m, 1H), 1.58-1.41 (m, 1H), 1.05 (d, J = 6.4 Hz, 3H). |

TABLE 1-continued

| No. | Structure | [M + 1]+ | RT [min] (HPLC method) | IC50 [μM] | Chemical Name | NMR |
|---|---|---|---|---|---|---|
| 162 | 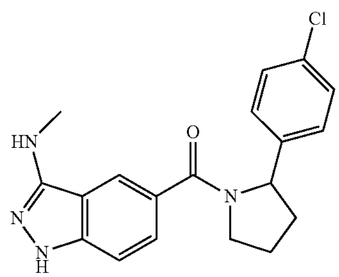 [SMILES: CNc1n[nH]c2ccc(C(=O)N3CCCC3c3ccc(Cl)cc3)cc12] | 405 | 3.43 (F) | C | (3-Methyl-1H-pyrazolo[3,4-b]pyridin-5-yl)-{2-[2-(2,2,2-trifluoro-ethoxy)-phenyl]-pyrrolidin-1-yl}-methanone | 1 H NMR (300 Hz, DMSO-d6) ppm = 13.09 (s, 1H), 8.51 (s, 1H), 8.22 (s, 1H), 7.26-7.19 (m, 2H), 7.04-6.99 (m, 2H), 5.36 (s, 1H), 4.70-4.60 (m, 2H), 3.84-3.80 (m, 1H), 3.69 (s, 1H), 2.48 (s, 3H), 2.38-2.32 (m, 1H), 1.91-1.76 (m, 3H). |
| 164 | 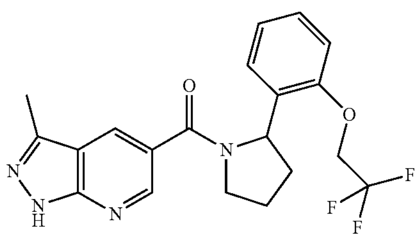 [SMILES: Cc1n[nH]c2ncc(C(=O)N3CCCC3c3ccccc3OCC(F)(F)F)cc12] | 355 | | | [2-(4-Chloro-phenyl)-pyrrolidin-1-yl]-(3-methylamino-1H-indazol-5-yl)-methanone | |
| 165 | 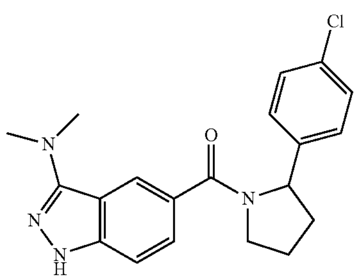 [SMILES: CN(C)c1n[nH]c2ccc(C(=O)N3CCCC3c3ccc(Cl)cc3)cc12] | 369 | | | [2-(4-Chloro-phenyl)-pyrrolidin-1-yl]-(3-dimethylamino-1H-indazol-5-yl)-methanone | |
| 166 | 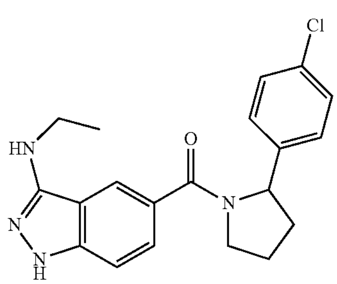 [SMILES: CCNc1n[nH]c2ccc(C(=O)N3CCCC3c3ccc(Cl)cc3)cc12] | 369 | | | [2-(4-Chloro-phenyl)-pyrrolidin-1-yl]-(3-ethylamino-1H-indazol-5-yl)-methanone | |
| 167 | 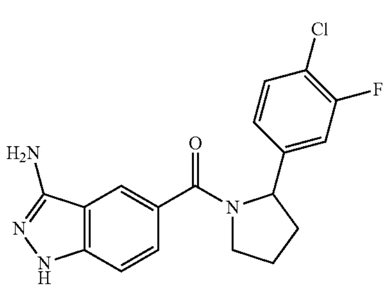 [SMILES: Nc1n[nH]c2ccc(C(=O)N3CCCC3c3ccc(Cl)c(F)c3)cc12] | 359 | 2.98 (F) | B | (3-Amino-1H-indazol-5-yl)-[2-(4-chloro-3-fluoro-phenyl)-pyrrolidin-1-yl] methanone | 1H NMR (300 Hz, DMSO-d6) ppm = 11.37 (s, 1H), 8.01 (s, 1H), 7.51-7.40 (m, 2H), 7.29-7.16 (m, 3H), 5.22 (s, 3H), 3.91-3.87 (m, 1H), 3.68-3.66 (m, 1H), 2.48-2.37 (m, 1H), 1.94-1.78 (m, 3H). |

TABLE 1-continued

| No. | Structure | [M + 1]⁺ | RT [min] (HPLC method) | IC50 [μM] | Chemical Name | NMR |
|---|---|---|---|---|---|---|
| 168 | 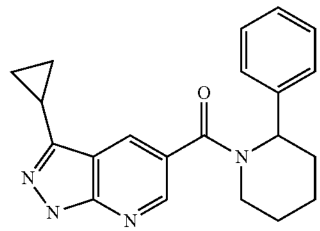 [SMILES: O=C(c1cnc2[nH]nc(C3CC3)c2c1)N1CCCCC1c1ccccc1] | 347 | 1.43 (D) | C | (3-Cyclopropyl-1H-pyrazolo[3,4-b]pyridin-5-yl)-(2-phenyl-piperidin-1-yl)-methanone | 1H NMR (400 MHz, DMSO-d6, TFA-Exchange) chemische Verschiebung 8.60 (d, J = 1.5 Hz, 1H), 8.39 (s, 1H) 7.41-7.28 (m, 4H), 7.22 (t, J = 7.1 Hz, 1H), 5.74-5.36 (m, 1H), 4.14-3.69 (m, 1H), 2.99-2.86 (m, 1H), 2.45-2.22 (m, 2H), 2.03-1.86 (m, 1H), 1.70-1.47 (m, 3H), 1.46-1.32 (m, 1H), 1.05-0.86 (m, 4H). |
| 169 | 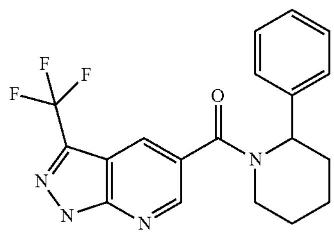 [SMILES: O=C(c1cnc2[nH]nc(C(F)(F)F)c2c1)N1CCCCC1c1ccccc1] | 375 | 2.30 (A) | C | (2-Phenyl-piperidin-1-yl)-(3-trifluoromethyl-1H-pyrazolo[3,4-b]pyridin-5-yl)-methanone | 1H NMR (400 MHz, T = 363 K, DMSO-d6) ? 14.55 (s, 1H), 8.73 (d, J = 1.9 Hz, 1H), 8.29-8.24 (m, 1H), 7.44-7.33 (m, 4H), 7.30-7.22 (m, 1H), 5.57-5.39 (m, 1H), 4.02-3.89 (m, 1H), 3.17-2.84 (1 × m + HDO, 1H), 2.40-2.28 (m, 1H), 2.06-1.91 (m, 1H), 1.73-1.39 (m, 4H). |
| 170 | 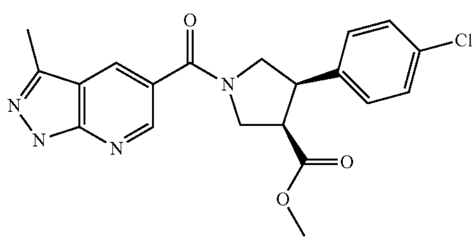 [SMILES: COC(=O)[C@H]1CN(C(=O)c2cnc3[nH]nc(C)c3c2)C[C@H]1c1ccc(Cl)cc1] | 399 | 1.00 (C) | | trans (+/−) 4-(4-Chloro-phenyl)-1-(3-methyl-1H-pyrazolo[3,4-b]pyridine-5-carbonyl)-pyrrolidine-3-carboxylic acid methyl ester | 1H NMR (500 MHz, DMSO-d6) ppm = 13.44-13.36 (m, 1H), 8.68-8.64 (m, 1H), 8.49-8.38 (m, 1H), 7.47-7.31 (m, 4H), 4.10-3.97 (m, 1H), 3.97-3.38 (m, 8H), 2.56-2.49 (m, 3H). |
| 171 | 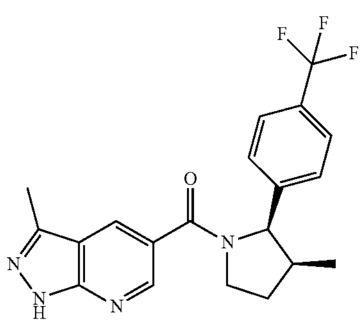 [SMILES: Cc1n[nH]c2ncc(C(=O)N3CC[C@H](C)[C@@H]3c3ccc(C(F)(F)F)cc3)cc12] | 389 | 1.43 (D) | B | (3-Methyl-1H-pyrazolo[3,4-b]pyridin-5-yl)-[(2S,3S)-3-methyl-2-(4-trifluoromethyl-phenyl)-pyrrolidin-1-yl]-methanone | 1H NMR (500 MHz, DMSO-d6) ppm = 13.47-13.16 (m, 1H), 8.73-8.19 (m, 2H), 7.80-7.14 (m, 4H), 4.59 (d, J = 7.9 Hz, 1H), 4.16-3.92 (m, 1H), 3.84-3.59 (m, 1H), 2.55 (s, 3H), 2.46-2.24 (m, 1H), 2.18-1.98 (m, 2H), 1.15-1.00 (m, 3H). |
| 172 | 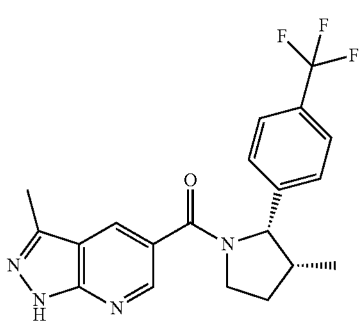 [SMILES: Cc1n[nH]c2ncc(C(=O)N3CC[C@@H](C)[C@H]3c3ccc(C(F)(F)F)cc3)cc12] | 389 | 1.42 (D) | A | (3-Methyl-1H-pyrazolo[3,4-b]pyridin-5-yl)-[(2S,3R)-3-methyl-2-(4-trifluoromethyl-phenyl)-pyrrolidin-1-yl]-methanone | 1H NMR (500 MHz, DMSO-d6) ppm = 13.42-13.23 (m, 1H), 8.72-8.18 (m, 2H), 7.73-7.20 (m, 4H), 5.32-4.88 (m, 1H), 4.06-3.54 (m, 2H), 2.66-2.52 (m, 3H), 2.25 (s, 1H), 2.12-1.98 (m, 1H), 1.72-1.57 (m, 1H), 0.65-0.52 (m, 3H). |

| No. | Structure | [M + 1]⁺ | RT [min] (HPLC method) | IC50 [µM] | Chemical Name | NMR |
|---|---|---|---|---|---|---|
| 173 | 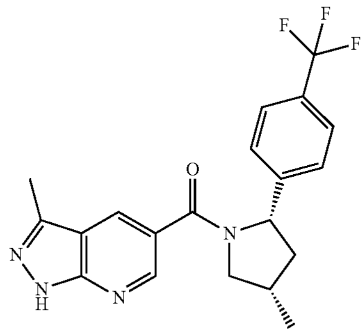 [SMILES: Cc1n[nH]c2ncc(C(=O)N3C[C@@H](C)C[C@H]3c3ccc(C(F)(F)F)cc3)cc12] | 389 | 1.42 (D) | C | (3-Methyl-1H-pyrazolo[3,4-b]pyridin-5-yl)-[(2R,3S)-3-methyl-2-(4-trifluoromethyl-phenyl)-pyrrolidin-1-yl]-methanone | 1H NMR (500 MHz, DMSO-d6) ppm = 13.44-13.23 (m, 1H), 8.70-8.16 (m, 2H), 7.73-7.18 (m, 4H), 5.34-4.88 (m, 1H), 4.04-3.55 (m, 2H), 2.68-2.52 (m, 3H), 2.25 (s, 1H), 2.13-1.97 (m, 1H), 1.71-1.56 (m, 1H), 0.64-0.51 (m, 3H). |
| 174 | 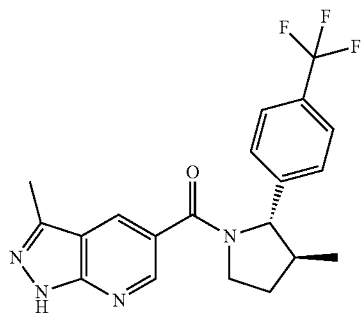 [SMILES: Cc1n[nH]c2ncc(C(=O)N3CC[C@H](C)[C@H]3c3ccc(C(F)(F)F)cc3)cc12] | 389 | 2.19 (A) | C | (3-Methyl-1H-pyrazolo[3,4-b]pyridin-5-yl)-[(2S,4S)-4-methyl-2-(4-trifluoromethyl-phenyl)-pyrrolidin-1-yl]-methanone | no NMR |
| 175 | 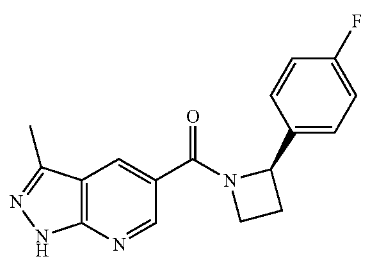 [SMILES: Cc1n[nH]c2ncc(C(=O)N3CC[C@@H]3c3ccc(F)cc3)cc12] | 311 | 1.78 (A) | C | [(R)-2-(4-Fluoro-phenyl)-azetidin-1-yl]-(3-methyl-1H-pyrazolo[3,4-b]pyridin-5-yl)-methanone | 1H NMR (400 MHz, DMSO-d6) ppm = 13.16 (s, 1H), 8.65 (s, 1H), 8.27 (s, 1H), 7.54-7.40 (m, 2H), 7.21-7.03 (m, 2H), 5.55 (dd, J = 8.8, 6.0 Hz, 1H), 4.54-4.44 (m, 1H), 4.20 (td, J = 9.1, 6.4 Hz, 1H), 2.84-2.72 (m, 1H), 2.47 (s, 3H), 2.22-2.08 (m, 1H). |
| 176 | 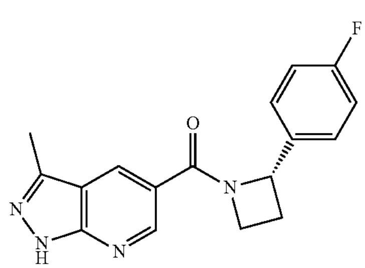 [SMILES: Cc1n[nH]c2ncc(C(=O)N3CC[C@H]3c3ccc(F)cc3)cc12] | 311 | 1.79 (A) | B | [(S)-2-(4-Fluoro-phenyl)-azetidin-1-yl]-(3-methyl-1H-pyrazolo[3,4-b]pyridin-5-yl)-methanone | 1H NMR (400 MHz, T = 363 K, DMSO-d6) ? 13.15 (s, 1H), 8.65 (s, 1H), 8.27 (s, 1H), 7.57-7.37 (m, 2H), 7.24-7.00 (m, 2H), 5.55 (dd, J = 8.8, 6.0 Hz, 1H), 4.62-4.38 (m, 1H), 4.32-4.08 (m, 1H), 2.87-2.71 (m, 1H), 2.47 (s, 3H), 2.25-2.07 (m, 1H). |

TABLE 1-continued

| No. | Structure | [M + 1]⁺ | RT [min] (HPLC method) | IC50 [μM] | Chemical Name | NMR |
|---|---|---|---|---|---|---|
| 177 | 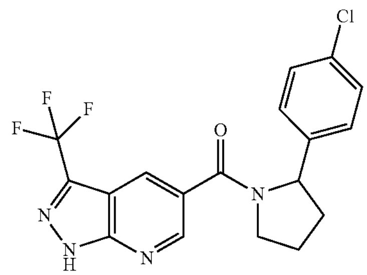 [SMILES: O=C(c1cnc2[nH]nc(C(F)(F)F)c2c1)N1CCCC1c1ccc(Cl)cc1] | 395 | 2.26 (A) | B | [2-(4-Chloro-phenyl)-pyrrolidin-1-yl]-(3-trifluoromethyl-1H-pyrazolo[3,4-b]pyridin-5-yl)-methanone | 1H NMR (400 MHz, DMSO-d6) ppm = 8.90, 8.55, 8.49, 7.84 (4 × s, 2H, ratio = 2:3 mixture of rotamers), 7.46, 7.38, 7.23, 7.02 (2 × d, J = 8.2 Hz, 2 × d, J = 7.7 Hz, 4H, ratio = 2:3 mixture of rotamers), 5.23-5.10, 4.98-4.87 (2 × m, 1H, ratio = 2:3 mixture of rotamers), 3.97-3.76, 3.66-3.24 (1 × m, 1 × m + HDO, 2H), 2.46-2.30 (m, 1H), 2.03-1.68 (m, 3H). |
| 178 | 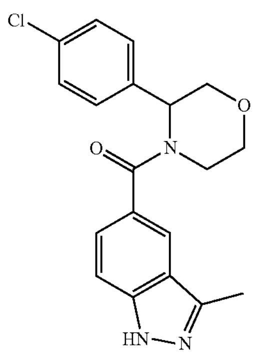 [SMILES: Cc1n[nH]c2ccc(C(=O)N3CCOCC3c3ccc(Cl)cc3)cc12] | 356/358 | 2.71 (L) | A | [3-(4-Chloro-phenyl)-morpholin-4-yl]-(3-methyl-1H-indazol-5-yl)-methanone | 1H NMR (500 MHz, CD3OD) ppm = 7.86-7.85 (m, 1H), 7.60-7.51 (m, 3H), 7.47-7.40 (m, 3H), 5.70-5.40 (bs, 1H), 4.49 (d, J = 12.4 Hz, 1H), 4.00-4.64 (bs, 1H), 4.00 (dd, J = 12.4, 3.6 Hz, 1H), 3.94-3.83 (m, 1H), 3.73-3.64 (m, 1H), 3.39-3.30 (m, 1H), 2.56 (s, 3H). |
| 179 | 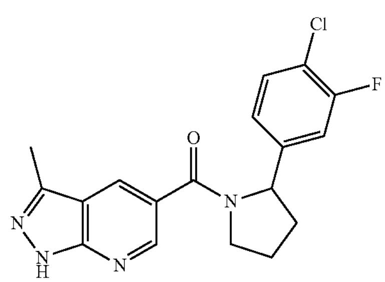 [SMILES: Cc1n[nH]c2ncc(C(=O)N3CCCC3c3ccc(Cl)c(F)c3)cc12] | 359 | 1.88 (J) | B | [2-(4-Chloro-3-fluoro-phenyl)-pyrrolidin-1-yl]-(3-methyl-1H-pyrazolo[3,4-b]pyridin-5-yl)-methanone | 1H NMR (300 MHz, DMSO-d6) ppm = 13.14 (s, 1H), 8.60 (s, 1H), 8.33 (s, 1H), 7.51-7.46 (m, 1H), 7.36-7.20 (m, 2H), 5.20-5.18 (m, 1H), 3.95-3.89 (m, 1H), 3.80-3.60 (m, 1H), 2.60-2.50 (m, 3H), 2.47-2.35 (m, 1H), 1.99-1.80 (m, 3H). |
| 180 | 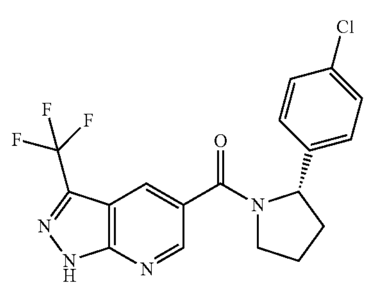 | 395 | 2.26 (A) | A | [(S)-2-(4-Chloro-phenyl)-pyrrolidin-1-yl]-(3-trifluoromethyl-1H-pyrazolo[3,4-b]pyridin-5-yl)-methanone | 1H NMR (400 MHz, DMSO-d6) ppm = 14.80 (s, 1H), 8.91, 8.56, 8.49, 7.86 (4 × s, 2H, ratio = 1:2 mixture of rotamers), 7.52-7.43, 7.43-7.34, 7.27-7.19, 7.09-6.97 (4 × m, 4H, ratio = 1:2 mixture of rotamers), 5.20-5.12, 5.00-4.85 (2 × m, 1H, ratio = 1:2), 3.98-3.76, 3.67-3.52 (2 × m, 2H), 2.46-2.31 (m, 1H), 2.04-1.69 (m, 3H). |

TABLE 1-continued

| No. | Structure | [M + 1]+ | RT [min] (HPLC method) | IC50 [μM] | Chemical Name | NMR |
|---|---|---|---|---|---|---|
| 181 | 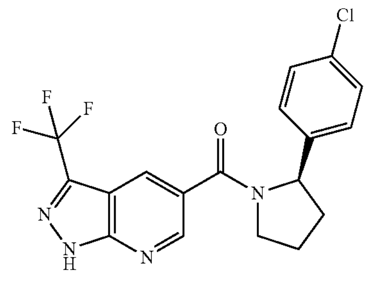 [SMILES: O=C(c1cnc2[nH]nc(C(F)(F)F)c2c1)N1CCC[C@@H]1c1ccc(Cl)cc1] | 395 | 2.26 (A) | C | [(R)-2-(4-Chloro-phenyl)-pyrrolidin-1-yl]-(3-trifluoromethyl-1H-pyrazolo[3,4-b]pyridin-5-yl)-methanone | 1H NMR (400 MHz, DMSO-d6) ppm = 14.78 (s, 1H), 8.91, 8.56, 8.49, 7.85 (4 × s, 2H, ratio = 2:1 mixture of rotamers), 7.55-7.44, 7.44-7.32, 7.32-7.18, 7.08-6.95 (4 × m, 4H, ratio = 2:1), 5.22-5.11, 4.99-4.84 (2 × m, 1H, ratio = 2:1 mixture of rotamers), 3.99-3.78, 3.66-3.52 (2 × m, 2H), 2.45-2.30 (m, 1H), 2.03-1.70 (m, 3H). |
| 182 | 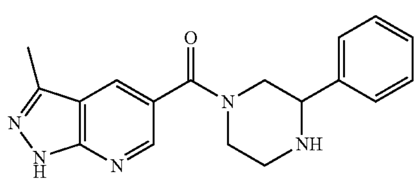 [SMILES: Cc1n[nH]c2ncc(C(=O)N3CCNC(c4ccccc4)C3)cc12] | 322 | 1.19 (A) | D | (3-Methyl-1H-pyrazolo[3,4-b]pyridin-5-yl)-(3-phenyl-piperazin-1-yl)-methanone | 1H NMR (400 MHz, DMSO-d6, 90° C.) ppm = 10.13-9.69 (m, 2H), 8.60 (d, J = 2.0 Hz, 1H), 8.34 (d, J = 2.0 Hz, 1H), 7.65-7.58 (m, 2H), 7.49-7.39 (m, 3H), 4.57-4.50 (m, 1H), 4.33-4.18 (m, 2H), 3.58-3.15 (m, 4H), 2.52 (s, 3H). |
| 183 | 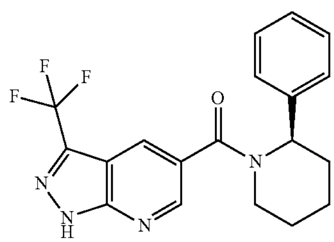 [SMILES: O=C(c1cnc2[nH]nc(C(F)(F)F)c2c1)N1CCCC[C@@H]1c1ccccc1] | 375 | 2.30 (A) | C | ((R)-2-Phenyl-piperidin-1-yl)-(3-trifluoromethyl-1H-pyrazolo[3,4-b]pyridin-5-yl)-methanone | 1H NMR (400 MHz, DMSO-d6) ppm = 8.76 (s, 1H), 8.36 (s, 1H), 7.45-7.32 (m, 4H), 7.28 (t, J = 7.2 Hz, 1H), 6.01-5.19 (m, 1H), 4.62-3.88 (m, 1H), 3.06-2.80 (m, 1H), 2.46-2.34 (m, 1H), 2.06-1.90 (m, 1H), 1.69-1.50 (m, 3H), 1.47-1.29 (m, 1H). |
| 184 | 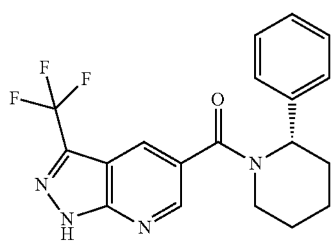 [SMILES: O=C(c1cnc2[nH]nc(C(F)(F)F)c2c1)N1CCCC[C@H]1c1ccccc1] | 375 | 2.30 (A) | C | ((S)-2-Phenyl-piperidin-1-yl)-(3-trifluoromethyl-1H-pyrazolo[3,4-b]pyridin-5-yl)-methanone | 1H NMR (400 MHz, DMSO-d6) ppm = 14.84 (s, 1H), 8.79 (s, 1H), 8.39 (s, 1H), 7.46-7.34 (m, 4H), 7.29 (t, J = 7.1 Hz, 1H), 6.04-5.11 (m, 1H), 4.28-3.60 (m, 1H), 2.98-2.85 (m, 1H), 2.42 (d, J = 14.0 Hz, 1H), 2.05-1.93 (m, 1H), 1.70-1.49 (m, 3H), 1.47-1.33 (m, 1H). |
| 185 | 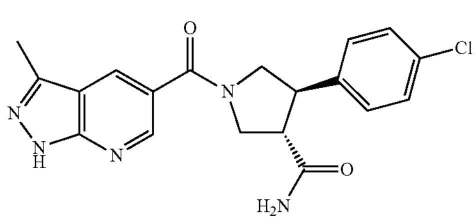 [SMILES: Cc1n[nH]c2ncc(C(=O)N3C[C@@H](C(N)=O)[C@H](c4ccc(Cl)cc4)C3)cc12] | 348.1 | 2.10 (B) | D | (3S,4R)-4-(4-Chloro-phenyl)-1-(3-methyl-1H-pyrazolo[3,4-b]pyridine-5-carbonyl)-pyrrolidine-3-carboxylic acid amide | 1H NMR (500 MHz, DMSO-d6) ppm = 13.52-13.26 (m, 1H), 8.67 (d, J = 2.0 Hz, 1H), 8.48-8.41 (m, 1H), 7.54-7.30 (m, 5H), 7.02-6.93 (m, 1H), 4.08-3.53 (m, 5H), 3.25-3.06 (m, 1H), 2.56-2.49 (m, 3H). |

TABLE 1-continued

| No. | Structure | [M + 1]+ | RT [min] (HPLC method) | IC50 [μM] | Chemical Name | NMR |
|---|---|---|---|---|---|---|
| 186 | 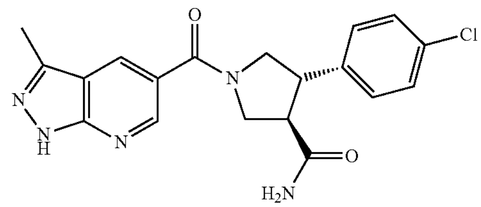 | 384.1 | 2.10 (B) | C | (3R,4S)-4-(4-Chloro-phenyl)-1-(3-methyl-1H-pyrazolo[3,4-b]pyridine-5-carbonyl)-pyrrolidine-3-carboxylic acid amide | 1H NMR (500 MHz, DMSO-d6) ppm = 13.55-13.29 (m, 1H), 8.66 (d, J = 2.0 Hz, 1H), 8.49-8.40 (m, 1H), 7.57-7.29 (m, 5H), 7.03-6.92 (m, 1H), 4.06-3.46 (m, 5H), 3.26-3.06 (m, 1H), 2.56-2.50 (m, 3H). |
| 188 | 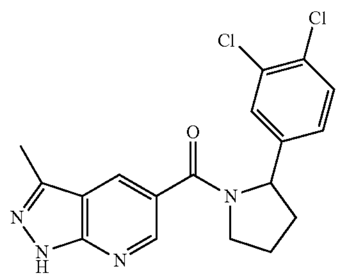 [SMILES: Cc1n[nH]c2ncc(C(=O)N3CCCC3c3ccc(Cl)c(Cl)c3)cc12] | 375 | 2.11 (A) | B | [2-(3,4-Dichloro-phenyl)-pyrrolidin-1-yl]-(3-methyl-1H-pyrazolo[3,4-b]pyridin-5-yl)-methanone | 1H NMR (400 MHz, DMSO-d6, TE = 363 K) ppm = 13.15 (s, br, 1H), 8.57 (s, br, 1H), 8.28 (s, br, 1H), 7.64-7.38 (m, 2H), 7.38-7.15 (m, 1H), 5.26-5.01 (m, 1H), 4.04-3.82 (m, 1H), 3.82-3.59 (m, 1H), 2.59-2.36 (m, 4H), 2.06-1.70 (m, 3H). |
| 189 | 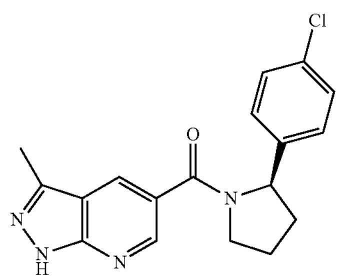 [SMILES: Cc1n[nH]c2ncc(C(=O)N3CCC[C@@H]3c3ccc(Cl)cc3)cc12] | 341 | | D | [(r)-2-(4-Chloro-phenyl)-pyrrolidin-1-yl]-(3-methyl-1H-pyrazolo[3,4-c]pyridin-5-yl)-methanone | 1H NMR (300 MHz, DMSO-d6) ppm = 13.40 (m, 1H), 9.00 (s, 0.67H), 8.72 (s, 0.33H), 8.14 (s, 0.67H), 7.83 (s, 0.33H), 7.40-7.32 (m, 3H), 7.15-6.98 (m, 1H), 5.84-5.82 (m, 0.33H), 5.26-5.21 (m, 0.67H), 4.10-4.02 (m, 0.67H), 3.87-3.70 (m, 1.33H), 2.55 (s, 2H), 2.41 (s, 1H), 2.38-2.27 (m, 1H), 1.87-1.68 (m, 3H). |
| 190 | 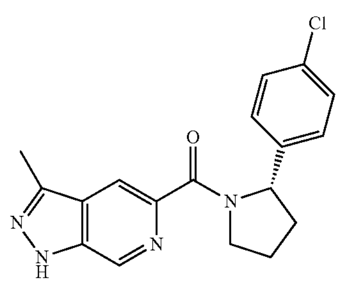 [SMILES: Cc1n[nH]c2cnc(C(=O)N3CCC[C@H]3c3ccc(Cl)cc3)cc12] | 341 | | B | [(s)-2-(4-Chloro-phenyl)-pyrrolidin-1-yl]-(3-methyl-1H-pyrazolo[3,4-c]pyridin-5-yl)-methanone | 1H NMR ((300 MHz, DMSO-d6) ppm = 13.42 (m, 1H), 8.99 (s, 0.67H), 8.72 (s, 0.33H), 8.13 (s, 0.67H), 7.83 (s, 0.33H), 7.40-7.31 (m, 3H), 7.15-6.90 (m, 1H), 5.85-5.82 (m, 0.33H), 5.26-5.21 (m, 0.67H), 4.10-4.00 (m, 0.67H), 3.87-3.68 (m, 1.33H), 2.55 (s, 2H), 2.44 (s, 1H), 2.41-2.30 (m, 1H), 1.91-1.70 (m, 3H). |
| 191 | 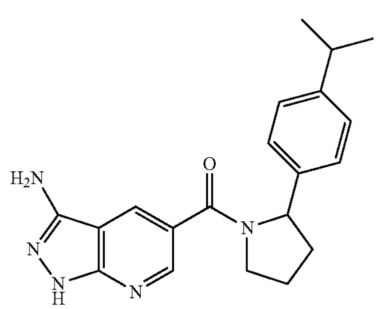 [SMILES: CC(C)c1ccc(C2CCCN2C(=O)c2cnc3[nH]nc(N)c3c2)cc1] | 349 | 2.06 (A) | B | (3-Amino-1H-indazol-5-yl)-[2-(4-isopropyl-phenyl)-pyrrolidin-1-yl]-methanone | racemic, enantiomeres desribed |

TABLE 1-continued

| No. | Structure | [M + 1]+ | RT [min] (HPLC method) | IC50 [μM] | Chemical Name | NMR |
|---|---|---|---|---|---|---|
| 192 | 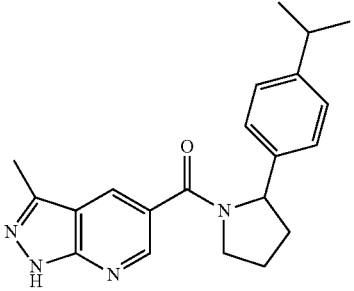 [SMILES: Cc1n[nH]c2ncc(C(=O)N3CCCC3c3ccc(C(C)C)cc3)cc12] | 349 | 2.18 (A) | A | [2-(4-Isopropyl-phenyl)-pyrrolidin-1-yl]-(3-methyl-1H-pyrazolo[3,4-b]pyridin-5-yl)-methanone | racemic, enantiomeres desribed |
| 193 | 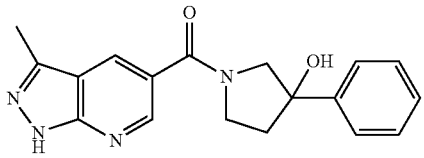 | 323 | 1.59 (A) | D | (3-Hydroxy-3-phenyl-pyrrolidin-1-yl)-(3-methyl-1H-pyrazolo[3,4-b]pyridin-5-yl)-methanone | racemic, enantiomeres desribed |
| 194 | 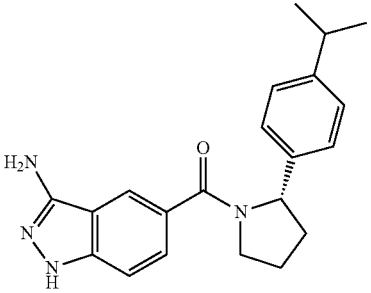 [SMILES: CC(C)c1ccc([C@@H]2CCCN2C(=O)c2ccc3[nH]nc(N)c3c2)cc1] | 349 | 2.07 (A) | A | (3-Amino-1H-indazol-5-yl)-[(S)-2-(4-isopropyl-phenyl)-pyrrolidin-1-yl]-methanone | 1H NMR (400 MHz, DMSO-d6, TE = 363 K) ppm = 11.32 (s, 1H), 7.94 (s, 1H), 7.43-7.29 (m, 1H), 7.29-7.04 (m, 5H), 5.24-5.05 (m, 3H), 3.91-3.73 (m, 1H), 3.73-3.53 (m, 1H), 2.94-2.79 (m, 1H), 2.42-2.28 (m, 1H), 2.01-1.72 (m, 3H), 1.21 (d, J = 6.9 Hz, 6H). |
| 195 | 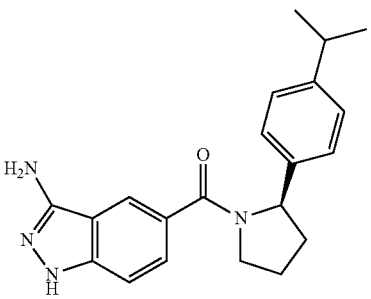 [SMILES: CC(C)c1ccc([C@H]2CCCN2C(=O)c2ccc3[nH]nc(N)c3c2)cc1] | 349 | 2.07 (A) | C | (3-Amino-1H-indazol-5-yl)-[(R)-2-(4-isopropyl-phenyl)-pyrrolidin-1-yl]-methanone | 1H NMR (400 MHz, DMSO-d6, TE = 363 K) ppm = 11.30 (s, 1H), 7.93 (s, 1H), 7.34 (d, J = 7.7 Hz, 1H), 7.25-7.02 (m, 5H), 5.29-5.03 (m, 3H), 3.90-3.72 (m, 1H), 3.72-3.50 (m, 1H), 2.93-2.77 (m, 1H), 2.39-2.25 (m, 1H), 1.94-1.68 (m, 3H), 1.19 (d, J = 6.9 Hz, 6H). |

TABLE 1-continued

| No. | Structure | [M + 1]+ | RT [min] (HPLC method) | IC50 [μM] | Chemical Name | NMR |
|---|---|---|---|---|---|---|
| 196 | 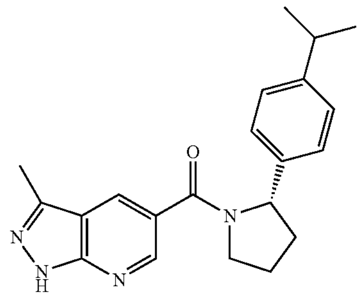 [SMILES: Cc1n[nH]c2ncc(C(=O)N3CCC[C@H]3c3ccc(C(C)C)cc3)cc12] | 349 | 2.18 (A) | A | [(S)-2-(4-Isopropyl-phenyl)-pyrrolidin-1-yl]-(3-methyl-1H-pyrazolo[3,4-b]pyridin-5-yl)-methanone | 1H NMR (400 MHz, DMSO-d6) ppm = 13.39, 13.23 (2 × s, br, 1H, ratio 2:1, mixture of rotamers), 8.68, 8.50, 8.30, 7.73 (4 × s, 2H, ratio 2:1, mixture of rotamers), 7.30, 7.20, 7.14-7.04, 7.04-6.80 (2 × d, J = 7.7 Hz, J = 7.4 Hz, 2 × m, 4H, ratio 2:1, mixture of rotamers), 5.26-5.09, 5.01-4.83 (2 × m, 1H, ratio 2:1, mixture of rotamers), 4.06-3.86, 3.86-3.70, 3.63-3.50 (3 × m, 2H), 2.96-2.73 (m, 1H), 2.55, 2.26 (2 × s, 3H, ratio 2:1, mixture of rotamers), 2.45-2.31 (m, 1H), 2.02-1.63 (m, 3H), 1.34-0.98 (m, 6H). |
| 197 | 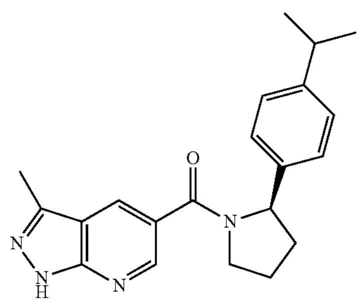 [SMILES: Cc1n[nH]c2ncc(C(=O)N3CCC[C@@H]3c3ccc(C(C)C)cc3)cc12] | 349 | 2.18 (A) | C | [(R)-2-(4-Isopropyl-phenyl)-pyrrolidin-1-yl]-(3-methyl-1H-pyrazolo[3,4-b]pyridin-5-yl)-methanone | 1H NMR (400 MHz, DMSO-d6) ppm = 13.39, 13.23 (2 × s, br, 1H, ratio 2:1, mixture of rotamers), 8.68, 8.50, 8.30, 7.73 (4 × s, 2H, ratio 2:1, mixture of rotamers), 7.30, 7.20, 7.14-7.04, 7.04-6.80 (2 × d, J = 7.7 Hz, J = 7.4 Hz, 2 × m, 4H, ratio 2:1, mixture of rotamers), 5.26-5.09, 5.01-4.83 (2 × m, 1H, ratio 2:1, mixture of rotamers), 4.06-3.86, 3.86-3.70, 3.63-3.50 (3 × m, 2H), 2.96-2.73 (m, 1H), 2.55, 2.26 (2 × s, 3H, ratio 2:1, mixture of rotamers), 2.45-2.31 (m, 1H), 2.02-1.63 (m, 3H), 1.34-0.98 (m, 6H). |
| 198 | 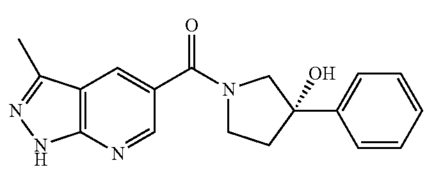 [SMILES: Cc1n[nH]c2ncc(C(=O)N3CC[C@](O)(c4ccccc4)C3)cc12] | 323 | 1.59 (A) | D | ((S)-3-Hydroxy-3-phenyl-pyrrolidin-1-yl)-(3-methyl-1H-pyrazolo[3,4-b]pyridin-5-yl)-methanone | 1H NMR (400 MHz, DMSO-d6, TE = 363 K) ppm = 13.16 (s, br, 1H), 8.66 (d, J = 1.9 Hz, 1H), 8.37 (s, 1H), 7.53 (d, J = 7.5 Hz, 2H), 7.35 (t, J = 7.5 Hz, 2H), 7.26 (t, J = 7.2 Hz, 1H), 5.25 (s, 1H), 3.98-3.60 (m, 4H), 2.53 (s, 3H), 2.39-2.28 (m, 1H), 2.23-2.12 (m, 1H). |

TABLE 1-continued

| No. | Structure | [M + 1]+ | RT [min] (HPLC method) | IC50 [μM] | Chemical Name | NMR |
|---|---|---|---|---|---|---|
| 199 | 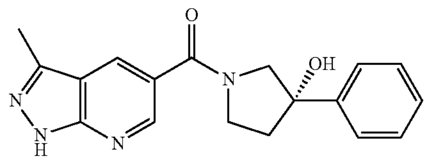 [SMILES: Cc1n[nH]c2ncc(C(=O)N3CC[C@](O)(c4ccccc4)C3)cc12] | 323 | 1.59 (A) | D | ((R)-3-Hydroxy-3-phenyl-pyrrolidin-1-yl)-(3-methyl-1H-pyrazolo[3,4-b]pyridin-5-yl)-methanone | 1H NMR (400 MHz, DMSO-d6, TE = 363 K) ppm = 13.16 (s, br, 1H), 8.66 (d, J = 1.8 Hz, 1H), 8.37 (s, 1H), 7.53 (d, J = 7.4 Hz, 2H), 7.35 (t, J = 7.5 Hz, 2H), 7.26 (t, J = 7.3 Hz, 1H), 5.25 (s, 1H), 3.97-3.57 (m, 4H), 2.53 (s, 3H), 2.38-2.26 (m, 1H), 2.23-2.11 (m, 1H). |
| 200 | 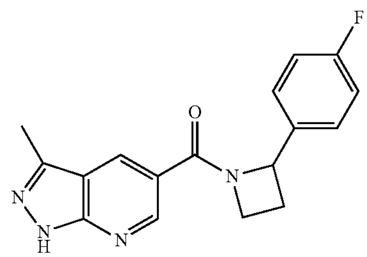 [SMILES: Cc1n[nH]c2ncc(C(=O)N3CCC3c3ccc(F)cc3)cc12] | 311 | 1.78 (A) | C | [2-(4-Fluoro-phenyl)-azetidin-1-yl]-(3-methyl-1H-pyrazolo[3,4-b]pyridin-5-yl)-methanone | 1H NMR (400 MHz, DMSO-d6, 90° C.) ppm = 13.27-13.08 (m, 1H), 8.70-8.63 (m, 1H), 8.34-8.23 (m, 1H), 7.51-7.43 (m, 2H), 7.18-7.08 (m, 2H), 5.60-5.53 (m, 1H), 4.54-4.45 (m, 1H), 4.27-4.17 (m, 1H), 2.86-2.74 (m, 1H), 2.49-2.47 (m, 3H), 2.23-2.12 (m, 1H). |
| 202 | 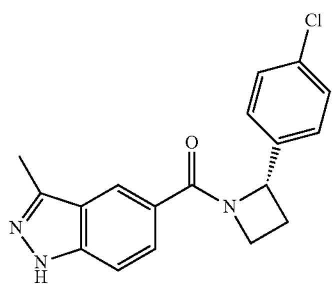 [SMILES: Cc1n[nH]c2ccc(C(=O)N3CC[C@H]3c3ccc(Cl)cc3)cc12] | 326 | 1.38 (J) | A | [(S)-2-(4-Chloro-phenyl)-azetidin-1-yl]-(3-methyl-1H-indazol-5-yl)-methanone | 1H NMR (300 MHz, DMSO-d6) ppm = 12.55 (s, 1H), 7.89 (s, 1H), 7.58-7.55 (m, 1H), 7.45-7.36 (m, 5H), 5.52-5.47 (m, 1H), 4.50-4.42 (m, 1H), 4.21-4.13 (m, 1H), 2.83-2.71 (m, 1H), 2.45 (s, 3H), 2.19-2.13 (m, 1H) |
| 203 | 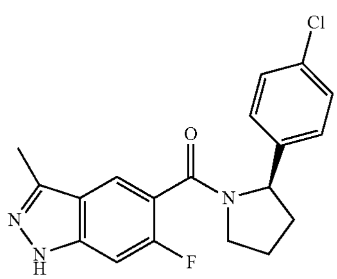 [SMILES: Cc1n[nH]c2cc(F)c(C(=O)N3CCC[C@@H]3c3ccc(Cl)cc3)cc12] | 358 | | D | [(R)-2-(4-Chloro-phenyl)-pyrrolidin-1-yl]-(6-fluoro-3-methyl-1H-indazol-5-yl)-methanone | 1H NMR (300 MHz, CDCl3) ppm = 7.78 (d, 0.646H), 7.33-7.12 (m, 2.33H), 7.09-7.06 (m, 1.90H), 6.93-6.78 (m, 1.17H), 5.36-5.32 (m, 0.69H), 4.72-4.68 (m, 0.38H), 4.00-3.90 (m, 0.75H), 3.70-3.66 (m, 0.65H), 3.49-3.45 (m, 0.65), 2.57-2.45 (s, 2H), 2.43-2.39 (m, 1.02H), 2.38-2.36 (s, 1.18H), 2.07-2.00 (m, 1.14H), 1.96-1.85 (m, 2.14H) |
| 204 | 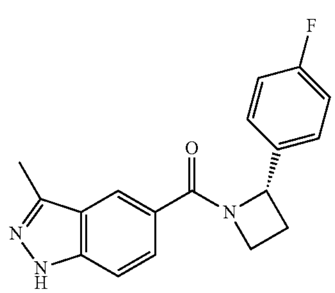 [SMILES: Cc1n[nH]c2ccc(C(=O)N3CC[C@H]3c3ccc(F)cc3)cc12] | 310 | 1.16 (J) | A | [(S)-2-(4-Fluoro-phenyl)-azetidin-1-yl]-(3-methyl-1H-indazol-5-yl)-methanone | 1H NMR (300 MHz, DMSO-d6) ppm = 12.84 (s, 1H), 8.10-7.50 (m, 5H), 7.19 (s, 2H), 5.50 (s, 1H), 4.61 (s, 1H), 4.20-4.11 (m, 1H), 2.90-2.73 (m, 1H), 2.51 (s, 3H), 2.22-2.06 (m, 1H) |

TABLE 1-continued

| No. | Structure | [M + 1]+ | RT [min] (HPLC method) | IC50 [μM] | Chemical Name | NMR |
|---|---|---|---|---|---|---|
| 205 | 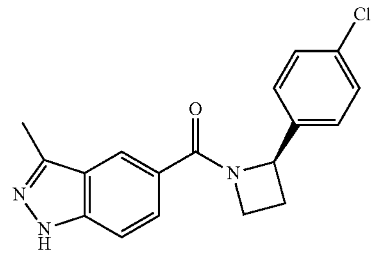 [SMILES: Cc1n[nH]c2ccc(C(=O)N3CC[C@@H]3c3ccc(Cl)cc3)cc12] | 326 | 1.38 (J) | C | [(R)-2-(4-Chloro-phenyl)-azetidin-1-yl]-(3-methyl-1H-indazol-5-yl)-methanone | 1H NMR (300 MHz, DMSO-d6) ppm = 12.55 (s, 1H), 7.89 (s, 1H), 7.58-7.55 (m, 1H), 7.45-7.36 (m, 5H), 5.52-5.47 (m, 1H), 4.50-4.42 (m, 1H), 4.21-4.13 (m, 1H), 2.83-2.71 (m, 1H), 2.45 (s, 3H), 2.19-2.10 (m, 1H) |
| 206 | 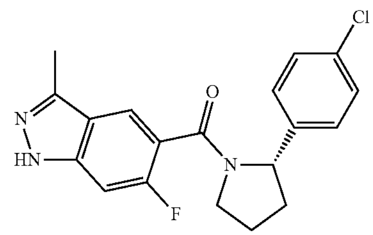 [SMILES: Cc1n[nH]c2cc(F)c(C(=O)N3CCC[C@H]3c3ccc(Cl)cc3)cc12] | 358 | | A | [(S)-2-(4-Chloro-phenyl)-pyrrolidin-1-yl]-(6-fluoro-3-methyl-1H-indazol-5-yl)-methanone | 1H NMR (300 MHz, CDCL3) ppm = 7.78 (d, 0.646H), 7.33-7.12 (m, 2.33H), 7.09-7.06 (m, 1.90H), 6.93-6.78 (m, 1.17H), 5.36-5.32 (m, 0.69H), 4.72-4.68 (m, 0.38H), 4.00-3.90 (m, 0.75H), 3.70-3.66 (m, 0.65H), 3.49-3.45 (m, 0.65H), 2.57-2.45 (s, 2H), 2.43-2.39 (m, 1.02H), 2.38-2.36 (s, 1.18H), 2.07-2.00 (m, 1.14H), 1.96-1.85 (m, 2.14H) |
| 207 | 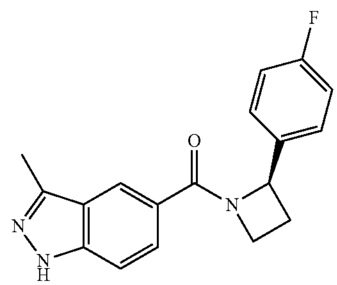 [SMILES: Cc1n[nH]c2ccc(C(=O)N3CC[C@@H]3c3ccc(F)cc3)cc12] | 310 | 1.17 (J) | B | [(R)-2-(4-Fluoro-phenyl)-azetidin-1-yl]-(3-methyl-1H-indazol-5-yl)-methanone | 1H NMR (300 MHz, DMSO-d6) ppm = 12.83 (s, 1H), 8.09-7.32 (m, 5H), 7.19 (s, 2H), 5.50 (s, 1H), 4.63 (s, 1H), 4.20-4.11 (m, 1H), 2.75-2.62 (m, 1H), 2.51 (s, 3H), 2.12-2.06 (m, 1H) |
| 208 | 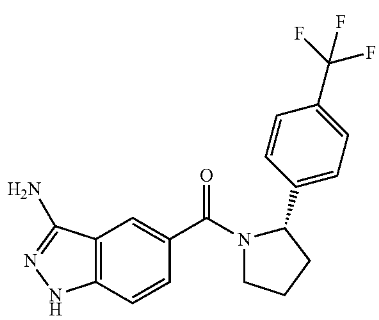 [SMILES: Nc1n[nH]c2ccc(C(=O)N3CCC[C@H]3c3ccc(C(F)(F)F)cc3)cc12] | | | B | (3-Amino-1H-indazol-5-yl)-[(S)-2-(4-trifluoromethyl-phenyl)-pyrrolidin-1-yl]-methanone | 1H NMR (400 MHz, DMSO-d6, TE = 363 K) ppm = 11.35 (s, 1H), 8.00 (s, 1H), 7.64 (d, J = 8.1 Hz, 2H), 7.51 (d, J = 7.9 Hz, 2H), 7.39 (d, J = 8.3 Hz, 1H), 7.21 (d, J = 8.6 Hz, 1H), 5.37-5.25 (m, 1H), 5.20 (s, 2H), 3.95-3.84 (m, 1H), 3.75-3.63 (m, 1H), 2.48-2.38 (m, 1H), 2.00-1.74 (m, 3H). |
| 209 | 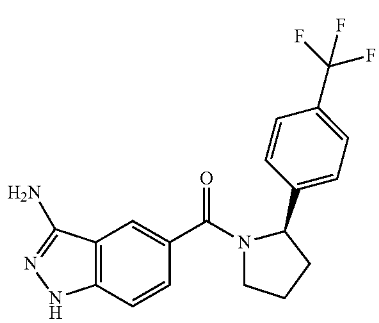 [SMILES: Nc1n[nH]c2ccc(C(=O)N3CCC[C@@H]3c3ccc(C(F)(F)F)cc3)cc12] | | | C | (3-Amino-1H-indazol-5-yl)-[(R)-2-(4-trifluoromethyl-phenyl)-pyrrolidin-1-yl]-methanone | 1H NMR (400 MHz, DMSO-d6, TE = 363 K) ppm = 11.35 (s, 1H), 8.00 (s, 1H), 7.64 (d, J = 8.0 Hz, 2H), 7.51 (d, J = 7.6 Hz, 2H), 7.39 (d, J = 7.8 Hz, 1H), 7.21 (d, J = 8.5 Hz, 1H), 5.28 (t, J = 6.8 Hz, 1H), 5.19 (s, 2H), 4.02-3.78 (m, 1H), 3.78-3.56 (m, 1H), 2.58-2.37 (m, 1H), 2.03-1.72 (m, 3H). |

TABLE 1-continued

| No. | Structure | [M + 1]+ | RT [min] (HPLC method) | IC50 [μM] | Chemical Name | NMR |
|---|---|---|---|---|---|---|
| 210 | 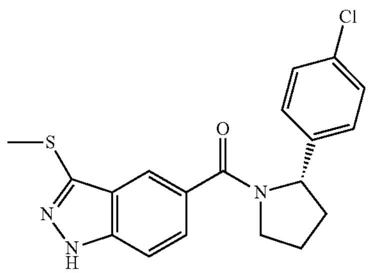 [SMILES: CSc1n[nH]c2ccc(C(=O)N3CCC[C@H]3c3ccc(Cl)cc3)cc12] | 372.1 | 2.88 (B) | A | [(S)-2-(4-Chloro-phenyl)-pyrrolidin-1-yl]-(3-methylsulfanyl-1H-indazol-5-yl)-methanone | no NMR |
| 211 | 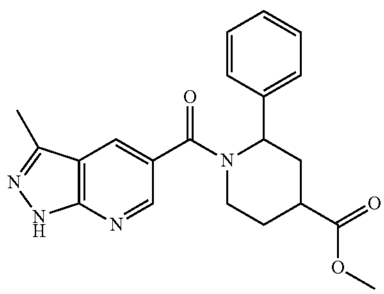 [SMILES: COC(=O)C1CCN(C(=O)c2cnc3[nH]nc(C)c3c2)C(c2ccccc2)C1] | 379.1 | 2.4 (B) | C | 1-(3-Methyl-1H-pyrazolo[3,4-b]pyridine-5-carbonyl)-2-phenyl-piperidine-4-carboxylic acid methyl ester | 1H NMR (500 MHz, DMSO-d6) ppm = 13.37 (s, 1H), 8.49 (d, J = 2.0 Hz, 1H), 8.28 (d, J = 2.0 Hz, 1H), 7.37-7.33 (m, 2H), 7.32-7.28 (m, 2H), 7.26-7.21 (m, 1H), 5.31 (t, J = 6.5 Hz, 1H), 3.99-3.90 (m, 1H), 3.58-3.48 (m, 1H), 3.34 (s, 3H), 2.83 (p, J = 6.2 Hz, 1H), 2.49 (s, 3H), 2.41-2.31 (m, 2H), 1.97-1.81 (m, 2H). |
| 214 | 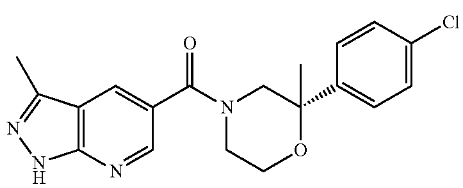 [SMILES: Cc1n[nH]c2ncc(C(=O)N3CCO[C@@](C)(c4ccc(Cl)cc4)C3)cc12] | 371.1 | 2.63 (B) | D | [(S)-2-(4-Chloro-phenyl)-2-methyl-morpholin-4-yl]-(3-methyl-1H-pyrazolo[3,4-b]pyridin-5-yl)-methanone | 1H NMR (500 MHz, DMSO-d6) ppm = 13.41 (s, 1H), 8.40 (d, J = 2.0 Hz, 1H), 8.21 (d, J = 2.0 Hz, 1H), 7.59-7.22 (m, 4H), 4.55-4.07 (m, 1H), 3.82-3.65 (m, 1H), 3.65-3.38 (m, 4H), 2.52 (s, 3H), 1.39 (s, 3H). |
| 215 | 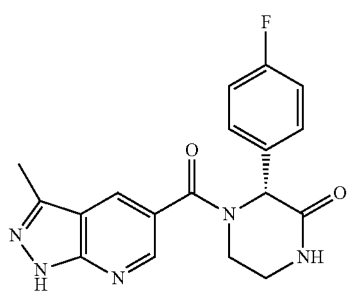 [SMILES: Cc1n[nH]c2ncc(C(=O)N3CCNC(=O)[C@H]3c3ccc(F)cc3)cc12] | 354.1 | 1.97 (B) | D | (R)-3-(4-Fluoro-phenyl)-4-(3-methyl-1H-pyrazolo[3,4-b]pyridine-5-carbonyl)-piperazin-2-one | 1H NMR (500 MHz, DMSO-d6) ppm = 13.42 (s, 1H), 8.54 (s, 1H), 8.39-8.29 (m, 2H), 7.59-7.43 (m, 2H), 7.26-7.17 (m, 2H), 6.09-5.58 (m, 1H), 3.99-3.64 (m, 1H), 3.54-3.40 (m, 2H), 3.22-3.14 (m, 1H), 2.51-2.50 (m, 3H). |
| 216 | 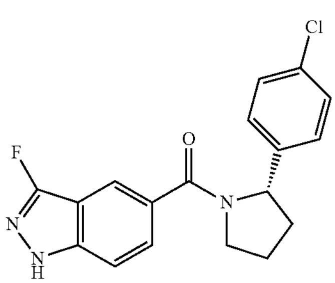 [SMILES: O=C(c1ccc2[nH]nc(F)c2c1)N1CCC[C@H]1c1ccc(Cl)cc1] | 344 | 2.17 (A) | A | [(S)-2-(4-Chloro-phenyl)-pyrrolidin-1-yl]-(3-fluoro-1H-indazol-5-yl)-methanone | 1H NMR (400 MHz, DMSO-d6, 90° C.) ppm = 12.43 (s, 1H), 7.78 (s, 1H), 7.54-7.39 (m, 2H), 7.34-7.18 (m, 4H), 5.12 (t, J = 6.7 Hz, 1H), 3.86-3.76 (m, 1H), 3.69-3.58 (m, 1H), 2.43-2.33 (m, 1H), 1.94-1.83 (m, 2H), 1.83-1.72 (m, 1H). |

TABLE 1-continued

| No. | Structure | [M + 1]+ | RT [min] (HPLC method) | IC50 [μM] | Chemical Name | NMR |
|---|---|---|---|---|---|---|
| 217 | 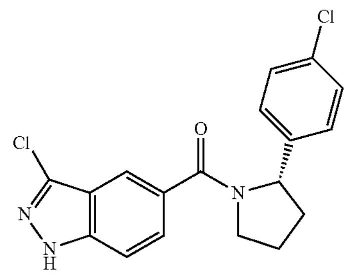 [SMILES: O=C(c1ccc2[nH]nc(Cl)c2c1)N1CCC[C@H]1c1ccc(Cl)cc1] | 360 | 2.22 (A) | B | (3-Chloro-1H-indazol-5-yl)-[(S)-2-(4-chloro-phenyl)-pyrrolidin-1-yl]-methanone | 1H NMR (400 MHz, DMSO-d6, 90° C.) ppm = 13.15 (s, 1H), 7.68 (s, 1H), 7.51 (s, 2H), 7.35-7.19 (m, 4H), 5.15-5.06 (m, 1H), 3.84-3.75 (m, 1H), 3.71-3.60 (m, 1H), 2.44-2.32 (m, 1H), 1.95-1.84 (m, 2H), 1.84-1.73 (m, 1H). |
| 218 | 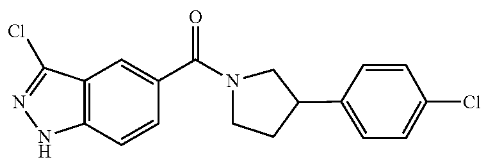 [SMILES: O=C(c1ccc2[nH]nc(Cl)c2c1)N1CCC(c2ccc(Cl)cc2)C1] | 360 | 2.27 (A) | B | (3-Chloro-1H-indazol-5-yl)-[3-(4-chloro-phenyl)-pyrrolidin-1-yl]-methanone | 1H NMR (400 MHz, DMSO-d6/90° C.) ppm = 13.19 (s, 1H), 7.83-7.75 (m, 1H), 7.61 (dd, J = 8.7, 1.5 Hz, 1H), 7.59-7.54 (m, 1H), 7.38-7.25 (m, 4H), 3.97-3.81 (m, 1H), 3.74-3.56 (m, 2H), 3.52-3.39 (m, 2H), 2.34-2.23 (m, 1H), 2.07-1.95 (m, 1H). |
| 219 | 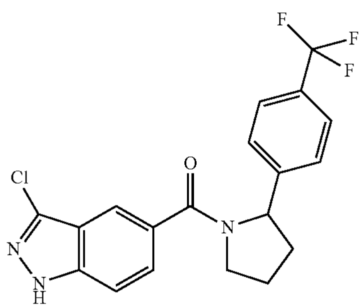 [SMILES: O=C(c1ccc2[nH]nc(Cl)c2c1)N1CCCC1c1ccc(C(F)(F)F)cc1] | 394 | 2.29 (A) | B | (3-Chloro-1H-indazol-5-yl)-[2-(4-trifluoromethyl-phenyl)-pyrrolidin-1-yl]-methanone | 1H NMR (400 MHz, DMSO-d6/90° C.) ppm = 13.16 (s, 1H), 7.79-7.64 (m, 1H), 7.64-7.57 (m, 2H), 7.57-7.38 (m, 4H), 5.24-5.13 (m, 1H), 3.89-3.79 (m, 1H), 3.75-3.62 (m, 1H), 2.47-2.38 (m, 1H), 1.96-1.86 (m, 2H), 1.85-1.76 (m, 1H). |
| 220 | 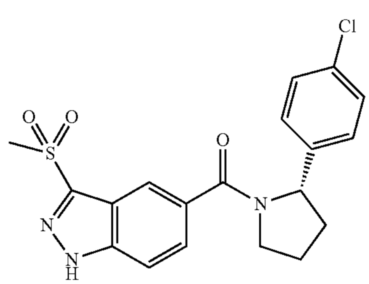 [SMILES: CS(=O)(=O)c1n[nH]c2ccc(C(=O)N3CCC[C@H]3c3ccc(Cl)cc3)cc12] | 404 | 2.6 (B) | B | [(S)-2-(4-Chloro-phenyl)-pyrrolidin-1-yl]-(3-methanesulfonyl-1H-indazol-5-yl)-methanone | 1H NMR (400 MHz, DMSO-d6) ppm = 14.61-14.05 (m, 1H), 8.17 (s, 1H), 7.82-7.70 (m, 2H), 7.58-6.97 (m, 4H), 5.20-4.87 (m, 1H), 4.11-3.47 (m, 2H), 3.44-3.35 (m, 3H), 2.43-2.32 (m, 1H), 1.99-1.69 (m, 3H). |
| 221 | 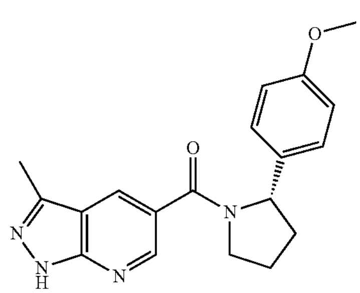 [SMILES: COc1ccc([C@@H]2CCCN2C(=O)c2cnc3[nH]nc(C)c3c2)cc1] | 337 | 1.12 (J) | A | [(S)-2-(4-Methoxy-phenyl)-pyrrolidin-1-yl]-(3-methyl-1H-pyrazolo[3,4-b]pyridin-5-yl)-methanone | 1H NMR (300 MHz, DMSO-d6) ppm = 13.08 (s, 1H), 8.48 (s, 1H), 8.15 (s, 1H), 7.11 (s, 2H), 6.84-6.81 (d, J = 9, 2H), 5.08 (s, 1H), 3.87-3.79 (m, 1H), 3.72 (s, 4H), 2.49-2.45 (m, 3H), 2.40-2.29 (m, 1H), 1.95-1.80 (m, 3H) |

TABLE 1-continued

| No. | Structure | [M + 1]+ | RT [min] (HPLC method) | IC50 [μM] | Chemical Name | NMR |
|---|---|---|---|---|---|---|
| 222 | 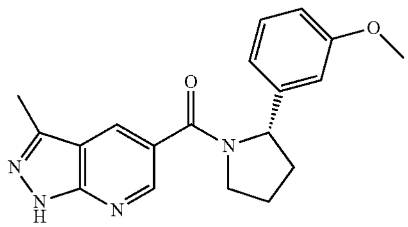 [SMILES: COc1cccc([C@@H]2CCCN2C(=O)c2cnc3[nH]nc(C)c3c2)c1] | 337 | 1.67 (G) | C | [(S)-2-(3-Methoxy-phenyl)-pyrrolidin-1-yl]-(3-methyl-1H-pyrazolo[3,4-b]pyridin-5-yl)-methanone | 1H NMR (300 MHz, DMSO-d6) ppm = 13.10 (s, 1H), 8.50 (s, 1H), 8.17 (s, 1H), 7.22-7.17 (m, 1H), 6.82-6.74 (m, 3H), 5.11 (s, 1H), 3.89-3.81 (m, 1H), 3.71 (s, 4H), 2.49-2.32 (m, 4H), 1.96-1.79 (m, 3H) |
| 223 | 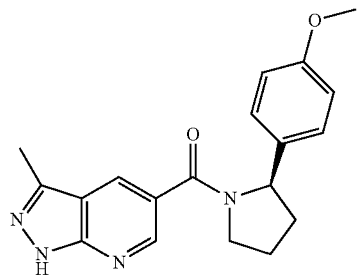 [SMILES: COc1ccc([C@H]2CCCN2C(=O)c2cnc3[nH]nc(C)c3c2)cc1] | 337 | 1.13 (J) | D | [(R)-2-(4-Methoxy-phenyl)-pyrrolidin-1-yl]-(3-methyl-1H-pyrazolo[3,4-b]pyridin-5-yl)-methanone | 1H NMR (300 MHz, DMSO-d6) ppm = 13.08 (s, 1H), 8.48 (s, 1H), 8.15 (s, 1H), 7.11 (s, 2H), 6.84-6.81 (d, J = 9, 2H), 5.08 (s, 1H), 3.87-3.79 (m, 1H), 3.72 (s, 4H), 2.49-2.45 (m, 3H), 2.40-2.29 (m, 1H), 1.95-1.74 (m, 3H) |
| 224 | 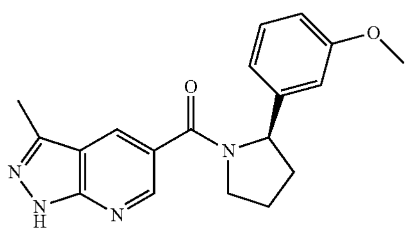 [SMILES: COc1cccc([C@H]2CCCN2C(=O)c2cnc3[nH]nc(C)c3c2)c1] | 337 | | D | [(R)-2-(3-Methoxy-phenyl)-pyrrolidin-1-yl]-(3-methyl-1H-pyrazolo[3,4-b]pyridin-5-yl)-methanone | 1H NMR (300 MHz, DMSO-d6) ppm = 13.10 (s, 1H), 8.50 (s, 1H), 8.17 (s, 1H), 7.22-7.17 (m, 1H), 6.82-6.74 (m, 3H), 5.11 (s, 1H), 3.89-3.81 (m, 1H), 3.71 (s, 4H), 2.49-2.32 (m, 4H), 1.96-1.79 (m, 3H) |
| 225 | 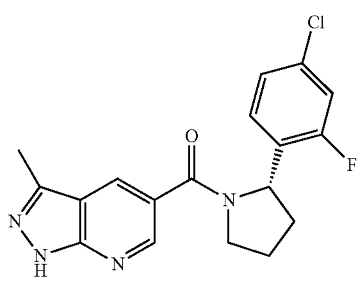 [SMILES: Cc1n[nH]c2ncc(C(=O)N3CCC[C@H]3c3ccc(Cl)cc3F)cc12] | 359 | | A | [(S)-2-(4-Chloro-2-fluoro-phenyl)-pyrrolidin-1 yl]-(3-methyl-1H-pyrazolo[3,4-b]pyridin-5-yl)-methanone | 1H NMR ((300 MHz, DMSO-d6) ppm = 13.15 (s, 1H), 8.55 (s, 1H), 8.25 (s, 1H), 7.49-7.30 (m, 1H), 7.30-7.16 (m, 2H), 5.38-5.20 (m, 1H), 3.97-3.78 (m, 1H), 3.76-3.58 (m, 1H), 2.44-2.30 (m, 4H), 2.01-1.88 (m, 2H), 1.86-1.73 (m, 1H). |
| 226 | 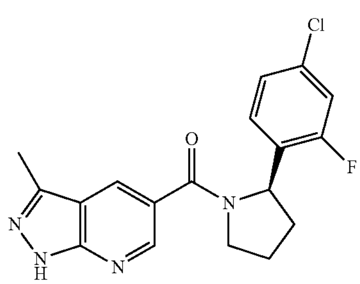 [SMILES: Cc1n[nH]c2ncc(C(=O)N3CCC[C@@H]3c3ccc(Cl)cc3F)cc12] | 359 | 1.36 (H) | D | [(R)-2-(4-Chloro-2-fluoro-phenyl)-pyrrolidin-1-yl]-(3-methyl-1H-pyrazolo[3,4-b]pyridin-5-yl)-methanone | 1H NMR ((300 MHz, DMSO-d6) ppm = 13.15 (s, 1H), 8.55 (s, 1H), 8.25 (s, 1H), 7.49-7.30 (m, 1H), 7.30-7.16 (m, 2H), 5.38-5.20 (m, 1H), 3.97-3.78 (m, 1H), 3.76-3.58 (m, 1H), 2.44-2.30 (m, 4H), 2.01-1.88 (m, 2H), 1.86-1.73 (m, 1H). |

| No. | Structure | [M + 1]⁺ | RT [min] (HPLC method) | IC50 [μM] | Chemical Name | NMR |
|---|---|---|---|---|---|---|
| 227 | 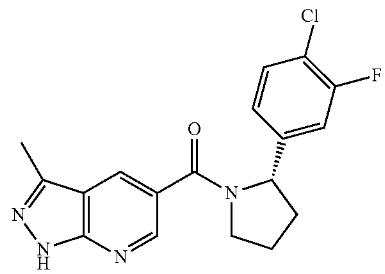 [SMILES: Cc1n[nH]c2ncc(C(=O)N3CCC[C@H]3c3ccc(Cl)c(F)c3)cc12] | 359 | 2.02 (A) | A | [(S)-2-(4-Chloro-3-fluoro-phenyl)-pyrrolidin-1-yl]-(3-methyl-1H-pyrazolo[3,4-b]pyridin-5-yl)-methanone | 1H NMR (400 MHz, DMSO-d6) ppm = 13.39 (s, br, 1H), 8.71, 8.56, 8.23, 7.90 (4 × s, 2H, ratio 4:1, mixture of rotamers), 7.57-7.44, 7.29, 7.40, 7.07, 6.90 (m, d, J = 7.6 Hz, 3 × s, 3H, ratio 4:1, mixture of rotamers), 5.16, 5.03 (t, J = 6.4 Hz, s, 1H, ratio 4:1, mixture of rotamers), 4.00, 3.82, 3.57 (q, J = 8.2 Hz, 2 × s, 2H, ratio 4:1, mixture of rotamers),, 2.55 (s, 3H), 2.46-2.32 (m, 1H), 2.01-1.68 (m, 3H). |
| 228 | 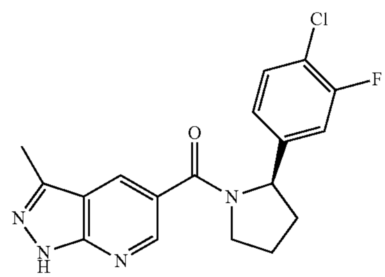 [SMILES: Cc1n[nH]c2ncc(C(=O)N3CCC[C@@H]3c3ccc(Cl)c(F)c3)cc12] | 359 | 2.01 (A) | D | [(R)-2-(4-Chloro-3-fluoro-phenyl)-pyrrolidin-1-yl]-(3-methyl-1H-pyrazolo[3,4-b]pyridin-5-yl)-methanone | 1H NMR (400 MHz, DMSO-d6) ppm = 13.39 (s, br, 1H), 8.71, 8.56, 8.23, 7.90 (4 × s, 2H, ratio 4:1, mixture of rotamers), 7.57-7.44, 7.29, 7.40, 7.07, 6.90 (m, d, J = 7.6 Hz, 3 × s, 3H, ratio 4:1, mixture of rotamers), 5.16, 5.03 (t, J = 6.4 Hz, s, 1H, ratio 4:1, mixture of rotamers), 4.00, 3.82, 3.57 (q, J = 8.2 Hz, 2 × s, 2H, ratio 4:1, mixture of rotamers),, 2.55 (s, 3H), 2.46-2.32 (m, 1H), 2.01-1.68 (m, 3H). |
| 229 | 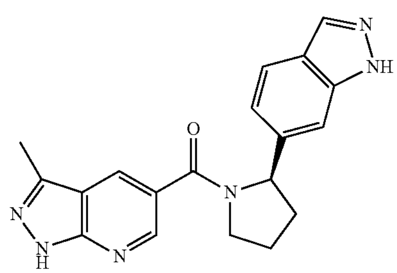 [SMILES: Cc1n[nH]c2ncc(C(=O)N3CCC[C@@H]3c3ccc4cn[nH]c4c3)cc12] | 347 | 1.08 (H) | D | [(R)-2-(1H-Indazol-6-yl)-pyrrolidin-1-yl]-(3-methyl-1H-pyrazolo[3,4-b]pyridin-5-yl)-methanone | 1H NMR ((300 MHz, DMSO-d6) ppm = 13.60-12.80 (m, 1H), 12.61 (s, 1H), 8.51 (s, 1H), 8.15 (s, 1H), 7.95 (s, 1H), 7.67-7.64 (m, 1H), 7.31 (s, 1H), 7.01-6.99 (m, 1H), 5.26 (s, 1H), 3.94-3.86 (m, 1H), 3.77-3.75 (m, 1H), 2.48-2.22 (m, 4H), 2.08-1.80 (m, 3H). |
| 230 | 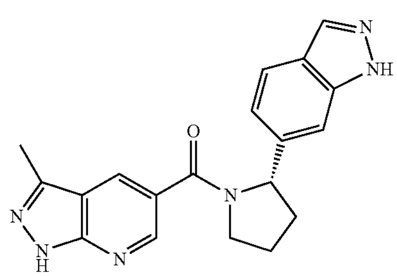 [SMILES: Cc1n[nH]c2ncc(C(=O)N3CCC[C@H]3c3ccc4cn[nH]c4c3)cc12] | 347 | | B | [(S)-2-(1H-Indazol-6-yl)-pyrrolidin-1-yl]-(3-methyl-1H-pyrazolo[3,4-b]pyridin-5-yl)-methanone | 1H NMR ((300 MHz, DMSO-d6) ppm = 13.60-12.80 (m, 1H), 12.61 (s, 1H), 8.51 (s, 1H), 8.15 (s, 1H), 7.95 (s, 1H), 7.67-7.64 (m, 1H), 7.31 (s, 1H), 7.01-6.99 (m, 1H), 5.26 (s, 1H), 3.94-3.86 (m, 1H), 3.77-3.75 (m, 1H), 2.48-2.22 (m, 4H), 2.08-1.80 (m, 3H). |

TABLE 1-continued

| No. | Structure | [M + 1]+ | RT [min] (HPLC method) | IC50 [µM] | Chemical Name | NMR |
|---|---|---|---|---|---|---|
| 231 | 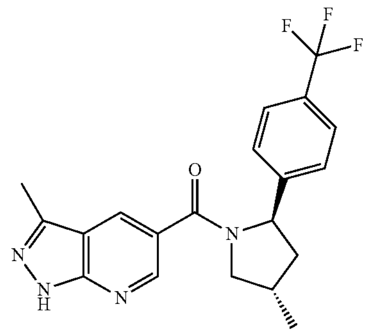 [SMILES: Cc1n[nH]c2ncc(C(=O)N3C[C@@H](C)C[C@@H]3c3ccc(C(F)(F)F)cc3)cc12] | 389 | 2.19 (A) | D | (3-Methyl-1H-pyrazolo[3,4-b]pyridin-5-yl)-[(2R,4S)-4-methyl-2-(4-trifluoromethyl-phenyl)-pyrrolidin-1-yl]-methanone | no NMR |
| 232 | 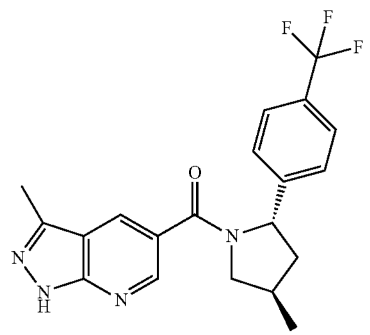 [SMILES: Cc1n[nH]c2ncc(C(=O)N3C[C@H](C)C[C@H]3c3ccc(C(F)(F)F)cc3)cc12] | 389 | 2.19 (A) | B | (3-Methyl-1H-pyrazolo[3,4-b]pyridin-5-yl)-[(2S,4R)-4-methyl-2-(4-trifluoromethyl-phenyl)-pyrrolidin-1-yl]-methanone | no NMR |
| 235 | 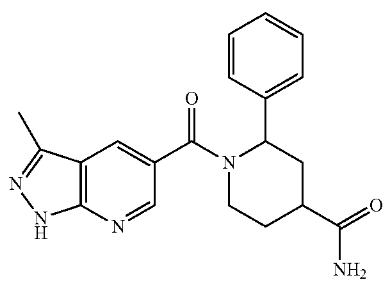 [SMILES: Cc1n[nH]c2ncc(C(=O)N3CCC(C(N)=O)CC3c3ccccc3)cc12] | 364.2 | 1.94 (B) | C | 1-(3-Methyl-1H-pyrazolo[3,4-b]pyridine-5-carbonyl)-2-phenyl-piperidine-4-carboxylic acid amide | 1H NMR (400 MHz, DMSO-d6) ppm = 13.40 (s, 1H), 8.68-8.25 (m, 2H), 7.53-7.22 (m, 5H), 6.81 (s, 2H), 6.13-5.85 (m, 1H), 5.16-4.49 (m, 1H), 3.89-3.47 (m, 1H), 2.59-2.52 (m, 3H), 2.39-2.18 (m, 1H), 2.08-1.85 (m, 2H), 1.80-1.56 (m, 2H). |
| 236 | 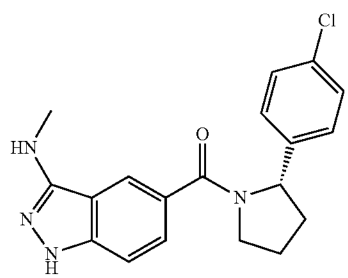 [SMILES: CNc1n[nH]c2ccc(C(=O)N3CCC[C@H]3c3ccc(Cl)cc3)cc12] | 355 | 1.93 (A) | A | [(S)-2-(4-Chloro-phenyl)-pyrrolidin-1-yl]-(3-methylamino-1H-indazol-5-yl)-methanone | 1H NMR (400 MHz, DMSO-d6) ppm = 12.32-12.09 (m, 1H), 8.28-8.13 (m, 1H), 7.69-7.55 (m, 1H), 7.46-6.94 (m, 7H), 5.19-5.11 (m, 1H), 3.81-3.60 (m, 2H), 2.93 (s, 3H), 2.46-2.35 (m, 1H), 1.94-1.68 (m, 3H). |
| 237 | 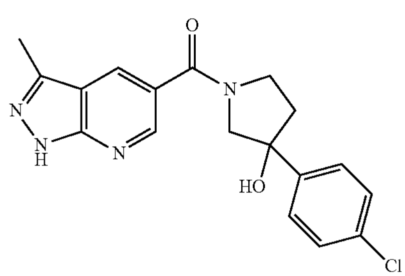 [SMILES: Cc1n[nH]c2ncc(C(=O)N3CCC(O)(c4ccc(Cl)cc4)C3)cc12] | 357.1 | 2.29 (B) | C | [3-(4-Chloro-phenyl)-3-hydroxy-pyrrolidin-1-yl]-(3-methyl-1H-pyrazolo[3,4-b]pyridin-5-yl)-methanone | 1H NMR (400 MHz, DMSO-d6) ppm = 13.43-13.36 (m, 1H), 8.69-8.64 (m, 1H), 8.48-8.38 (m, 1H), 7.61-7.50 (m, 2H), 7.46-7.36 (m, 2H), 5.69-5.51 (m, 1H), 4.02-3.78 (m, 2H), 3.78-3.49 (m, 2H), 2.57-2.50 (m, 3H), 2.39-2.25 (m, 1H), 2.17-2.05 (m, 1H). |

TABLE 1-continued

| No. | Structure | [M + 1]+ | RT [min] (HPLC method) | IC50 [µM] | Chemical Name | NMR |
|---|---|---|---|---|---|---|
| 238 | 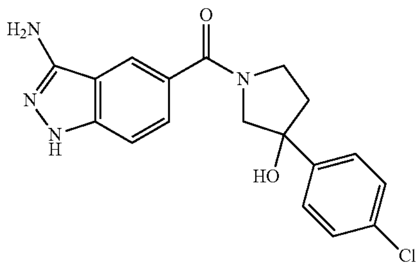 [SMILES: Nc1n[nH]c2ccc(C(=O)N3CCC(O)(c4ccc(Cl)cc4)C3)cc12] | 357.1 | 2.10 (B) | C | (3-Amino-1H-indazol-5-yl)-[3-(4-chloro-phenyl)-3-hydroxy-pyrrolidin-1-yl]-methanone | 1H NMR (400 MHz, DMSO-d6) ppm = 11.55 (s, 1H), 8.10-7.93 (m, 1H), 7.62-7.35 (m, 5H), 7.29-7.18 (m, 1H), 5.66-5.40 (m, 3H), 4.04-3.72 (m, 2H), 3.72-3.52 (m, 2H), 2.41-2.22 (m, 1H), 2.16-2.02 (m, 1H). |
| 239 | 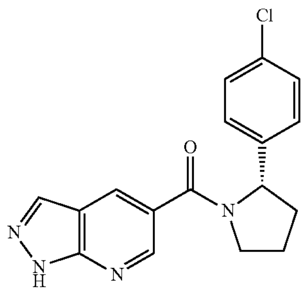 [SMILES: O=C(c1cnc2[nH]ncc2c1)N1CCC[C@H]1c1ccc(Cl)cc1] | 327.1 | 2.46 (B) | C | [(S)-2-(4-Chloro-phenyl)-pyrrolidin-1-yl]-(1H-pyrazolo[3,4-b]pyridin-5-yl)-methanone | 1H NMR (400 MHz, DMSO-d6) ppm = 13.96-13.58 (m, 1H), 8.79-8.01 (m, 3H), 7.46-7.29 (m, 3H), 7.26-6.94 (m, 1H), 5.22-4.98 (m, 1H), 3.98-3.75 (m, 1H), 3.64-3.53 (m, 1H), 2.45-2.34 (m, 1H), 1.98-1.80 (m, 2H), 1.80-1.68 (m, 1H). |
| 240 | 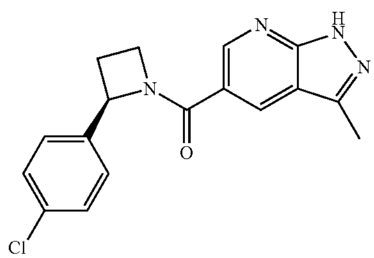 [SMILES: Cc1n[nH]c2ncc(C(=O)N3CC[C@@H]3c3ccc(Cl)cc3)cc12] | 327 | 1.91 (A) | D | [(R)-2-(4-Chloro-phenyl)-azetidin-1-yl]-(3-methyl-1H-pyrazolo[3,4-b]pyridin-5-yl)-methanone | no NMR |
| 241 | 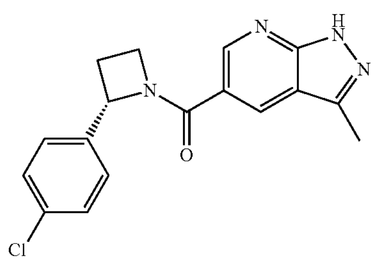 | 327 | 1.91 (A) | B | [(S)-2-(4-Chloro-phenyl)-azetidin-1-yl]-(3-methyl-1H-pyrazolo[3,4-b]pyridin-5-yl)-methanone | 1H NMR (400 MHz, DMSO-d6) ppm = 13.45 (s, 1H), 8.78 (s, 1H), 8.55 (s, 1H), 7.65-7.25 (m, 4H), 5.71-5.42 (m, 1H), 4.78-4.14 (m, 2H), 2.88-2.66 (m, 1H), 2.54 (s, 3H), 2.43-2.26 (m, 1H). |
| 242 | 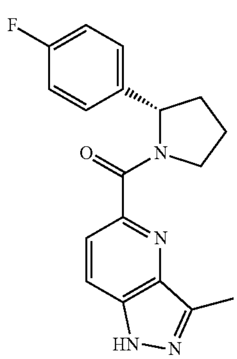 [SMILES: Cc1n[nH]c2ccc(C(=O)N3CCC[C@H]3c3ccc(F)cc3)nc12] | 325 | 2.55 (L) | A | [(S)-2-(4-Fluoro-phenyl)-pyrrolidin-1-yl]-(3-methyl-1H-pyrazolo[4,3-b]pyridin-5-yl)-methanone | 1H NMR (500 MHz, CDCl3) ppm = 7.97 (d, J = 8.7 Hz, 0.45H), 7.79 (d, J = 8.7 Hz, 0.45H), 7.66 (d, J = 8.7 Hz, 0.55H), 7.59 (d, J = 8.7 Hz, 0.55H), 7.32-7.26 (m, 0.90H), 7.01-6.93 (m, 2H), 6.82-6.76 (m, 1.1H), 5.89-5.84 (m, 0.55H), 5.42-5.37 (m, 0.45H), 4.39 (dt, J = 12.3, 6.8 Hz, 0.45H), 4.11 (dt, J = 12.3, 6.8 Hz, 0.45H), 4.06-3.94 (m, 1.1H), 2.73 (s, 1.35H), 2.48 (s, 1.65H), 2.52-2.37 (m, 1.1H), 2.10-1.85 (m, 2.9H). |

TABLE 1-continued

| No. | Structure | [M + 1]+ | RT [min] (HPLC method) | IC50 [μM] | Chemical Name | NMR |
|---|---|---|---|---|---|---|
| 243 | 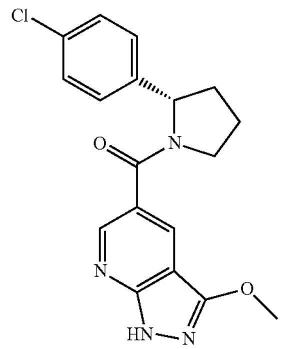 [SMILES: COc1n[nH]c2ncc(C(=O)N3CCC[C@H]3c3ccc(Cl)cc3)cc12] | 357/359 | 2.67 (L) | B | [(S)-2-(4-Chloro-phenyl)-pyrrolidin-1-yl]-(3-methoxy-1H-pyrazolo[3,4-b]pyridin-5-yl)-methanone | 1H NMR (500 MHz, CD3OD) ppm = 8.72 (s, 0.6H), 8.39 (s, 0.6H), 8.26 (s, 0.4H), 7.86 (s, 0.4H), 7.37 (d, J = 8.1 Hz, 1.2H), 7.32 (d, J = 8.1 Hz, 1.2H), 7.17 (d, J = 8.0 Hz, 0.8H), 6.97 (d, J = 8.0 Hz, 0.8H), 5.21 (t, J = 7.3 Hz, 0.6H), 5.02-4.96 (m, 0.4H), 4.09 (s, 1.8H), 4.01 (s, 1.2H), 4.00-3.85 (m, 1.4H), 3.75-3.68 (m, 0.6H), 2.50-2.40 (m, 1H), 2.08-1.98 (m, 1.4H), 1.96-1.83 (m, 1.6H). |
| 244 | 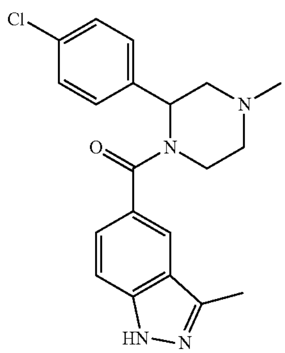 [SMILES: Cc1n[nH]c2ccc(C(=O)N3CCN(C)CC3c3ccc(Cl)cc3)cc12] | 361/371 | 0.96 (L) | B | [2-(4-Chloro-phenyl)-4-methyl-piperazin-1-yl]-(3-methyl-1H-indazol-5-yl)-methanone | 1H NMR (500 MHz, CD3OD) ppm = 7.84 (s, 1H), 7.55-7.34 (m, 6H), 5.64 (bs, 1H), 3.92 (bs, 1H), 3.51-3.44 (m, 1H), 3.27-3.18 (m, 1H), 2.78-2.72 (m, 1H), 2.54 (s, 3H), 2.53-2.48 (m, 1H), 2.29 (s, 3H), 2.20-2.14 (m, 1H). |
| 245 | 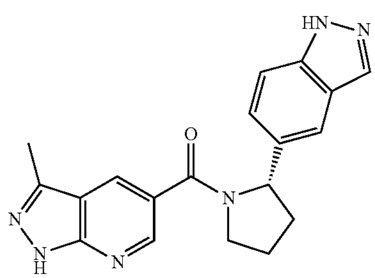 [SMILES: Cc1n[nH]c2ncc(C(=O)N3CCC[C@H]3c3ccc4[nH]ncc4c3)cc12] | 347 | 1.34 (H) | B | [(S)-2-(1H-Indazol-5-yl)-pyrrolidin-1-yl]-(3-methyl-1H-pyrazolo[3,4-b]pyridin-5-yl)-methanone | 1H NMR ((300 MHz, DMSO-d6) ppm = 13.11 (s, 1H), 12.76 (s, 1H), 8.52 (s, 1H), 8.40-8.09 (m, 1H), 7.95 (s, 1H), 7.62-7.50 (m, 1H), 7.50-7.35 (m, 1H), 7.22 (s, 1H), 5.24 (s, 1H), 3.92-3.90 (m, 1H), 3.79-3.72 (m, 1H), 2.42-2.31 (m, 4H), 1.97-1.90 (m, 3H). |
| 246 | 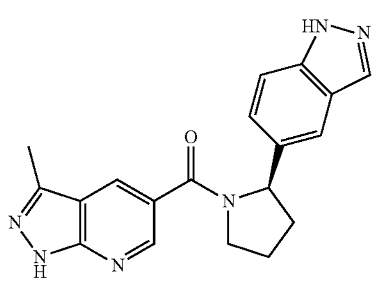 [SMILES: Cc1n[nH]c2ncc(C(=O)N3CCC[C@@H]3c3ccc4[nH]ncc4c3)cc12] | 347 | 1.44 (H) | D | [(R)-2-(1H-Indazol-5-yl)-pyrrolidin-1-yl]-(3-methyl-1H-pyrazolo[3,4-b]pyridin-5-yl)-methanone | 1H NMR ((300 MHz, DMSO-d6) ppm = 13.11 (s, 1H), 12.76 (s, 1H), 8.52 (s, 1H), 8.40-8.09 (m, 1H), 7.95 (s, 1H), 7.62-7.50 (m, 1H), 7.50-7.35 (m, 1H), 7.22 (s, 1H), 5.24 (s, 1H), 3.92-3.90 (m, 1H), 3.79-3.72 (m, 1H), 2.42-2.31 (m, 4H), 1.97-1.90 (m, 3H). |

TABLE 1-continued

| No. | Structure | [M + 1]+ | RT [min] (HPLC method) | IC50 [µM] | Chemical Name | NMR |
|---|---|---|---|---|---|---|
| 247 | 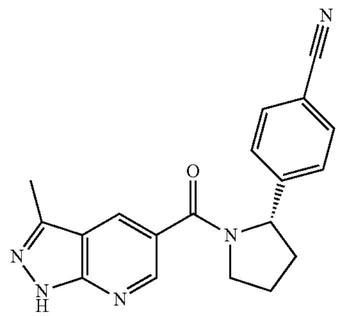 [SMILES: Cc1n[nH]c2ncc(C(=O)N3CCC[C@H]3c3ccc(C#N)cc3)cc12] | 332 | | B | 4-[(S)-1-(3-Methyl-1H-pyrazolo[3,4-b]pyridine-5-carbonyl)-pyrrolidin-2-yl]-benzonitrile | 1H NMR (300 MHz, DMSO-d6) ppm = 13.13 (s, 1H), 8.59 (s, 1H), 8.29 (s, 1H), 7.72-7.69 (m, 2H), 7.49 (s, 2H), 5.30-5.10 (m, 1H), 3.97-3.78 (m, 1H), 3.76-3.58 (m, 1H), 2.55-2.35 (m, 4H), 2.01-1.88 (m, 2H), 1.82-1.69 (m, 1H). |
| 248 | 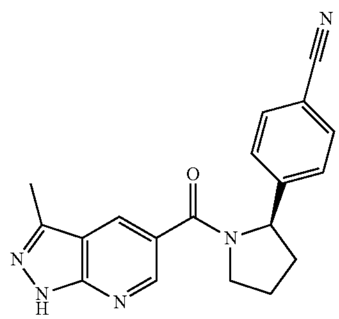 [SMILES: Cc1n[nH]c2ncc(C(=O)N3CCC[C@@H]3c3ccc(C#N)cc3)cc12] | 332 | 1.19 (H) | D | 4-[(R)-1-(3-Methyl-1H-pyrazolo[3,4-b]pyridine-5-carbonyl)-pyrrolidin-2-yl]-benzonitrile | 1H NMR ((300 MHz, DMSO-d6) ppm = 13.13 (s, 1H), 8.59 (s, 1H), 8.29 (s, 1H), 7.72-7.69 (m, 2H), 7.49 (s, 2H), 5.30-5.10 (m, 1H), 3.97-3.78 (m, 1H), 3.76-3.58 (m, 1H), 2.55-2.35 (m, 4H), 2.01-1.88 (m, 2H), 1.82-1.69 (m, 1H). |
| 249 | 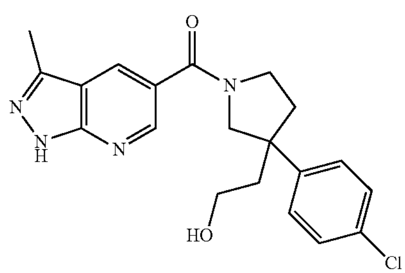 [SMILES: Cc1n[nH]c2ncc(C(=O)N3CCC(CCO)(c4ccc(Cl)cc4)C3)cc12] | 385.2 | 2.32 (B) | B | [3-(4-Chloro-phenyl)-3-(2-hydroxy-ethyl)-pyrrolidin-1-yl]-(3-methyl-1H-pyrazolo[3,4-b]pyridin-5-yl)-methanone | 1H NMR (400 MHz, DMSO-d6, 90° C.) ppm = 13.14 (s, 1H), 8.59 (d, J = 2.1 Hz, 1H), 8.30 (d, J = 2.1 Hz, 1H), 7.40-7.23 (m, 4H), 4.02 (t, J = 5.1 Hz, 1H), 3.88-3.82 (m, 2H), 3.72-3.62 (m, 1H), 3.51-3.39 (m, 1H), 3.27-3.17 (m, 1H), 3.16-3.06 (m, 1H), 2.52 (s, 3H), 2.34-2.15 (m, 2H), 1.97-1.78 (m, 2H). |
| 250 | 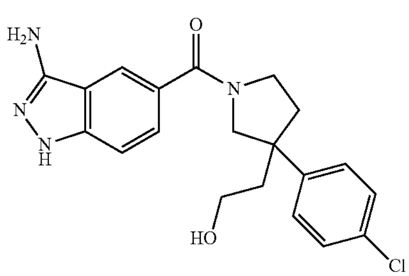 [SMILES: Nc1n[nH]c2ccc(C(=O)N3CCC(CCO)(c4ccc(Cl)cc4)C3)cc12] | 385.2 | 2.13 (B) | C | (3-Amino-1H-indazol-5-yl)-[3-(4-chloro-phenyl)-3-(2-hydroxy-ethyl)-pyrrolidin-1-yl]-methanone | 1H NMR (400 MHz, DMSO-d6) ppm = 11.65-11.47 (m, 1H), 7.98 (s, 1H), 7.48-7.11 (m, 6H), 5.48 (s, 2H), 4.41-4.30, 4.30-4.20 (2 × m, 1H, mixture of rotamers ratio = 1:1), 3.88-3.74 (m, 2H), 3.70-3.57 (m, 1H), 3.45-3.33 (m, 1H), 3.21-3.07, 3.01-2.89 (2 × m, 1H, mixture of rotamers, ratio = 1:1), 2.37-1.64 (m, 4H). |

TABLE 1-continued

| No. | Structure | [M + 1]+ | RT [min] (HPLC method) | IC50 [μM] | Chemical Name | NMR |
|---|---|---|---|---|---|---|
| 251 | 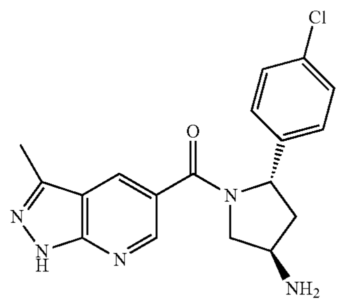 [SMILES: Cc1n[nH]c2ncc(C(=O)N3C[C@H](N)C[C@H]3c3ccc(Cl)cc3)cc12] | 356 | 0.93 (H) | C | [(2S,4R)-4-Amino-2-(4-chloro-phenyl)-pyrrolidin-1-yl]-(3-methyl-1H-pyrazolo[3,4-b]pyridin-5-yl)-methanone | 1H NMR (400 MHz, DMSO-d6) ppm = 8.70 (s, 1H), 8.51 (s, 1H), 7.44 (d, J = 8 Hz, 2H), 7.38 (d, J = 8 Hz, 2H), 5.28 (m, 1H), 4.11-4.05 (m, 1H), 3.52 (m, 2H), 3.31 (m, 3H), 2.55 (s, 3H), 2.15 (m, 1H), 1.84 (m, 3H). |
| 252 | 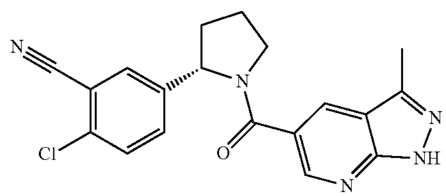 [SMILES: Cc1n[nH]c2ncc(C(=O)N3CCC[C@H]3c3ccc(Cl)c(C#N)c3)cc12] | 366 | 1.34 (H) | C | 2-Chloro-5-[(S)-1-(3-methyl-1H-pyrazolo[3,4-b]pyridine-5-carbonyl)-pyrrolidin-2-yl]-benzonitrile | 1H NMR (300 MHz, DMSO-d6) ppm = 13.14 (s, 1H), 8.59 (s, 1H), 8.31 (s, 1H), 7.85 (s, 1H), 7.64-7.59 (m, 2H), 5.19-5.15 (m, 1H), 3.97-3.89 (m, 1H), 3.67-3.62 (m, 1H)2.50-2.47 (m, 3H), 2.43-2.37 (m, 1H), 1.98-1.83 (m, 3H) |
| 253 | 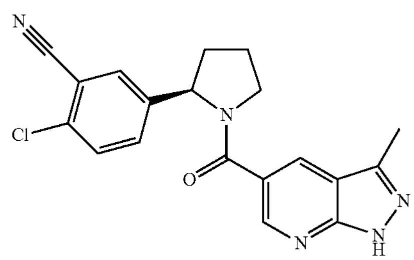 [SMILES: Cc1n[nH]c2ncc(C(=O)N3CCC[C@@H]3c3ccc(Cl)c(C#N)c3)cc12] | 366 | 1.33 (H) | D | 2-Chloro-5-[(R)-1-(3-methyl-1H-pyrazolo[3,4-b]pyridine-5-carbonyl)-pyrrolidin-2-yl]-benzonitrile | 1H NMR (300 MHz, DMSO-d6) ppm = 13.14 (s, 1H), 8.59 (s, 1H), 8.31 (s, 1H), 7.85 (s, 1H), 7.62-7.59 (m, 2H), 5.19-5.15 (m, 1H), 3.95-3.89 (m, 1H), 3.67-3.65 (m, 1H) 2.48-2.47 (m, 3H), 2.39-2.37 (m, 1H), 1.96-1.77 (m, 3H) |
| 254 | 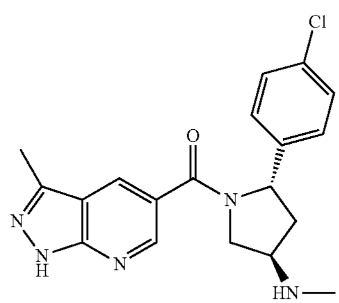 [SMILES: CN[C@@H]1C[C@@H](c2ccc(Cl)cc2)N(C(=O)c2cnc3[nH]nc(C)c3c2)C1] | 369 | | C | [(2S,4R)-2-(4-Chloro-phenyl)-4-methylamino-pyrrolidin-1-yl]-(3-methyl-1H-pyrazolo[3,4-b]pyridin-5-yl)-methanone | 1H NMR (400 MHz, DMSO-d6) ppm = 13.38 (s, 1H), 8.69 (s, 1H), 8.52 (s, 1H), 7.46 (d, J = 8 Hz, 2H), 7.38 (d, J = 8 Hz, 2H), 5.20 (m, 1H), 4.11-4.07 (m, 1H), 3.46-3.41 (m, 2H), 2.59 (s, 3H), 2.37-2.15 (m, 5H), 1.84 (m, 2H). |
| 255 | 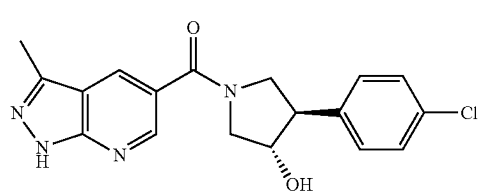 [SMILES: Cc1n[nH]c2ncc(C(=O)N3C[C@@H](O)[C@H](c4ccc(Cl)cc4)C3)cc12] | 357 | | D | [(3R,4S)-3-(4-Chloro-phenyl)-4-hydroxy-pyrrolidin-1-yl]-(3-methyl-1H-pyrazolo[3,4-b]pyridin-5-yl)-methanone | 1H NMR ((300 MHz, DMSO-d6) ppm = 13.15 (s, 1H), 8.65-8.64 (m, 1H), 8.36-8.35 (m, 1H), 7.38-7.33 (m, 4H), 5.30-5.00 (m, 1H), 4.27-4.25 (m, 1H), 4.04-3.98 (m, 1H), 3.86-3.80 (m, 1H), 3.65-3.59 (m, 1H), 3.46-3.40 (m, 1H), 3.32-3.24 (m, 1H), 2.52 (s, 3H). |

TABLE 1-continued

| No. | Structure | [M + 1]+ | RT [min] (HPLC method) | IC50 [μM] | Chemical Name | NMR |
|---|---|---|---|---|---|---|
| 256 | 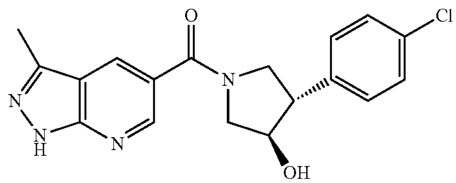 [SMILES: Cc1n[nH]c2ncc(C(=O)N3C[C@H](c4ccc(Cl)cc4)[C@@H](O)C3)cc12] | 356 | 0.90 (J) | A | Trans-[3-(4-Chloro-phenyl)-4-hydroxy-pyrrolidin-1-yl]-(3-methyl-1H-pyrazolo[3,4-b]pyridin-5-yl)-methanone | 1H NMR (300 Hz, DMSO-d6) ppm = 13.15 (s, 1H), 8.65-8.64 (m, 1H), 8.36-8.35 (m, 1H), 7.38-7.33 (m, 4H), 5.30-5.00 (m, 1H), 4.27-4.25 (m, 1H), 4.04-3.98 (m, 1H), 3.86-3.80 (m, 1H), 3.65-3.59 (m, 1H), 3.46-3.40 (m, 1H), 3.32-3.24 (m, 1H), 2.52 (s, 3H). |
| 257 | 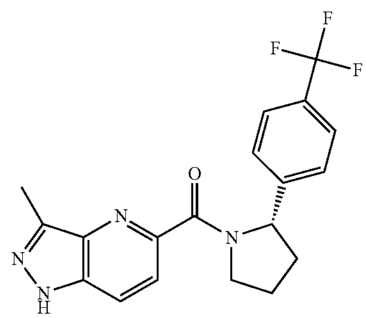 [SMILES: Cc1n[nH]c2ccc(C(=O)N3CCC[C@H]3c3ccc(C(F)(F)F)cc3)nc12] | 375 | 1.31 (M) | A | (3-Methyl-1H-pyrazolo[4,3-b]pyridin-5-yl)-[(S)-2-(4-trifluoromethyl-phenyl)-pyrrolidin-1-yl]-methanone | 1H NMR (500 MHz, CDCl3) δ 7.98 (d, J = 8.7 Hz, 1H), 7.82-7.74 (m, 2H), 8.00-7.55 (m, 3H), 7.47-7.42 (m, 4H), 7.21 (d, J = 8.0 Hz, 2H), 6.02-5.97 (m, 1H), 5.47 (br dd, J = 7.8, 5.2 Hz, 1H), 4.45 (dt, J = 12.0, 6.9 Hz, 1H), 4.19 (dt, J = 12.4, 6.8 Hz, 1H), 4.08-4.01 (m, 2H), 2.72 (s, 3H), 2.51-2.42 (m, 2H), 2.32 (s, 3H), 2.10-1.98 (m, 4H), 1.96-1.89 (m, 2H). |
| 258 | 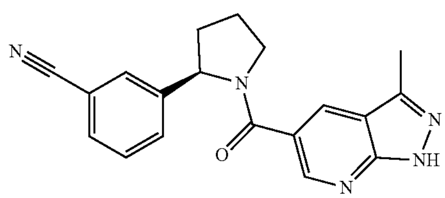 [SMILES: Cc1n[nH]c2ncc(C(=O)N3CCC[C@@H]3c3cccc(C#N)c3)cc12] | 332 | 1.10 (H) | D | 3-[(R)-1-(3-Methyl-1H-pyrazolo[3,4-b]pyridine-5-carbonyl)-pyrrolidin-2-yl]-benzonitrile | 1H NMR (300 MHz, DMSO-d6) ppm = 13.12 (s, 1H), 8.57 (s, 1H), 8.28-8.24 (s, 1H), 7.70-7.46 (m, 4H), 5.21-5.19 (m, 1H), 3.94-3.89 (m, 1H), 3.68-3.63 (m, 1H), 2.48 (s, 3H), 1.92 (s, 1H), 1.90-1.78 (m, 3H) |
| 259 | 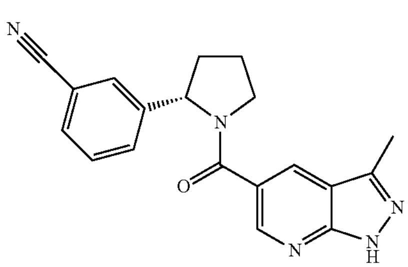 [SMILES: Cc1n[nH]c2ncc(C(=O)N3CCC[C@H]3c3cccc(C#N)c3)cc12] | 332 | 1.10 (H) | C | 3-[(S)-1-(3-Methyl-1H-pyrazolo[3,4-b]pyridine-5-carbonyl)-pyrrolidin-2-yl]-benzonitrile | 1H NMR (300 MHz, DMSO-d6) ppm = 13.14-13.12 (s, 1H), 8.58 (s, 1H), 8.29 (s, 1H), 7.70-7.60 (m, 3H), 7.51-7.46 (m, 1H), 5.21-5.17 (m, 1H), 3.97-3.89 (m, 1H), 3.68-3.67 (m, 1H), 2.488-2.482 (s, 3H), 2.250 (s, 1H), 1.94-1.77 (m, 3H) |

| No. | Structure | [M + 1]+ | RT [min] (HPLC method) | IC50 [µM] | Chemical Name | NMR |
|---|---|---|---|---|---|---|
| 260 | 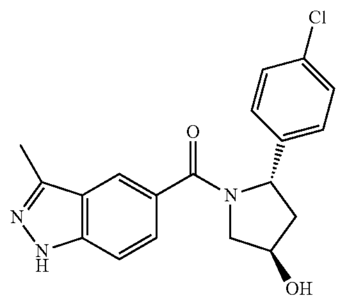 | 359/361 | 1.40 (K) | A | [2-(4-Chloro-3-fluoro-phenyl)-pyrrolidin-1-yl]-(3-methyl-1H-pyrazolo[4,3-b]pyridin-5-yl)-methanone | 1H NMR (500 MHz, CDCl3) ppm = 7.98 (d, J = 8.8 Hz, 0.5H), 7.85 (dd, J = 8.8, 5.5 Hz, 1H), 7.71 (d, J = 8.8 Hz, 0.5H), 7.29 (t, J = 8.1 Hz, 0.5H), 7.17 (dd, J = 8.3, 7.4 Hz, 0.5H), 7.09 (dd, J = 10.0, 2.0 Hz, 0.5H), 7.05 (dd, J = 8.1, 2.1 Hz, 0.5H), 6.88 (dd, J = 10.0, 2.0 Hz, 0.5H), 6.81 (dd, J = 8.3, 2.1 Hz, 0.5H), 5.92 (dd, J = 7.5, 2.7 Hz, 0.5H), 5.34 (dd, J = 7.8, 5.3 Hz, 0.5H), 4.38 (dt, J = 11.7, 6.9 Hz, 0.5H), 4.11 (dt, J = 11.7, 6.9 Hz, 0.5H), 4.02-3.94 (m, 1H), 2.75 (s, 1.5H), 2.49-2.34 (m, 2.5H), 2.10-1.82 (m, 3H). |
| 261 | 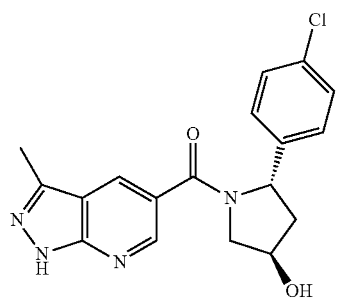 [SMILES: Cc1n[nH]c2ncc(C(=O)N3C[C@H](O)C[C@H]3c3ccc(Cl)cc3)cc12] | 357 | 1.02 (H) | C | [(2S,4R)-2-(4-Chloro-phenyl)-4-hydroxy-pyrrolidin-1-yl]-(3-methyl-1H-pyrazolo[3,4-b]pyridin-5-yl)-methanone | 1H NMR (300 MHz, CD3OD) ppm = 8.49 (s, 1H), 8.23 (s, 1H), 7.86 (s, 0.48H), 7.43 (s, 0.43H), 7.43-7.40 (m, 2H), 7.33-7.30 (m, 2H), 7.01-6.98 (m, 1H), 6.82-6.80 (d, J = 4 Hz, 0.87H), 5.37-5.32 (m, 1H), 5.09-5.04 (m, 0.39H), 4.55 (s, 0.44H), 4.40 (s, 1H), 4.19-4.14 (m, 1H), 3.97 (s, 1H), 3.59-3.56 (m, 1H), 3.28-3.23 (s, 0.38H), 2.58 (m, 3H), 2.52-2.43 (m, 3H), 2.08-1.97 (m, 2H), 1.39-1.37 (m, 0.5H), 1.34-1.32 (m, 0.66H), 1.25-1.22 (s, 2H), 1.02-0.99 (m, 0.5H), 0.87-0.82 (m, 1H) |
| 262 | 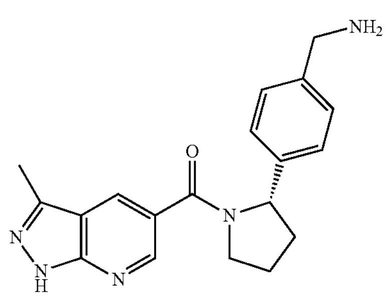 [SMILES: Cc1n[nH]c2ncc(C(=O)N3CCC[C@H]3c3ccc(CN)cc3)cc12] | 336 | 1.18 (G) | C | [(S)-2-(4-Aminomethyl-phenyl)-pyrrolidin-1-yl]-(3-methyl-1H-pyrazolo[3,4-b]pyridin-5-yl)-methanone | 1H NMR (300 MHz, DMSO-d6) ppm = 8.54-8.50 (s, 1H), 8.18-8.17 (s, 1H), 7.24-7.16 (m, 4H), 5.12 (s, 1H), 3.82 (m, 1H), 3.68 (s, 3H), 2.48-2.33 (m, 5H), 1.92-1.78 (m, 4H) |

TABLE 1-continued

| No. | Structure | [M + 1]⁺ | RT [min] (HPLC method) | IC50 [μM] | Chemical Name | NMR |
|---|---|---|---|---|---|---|
| 263 | 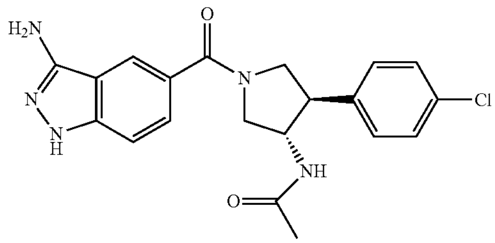 [SMILES: CC(=O)N[C@@H]1CN(C(=O)c2ccc3[nH]nc(N)c3c2)C[C@H]1c1ccc(Cl)cc1] | 398 | 1.64 (A) | B | N-[(3S,4R)-1-(3-Amino-1H-indazole-5-carbonyl)-4-(4-chloro-phenyl)-pyrrolidin-3-yl]-acetamide (racemic) | 1H NMR (400 MHz, DMSO-d6, T = 363 K) ppm = 7.98 (s, 1H), 7.91 (d, br, J = 7.1 Hz, 1H), 7.46 (dd, J = 8.7, 1.5 Hz, 1H), 7.34 (s, 4H), 7.25 (d, J = 8.7 Hz, 1H), 4.47-4.36 (m, 1H), 3.99 (dd, J = 11.3, 7.9 Hz, 1H), 3.91 (dd, J = 11.3, 7.4 Hz, 1H), 3.65-3.58 (m, 1H), 3.42-3.36 (m, 2H), 1.76 (s, 3H), three mobile protons were not visible to exchange effects. |
| 264 | 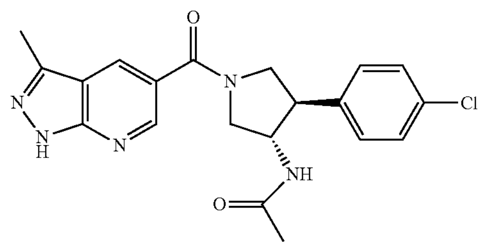 [SMILES: CC(=O)N[C@@H]1CN(C(=O)c2cnc3[nH]nc(C)c3c2)C[C@H]1c1ccc(Cl)cc1] | 398 | 1.73 (A) | B | N-[(3S,4R)-4-(4-Chloro-phenyl)-1-(3-methyl-1H-pyrazolo[3,4-b]pyridine-5-carbonyl)-pyrrolidin-3-yl]-acetamide (racemic) | 1H NMR (400 MHz, DMSO-d6) ppm = 13.14 (s, 1H), 8.64 (d, J = 2.0 Hz, 1H), 8.34 (d, J = 2.0 Hz, 1H), 7.89 (d, J = 7.2 Hz, 1H), 7.34 (s, 4H), 4.59-4.35 (m, 1H), 4.09-3.95 (m, 1H), 3.95-3.84 (m, 1H), 3.69-3.56 (m, 1H), 3.48-3.32 (m, 2H), 2.51 (s, 3H), 1.76 (s, 3H). |
| 265 | 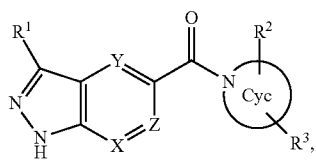 | 342 | 1.17 (J) | 0.34 | (3-Amino-1H-pyrazolo[4,3-b]pyridin-5-yl)-[(S)-2-(4-chloro-phenyl)-pyrrolidin-1-yl]-methanone | 1H NMR (300 Hz, DMSO-d6) ppm = 11.84 (s, 1H), 8.65-8.64 (m, 1H), 8.13 (s, 1H), 7.27 (s, 4H), 5.60-5.20 (m, 3H), 4.12-3.90 (m, 1H), 3.90-3.70 (m, 1H), 2.41-2.29 (m, 1H), 1.99-1.77 (m, 4H). |

Example numbers 7, 8, 42, 75, 119, 126, 128, 140, 146, 151, 161, 163, 187, 201, 212, 213, 233 and 234 were omitted intentionally.

The invention claimed is:

1. A compound of Formula (I)

(I)

wherein:
X, Y independently are CH or N,
Z is CH, C-Hal or N,
$R^1$ is H, LA, CA, $NH_2$, NH(LA) or (LA)NH(LA), Hal, —S(LA), —SO2(LA), O(LA),
Cyc is a 3, 4, 5, 6 or 7 membered aliphatic heterocycle having 1 or 2 N atoms, or 1 N atom and 1 O atom, $R^2$ is -LA-Ar or Ar, which is in the 2-, or 3-position with respect to the ring N atom of Cyc, $R^3$ is H, OH, $NH_2$, COO(LA), $CONH_2$, CONH(LA) NHCO(LA), (LA)OH, NH(LA) or LA, which is in any position of Cyc, Ar is a mono- or binuclear, aliphatic or aromatic 3, 4, 5, 6, 7, 8, 9 or 10 membered homo- or heterocycle, having 0, 1, 2, 3 or 4 N, O and/or S atoms, which is unsubstituted, or mono- or independently disubstituted by Hal, OH, CN, LA, O(LA), or S(LA), LA is unbranched or branched alkyl, having 1, 2, 3, 4 or 5 carbon atoms, which is saturated or partially unsaturated, wherein 1, 2 or 3 H atoms are optionally replaced by Hal, CA is cycloalkyl having 3, 4, 5 or 6 carbon atoms, or cycloalkyl alkyl having 3, 4, 5 or 6 ring carbon atoms and 1 or 2 non-ring carbon atoms, and Hal is F, Cl, Br or I, or a stereoisomer or tautomer or pharmaceutically acceptable salt thereof.

2. The compound according to claim 1, wherein
X, Y, Z independently are CH or N,
$R^1$ is H, LA, CA, $NH_2$, NH(LA) or (LA)NH(LA),
Cyc is a 3, 4, 5, 6 or 7 membered aliphatic heterocycle having 1 N atom,
$R^2$ is -LA-Ar or Ar, which is in the 2-, or 3-position with respect to the ring N atom of Cyc,
$R^3$ is H, OH, $NH_2$, COO(LA), $CONH_2$, CONH(LA) or LA, which is in any position of Cyc,
Ar is a mono- or binuclear, aliphatic or aromatic 3, 4, 5, 6, 7, 8, 9 or 10 membered homo- or heterocycle, having 0, 1, 2, 3 or 4 N, O and/or S atoms, which is unsubstituted, or mono- or independently disubstituted by Hal, OH, CN, LA, O(LA), or S(LA),
LA is unbranched or branched alkyl, having 1, 2, 3, 4 or 5 carbon atoms,
which is saturated or partially unsaturated, wherein 1, 2 or 3 H atoms are optionally replaced by Hal,
CA is cycloalkyl having 3, 4, 5 or 6 carbon atoms, or cycloalkyl alkyl having 3, 4, 5 or 6 ring carbon atoms and 1 or 2 non-ring carbon atoms, and
Hal is F, Cl, Br or I,
or a pharmaceutically acceptable salt thereof.

3. The compound according to claim 2, wherein
X, Y independently are CH or N,
Z is CH,
$R^1$ is H, LA, CA, $NH_2$, NH(LA) or (LA)NH(LA),
Cyc is a 3, 4, 5, 6 or 7 membered aliphatic heterocycle having 1 N atom,
$R^2$ is -LA-Ar or Ar, which is in the 2-, or 3-position with respect to the ring N atom of Cyc,
$R^3$ is H, $NH_2$ or LA, which is in any position of Cyc,
Ar is a mononuclear, aromatic, 6 membered homo- or heterocycle,
having 0, 1 or 2 N atoms, which is unsubstituted, or mono- or independently disubstituted by Hal, OH, CN, LA, O(LA), or S(LA),
LA is unbranched or branched alkyl, having 1, 2, 3, 4 or 5 carbon atoms,
which is saturated or partially unsaturated, wherein 1, 2 or 3 H atoms are optionally replaced by Hal,
CA is cycloalkyl having 3, 4, 5 or 6 carbon atoms, or cycloalkyl alkyl having 3, 4, 5 or 6 ring carbon atoms and 1 or 2 non-ring carbon atoms, and
Hal is F, Cl, Br or I,
or a pharmaceutically acceptable salt thereof.

4. The compound according to claim 1, which is of formula (IIa) or (IIb),

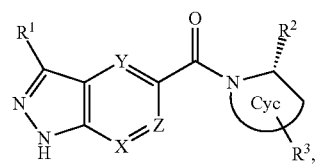

(IIa)

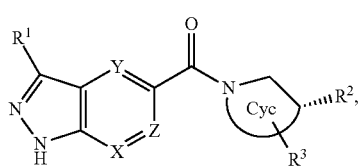

(IIb)

or a pharmaceutically acceptable salt thereof.

5. The compound according to claim 1, in which
Ar is a mononuclear, aromatic, 6 membered homo- or heterocycle, having 0, 1 or 2 N atoms, which is unsubstituted, or monosubstituted by Hal, LA, or O(LA),
or
X is N,
or
X is CH,
or
Y is CH,
or
Y is N,
or
Z is CH,
or
X is CH,
Y is N, and
Z is CH,
or
X is N,
Y is CH, and
Z is CH,
or
Ar is a mononuclear, aromatic, 6 membered homo- or heterocycle, having 0, 1 or 2 N atoms, which is unsubstituted, or mono- or independently disubstituted by Hal, OH, CN, LA, O(LA), or S(LA),
X is CH,
Y is N, and
Z is CH,
or
Ar is a mononuclear, aromatic, 6 membered homo- or heterocycle, having 0, 1 or 2 N atoms, which is unsubstituted, or mono- or independently disubstituted by Hal, OH, CN, LA, O(LA), or S(LA),
X is N,
Y is CH, and
Z is CH,
or
$R^1$ is LA, $NH_2$, or NHLA
or
Cyc has 4, 5 or 6 ring atoms,
or
$R^3$ is H, OH, $NH_2$ or methyl,
or
$R^3$ is H,
or
$R^2$ is benzyl,
$R^3$ is H, $NH_2$ or methyl, and
Cyc has 6 ring atoms,
or
Cyc has 5 or 6 ring atoms, and
$R^2$ is phenyl, which is unsubstituted, or mono- or independently disubstituted by Hal or LA,
or
Z is CH, and
$R^2$ is benzyl or phenyl, which phenyl is unsubstituted, or mono- or independently disubstituted by Hal or LA,
or
X is N or CH,
Y is CH,
Z is CH, and
$R^1$ is methyl, n-propyl, i-propyl, cyclopropyl, $NH_2$, or NHLA,
or
Z is CH,
Cyc has 5 ring atoms, or Z is CH, R² is phenyl, which is unsubstituted or monosubstituted by Br, Cl, methyl or CF₃, and R³ is H, or Z is CH, R² is phenyl, which is unsubstituted or monosubstituted by Br, Cl, methyl or CF₃, and R³ is H, or Z is CH, R² is phenyl, which is unsubstituted or para-substituted by Br, Cl, methyl or CF₃, and R³ is H, or Y is CH, Z is CH, and R¹ is methyl, n-propyl, i-propyl, cyclopropyl or NH₂, or X is N or CH, Y is CH, Z is CH, R¹ is methyl, n-propyl, i-propyl, cyclopropyl or NH₂, and Cyc has 4, 5 or 6 ring atoms, or X is N or CH, Y is CH, Z is CH, R¹ is methyl, n-propyl, i-propyl, cyclopropyl or NH₂, Cyc has 4, 5 or 6 ring atoms, R² is phenyl, which is unsubstituted or para-substituted by Br, Cl, methyl or CF₃, and R³ is H, or X is N or CH, Y is CH, Z is CH, R¹ is methyl, n-propyl, i-propyl, cyclopropyl or NH₂, Cyc has 5 ring atoms, R² is phenyl, which is unsubstituted or para-substituted by Br, Cl, methyl or CF₃, and R³ is H, or R¹ is methyl, n-propyl, i-propyl, cyclopropyl, methylsulfanyl, methanesulfonyl, methoxy, F or NH₂, or R³ is H, OH, NH₂, methyl, acetamido, 2-hydroxyethyl or methylamino, or Z is CH or C(Hal), Cyc has 4, 5 or 6 ring atoms, of which 1 atom is N and the other atoms are C, R² is phenyl, which is unsubstituted or para-substituted by Br, Cl, F, methyl, methoxy, isopropyl or CF₃, or independently meta-/para-disubstituted by Cl and F, and R³ is H, or Z is CH or C(Hal), Cyc has 4 or 5 ring atoms, of which 1 atom is N and the other atoms are C, R² is phenyl, which is unsubstituted or para-substituted by Br, Cl, F, methyl, methoxy, isopropyl or CF₃, or meta-substituted by F and para-substituted by Cl, and R³ is H, or a pharmaceutically acceptable salt thereof.

6. A compound, which is one of the following compounds:

[2-(4-Bromo-phenyl)-pyrrolidin-1-yl]-(3-methyl-1H-pyrazolo[3,4-b]pyridin-5-yl)-methanone,

[(S)-2-(4-Bromo-phenyl)-pyrrolidin-1-yl]-(3-methyl-1H-pyrazolo[3,4-b]pyridin-5-yl)-methanone,

[2-(4-Bromo-phenyl)-pyrrolidin-1-yl]-(3-propyl-1H-indazol-5-yl)-methanone,

[(S)-2-(4-Bromo-phenyl)-pyrrolidin-1-yl]-(3-propyl-1H-indazol-5-yl)-methanone,

[2-(4-Chloro-phenyl)-pyrrolidin-1-yl]-(3-propyl-1H-indazol-5-yl)-methanone,

[2-(4-Chloro-phenyl)-pyrrolidin-1-yl]-(3-methyl-1H-pyrazolo[3,4-b]pyridin-5-yl)-methanone,

[(S)-2-(4-Chloro-phenyl)-pyrrolidin-1-yl]-(3-propyl-1H-indazol-5-yl)-methanone,

[(S)-2-(4-Chloro-phenyl)-pyrrolidin-1-yl]-(3-methyl-1H-pyrazolo[3,4-b]pyridin-5-yl)-methanone,

[2-(4-Fluoro-phenyl)-piperidin-1-yl]-(3-methyl-1H-pyrazolo[3,4-b]pyridin-5-yl)-methanone,

[(S)-2-(4-Fluoro-phenyl)-piperidin-1-yl]-(3-methyl-1H-pyrazolo[3,4-b]pyridin-5-yl)-methanone, (3-Methyl-1H-pyrazolo[3,4-b]pyridin-5-yl)-(2-phenyl-piperidin-1-yl)-methanone, (3-Methyl-1H-pyrazolo[3,4-b]pyridin-5-yl)-(2-phenyl-pyrrolidin-1-yl)-methanone,

[2-(3-Chloro-phenyl)-pyrrolidin-1-yl]-(3-methyl-1H-pyrazolo[3,4-b]pyridin-5-yl)-methanone, (3-Methyl-1H-pyrazolo[3,4-b]pyridin-5-yl)-(3-phenyl-pyrrolidin-1-yl)-methanone,

[2-(2-Chloro-phenyl)-pyrrolidin-1-yl]-(3-methyl-1H-pyrazolo[3,4-b]pyridin-5-yl)-methanone,

[2-(4-Fluoro-phenyl)-pyrrolidin-1-yl]-(3-methyl-1H-pyrazolo[3,4-b]pyridin-5-yl)-methanone, (3-Methyl-1H-pyrazolo[3,4-b]pyridin-5-yl)-((S)-2-phenyl-piperidin-1-yl)-methanone,

[(S)-2-(4-Chloro-phenyl)-pyrrolidin-1-yl]-(3-isobutyl-1H-indazol-5-yl)-methanone,

[(S)-2-(2-Chloro-phenyl)-pyrrolidin-1-yl]-(3-methyl-1H-pyrazolo[3,4-b]pyridin-5-yl)-methanone, (3-Methyl-1H-pyrazolo[3,4-b]pyridin-5-yl)-((S)-2-phenyl-pyrrolidin-1-yl)-methanone, (3-Methyl-1H-pyrazolo[3,4-b]pyridin-5-yl)-((S)-3-phenyl-pyrrolidin-1-yl)-methanone,

[(S)-2-(4-Fluoro-phenyl)-pyrrolidin-1-yl]-(3-methyl-1H-pyrazolo[3,4-b]pyridin-5-yl)-methanone,

[(S)-2-(3-Chloro-phenyl)-pyrrolidin-1-yl]-(3-methyl-1H-pyrazolo[3,4-b]pyridin-5-yl)-methanone,

[(S)-2-(4-Chloro-phenyl)-pyrrolidin-1-yl]-(3-methyl-1H-indazol-5-yl)-methanone,

[(S)-2-(4-Bromo-phenyl)-pyrrolidin-1-yl]-(3-methyl-1H-indazol-5-yl)-methanone,

[(S)-2-(4-Chloro-phenyl)-pyrrolidin-1-yl]-(3-methyl-1H-pyrazolo[4,3-b]pyridin-5-yl)-methanone,

[(S)-2-(4-Bromo-phenyl)-pyrrolidin-1-yl]-(3-methyl-1H-pyrazolo[4,3-b]pyridin-5-yl)-methanone,

[2-(4-Chloro-phenyl)-azetidin-1-yl]-(3-methyl-1H-pyrazolo[3,4-b]pyridin-5-yl)-methanone, (3-Methyl-1H-pyrazolo[3,4-b]pyridin-5-yl)-(2-p-tolyl-pyrrolidin-1-yl)-methanone, (3-Methyl-1H-pyrazolo[3,4-b]pyridin-5-yl)-[2-(4-trifluoromethyl-phenyl)-pyrrolidin-1-yl]-methanone,

[3-(4-Chloro-phenyl)-piperidin-1-yl]-(3-methyl-1H-pyrazolo[3,4-b]pyridin-5-yl)-methanone,

[3-(4-Chloro-phenyl)-pyrrolidin-1-yl]-(3-methyl-1H-pyrazolo[3,4-b]pyridin-5-yl)-methanone,

[2-(4-Chloro-phenyl)-pyrrolidin-1-yl]-(3-cyclopropyl-1H-pyrazolo[3,4-b]pyridin-5-yl)-methanone,
(3-Amino-1H-indazol-5-yl)-[2-(4-bromo-phenyl)-pyrrolidin-1-yl]-methanone,
(3-Amino-1H-indazol-5-yl)-[(S)-2-(4-bromo-phenyl)-pyrrolidin-1-yl]-methanone,
(3-Amino-1H-indazol-5-yl)-[2-(4-chloro-phenyl)-pyrrolidin-1-yl]-methanone,
(3-Amino-1H-indazol-5-yl)-[(S)-2-(4-chloro-phenyl)-pyrrolidin-1-yl]-methanone,
(3-Amino-1H-indazol-5-yl)-(2-phenyl-piperidin-1-yl)-methanone,
(3-Amino-1H-indazol-5-yl)-(2-phenyl-pyrrolidin-1-yl)-methanone,
(3-Amino-1H-indazol-5-yl)-[2-(4-fluoro-phenyl)-pyrrolidin-1-yl]-methanone,
(3-Amino-1H-indazol-5-yl)-((S)-2-benzyl-piperidin-1-yl)-methanone,
(3-Amino-1H-indazol-5-yl)-((S)-2-phenyl-piperidin-1-yl)-methanone,
(3-Amino-1H-indazol-5-yl)-((R)-2-phenyl-piperidin-1-yl)-methanone,
(3-Amino-1H-indazol-5-yl)-[(S)-2-(4-fluoro-phenyl)-piperidin-1-yl]-methanone,
(3-Amino-1H-pyrazolo[3,4-b]pyridin-5-yl)-[(S)-2-(4-chloro-phenyl)-pyrrolidin-1-yl]-methanone,
(3-Amino-1H-pyrazolo[3,4-b]pyridin-5-yl)-[(S)-2-(4-bromo-phenyl)-pyrrolidin-1-yl]-methanone,
(3-Amino-1H-indazol-5-yl)-[2-(4-chloro-phenyl)-azetidin-1-yl]-methanone,
(3-Amino-1H-indazol-5-yl)-[2-(4-fluoro-phenyl)-azetidin-1-yl]-methanone,
(3-Amino-1H-indazol-5-yl)-[3-(4-chloro-phenyl)-pyrrolidin-1-yl]-methanone,
(3-Amino-1H-indazol-5-yl)-[(S)-2-(4-fluoro-phenyl)-pyrrolidin-1-yl]-methanone,
(3-Amino-1H-indazol-5-yl)-[(S)-2-(4-fluoro-phenyl)-azetidin-1-yl]-methanone,
(3-Methyl-1H-pyrazolo[3,4-b]pyridin-5-yl)-((S)-2-p-tolyl-pyrrolidin-1-yl)-methanone,
[(S)-2-(2-Methoxy-phenyl)-pyrrolidin-1-yl]-(3-methyl-1H-pyrazolo[3,4-b]pyridin-5-yl)-methanone,
[(2R,3R)-3-Amino-2-(4-fluoro-phenyl)-pyrrolidin-1-yl]-(3-methyl-1H-pyrazolo[3,4-b]pyridin-5-yl)-methanone,
[(S)-2-(4-Chloro-phenyl)-pyrrolidin-1-yl]-(3-cyclopropyl-1H-pyrazolo[3,4-b]pyridin-5-yl)-methanone,
[2-(4-Bromo-phenyl)-pyrrolidin-1-yl]-(1H-indazol-5-yl)-methanone,
[(S)-2-(4-Bromo-phenyl)-pyrrolidin-1-yl]-(1H-indazol-5-yl)-methanone,
(3-Methyl-1H-pyrazolo[3,4-b]pyridin-5-yl)-[(S)-2-(4-trifluoromethyl-phenyl)-pyrrolidin-1-yl]-methanone,
(3-Methyl-1H-pyrazolo[3,4-b]pyridin-5-yl)-[3-methyl-2-(4-trifluoromethyl-phenyl)-pyrrolidin-1-yl]-methanone,
N-4-(4-Chloro-phenyl)-1-(3-methyl-1H-pyrazolo[3,4-b]pyridine-5-carbonyl)-pyrrolidin-3-yl]-acetamide,
(3-Amino-1H-indazol-5-yl)-[2-(4-trifluoromethyl-phenyl)-pyrrolidin-1-yl]-methanone,
[(S)-2-(1H-Indazol-6-yl)-pyrrolidin-1-yl]-(3-methyl-1H-pyrazolo[3,4-b]pyridin-5-yl)-methanone,
(3-Chloro-1H-indazol-5-yl)-[(S)-2-(4-chloro-phenyl)-pyrrolidin-1-yl]-methanone,
[(S)-2-(4-Fluoro-phenyl)-azetidin-1-yl]-(3-methyl-1H-pyrazolo[3,4-b]pyridin-5-yl)-methanone,
[(S)-2-(4-Chloro-phenyl)-pyrrolidin-1-yl]-(3-methoxy-1H-pyrazolo[3,4-b]pyridin-5-yl)-methanone,
(3-Chloro-1H-indazol-5-yl)-[3-(4-chloro-phenyl)-pyrrolidin-1-yl]-methanone,
[2-(4-Chloro-phenyl)-4-methyl-piperazin-1-yl]-(3-methyl-1H-indazol-5-yl)-methanone,
[2-(4-Chloro-phenyl)-pyrrolidin-1-yl]-(3-trifluoromethyl-1H-pyrazolo[3,4-b]pyridin-5-yl)-methanone,
(3-Amino-1H-indazol-5-yl)-[(S)-2-(4-trifluoromethyl-phenyl)-pyrrolidin-1-yl]-methanone,
(3-Amino-1H-indazol-5-yl)-[2-(4-isopropyl-phenyl)-pyrrolidin-1-yl]-methanone,
(3-Chloro-1H-indazol-5-yl)-[2-(4-trifluoromethyl-phenyl)-pyrrolidin-1-yl]-methanone,
[(S)-2-(4-Chloro-phenyl)-azetidin-1-yl]-(3-methyl-1H-pyrazolo[3,4-b]pyridin-5-yl)-methanone,
[(s)-2-(4-Chloro-phenyl)-pyrrolidin-1-yl]-(3-methyl-1H-pyrazolo[3,4-c]pyridin-5-yl)-methanone,
[2-(4-Chloro-3-fluoro-phenyl)-pyrrolidin-1-yl]-(3-methyl-1H-pyrazolo[3,4-b]pyridin-5-yl)-methanone,
[(S)-2-(4-Chloro-2-fluoro-phenyl)-pyrrolidin-1-yl]-(3-methyl-1H-pyrazolo[3,4-b]pyridin-5-yl)-methanone,
[3-(4-Chloro-phenyl)-morpholin-4-yl]-(3-methyl-1H-indazol-5-yl)-methanone,
[(S)-2-(4-Chloro-phenyl)-pyrrolidin-1-yl]-(3-fluoro-1H-indazol-5-yl)-methanone,
[(S)-2-(4-Methoxy-phenyl)-pyrrolidin-1-yl]-(3-methyl-1H-pyrazolo[3,4-b]pyridin-5-yl)-methanone,
(3-Methyl-1H-pyrazolo[3,4-b]pyridin-5-yl)-[(2S,3R)-3-methyl-2-(4-trifluoromethyl-phenyl)-pyrrolidin-1-yl]-methanone,
[(S)-2-(4-Chloro-phenyl)-pyrrolidin-1-yl]-(3-trifluoromethyl-1H-pyrazolo[3,4-b]pyridin-5-yl)-methanone,
[(S)-2-(4-Chloro-phenyl)-pyrrolidin-1-yl]-(3-methylsulfanyl-1H-indazol-5-yl)-methanone,
[2-(4-Isopropyl-phenyl)-pyrrolidin-1-yl]-(3-methyl-1H-pyrazolo[3,4-b]pyridin-5-yl)-methanone,
Trans-[3-(4-Chloro-phenyl)-4-hydroxy-pyrrolidin-1-yl]-(3-methyl-1H-pyrazolo[3,4-b]pyridin-5-yl)-methanone,
(3-Amino-1H-indazol-5-yl)-[(S)-2-(4-isopropyl-phenyl)-pyrrolidin-1-yl]-methanone,
[(S)-2-(4-Fluoro-phenyl)-pyrrolidin-1-yl]-(3-methyl-1H-pyrazolo[4,3-b]pyridin-5-yl)-methanone,
(3-Methyl-1H-pyrazolo[4,3-b]pyridin-5-yl)-[(S)-2-(4-trifluoromethyl-phenyl)-pyrrolidin-1-yl]-methanone,
[(S)-2-(4-Chloro-3-fluoro-phenyl)-pyrrolidin-1-yl]-(3-methyl-1H-pyrazolo[3,4-b]pyridin-5-yl)-methanone,
[2-(4-Chloro-3-fluoro-phenyl)-pyrrolidin-1-yl]-(3-methyl-1H-pyrazolo[4,3-b]pyridin-5-yl)-methanone,
[(S)-2-(4-Isopropyl-phenyl)-pyrrolidin-1-yl]-(3-methyl-1H-pyrazolo[3,4-b]pyridin-5-yl)-methanone,
[(S)-2-(4-Fluoro-phenyl)-azetidin-1-yl]-(3-methyl-1H-indazol-5-yl)-methanone,
[(S)-2-(4-Chloro-phenyl)-pyrrolidin-1-yl]-(3-methylamino-1H-indazol-5-yl)-methanone,
[(S)-2-(4-Chloro-phenyl)-pyrrolidin-1-yl]-(6-fluoro-3-methyl-1H-indazol-5-yl)-methanone,
[(S)-2-(4-Chloro-phenyl)-azetidin-1-yl]-(3-methyl-1H-indazol-5-yl)-methanone,
or a stereoisomer or tautomer or pharmaceutically acceptable salt thereof.

7. A pharmaceutical composition comprising a compound according to claim 1, or a pharmaceutically acceptable salt thereof and a pharmaceutically acceptable carrier.

8. A method for treating a hyperproliferative, inflammatory or degenerative disease, comprising administering to a subject in need thereof an effective amount of a compound of claim 1 or a pharmaceutically acceptable salt thereof.

9. The method of claim 8, wherein the hyperproliferative disease is cancer of the brain, lung, colon, epidermoid, squamous cell, bladder, gastric, pancreatic, breast, head & neck, renal, kidney, liver, ovarian, prostate, uterine, oesophageal, testicular, gynecological, thyroid cancer, melanoma, acute myelogenous leukemia, multiple myeloma, chronic myelogneous leukemia, myeloid cell leukemia, or Kaposi's sarcoma.

10. A kit comprising separate packs of
a) a compound according to claim 1 or a pharmaceutically acceptable salt thereof, and
b) a further pharmaceutically active ingredient.

11. A process for preparing a compound according to claim 1, comprising reacting a compound of Formula (IV)

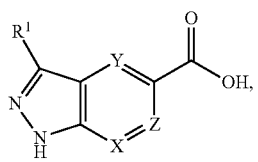

(IV)

optionally in the presence of an activating agent, with a compound of Formula (III),

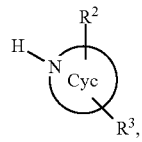

(III)

to yield a compound of Formula (I).

12. A method for treating a hyperproliferative, inflammatory or degenerative disease, comprising administering to a subject in need thereof an effective amount of a compound of claim 6 or pharmaceutically acceptable salt thereof.

13. The method of claim 12, wherein the hyperproliferative disease is cancer of the brain, lung, colon, epidermoid, squamous cell, bladder, gastric, pancreatic, breast, head & neck, renal, kidney, liver, ovarian, prostate, uterine, oesophageal, testicular, gynecological, thyroid cancer, melanoma, acute myelogenous leukemia, multiple myeloma, chronic myelogneous leukemia, myeloid cell leukemia, or Kaposi's sarcoma.

14. The compound according to claim 1, or a pharmaceutically acceptable salt thereof.

15. The compound according to claim 6, or a pharmaceutically acceptable salt thereof.

* * * * *